(12) United States Patent
Heo et al.

(10) Patent No.: US 8,877,747 B2
(45) Date of Patent: Nov. 4, 2014

(54) INDENONE DERIVATIVE AND PHARMACEUTICAL COMPOSITION COMPRISING SAME

(75) Inventors: Jung Nyoung Heo, Daejeon (KR); Myung Ae Bae, Daejeon (KR); Nack Jeong Kim, Daejeon (KR); Sung Youn Chang, Daejeon (KR); Nam Sook Kang, Daejeon (KR); Sung Eun Yoo, Chungcheongnam-do (KR); Eun Sook Hwang, Seoul (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 240 days.

(21) Appl. No.: 13/394,102

(22) PCT Filed: Oct. 21, 2009

(86) PCT No.: PCT/KR2009/006085
§ 371 (c)(1),
(2), (4) Date: May 7, 2012

(87) PCT Pub. No.: WO2011/030955
PCT Pub. Date: Mar. 17, 2011

(65) Prior Publication Data
US 2012/0214991 A1    Aug. 23, 2012

(30) Foreign Application Priority Data

Sep. 11, 2009 (KR) .................... 10-2009-0085954

(51) Int. Cl.
| | |
|---|---|
| *C07D 417/12* | (2006.01) |
| *C07D 295/08* | (2006.01) |
| *C07D 401/12* | (2006.01) |
| *C07D 403/12* | (2006.01) |
| *C07D 413/12* | (2006.01) |
| *C07D 295/26* | (2006.01) |
| *A61K 31/5375* | (2006.01) |
| *A61K 31/5377* | (2006.01) |
| *A61K 31/541* | (2006.01) |
| *A61K 31/54* | (2006.01) |

(52) U.S. Cl.
USPC ................. 514/227.5; 514/237.8; 514/238.8; 514/253.01; 514/252.01; 544/58.2; 544/131; 544/174; 544/128; 544/163; 544/122; 544/360; 544/383; 544/295; 544/82; 546/82; 546/194

(58) Field of Classification Search
USPC ........ 544/58.2, 131, 174, 128, 169, 163, 122, 544/360, 383, 295, 82; 546/82, 194; 514/227.5, 237.8, 238.8, 253.01, 514/252.01
See application file for complete search history.

(56) References Cited

U.S. PATENT DOCUMENTS

| | | |
|---|---|---|
| 2003/0166643 A1 | 9/2003 | McDevitt et al. |
| 2005/0130221 A1 | 6/2005 | Flynn et al. |

FOREIGN PATENT DOCUMENTS

WO    WO 2009/038731 A2    3/2009

OTHER PUBLICATIONS

Dalev et al. Nauchni Tr., Visshiya Med. Inst. Sofia (1962), 41(4), 13-19.*
Kerr, et al., "The concise synthesis of chalcone, indanone and indenone analogues of combretastatin A4", *Bioorganic & Medicinal Chemistry*, ( 2007) pp. 3290-3298.
McDevitt, et al."Estrogen receptor ligands: design and synthesis of new 2-arylindene-1-ones"4" , Bioorganic & Medicinal Chemistry, Letters (2007) pp. 3137-3142.
Dalev, D. et al., "Interaction of 5(or 6)-Ethoxybenzalphthalides with Aryl and Alkyl Magnesium Bromides" Nauchni Tr. Viss. Med. Inst. Sofia, 41(4), 1-11, 1962.
Dalev, D., et al. "Structre of the Isomeric Indones fo the Phthalide of Beta-ethoxyphthalic Anhydride" Nauchni Tr. Vissiya Med. Inst. Sofia, 41(4), 13-19, 1962.

* cited by examiner

*Primary Examiner* — Kahsay Habte
(74) *Attorney, Agent, or Firm* — Clark G. Sullivan; Troutman Sanders LLP

(57) ABSTRACT

An indenone derivative of formula (1) is effective in enhancing the activity of osteoblastic cells and inhibiting bone resorption by osteoclastic cells, and a pharmaceutical composition comprising the indenone derivative or a pharmaceutically acceptable salt thereof is useful for preventing or treating bone diseases such as osteoporosis.

20 Claims, 3 Drawing Sheets

INDENONE DERIVATIVE AND PHARMACEUTICAL COMPOSITION COMPRISING SAME

FIELD OF THE INVENTION

The present invention relates to an indenone derivative and a pharmaceutical composition comprising the same which is used for preventing or treating bone diseases such as osteoporosis.

BACKGROUND OF THE INVENTION

Osteoporosis is caused by reduced bone mass, leading to weakening of the bone strength and an increased risk of bone fracture. The bone mass is controlled by the continuous bone resorption and bone formation processes. The peak bone mass is achieved at about 25 ages in healthy people, and decreases slowly with advancing age. Women generally have a lower bone mass than men, and the bone loss becomes increasing more pronounced after menopause. Ten million people are presumed to suffer from osteoporosis in U.S., and about thirty-four million people in the world have the problem of low bone mass, and they are under the risk of osteoporosis. Clinical studies showed that the death rate within two years from the appearance of symptoms of osteoporosis is currently about 12%, and many osteoporosis patients (about 30%) are faced to stay home due to bone fracture. Recently, the number of osteoporosis patients has increased due to the aging of global population, and accordingly, there has existed a need for developing an efficacious medicament for preventing and treating osteoporosis.

Bone is a living tissue which is composed of several different types of cells. In healthy individuals, the amount of bone removed or resorbed by the osteoclastic cells is compensated by new bone made by the osteoblastic cells. The overall bone formation and bone resorption occur to the extent of about 14% of bones over a year to maintain a steady bone mass, but for individuals suffering from a bone-resorbing disease, such balance cannot be achieved. In women, about 5% a year bone loss from the spine occurs after menopause. Such symptom has been attributed to estrogen deficiency associated with menopause. However, the question as to what mechanism is involved between the loss of estrogen and increased bone resorption remains unresolved.

In order to reduce the risk of bone fracture, various methods for maintaining or increasing the bone mass are currently used, by reducing the bone resorption rate, increasing the bone formation rate, or a combination thereof. As therapeutic agents for blocking bone resorption, integrin $\alpha_v\beta_3$ antagonists, cathepsin K inhibitors, and inhibitors against OPG/PANKL/RANK system have been investigated. Further, as therapeutic agents for enhancing the bone formation, parathyroid hormones and their derivatives structure have been reported. Exemplary therapeutic agents include new parathyroid hormonal products, calcium sensing receptor antagonists which regulate the secretion of parathyroid hormone, selective androgen receptor modulators (SARMs), growth hormone secretagogues, insulin-like growth elements, proteosome inhibitors, and statins.

The currently methods for treating bone loss generally involve the administration of compounds such as estrogen, bisphosphonates, calcitonin, and raloxifene. These compounds, however, are generally used for long-term treatments, and they induce undesirable side effects. Further, such treatments are typically directed to the activity of mature osteoclasts, rather than reducing their formation. For example, estrogen induces the apoptosis of osteoclasts, while calcitonin causes the osteoclasts to shrink and detach from the bone surface (Hughes et al., *Nat. Med.* 2:1132-1136, 1996; Jilka et al., *Exp. Hematol.* 23:500-506, 1995). Similarly, bisphosphonates reduce the osteoclast activity, change their morphology, and increase the apoptosis of osteoclasts (Parfitt et al., *J. Bone Miner Res.* 11:150-159, 1996; Suzuki et al., *Endocrinology* 137: 4685-4690, 1996).

Currently available therapeutic agents for treating osteoporosis include bisphosphonates, hormonal drugs, vitamin D and its analogues, calcitonin, and calcium. Representative bisphosphonates include alendronate (Merck Co., Ltd.), risedronate (Hoffman-La Roche Ltd.), zoledronate (Novartis AG; EP Patent No. 275,821), ibandronate (Hoffman-La Roche Ltd.; U.S. Pat. No. 4,942,157), and minodronate (Yamanouchi Pharmaceutical Co., Ltd.; EP Patent No. 354,806). Bisphosphonates, however, suffers from the problems of low absorption rates through the gastrointestinal tract (10% or less) and the tendency to cause esophagitis when the patients do not follow the complicated administration guidance. In particular, it has been reported that alendronate causes some side effects, e.g., gastrointestinal disorders and osteonecrosis of the jaw, besides the fact that long-term administration of bisphosphonates osteonecrosis. Accordingly, novel therapeutic agents for osteoporosis are required.

Exemplary hormonal drugs include raloxifene (Eli Lilly Co.), droloxyfene (Pfizer Inc.; EP Patent No. 54168), lasopoxifene (Pfizer Inc.; WO 97/16434), FC-1271 (homosmedical Co. and Orion Corp.; WO 96/07402), TES-424 (Ligand Co. and Weyers Co.; U.S. Pat. No. 5,948,755), and SERMs, which are at the stage of clinical studies. However, these drugs bring the risk of causing breast or uterine cancer, and accordingly, they are not suitable for use as a therapeutic agent for osteoporosis which requires a long-term administration.

Further, vitamin D and its analogues are expensive and its therapeutic efficacy for osteoporosis is not clearly established; calcitonin is relatively expensive and requires a complicated administration procedure; and calcium is effective only for the prevention of osteoporosis, having no therapeutic effect.

SUMMARY OF THE INVENTION

Accordingly, it is an object of the present invention to provide a novel indenone derivative and a pharmaceutical composition comprising the same for effectively preventing or treating bone diseases such as osteoporosis.

In accordance with one aspect of the present invention, there is provided an indenone derivative of formula (1) or a pharmaceutically acceptable salt thereof:

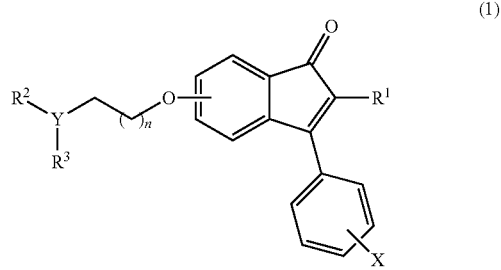

wherein, n is 0, 1 or 2;

X is one or more substituents introduced to the ortho-, meta- or para-position of the phenyl group, each selected independently from the group consisting of hydrogen, halogen, —CN, —CF$_3$, C$_{1-6}$alkyl, C$_{1-6}$alkoxy, C$_{3-10}$cycloalkyl, and C$_{3-8}$cycloalkoxy;

R$^1$ is C$_{6-10}$aryl or 5 to 10-membered heteroaryl;

Y is CH, N, N$^+$(—C$_{1-6}$alkyl), or N$^+$(—O$^-$); and

R$^2$ and R$^3$ are each independently hydrogen, C$_{1-6}$alkyl, C$_{1-6}$alkoxy, C$_{6-10}$aryl, or 5 to 10-membered heteroaryl, or are fused together with Y to form C$_{3-10}$cycloalkyl or 5 to 10-membered heterocycloalkyl, in which the C$_{6-10}$aryl, 5 to 10-membered heteroaryl, C$_{3-10}$cycloalkyl, and 5 to 10-membered heterocycloalkyl are each independently and optionally substituted with at least one substituent selected from the group consisting of halogen, oxo, —CF$_3$, —CN, amino, hydroxy, carboxy, carbamoyl, nitro, thiol, C$_{1-6}$alkyl, C$_{2-6}$alkenyl, C$_{1-6}$alkoxy, C$_{3-10}$cycloalkyl, C$_{3-8}$cycloalkoxy, C$_{6-10}$aryl, C$_{6-10}$aryloxy, —C(O)R$^4$, —C(O)OR$^4$, —C(O)NR$^4$R$^5$, —S(O)R$^4$, —S(O$_2$)R$^4$, —S(O$_2$)NR$^4$R$^5$, —NR$^4$R$^5$, and —NR$^4$C(O)R$^5$, R$^4$ and R$^5$ being each independently hydrogen, C$_{1-6}$alkyl, or C$_{3-10}$cycloalkyl.

The indenone derivative of formula (1) or a pharmaceutically acceptable salt thereof is effective in increasing the activity of osteoblastic cells and inhibiting bone resorption by osteoclastic cells, so that the inventive pharmaceutical composition is useful for preventing or treating bone diseases such as osteoporosis.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
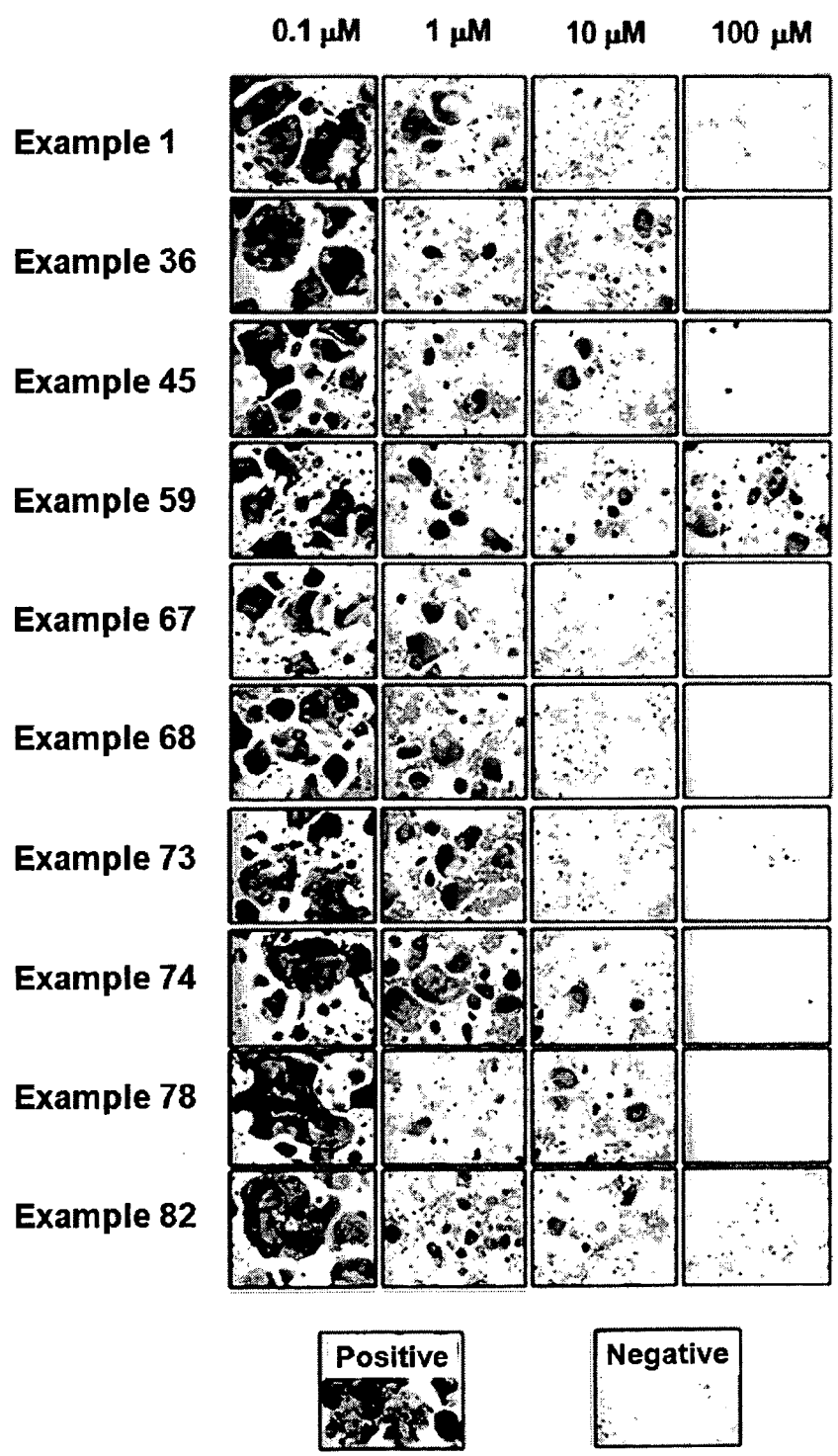
FIG. 1: TRAP staining results showing the inhibitory effects of the inventive indenone derivatives on the activity of the osteoclast cells.

The present invention provides an indenone derivative of formula (1) and a pharmaceutically acceptable salt thereof.

The pharmaceutically acceptable salt of the compound of formula (1) may be prepared using any of the conventional methods, and it may be a salt of an inorganic acid such as hydrochloric acid, hydrobromic acid, sulfuric acid, sodium hydrogen sulfate, phosphoric acid, nitric acid, and carbonic acid; a salt of an organic acid such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, and acetylsalicylic acid (aspirin); a salt of an amino acid such as glycine, alanine, vaniline, isoleucine, serine, cystein, cystine, aspartic acid, glutamine, lysine, arginine, tyrosine, and proline; a salt of a sulfonic acid such as methanesulfonic acid, ethanesulfonic acid, benzenesulfonic acid, and toluenesulfonic acid; a metal salt formed by a reaction with an alkali metal such as sodium and potassium; or an ammonium salt.

The term "aryl" as used herein comprises an aromatic group such as phenyl and substituted phenyl as well as a bicyclic aromatic group such as naphthyl and phenanthrenyl.

The term "cycloalkyl" as used herein refers to a cycloalkyl or cycloalkenyl group such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octanyl, and norbornanyl.

The term "heterocycloalkyl" as used herein refers to a ring containing at least one hetero atom selected from the group consisting of N, S, and O, e.g., pyrrolidinyl, tetrahydrofuranyl, dihydrofuranyl, tetrahydropyranyl, pyranyl, thiopyranyl, aziridinyl, oxiranyl, dioxolanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, and piperazinyl.

The term "heteroaryl" as used herein refers to an aromatic ring containing at least one hetero atom selected from the group consisting of N, S, and O, e.g., furyl, thienyl, thiazolyl, pyrazolyl, isothiazolyl, oxazolyl, isooxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5,6,7,8-tetrahydro-quinolin-3-yl, benzooxazolyl, benzo[d][1,3]dioxolyl, benzothiazolyl, benzisothiazolyl, benzisooxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl.

The aryl, heteroaryl, cycloalkyl, or heterocycloalkyl group may be optionally substituted with at least one substituent selected from the group consisting of halogen, oxo, —CF$_3$, —CN, amino, hydroxy, carboxy, carbamoyl, nitro, thiol, C$_{1-6}$alkyl, C$_{2-6}$alkenyl, C$_{1-6}$alkoxy, C$_{3-10}$cycloalkyl, C$_{3-6}$cycloalkoxy, C$_{6-20}$aryl, C$_{6-20}$aryloxy, —C(O)R$^4$, —C(O)OR$^4$, —C(O)NR$^4$R$^5$, —S(O)R$^4$, —S(O$_2$)R$^4$, —S(O$_2$)NR$^4$R$^5$, —NR$^4$R$^5$, and —NR$^4$C(O)R$^5$, wherein R$^4$ and R$^5$ are each independently hydrogen, C$_{1-6}$alkyl, or C$_{3-8}$cycloalkyl.

In the compound of formula (1) according to the present invention, R$^1$ is preferably C$_6$-aryl or 6 to 10-membered heteroaryl, which is unsubstituted or substituted with at least one selected from halogen and C$_{1-6}$alkoxy. More preferably, R$^1$ is phenyl which is substituted with at least one selected from fluoro and methoxy; or pyridyl, pyrimidyl, quinolyl, or isoquinolyl, each of which is unsubstituted or substituted with at least one selected from fluoro and methoxy.

Further, R$^2$ and R$^3$ are preferably fused together with Y to form a 5 to 10-membered heterocycloalkyl group which is unsubstituted or substituted with —S(O$_2$)R$^4$, wherein R$^4$ being C$_{1-6}$alkyl. More preferably, R$^2$ and R$^3$ are fused together with Y to form morpholinyl;

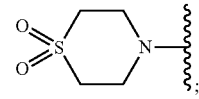 [SMILES: *N1CCS(=O)(=O)CC1]

or a piperidinyl or piperazinyl group substituted with —S(O₂)CH₃.

Furthermore, X is one or more substituents introduced to the ortho-, meta-, or para-position of the phenyl group, each selected independently from hydrogen and halogen. More preferably, X is hydrogen, 2,4-difluoro, or 3,5-difluoro.

Furthermore, n is preferably 1 or 2, and Y is preferably CH or N.

According to an example of the compound according to the present invention, the indenone derivative is preferably in the form of formula (1a):

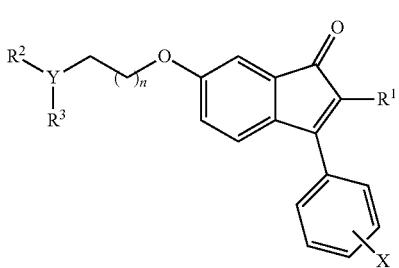

(1a)

wherein, n, X, Y, $R^1$, $R^2$ and $R^3$ have the same meanings as defined in formula (1).

In the compound of formula (Ia) according to the present invention, $R^1$ is preferably $C_6$-aryl or 6 to 10-membered heteroaryl, which is unsubstituted or substituted with at least one selected from halogen and $C_{1-6}$alkoxy. More preferably, $R^1$ is phenyl which is substituted with at least one selected from fluoro and methoxy; or pyridyl, pyrimidyl, quinolyl, or isoquinolyl, each of which is unsubstituted or substituted with at least one selected from fluoro and methoxy.

Further, $R^2$ and $R^3$ are preferably fused together with Y to form a 5 to 10-membered heterocycloalkyl group, which is unsubstituted or substituted with —S(O₂)$R^4$, $R^4$ being $C_{1-6}$alkyl. More preferably, $R^2$ and $R^3$ are fused together with Y to form morpholinyl;

or a piperidinyl or piperazinyl group substituted with —S(O₂)CH₃.

Furthermore, X is preferably one or more substituents introduced to the ortho-, meta- or para-position of the phenyl group, each selected independently from hydrogen and halogen. More preferably, X is hydrogen, 2,4-difluoro, or 3,5-difluoro.

Exemplary compounds according to the present invention are indenone derivatives listed below and pharmaceutical acceptable salts thereof:
1) 6-(2-morpholinoethoxy)-3-phenyl-2-(pyridin-3-yl)-1H-inden-1-one;
2) 6-(2-morpholinoethoxy)-2-(3-fluoro-4-methoxyphenyl)-3-phenyl-1H-inden-1-one;
3) 6-(2-morpholinoethoxy)-3-phenyl-2-(quinolin-3-yl)-1H-inden-1-one;
4) 4-(6-(2-morpholinoethoxy)-1-oxo-3-phenyl-1H-inden-2-yl)benzamide;
5) 3-(6-(2-morpholinoethoxy)-1-oxo-3-phenyl-1H-inden-2-yl)benzonitrile;
6) 6-(2-morpholinoethoxy)-2-(6-methoxypyridin-3-yl)-3-phenyl-1H-inden-1-one;
7) 6-(2-morpholinoethoxy)-3-phenyl-2-(pyrimidin-5-yl)-1H-inden-1-one;
8) 6-(2-morpholinoethoxy)-3-phenyl-2-(pyridin-4-yl)-1H-inden-1-one;
9) 6-(2-morpholinoethoxy)-2-(6-fluoropyridin-3-yl)-3-phenyl-1H-inden-1-one;
10) 6-(2-morpholinoethoxy)-2-(4-(phenyl)phenyl)-3-phenyl-1H-inden-1-one;
11) 6-(2-morpholinoethoxy)-3-phenyl-2-p-tolyl-1H-inden-1-one;
12) 2-(6-(2-morpholinoethoxy)-1-oxo-3-phenyl-1H-inden-2-yl)benzonitrile;
13) 6-(2-morpholinoethoxy)-2-(4-(trifluoromethyl)phenyl)-3-phenyl-1H-inden-1-one;
14) N-(3-(6-(2-morpholinoethoxy)-1-oxo-3-phenyl-1H-inden-2-yl)phenyl)acetamide;
15) 6-(2-morpholinoethoxy)-2-(isoquinolin-4-yl)-3-phenyl-1H-inden-1-one;
16) 6-(2-morpholinoethoxy)-2-(naphthalen-3-yl)-3-phenyl-1H-inden-1-one;
17) 6-(2-morpholinoethoxy)-2-(4-fluorophenyl)-3-phenyl-1H-inden-1-one;
18) 6-(2-morpholinoethoxy)-2-(3,4-difluorophenyl)-3-phenyl-1H-inden-1-one;
19) 6-(2-morpholinoethoxy)-2-(3-fluoro-4-methylphenyl)-3-phenyl-1H-inden-1-one;
20) 6-(2-morpholinoethoxy)-2-(3-aminophenyl)-3-phenyl-1H-inden-1-one;
21) 6-(2-morpholinoethoxy)-2-(4-phenoxyphenyl)-3-phenyl-1H-inden-1-one;
22) 6-(2-morpholinoethoxy)-2-(4-methoxyphenyl)-3-phenyl-1H-inden-1-one;
23) 6-(2-morpholinoethoxy)-2-(4-chlorophenyl)-3-phenyl-1H-inden-1-one;
24) 6-(2-morpholinoethoxy)-3-(4-fluorophenyl)-2-(pyridin-3-yl)-1H-inden-1-one;
25) 6-(2-morpholinoethoxy)-3-(4-fluorophenyl)-2-(pyrimidin-5-yl)-1H-inden-1-one;
26) 6-(2-morpholinoethoxy)-2-(3,4-difluorophenyl)-3-(4-fluorophenyl)-1H-inden-1-one;
27) 6-(2-morpholinoethoxy)-2-(4-(trifluoromethyl)phenyl)-3-(4-fluorophenyl)-1H-inden-1-one;
28) 6-(2-morpholinoethoxy)-3-(4-chlorophenyl)-2-(pyridin-3-yl)-1H-inden-1-one;
29) 6-(2-morpholinoethoxy)-3-(4-chlorophenyl)-2-(3,4-difluorophenyl)-1H-inden-1-one;
30) 6-(2-morpholinoethoxy)-3-(4-chlorophenyl)-2-(pyrimidin-5-yl)-1H-inden-1-one;
31) 6-(2-morpholinoethoxy)-3-(4-chlorophenyl)-2-(4-(trifluoromethyl)phenyl)-1H-inden-1-one;
32) 6-(2-morpholinoethoxy)-3-(4-(trifluoromethyl)phenyl)-2-(pyridin-3-yl)-1H-inden-1-one;
33) 6-(2-morpholinoethoxy)-2,3-bis(4-(trifluoromethyl)phenyl)-1H-inden-1-one;
34) 6-(2-morpholinoethoxy)-3-(4-(trifluoromethyl)phenyl)-2-(3,4-difluorophenyl)-1H-inden-1-one;
35) 6-(2-morpholinoethoxy)-3-(4-(trifluoromethyl)phenyl)-2-(pyrimidin-5-yl)-1H-inden-1-one;
36) 6-(2-morpholinoethoxy)-3-(3,5-difluorophenyl)-2-(pyridin-3-yl)-1H-inden-1-one;
37) 6-(2-morpholinoethoxy)-2-(4-(trifluoromethyl)phenyl)-3-(3,5-difluorophenyl)-1H-inden-1-one;
38) 6-(2-morpholinoethoxy)-2-(3,4-difluorophenyl)-3-(3,5-difluorophenyl)-1H-inden-1-one;

39) 6-(2-morpholinoethoxy)-3-(3,5-difluorophenyl)-2-(pyrimidin-5-yl)-1H-inden-1-one;
40) 4-methyl-4-(2-{[2-(1-methylpyridin-1-ium-3-yl)-1-oxo-3-phenyl-1H-inden-6-yl]oxy}ethyl)morpholin-4-ium diiodide;
41) 1-methyl-3-{6-[2-(morpholin-4-yl)ethoxy]-1-oxo-3-phenyl-1H-inden-2-yl}pyridin-1-ium iodide;
42) 4-oxido-4-(2-{[1-oxo-3-phenyl-2-(pyridin-3-yl)-1H-inden-6-yl]oxy}ethyl)morpholin-4-ium;
43) 4-oxido-4-(2-{[2-(1-oxidopyridin-1-ium-3-yl)-1-oxo-3-phenyl-1H-inden-6-yl]oxy}ethyl)morpholin-4-ium;
44) tert-butyl 4-(2-(1-oxo-3-phenyl-2-(pyridin-3-yl)-1H-inden-6-yloxy)ethyl)piperazine-1-carboxylate;
45) 6-[2-(4-(methylsulfonyl)piperazin-1-yl)ethoxy]-3-phenyl-2-(pyridin-3-yl)-1H-inden-1-one;
46) 6-(2-(piperazin-1-yl)ethoxy)-3-phenyl-2-(pyridin-3-yl)-1H-inden-1-one;
47) 6-[2-(4-(methylsulfonyl)piperazin-1-yl)ethoxy]-2,3-bis[4-(trifluoromethyl)phenyl]-1H-inden-1-one;
48) 2-(3,4-difluorophenyl)-6-(2-(4-(methylsulfonyl)piperazin-1-yl)ethoxy)-3-(4-(trifluoromethyl)phenyl)-1H-inden-1-one;
49) 6-(2-(4-(methylsulfonyl)piperazin-1-yl)ethoxy)-2-(pyrimidin-5-yl)-3-(4-(trifluoromethyl)phenyl)-1H-inden-1-one;
50) 3-(3,5-difluorophenyl)-6-(2-(4-(methylsulfonyl)piperazin-1-yl)ethoxy)-2-(4-(trifluoromethyl)phenyl)-1H-inden-1-one;
51) 2-(3,4-difluorophenyl)-3-(3,5-difluorophenyl)-6-(2-(4-(methylsulfonyl)piperazin-1-yl)ethoxy)-1H-inden-1-one;
52) 3-(3,5-difluorophenyl)-6-(2-(4-(methylsulfonyl)piperazin-1-yl)ethoxy)-2-(pyrimidin-5-yl)-1H-inden-1-one;
53) 3-(4-chlorophenyl)-2-(3,4-difluorophenyl)-6-(2-(4-(methylsulfonyl)piperazin-1-yl)ethoxy)-1H-inden-1-one;
54) 3-(4-chlorophenyl)-6-(2-(4-(methylsulfonyl)piperazin-1-yl)ethoxy)-2-(pyrimidin-5-yl)-1H-inden-1-one;
55) tert-butyl 4-(3-(1-oxo-3-phenyl-2-(pyridin-3-yl)-1H-inden-6-yloxy)propyl)piperazine-1-carboxylate;
56) 6-(2-(dimethylamino)ethoxy)-3-phenyl-2-(pyridin-3-yl)-1H-inden-1-one;
57) 6-(3-(dimethylamino)propoxy)-3-phenyl-2-(pyridin-3-yl)-1H-inden-1-one;
58) tert-butyl 4-(2-(3-(3,5-difluorophenyl)-1-oxo-2-(pyridin-3-yl)-1H-inden-6-yloxy)ethyl)piperazine-1-carboxylate;
59) 3-(3,5-difluorophenyl)-6-(2-(4-(methylsulfonyl)piperazin-1-yl)ethoxy)-2-(pyridin-3-yl)-1H-inden-1-one;
60) 3-(3,5-difluorophenyl)-6-(3-(dimethylamino)propoxy)-2-(pyridin-3-yl)-1H-inden-1-one;
61) 3-(3,5-difluorophenyl)-6-phenethoxy-2-(pyridin-3-yl)-1H-inden-1-one;
62) 3-(3,5-difluorophenyl)-6-(2-(pyridin-2-yl)ethoxy)-2-(pyridin-3-yl)-1H-inden-1-one;
63) 3-(3,5-difluorophenyl)-6-(2-(piperidin-1-yl)ethoxy)-2-(pyridin-3-yl)-1H-inden-1-one;
64) tert-butyl 4-(3-(3-(3,5-difluorophenyl)-1-oxo-2-(pyridin-3-yl)-1H-inden-6-yl oxy)propyl)piperazine-1-carboxylate;
65) 6-(3-(4-methylpiperazin-1-yl)propoxy)-3-(3,5-difluorophenyl)-2-(pyridin-3-yl)-1H-inden-1-one;
66) 6-(3-(piperazin-1-yl)propoxy)-3-(3,5-difluorophenyl)-2-(pyridin-3-yl)-1H-inden-1-one;
67) 6-(3-(4-acetylpiperazin-1-yl)propoxy)-3-(3,5-difluorophenyl)-2-(pyridin-3-yl)-1H-inden-1-one;
68) 3-(3,5-difluorophenyl)-6-(3-(4-(methylsulfonyl)piperazin-1-yl)propoxy)-2-(pyridin-3-yl)-1H-inden-1-one;
69) tert-butyl 4-(2-(3-(3,5-difluorophenyl)-1-oxo-2-(pyridin-3-yl)-1H-inden-6-yloxy)ethyl)piperidine-1-carboxylate;
70) 3-(3,5-difluorophenyl)-6-(2-(piperidin-4-yl)ethoxy)-2-(pyridin-3-yl)-1H-inden-1-one;
71) 3-(3,5-difluorophenyl)-6-(2-(1-methylpiperidin-4-yl)ethoxy)-2-(pyridin-3-yl)-1H-inden-1-one;
72) 6-(2-(1-acetylpiperidin-4-yl)ethoxy)-3-(3,5-difluorophenyl)-2-(pyridin-3-yl)-1H-inden-1-one;
73) 3-(3,5-difluorophenyl)-6-(2-(1-(methylsulfonyl)piperidin-4-yl)ethoxy)-2-(pyridin-3-yl)-1H-inden-1-one;
74) 6-[2-(1,1-dioxothiomorpholin-4-yl)ethoxy]-3-(3,5-difluorophenyl)-2-(pyridin-3-yl)-1H-inden-1-one;
75) 3-(3,5-difluorophenyl)-6-(isopentyloxy)-2-(pyridin-3-yl)-1H-inden-1-one;
76) 6-(2-cyclohexylethoxy)-3-(3,5-difluorophenyl)-2-(pyridin-3-yl)-1H-inden-1-one;
77) 6-(2-cyclopentylethoxy)-3-(3,5-difluorophenyl)-2-(pyridin-3-yl)-1H-inden-1-one;
78) 3-(3,5-difluorophenyl)-2-(pyridin-3-yl)-6-(2-(tetrahydro-2H-pyran-4-yl)ethoxy)-1H-inden-1-one;
79) 3-(3,5-difluorophenyl)-2-(pyridin-3-yl)-6-((tetrahydrofuran-2-yl)methoxy)-1H-inden-1-one;
80) 6-(2-morpholinoethoxy)-3-(2-fluorophenyl)-2-(pyridin-3-yl)-1H-inden-1-one;
81) 6-(2-morpholinoethoxy)-3-(3-fluorophenyl)-2-(pyridin-3-yl)-1H-inden-1-one;
82) 6-(2-morpholinoethoxy)-3-(2,4-difluorophenyl)-2-(pyridin-3-yl)-1H-inden-1-one;
83) 6-(2-morpholinoethoxy)-3-phenyl-2-(pyridin-2-yl)-1H-inden-1-one;
84) 2-(benzo[b]thiophen-3-yl)-6-(2-morpholinoethoxy)-3-phenyl-1H-inden-1-one;
85) 2-(benzo[1,3]dioxol-5-yl)-6-(2-morpholinoethoxy)-3-phenyl-1H-inden-1-one;
86) 2-(5-chlorothiophen-2-yl)-6-(2-morpholinoethoxy)-3-phenyl-1H-inden-1-one;
87) 2-(1-methyl-1H-indol-5-yl)-6-(2-morpholinoethoxy)-3-phenyl-1H-inden-1-one;
88) 2-(1H-indol-2-yl)-6-(2-morpholinoethoxy)-3-phenyl-1H-inden-1-one;
89) 6-(2-morpholinoethoxy)-2-(6-(morpholin-4-yl)pyridin-3-yl)-3-phenyl-1H-inden-1-one;
90) 6-(2-morpholinoethoxy)-3-phenyl-2-(1H-pyrrol-2-yl)-1H-inden-1-one;
91) 6-(2-morpholinoethoxy)-2-(benzofuran-2-yl)-3-phenyl-1H-inden-1-one;
92) 3-(3,5-difluorophenyl)-6-[2-(1,1-dioxothiomorpholin-4-yl)ethoxy]-2-(quinolin-3-yl)-1H-inden-1-one;
93) 3-(3,5-difluorophenyl)-2-(6-methoxypyridin-3-yl)-6-[2-(1,1-dioxothiomorpholin-4-yl)ethoxy]-1H-inden-1-one;
94) 3-(3,5-difluorophenyl)-6-[2-(1,1-dioxothiomorpholin-4-yl)ethoxy]-2-p-tolyl-1H-inden-1-one;
95) 2-(3-fluoro-4-methoxyphenyl)-3-(3,5-difluorophenyl)-6-[2-(1,1-dioxothiomorpholin-4-yl)ethoxy]-1H-inden-1-one;
96) 3-(3,5-difluorophenyl)-6-{2-[4-(methylsulfonyl)piperazin-1-yl]ethoxy}-2-(quinolin-3-yl)-1H-inden-1-one;
97) 3-(3,5-difluorophenyl)-2-(6-methoxypyridin-3-yl)-6-{2-[4-(methylsulfonyl)piperazin-1-yl]ethoxy}-1H-inden-1-one;
98) 3-(3,5-difluorophenyl)-6-{2-[4-(methylsulfonyl)piperazin-1-yl]ethoxy}-2-p-tolyl-1H-inden-1-one;
99) 2-(3-fluoro-4-methoxyphenyl)-3-(3,5-difluorophenyl)-6-{2-[4-(methylsulfonyl)piperazin-1-yl]ethoxy}-1H-inden-1-one;

100) 3-(3,5-difluorophenyl)-2-(6-methoxypyridin-3-yl)-6-{2-[1-(methylsulfonyl)piperidin-4-yl]ethoxy}-1H-inden-1-one;

101) 3-(3,5-difluorophenyl)-6-{2-[1-(methylsulfonyl)piperidin-4-yl]ethoxy}-2-(quinolin-3-yl)-1H-inden-1-one;

102) 2-(3-fluoro-4-methoxyphenyl)-3-(3,5-difluorophenyl)-6-{2-[1-(methylsulfonyl)piperidin-4-yl]ethoxy}-1H-inden-1-one;

103) 3-(3,5-difluorophenyl)-6-{2-[1-(methylsulfonyl)piperidin-4-yl]ethoxy}-2-p-tolyl-1H-inden-1-one;

104) 3-(3,5-difluorophenyl)-6-{3-[4-(methylsulfonyl)piperazin-1-yl]propoxy}-2-(quinolin-3-yl)-1H-inden-1-one;

105) 3-(3,5-difluorophenyl)-6-{3-[4-(methylsulfonyl)piperazin-1-yl]propoxy}-2-p-tolyl-1H-inden-1-one;

106) 2-(3-fluoro-4-methoxyphenyl)-3-(3,5-difluorophenyl)-6-{3-[4-(methylsulfonyl)piperazin-1-yl]propoxy}-1H-inden-1-one;

107) 3-(3,5-difluorophenyl)-2-(6-methoxypyridin-3-yl)-6-{3-[4-(methylsulfonyl)piperazin-1-yl]propoxy}-1H-inden-1-one;

108) 3-(2,4-difluorophenyl)-6-{3-[4-(methylsulfonyl)piperazin-1-yl]propoxy}-2-p-tolyl-1H-inden-1-one;

109) 3-(2,4-difluorophenyl)-2-(6-methoxypyridin-3-yl)-6-{3-[4-(methylsulfonyl)piperazin-1-yl]propoxy}-1H-inden-1-one;

110) 2-(3-fluoro-4-methoxyphenyl)-3-(2,4-difluorophenyl)-6-{3-[4-(methylsulfonyl)piperazin-1-yl]propoxy}-1H-inden-1-one;

111) 3-(2,4-difluorophenyl)-6-{3-[4-(methylsulfonyl)piperazin-1-yl]propoxy}-2-(quinolin-3-yl)-1H-inden-1-one;

112) 3-(2,4-difluorophenyl-6-[2-(1,1-dioxothiomorpholin-4-yl)ethoxy]-2-p-tolyl-1H-inden-1-one;

113) 3-(2,4-difluorophenyl)-2-(6-methoxypyridin-3-yl)-6-[2-(1,1-dioxothiomorpholin-4-yl)ethoxy]-1H-inden-1-one;

114) 2-(3-fluoro-4-methoxyphenyl)-3-(2,4-difluorophenyl)-6-[2-(1,1-dioxothiomorpholin-4-yl)ethoxy]-1H-inden-1-one;

115) 3-(2,4-difluorophenyl)-6-[2-(1,1-dioxothiomorpholin-4-yl)ethoxy]-2-(quinolin-3-yl)-1H-inden-1-one;

116) 3-(2,4-difluorophenyl)-6-{2-[4-(methylsulfonyl)piperazin-1-yl]ethoxy}-2-p-tolyl-1H-inden-1-one;

117) 3-(2,4-difluorophenyl)-2-(6-methoxypyridin-3-yl)-6-{2-[4-(methylsulfonyl)piperazin-1-yl]ethoxy}-1H-inden-1-one;

118) 2-(3-fluoro-4-methoxyphenyl)-3-(2,4-difluorophenyl)-6-{2-[4-(methylsulfonyl)piperazin-1-yl]ethoxy}-1H-inden-1-one;

119) 3-(2,4-difluorophenyl)-6-{2-[4-(methylsulfonyl)piperazin-1-yl]ethoxy}-2-(quinolin-3-yl)-1H-inden-1-one;

120) 3-(2,4-difluorophenyl)-6-{2-[1-(methylsulfonyl)piperidin-4-yl]ethoxy}-2-p-tolyl-1H-inden-1-one;

121) 3-(2,4-difluorophenyl)-2-(6-methoxypyridin-3-yl)-6-{2-[1-(methylsulfonyl)piperidin-4-yl]ethoxy}-1H-inden-1-one;

122) 2-(3-fluoro-4-methoxyphenyl)-3-(2,4-difluorophenyl)-6-{2-[1-(methylsulfonyl)piperidin-4-yl]ethoxy}-1H-inden-1-one;

123) 3-(2,4-difluorophenyl)-6-{2-[1-(methylsulfonyl)piperidin-4-yl]ethoxy}-2-(quinolin-3-yl)-1H-inden-1-one;

124) 3-(2,4-difluorophenyl)-6-[2-(morpholin-4-yl)ethoxy]-2-p-tolyl-1H-inden-1-one;

125) 3-(2,4-difluorophenyl)-2-(6-methoxypyridin-3-yl)-6-[2-(morpholin-4-yl)ethoxy]-1H-inden-1-one;

126) 2-(3-fluoro-4-methoxyphenyl)-3-(2,4-difluorophenyl)-6-[2-(morpholin-4-yl)ethoxy]-1H-inden-1-one;

127) 3-(2,4-difluorophenyl)-6-[2-(morpholin-4-yl)ethoxy]-2-(quinolin-3-yl)-1H-inden-1-one;

128) 3-(3,5-difluorophenyl)-5-[2-(morpholin-4-yl)ethoxy]-2-(pyridin-3-yl)-1H-inden-1-one;

129) 5-(2-morpholinoethoxy)-3-phenyl-2-(pyridin-3-yl)-1H-inden-1-one;

130) 542-morpholino ethoxy)-3-phenyl-2-(pyridin-4-yl)-1H-inden-1-one;

131) 5-(2-morpholinoethoxy)-3-phenyl-2-p-tolyl-1H-inden-1-one;

132) 5-(2-morpholinoethoxy)-2-(3-fluoro-4-methylphenyl)-3-phenyl-1H-inden-1-one;

133) 3-(3,5-difluorophenyl)-5-[2-(4-(methylsulfonyl)piperazin-1-yl)ethoxy]-2-(pyridin-3-yl)-1H-inden-1-one;

134) 5-[2-(4-(methylsulfonyl)piperazin-1-yl)ethoxy]-3-phenyl-2-(pyridin-3-yl)-1H-inden-1-one;

135) 5-[2-(4-(methylsulfonyl)piperazin-1-yl)ethoxy]-3-phenyl-2-p-tolyl-1H-inden-1-one; and 136) 5-[2-(4-(methylsulfonyl)piperazin-1-yl)ethoxy]-2-(3-fluoro-4-methylphenyl)-3-phenyl-1H-inden-1-one.

Further, representative exemplary compounds according to the present invention are indenone derivatives listed below and pharmaceutical acceptable salts thereof:

1) 6-(2-morpholinoethoxy)-3-phenyl-2-(pyridin-3-yl)-1H-inden-1-one;

45) 6-[2-(4-(methylsulfonyl)piperazin-1-yl)ethoxy]-3-phenyl-2-(pyridin-3-yl)-1H-inden-1-one;

73) 3-(3,5-difluorophenyl)-6-(2-(1-(methylsulfonyl)piperidin-4-yl)ethoxy)-2-(pyridin-3-yl)-1H-inden-1-one;

74) 6-[2-(1,1-dioxothiomorpholin-4-yl)ethoxy]-3-(3,5-difluorophenyl)-2-(pyridin-3-yl)-1H-inden-1-one;

82) 6-(2-morpholinoethoxy)-3-(2,4-difluorophenyl)-2-(pyridin-3-yl)-1H-inden-1-one;

97) 3-(3,5-difluorophenyl)-2-(6-methoxypyridin-3-yl)-6-{2-[4-(methylsulfonyl)piperazin-1-yl]ethoxy}-1H-inden-1-one;

102) 2-(3-fluoro-4-methoxyphenyl)-3-(3,5-difluorophenyl)-6-{2-[1-(methylsulfonyl)piperidin-4-yl]ethoxy}-1H-inden-1-one;

113) 3-(2,4-difluorophenyl)-2-(6-methoxypyridin-3-yl)-6-[2-(1,1-dioxothiomorpholin-4-yl)ethoxy]-1H-inden-1-one;

114) 2-(3-fluoro-4-methoxyphenyl)-3-(2,4-difluorophenyl)-6-[2-(1,1-dioxothiomorpholin-4-yl)ethoxy]-1H-inden-1-one; and 122) 2-(3-fluoro-4-methoxyphenyl)-3-(2,4-difluorophenyl)-6-{2-[1-(methylsulfonyl)piperidin-4-yl]ethoxy}-1H-inden-1-one.

The present invention also provides a pharmaceutical composition for treating or preventing of a bone disease comprising the compound or salt according to the present invention as an active ingredient.

The composition of the present invention may be useful to prevent or treat osteoporosis, bone growth disorder, bone fractures, periodontal disease, Paget's disease, metastatic carcinoma, or rheumatoid arthritis.

Hereinafter, the methods for preparing the indenone derivatives according to the present invention are described in detail.

According to an embodiment of the present invention, the inventive compound of formula 1a may be prepared as shown in Reaction Scheme 1:

Reaction Scheme 1

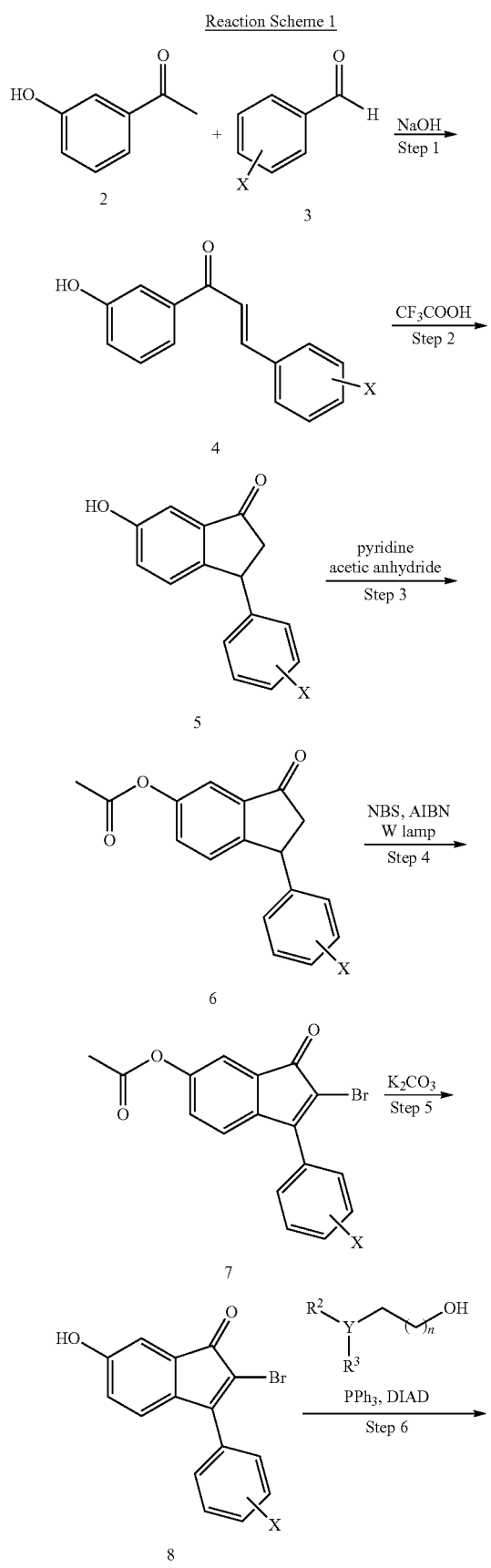

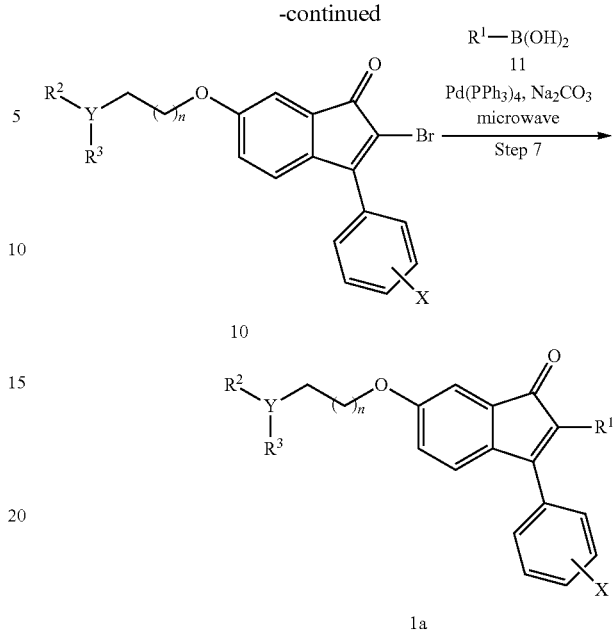

wherein, n, X, Y, $R^1$, $R^2$ and $R^3$ have the same meanings as defined in formula (1).

Step 1: 1-(3-hydroxyphenyl)ethanone of formula 2 is dissolved in NaOH solution and ethanol, and then the benzaldehyde of formula 3 (1 to 2 eq) is added thereto. The resulting mixture was maintained at 10° C. or less for 30 min to 1 h and then stirred for 22 to 36 h at room temperature, to obtain the α,β-unsaturated carbonyl compound of formula 4.

Step 2: The α,β-unsaturated carbonyl compound prepared in Step 1 is allowed to reflux for 1 to 5 days with stirring using 10 to 30 eq of trifluoroacetic acid as a solvent, to obtain the indanone compound of formula 5.

Step 3: The indanone compound prepared in Step 2 is dissolved in $CH_2Cl_2$, pyridine (3 to 5 eq) and acetic anhydride (3 to 5 eq) are added dropwise thereto in an icebath. The resulting mixture is stirred for 1 to 8 h, to obtain the compound of formula 6 which is protected with acetyl group.

Step 4: The indanone compound of formula 6 prepared in Step 3, NBS (2 to 3 eq), and AIBN (1 to 0.2 eq) are dissolved in $CCl_4$. Then, the mixture is allowed to reflux for 30 min to 1 h with stirring and then is further irradiated by a tungsten lamp (375 W) for 1 to 2 h with stirring, to obtain the 2-bromo-1H-indenone of formula 7. In other way, the mixture may be allowed to reflux for 2 to 9 h with stirring while being irradiated by a tungsten lamp (375 W), to obtain the 2-bromo-1H-indenone of formula 7.

Step 5: 1 to 1.2 eq of the 2-bromo-1H-indenone prepared in Step 4 is dissolved in MeOH, and then $K_2CO_3$ (1 to 2 eq) is added thereto. The resulting mixture is stirred at room temperature for 2 to 7 h, to obtain the 2-bromo-6-hydroxy-1H-indenone of formula 8 in which acetyl group is removed.

Step 6: The 2-bromo-6-hydroxy-1H-indenone prepared in Step 5, $PPh_3$ (1 to 2 eq), and the compound of formula 9 (1 to 2 eq) are dissolved in THF. The mixture is cooled to 0° C. and stirred for 5 to 10 min, diisopropyl azodicarboxylate (DIAD, 1 to 2 eq) is added thereto, followed by stirring at 0° C. for 30 min. The resulting mixture is allowed to increase to room temperature and then stirred for 2 h to 7 days, to obtain the ether of formula 10.

Step 7: The 2-bromo-3-phenyl-1H-inden-1-one prepared in Step 6, the boronic acid of formula 11 (1 to 1.5 eq), Pd(PPh$_3$)$_4$ (5 to 6 mol %), and Na$_2$CO$_3$ (2 to 3 eq) are dissolved in dioxane/H$_2$O (4:1), followed by stirring for 10 min. The resulting mixture is placed into a microwave reactor and irradiated at 150° C. for 10 to 20 min, to obtain the compound of formula 1a.

According to another embodiment of the present invention, the inventive compound of formula 1a may be prepared as shown in Reaction Scheme 2:

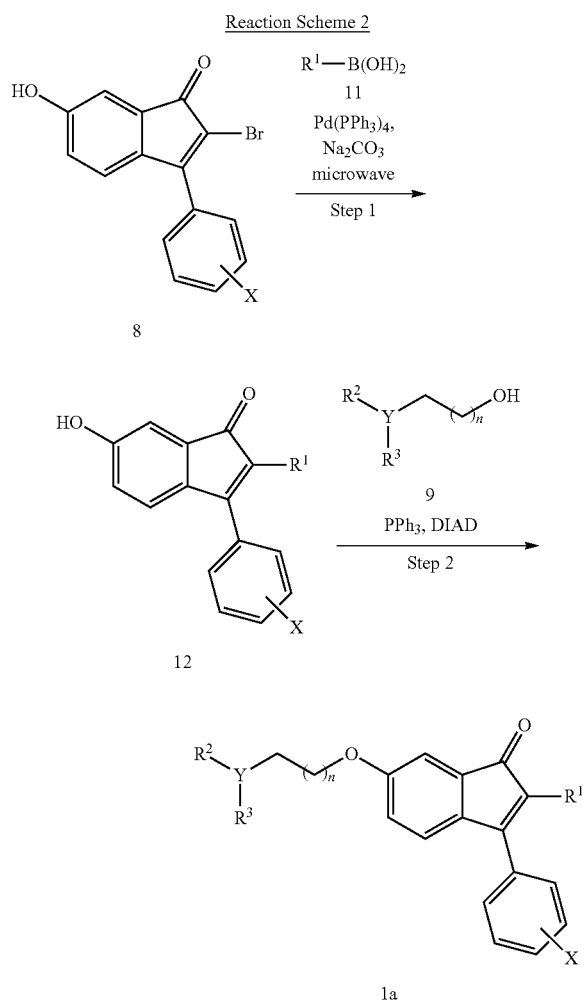

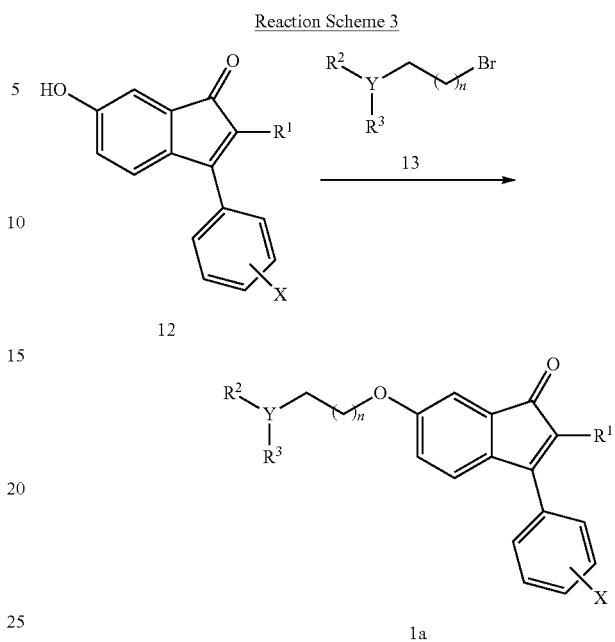

wherein, n, X, Y, R$^1$, R$^2$ and R$^3$ have the same meanings as defined in formula (1).

The 6-hydroxy-1H-indenone substituted with R$^1$ of formula 12 prepared in Step 1 of Reaction Scheme 2, is dissolved in acetonitrile, and then K$_2$CO$_3$ (1 to 1.5 eq) and the compound of formula 13 (1.5 to 2 eq) are added thereto. The resulting mixture is allowed to reflux for 1 to 3 days with stirring, to obtain the compound of formula 1a.

According to an embodiment of the present invention, the inventive compounds of formulas 1c and 1d may be prepared as shown in Reaction Scheme 4:

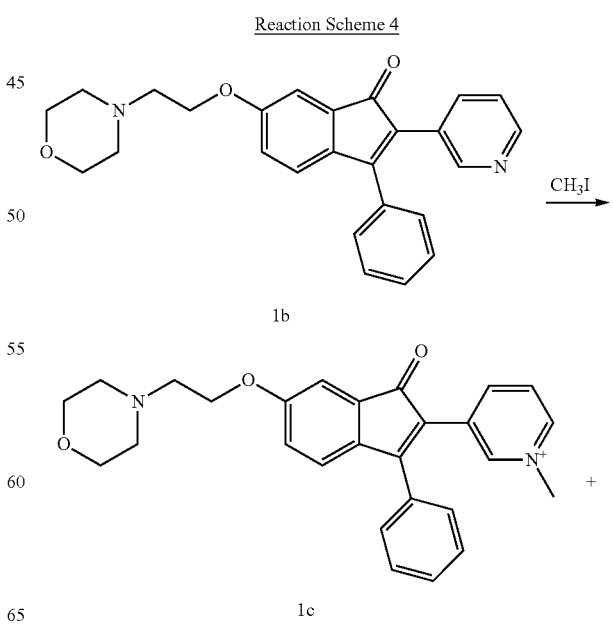

wherein, n, X, Y, R$^1$, R$^2$ and R$^3$ have the same meanings as defined in formula (1).

Step 1: The 2-bromo-6-hydroxy-1H-indenone of formula 8 prepared in Step 5 of Reaction Scheme 1, is subjected to the Suzuki coupling reaction in the same manner as in Step 7 of Reaction Scheme 1, to obtain the 6-hydroxy-1H-indenone substituted with R$^1$ of formula 12.

Step 2: The 6-hydroxy-1H-indenone substituted with R$^1$ of formula 12 prepared in Step 1, is subjected to the Mitsunobu reaction in the same manner as in Step 6 of Reaction Scheme 1, to obtain the compound of formula 1a.

According to a further embodiment of the present invention, the inventive compound of formula 1a may be prepared as shown in Reaction Scheme 3:

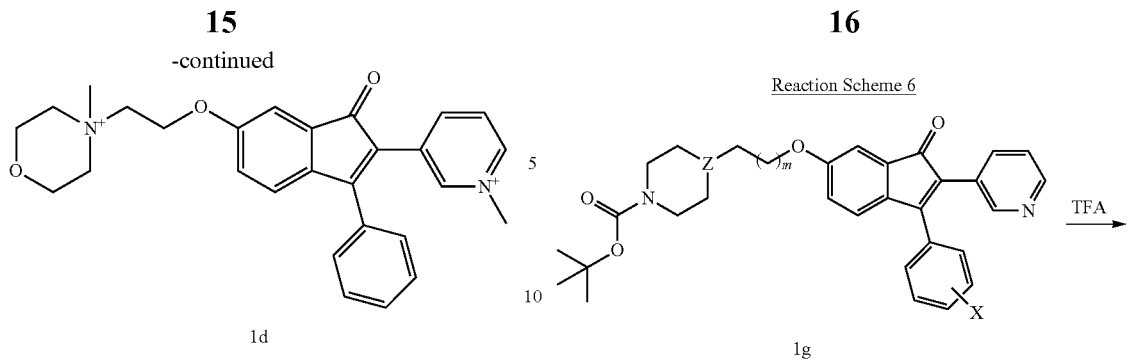

6-(2-mopholinoethoxy)-3-phenyl-2-(pyridin-3-yl)-1H-inden-1-one of formula Ib prepared in Reaction Scheme 1, is dissolved in CH$_2$Cl$_2$, and then CH$_3$I (5 to 10 eq) is added thereto at room temperature. The resulting mixture is allowed to reflux for 30 min to 1 h with stirring, to obtain the compounds of formulas 1c and 1d.

According to an embodiment of the present invention, the inventive compounds of formulas 1e and 1f may be prepared as shown in Reaction Scheme 5:

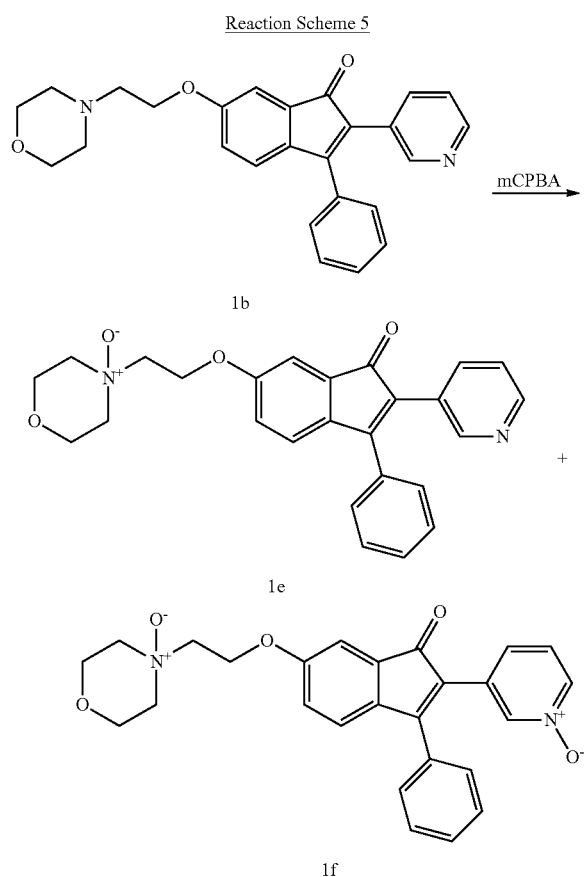

6-(2-mopholinoethoxy)-3-phenyl-2-(pyridin-3-yl)-1H-inden-1-one of formula Ib prepared in Reaction Scheme 1, is dissolved in CH$_2$Cl$_2$, and then mCPBA (1 to 1.5 eq) is added thereto at 10° C. The resulting mixture is allowed to react for 2 to 3 h at room temperature, to obtain the compounds of formulas 1e and 1f.

According to an embodiment of the present invention, the inventive compound of formula 1h may be prepared as shown in Reaction Scheme 6:

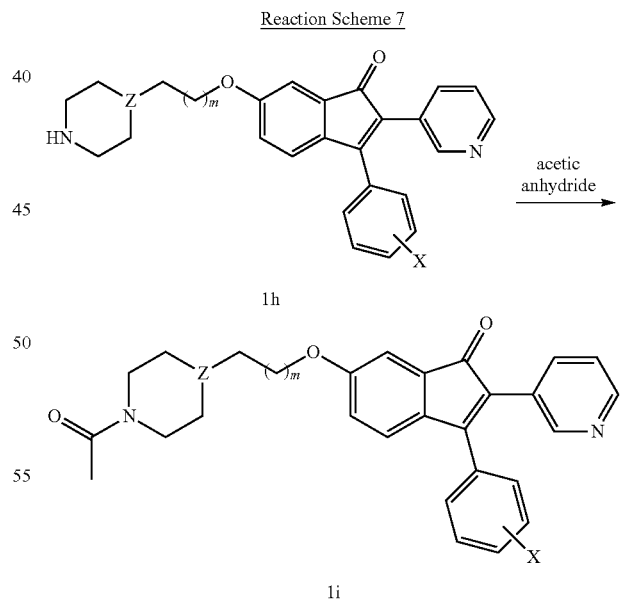

wherein, X has the same meaning as defined in formula (1); Z is CH or N; and m is 1 or 2.

The compound of formula 1g prepared in Reaction Scheme 1 is dissolved in CH$_2$Cl$_2$, and then trifluoroacetic acid (20 to 40 eq) is added thereto. The resulting mixture is stirred for 30 min to 2 h at room temperature, to obtain the compound of formula 1h.

According to an embodiment of the present invention, the inventive compound of formula 1i may be prepared as shown in Reaction Scheme 7:

wherein, X has the same meaning as defined in formula (1); Z is CH or N; and m is 1 or 2.

The compound of formula 1h prepared in Reaction Scheme 6 is dissolved in CH$_2$Cl$_2$, and then pyridine (1.2 to 1.5 eq) is added thereto. The mixture is cooled to 0° C., acetic anhydride (1.2 to 1.5 eq) is added thereto, and then the resulting mixture is allowed to react for 15 to 20 h at room temperature, so as to obtain the compound of formula 1i.

According to an embodiment of the present invention, the inventive compound of formula 1j may be prepared as shown in Reaction Scheme 8:

Reaction Scheme 8

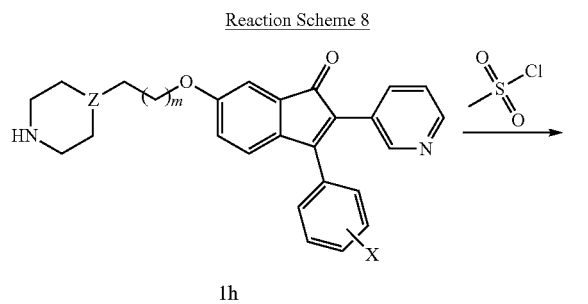

1h

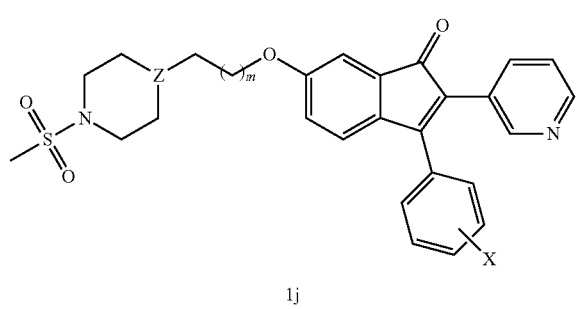

1j wherein, X has the same meaning as defined in formula (1); Z is CH or N; and m is 1 or 2.

The compound of formula 1g prepared in Reaction Scheme 1 is dissolved in CH$_2$Cl$_2$, and then triethylamine (1.5 to 3 eq) is added thereto. The mixture is cooled to 0° C., methanesulfonyl chloride (3 to 5 eq) dissolved in CH$_2$Cl$_2$ is added slowly thereto for 5 to 10 min, and then the resulting mixture is allowed to react for 3 to 18 h at room temperature, so as to obtain the compound of formula 1j.

According to an embodiment of the present invention, the inventive compound of formula 1k may be prepared as shown in Reaction Scheme 9:

Reaction Scheme 9

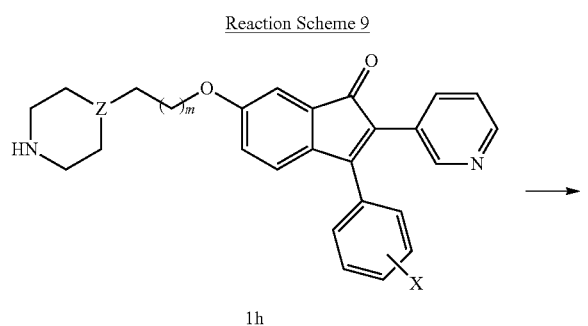

1h

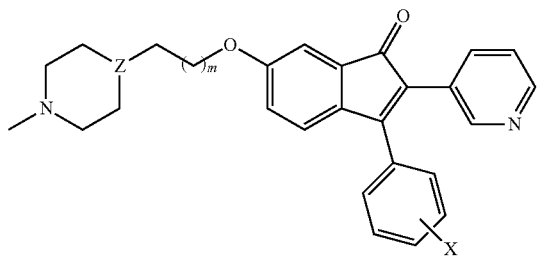

1k wherein, X has the same meaning as defined in formula (1); Z is CH or N; and m is 1 or 2.

The compound of formula 1h prepared in Reaction Scheme 6 and formaldehyde (37% aqueous solution, 1 to 1.2 eq) are dissolved in CH$_2$Cl$_2$, and then sodium triacetoxyborohydride (3 to 4 eq) is added thereto. The resulting mixture is allowed to react for 2 to 3 h at room temperature, so as to obtain the compound of formula 1k.

According to an embodiment of the present invention, the inventive compound of formula 1l may be prepared as shown in Reaction Scheme 10:

Reaction Scheme 10

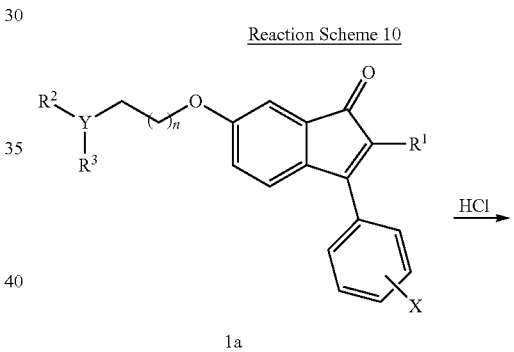

1a

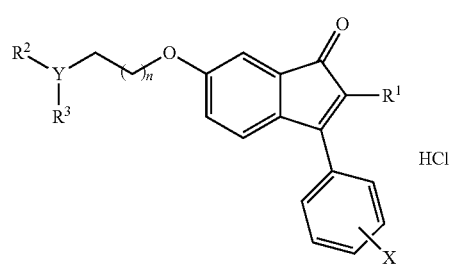

1l wherein, n, X, Y, R$^1$, R$^2$ and R$^3$ have the same meanings as defined in formula (1).

The compound of formula 1a prepared in Reaction Schemes 1 to 3 is dissolved in CH$_2$Cl$_2$, and then 1.0 M HCl solution (dissolved in ether, 1 eq) is added thereto, to obtain the compound in the form of HCl salt of formula 1l.

According to an embodiment of the present invention, the inventive compound of formula 1m may be prepared as shown in Reaction Scheme 11:

Reaction Scheme 11

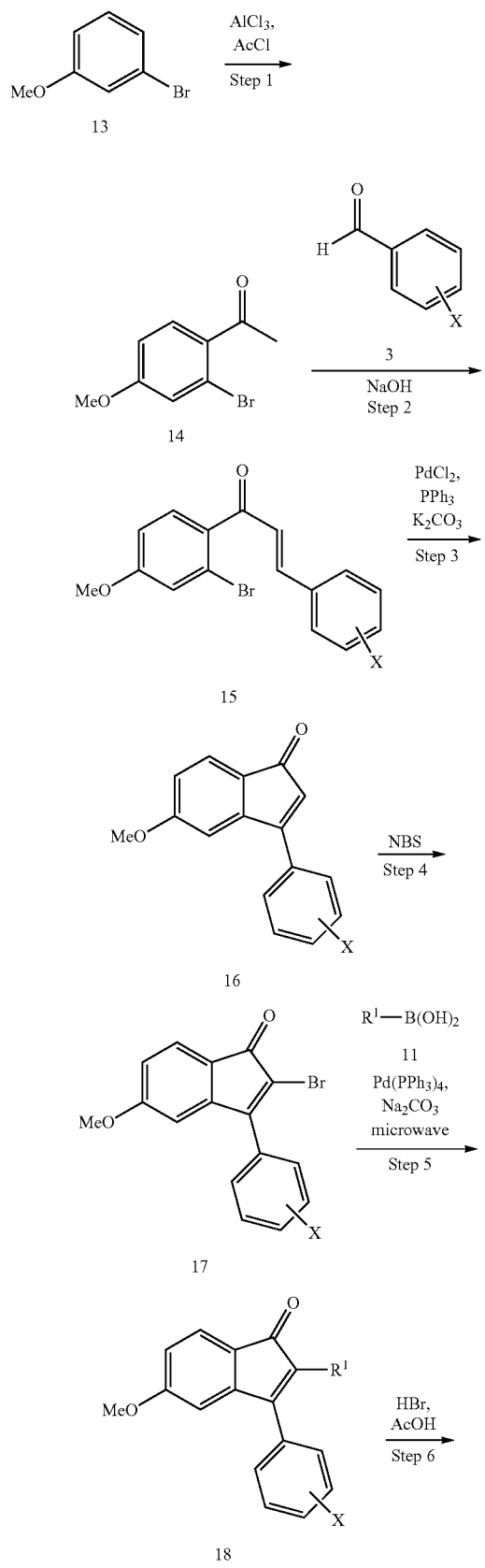

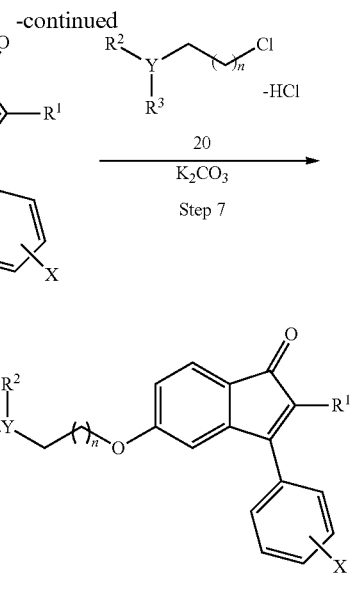

1m wherein, n, X, Y, $R^1$, $R^2$ and $R^3$ have the same meanings as defined in formula (1).

Step 1: Acetyl chloride (1 to 1.2 eq) and $AlCl_3$ (1 to 1.2 eq) are mixed with carbon disulfide, 3-bromoanisole dissolved in carbon disulfide is added thereto. The resulting mixture is stirred for 10 to 16 h at room temperature, to obtain 1-(2-bromo-4-methoxyphenyl)ethanone of formula 14.

Step 2: 1-(2-bromo-4-methoxyphenyl)ethanone prepared in Step 1 is dissolved in ethanol, 10 N NaOH (2 to 4 eq) and the benzaldehyde of formula 3 (1 to 1.2 eq) are sequentially added thereto at 0° C. The resulting mixture is allowed to increase to room temperature and stirred for 4 to 6 h, to obtain the α,β-unsaturated carbonyl compound of formula 15.

Step 3: The α,β-unsaturated carbonyl compound of formula 15 prepared in Step 2, is dissolved in N,N-dimethylformamide, and then triphenylphosphine (0.2 to 0.3 eq), potassium carbonate (2 to 3 eq), and palladium dichloride (0.1 to 0.2 eq) are added thereto. The resulting mixture is stirred for 2 to 4 h at 110° C., to obtain the indenone compound of formula 16.

Step 4: The indenone compound of formula 16 prepared in Step 3 is dissolved in $CCl_4$, N-bromosuccinimide (1 to 1.2 eq) and 2,2'-azobisisobutyronitrile (10 to 15 wt %) are added thereto. The resulting mixture is allowed to reflux for 2 to 3 h with stirring, to obtain the 2-bromoindenone of formula 17.

Step 5: The 2-bromoindenone of formula 17 prepared in Step 4, boron acid of formula 11 (1 to 1.5 eq), $Pd(PPh_3)_4$ (5 to 6 mol %), and $Na_2CO_3$ (2 to 3 eq) are dissolved in dioxane/$H_2O$ (4:1). The resulting mixture is placed into a microwave reactor and irradiated at 150° C. for 10 to 20 min, to obtain the indenone compound of formula 18.

Step 6: The indenone compound prepared in Step 5 is mixed with HBr/AcOH (1:2), and then the resulting mixture is allowed to reflux for 14 to 16 h with stirring, to obtain the 5-hydroxyindenone of formula 19.

Step 7: The compound of formula 19 prepared in Step 6 is dissolved in dimethylformamide, $K_2CO_3$ (2 to 3 eq) and the compound of formula 20 (1 to 2 eq) are added thereto. The resulting mixture is stirred for 3 to 5 h at 80° C., to obtain the compound of formula 1 m.

According to another embodiment of the present invention, the inventive compound of formula 1m may be prepared as shown in Reaction Scheme 12:

Reaction Scheme 12

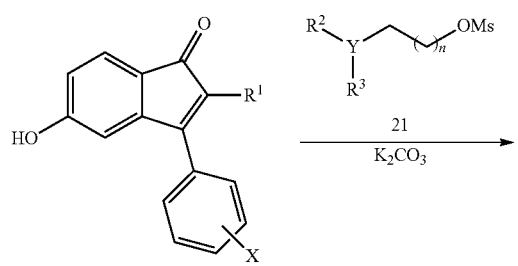

wherein, n, X, Y, R¹, R² and R³ have the same meanings as defined in formula (1).

The 5-hydroxyindenone of formula 19 prepared in Step 6 of Reaction Scheme 11, is dissolved in dimethylformamide, K$_2$CO$_3$ (2 to 3 eq) and the ether substituted with methanesulfonyl group of formula 21 (1 to 1.5 eq) are added thereto. The resulting mixture is stirred for 3 to 5 h at 70 to 80° C., to obtain the compound of formula 1m.

According to another embodiment of the present invention, the 2-bromo-5-methoxyindenone compound of formula 17 may be prepared as shown in Reaction Scheme 13:

Reaction Scheme 13

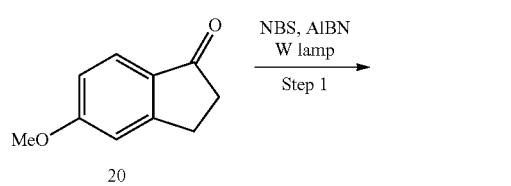

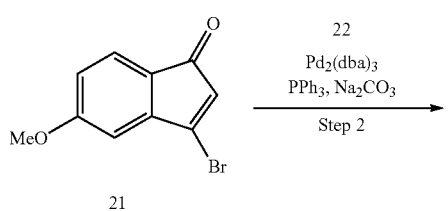

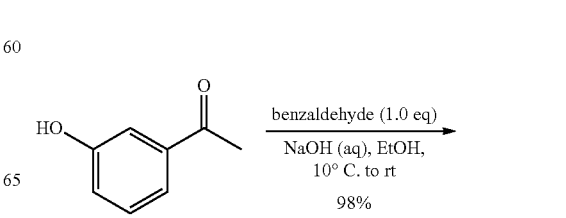

wherein, X has the same meaning as defined in formula (1).

Step 1: 5-methoxyindanone of formula 20 is dissolved in CCl$_4$, N-bromosuccinimide (2 to 2.2 eq) and 2,2'-azobisisobutyronitrile (0.2 to 0.3 eq) are added thereto. The resulting mixture is further irradiated by a tungsten lamp (375W) for 3 to 5 h with stirring, to obtain the 3-bromoindenone of formula 21.

Step 2: The 3-bromoindenone of formula 21 prepared in Step 1 is dissolved in ethylene glycol dimethyl ether, the boronic acid of formula 22 (1 to 1.5 eq), triphenylphosphine (0.1 to 0.2 eq), tris(dibenzylideneacetone)dipalladium (4 to 5 mol %), and sodium carbonate (2 to 2.5 eq) are added thereto. The resulting mixture is allowed to reflux for 3 to 4 h with stirring, to obtain the indenone of formula 23.

Step 3: The indenone of formula 23 prepared in Step 2 is dissolved in CH$_2$Cl$_2$, 1M Br$_2$ solution (dissolved in CH$_2$Cl$_2$) is added thereto. The resulting mixture is stirred for 2 to 3 h at room temperature, to obtain the 2-bromoindenone of formula 17.

EXAMPLE

The following Examples are intended to further illustrate the present invention without limiting its scope.

Example 1

Synthesis of 6-(2-morpholinoethoxy)-3-phenyl-2-(pyridin-3-yl)-1H-inden-1-one hydrochloride salt Step 1. (E)-1-(3-Hydroxyphenyl)-3-phenylprop-2-en-1-one -continued

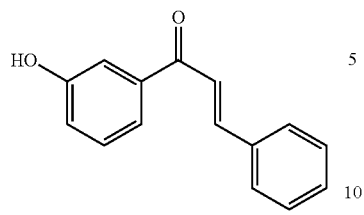

A 250 mL round-bottomed flask was charged sequentially aq. NaOH solution (NaOH 7.1 g/H$_2$O 50 mL) and EtOH (40 mL). The solution was maintained below 10° C. in an ice bath. 1-(3-hydroxyphenyl)ethanone (20.0 g, 147 mmol) was added and stirred for 30 min at 10° C. To the resulting mixture was then added benzaldehyde (15 mL, 1.0 eq). After being stirred for additional 1 h at 10° C., the reaction mixture was stirred at room temperature for further 26 h. The solution was concentrated by rotary evaporation under reduced pressure. The residue was dissolved in EtOAc. The organic layer was washed with 3N HCl and H$_2$O, dried over MgSO$_4$, and concentrated in vacuo to obtain the desired product (32.5 g, 98%).

$^1$H NMR (CDCl$_3$, 300 MHz) δ 7.8 (d, J=15.7 Hz, 1H), 7.7 (m, 2H), 7.6 (m, 1H), 7.6 (m, 1H), 7.5 (d, J=18.7 Hz, 1H), 7.4 (m, 3H), 7.4 (d, J=7.8 Hz, 1H), 7.1 (dd, J=2.6 Hz, 11 Hz, 1H)

Step 2. 2,3-Dihydro-6-hydroxy-3-phenylinden-1-one

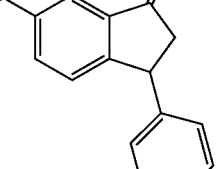

(E)-1-(3-Hydroxyphenyl)-3-phenylprop-2-en-1-one (48.7 g, 217 mmol) obtained in Step 1 and CF$_3$COOH (161 mL, 10 eq) were placed into a flask and stirred for 24 h at 80° C. After cooling to room temperature, toluene (200 mL) was added and the solution was concentrated to remove TFA under reduced pressure. The residue was dissolved in EtOAc, washed with H$_2$O, dried over MgSO$_4$, and concentrated in vacuo to obtain the desired product (48.0 g, 99%).

$^1$H NMR (CDCl$_3$, 300 MHz) δ 7.3 (m, 5H), 7.1 (m, 3H), 4.5 (q, J=3.8 Hz, 1H), 3.3 (dd, J=7.9 Hz, 19.2 Hz, 1H), 2.7 (dd, J=3.7 Hz, 19.2 Hz, 1H)

Step 3. 2,3-Dihydro-1-oxo-3-phenyl-1H-inden-6-yl acetate

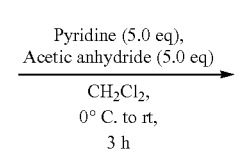

2,3-Dihydro-6-hydroxy-3-phenylinden-1-one (22.5 g, 100 mmol) obtained in Step 2 was placed into a flask and dissolved in CH$_2$Cl$_2$ (300 mL). To the solution at 0° C., pyridine (40 mL, 5.0 eq) and acetic anhydride (47 mL, 5.0 eq) were added dropwise. The mixture was stirred for 8 h at room temperature. The reaction mixture was diluted with EtOAc and washed with H$_2$O. The organic layer was dried over MgSO$_4$ and concentrated in vacuo to give the desired product (20.0 g, 77%).

$^1$H NMR (CDCl$_3$, 300 MHz) δ 7.5 (m, 1H), 7.3 (d, J=1.7 Hz, 1H), 7.3 (d, J=1.4 Hz, 1H), 7.3 (d, J=2.0 Hz, 2H), 7.3 (m, 1H), 7.1 (m, 2H), 4.6 (d, J=3.8 Hz, 1H), 3.3 (dd, J=6.6 Hz, 17.9 Hz, 1H), 2.7 (dd, J=3.9 Hz, 19.3 Hz, 1H), 2.3 (s, 3H)

Step 4. 2-Bromo-1-oxo-3-phenyl-1H-inden-6-yl acetate

-continued

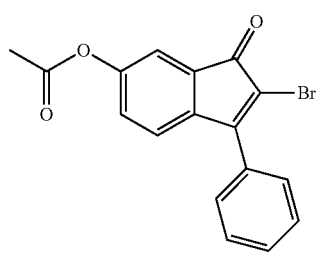

2,3-Dihydro-1-oxo-3-phenyl-1H-inden-6-yl acetate (10.1 g, 37.9 mmol) obtained in Step 3 was placed into a flask and dissolved in CCl₄ (200 mL). To the resulting solution, NBS (14.8 g, 2.2 eq) and AIBN (0.62 g, 10 mol %) were added. The resulting mixture was allowed to reflux for 1 h. Then the mixture was further irradiated by a tungsten lamp (375W) for 1.5 h. After cooling to room temperature, the precipitate was collected using a Buchner funnel. The solid was dissolved in CH₂Cl₂ and washed with sat. Na₂S₂O₃, H₂O, and brine. The organic layer was dried over MgSO₄ and concentrated in vacuo to give the desired product (12.0 g, 92%).

¹H NMR (CDCl₃, 300 MHz) δ 7.7 (m, 2H), 7.6 (m, 2H), 7.3 (d, J=6.1 Hz, 1H), 7.3 (s, 1H), 7.2 (d, J=8.0 Hz, 1H), 7.1 (dd, J=2.1 Hz, 8.1 Hz, 1H), 2.3 (s, 3H)

Step 5.
2-Bromo-6-hydroxy-3-phenyl-1H-inden-1-one

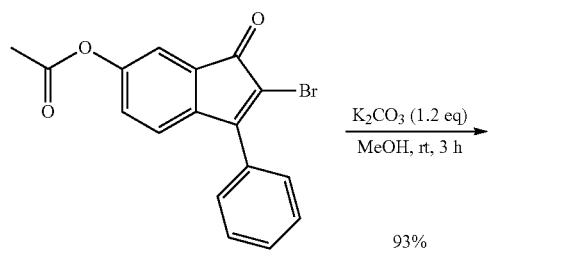

2-Bromo-1-oxo-3-phenyl-1H-inden-6-yl acetate (24 g, 70.0 mmol) obtained in Step 4 was placed into a flask and dissolved in MeOH (350 mL). The solution was charged with K₂CO₃ (11.64 g, 1.2 eq) and stirred at room temperature for 2 h. The reaction mixture was diluted with EtOAc and washed with a brine solution. The organic layer was dried over MgSO₄ and concentrated in vacuo to give the desired product (19.5 g, 93%).

¹H NMR (DMSO, 300 MHz) δ 7.6 (m, 5H), 7.0 (d, J=8 Hz, 1H), 6.9 (d, J=2.3 Hz, 1H), 6.7 (dd, J=2.4 Hz, 8.0 Hz, 1H)

Step 6. 6-(2-Morpholinoethoxy)-2-bromo-3-phenyl-1H-inden-1-one

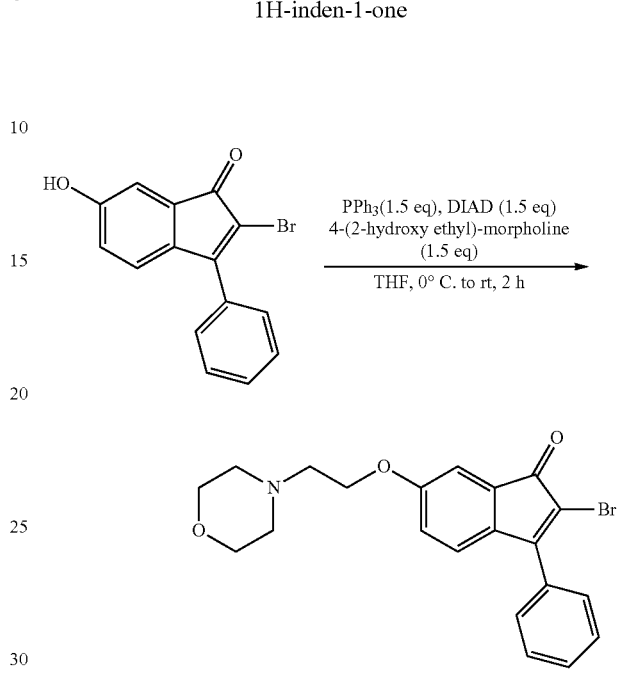

A flask was charged with 2-bromo-6-hydroxy-3-phenyl-1H-inden-1-one (3.0 g, 10.0 mmol) obtained in Step 5, PPh₃ (3.93 g, 1.5 eq), 4-(2-hydroxyethyl)morpholine (1.8 mL, 1.5 eq), and THF (33 mL, 0.3M). The resulting mixture was cooled to 0° C. and diisopropyl azodicarboxylate (DIAD, 2.9 mL, 1.5 eq) was added. The reaction mixture was stirred at 0° C. for 30 min and allowed to increase to ambient temperature. After being stirred for 2 h, the solution was concentrated by rotary evaporation under reduced pressure. The residue was dissolved in EtOAc, washed with H₂O and brine, dried over MgSO₄, and concentrated in vacuo. The crude product was purified by silica gel column chromatography (EtOAc/hexanes=4:1) to afford the desired product (3.2 g, 78%).

¹H NMR (CDCl₃, 300 MHz) δ 7.64 (m, 2H), 7.52 (m, 1H), 7.18 (d, J=2.4 Hz, 1H), 7.03 (d, J=8 Hz, 1H), 6.76 (dd, J=8.1 Hz, 2.5 Hz, 1H), 4.13 (t, J=5.7 Hz, 2H), 3.74 (t, J=4.7 Hz, 4H), 2.80 (t, J=5.7 Hz, 2H), 2.58 (t, J=4.7 Hz, 4H)

Step 7. 6-(2-Morpholinoethoxy)-3-phenyl-2-(pyridin-3-yl)-1H-inden-1-one

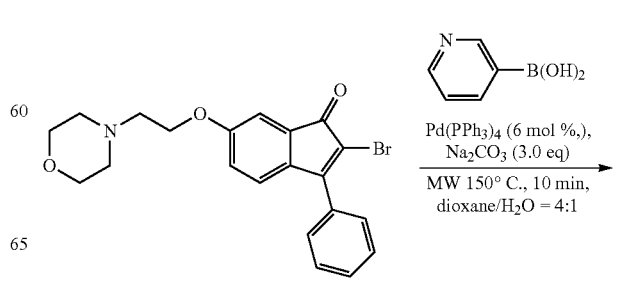

-continued

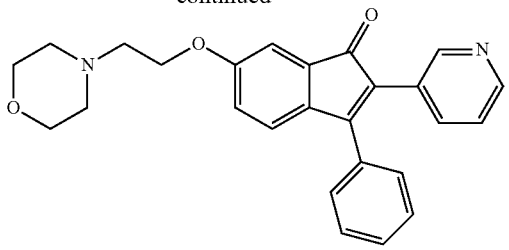

To a microwave reaction vial, 6-(2-morpholinoethoxy)-2-bromo-3-phenyl-1H-inden-1-one (1.0 g, 2.5 mmol) obtained in Step 6,3-pyridinylboronic acid (470 mg, 3.8 mmol, 1.5 eq), Pd(PPh$_3$)$_4$ (180 mg, 6 mol %), Na$_2$CO$_3$ (800 mg, 3.0 eq), and dioxane/H$_2$O (4:1, 5 mL) were sequentially charged. The reaction vial was placed into a microwave reactor and irradiated at 150° C. for 20 min. After cooling to room temperature, the reaction was diluted with EtOAc and dried over MgSO$_4$. The mixture was filtered through a Celite pad while rinsing with EtOAc and then concentrated in vacuo. The residue was purified by prep HPLC (CH$_3$CN/H$_2$O=1:1) to afford the desired product (640 mg, 64%).

$^1$H NMR (CDCl$_3$, 300 MHz) δ 8.44 (dd, J=0.9, 4.7 Hz, 1H), 8.42 (s, 1H), 7.64 (d, J=7.9 Hz, 1H), 7.47-7.40 (m, 3H), 7.40-7.34 (m, 2H), 7.25-7.17 (m, 2H), 7.07 (d, J=8.1 Hz, 1H), 6.83 (dd, J=2.2, 8.0 Hz, 1H), 4.17 (t, J=5.5 Hz, 2H), 3.75 (t, J=4.5 Hz, 4H), 2.83 (t, J=5.5, 2H), 2.60 (t, J=4.5 Hz, 4H)

Step 8. 6-(2-Morpholinoethoxy)-3-phenyl-2-(pyridin-3-yl)-1H-inden-1-one hydrochloride salt 6-(2-Morpholinoethoxy)-3-phenyl-2-(pyridin-3-yl)-1H-inden-1-one (500 mg, 1.21 mmol) obtained in Step 7 was placed into a flask and dissolved in CH$_2$Cl$_2$ (4.0 mL). To the resulting solution was added 1.0M HCl in diethyl ether (1.21 mL, 1 eq). The solvents were removed by rotary evaporation under reduced pressure to give the desired product in quantitative yield.

$^1$H NMR (CDCl$_3$, 300 MHz) δ 8.5-8.4 (2H, m), 7.67 (1H, d, J=7.5 Hz), 7.6 (1H, dt, J=1.8 Hz, 7.9 Hz), 7.45-7.36 (5H, m), 7.2 (1H, s), 7.1 (1H, d, J=8.0 Hz), 6.85 (1H, dd, J=5.7 Hz, 6.8 Hz), 4.6 (2H, s), 4.1 (4H, s), 4.0 (2H, s), 3.2 (4H, s)

Example 2

Synthesis of 6-(2-morpholinoethoxy)-2-(3-fluoro-4-methoxyphenyl)-3-phenyl-1H-inden-1-one The procedure of Step 7 of Example 1 was repeated except for using 3-fluoro-4-methoxyphenylboronic acid instead of 3-pyridinylboronic acid to obtain the title compound (13%).

$^1$H NMR (CDCl$_3$, 300 MHz) δ 7.44-7.39 (3H, m), 7.37-7.36 (2H, m), 7.18 (1H, d, J=2.4 Hz), 7.04-6.96 (3H, m). 6.86 (1H, d, J=8.4 Hz), 6.80 (1H, dd, J=8.3 Hz, 2.6 Hz), 4.15 (2H, t, J=5.7 Hz), 3.86 (3H, s), 3.75 (4H, t, J=4.7 Hz), 2.82 (2H, t, J=5.7 Hz), 2.59 (4H, t, J=4.5 Hz)

Example 3

Synthesis of 6-(2-morpholinoethoxy)-3-phenyl-2-(quinolin-3-yl)-1H-inden-1-one

The procedure of Step 7 of Example 1 was repeated except for using 3-quinolinylboronic acid instead of 3-pyridinylboronic acid and being recrystallized with EtOAc to obtain the title compound (75%).

$^1$H NMR (CDCl$_3$, 300 MHz) δ 8.54 (1H, d, J=2.1 Hz), 8.31 (1H, d, J=2.1 Hz), 8.00 (1H, d, J=8.4 Hz), 7.81 (1H, d, J=8.1 Hz). 7.68 (1H, dt, J=7.1 Hz, 1.3 Hz), 7.55 (1H, t, J=7.4 Hz), 7.44-7.40 (5H, m), 7.25 (1H, d, J=2.4 Hz), 7.11 (1H, d, J=8.1 Hz), 6.85 (1H, dd, J=8.1 Hz, 2.4 Hz), 4.19 (2H, t, J=5.6 Hz), 3.76 (4H, t, J=4.7 Hz), 2.84 (2H, t, J=5.6 Hz), 2.61 (2H, t, J=5.6 Hz)

Example 4

Synthesis of 4-(6-(2-morpholinoethoxy)-1-oxo-3-phenyl-1H-inden-2-yl)benzamide

The procedure of Step 7 of Example 1 was repeated except for using 4-carbamoylphenylboronic acid instead of 3-pyridinylboronic acid and being recrystallized with EtOAc to obtain the title compound (36%).

$^1$H NMR (CDCl$_3$, 300 MHz) δ 7.69 (2H, d, J=8.1 Hz), 7.42-7.30 (7H, m), 7.36-7.30 (4H, m), 7.20 (1H, d, J=0.75 Hz). 7.06 (1H, d, J=8.0 Hz), 6.82 (1H, dd, J=8.1 Hz, 1.8 Hz), 6.00 (2H, NH$_2$, J=79 Hz), 4.16 (2H, t, J=5.4 Hz), 3.75 (4H, t, J=4.4 Hz), 2.82 (2H, t, J=5.6 Hz), 2.59 (4H, t, J=4.4 Hz)

Example 5

Synthesis of 3-(6-(2-morpholinoethoxy)-1-oxo-3-phenyl-1H-inden-2-yl)benzonitrile The procedure of Step 7 of Example 1 was repeated except for using 3-cyanophenylboronic acid (1.2 eq) instead of 3-pyridinylboronic acid, Pd(PPh$_3$)$_4$ (4 mol %), Na$_2$CO$_3$ (2.4 eq), and being purified by silica gel column chromatography (EtOAc/hexanes=1:1) to obtain the title compound (67%).

$^1$H NMR (CDCl$_3$, 300 MHz) δ 7.55 (s, 1H), 7.51 (t, 1H, J=1.3 Hz), 7.49-7.42 (m, 4H), 7.36-7.31 (m, 3H), 7.21 (d, 1H, J=2.3 Hz), 7.06 (s, 1H, J=8.1 Hz), 6.83 (dd, 1H, J=8.1, 2.4 Hz), 4.16 (t, 2H, J=5.6 Hz), 3.74 (t, 4H, J=4.5 Hz), 2.82 (t, 2H, J=5.6 Hz), 2.59 (t, 4H, J=4.7 Hz)

Example 6

Synthesis of 6-(2-morpholinoethoxy)-2-(6-methoxypyridin-3-yl)-3-phenyl-1H-inden-1-one The procedure of Step 7 of Example 1 was repeated except for using 2-methoxy-5-pyridinylboronic acid (1.2 eq) instead of 3-pyridinylboronic acid, Pd(PPh$_3$)$_4$ (4 mol %), Na$_2$CO$_3$ (2.4 eq), and being purified by silica gel column chromatography (EtOAc/hexanes=1:1) to obtain the title compound (85%).

$^1$H NMR (CDCl$_3$, 300 MHz) δ 8.09 (d, 1H, J=2.1 Hz), 7.48-7.36 (m, 6H), 7.18 (d, 1H, J=2.3 Hz), 7.01 (d, 1H, J=8.0 Hz), 6.80 (dd, 1H, J=8.1, 2.4 Hz), 6.64 (d, 1H, J=8.6 Hz), 4.15 (t, 2H, J=5.6 Hz), 3.90 (2, 3H), 3.74 (t, 4H, J=4.8 Hz), 2.81 (t, 2H, J=5.7 Hz), 2.58 (t, 4H, J=4.6 Hz)

Example 7

Synthesis of 6-(2-morpholinoethoxy)-3-phenyl-2-(pyrimidin-5-yl)-1H-inden-1-one

The procedure of Step 7 of Example 1 was repeated except for using 5-pyrimidinylboronic acid (1.2 eq) instead of 3-pyridinylboronic acid, Pd(PPh$_3$)$_4$ (4 mol %), Na$_2$CO$_3$ (2.4 eq), and being purified by silica gel column chromatography (EtOAc/hexanes=1:1) to obtain the title compound (70%).

¹H NMR (CDCl₃, 300 MHz) δ 9.05 (s, 1H), 8.63 (s, 2H), 7.49-7.47 (m, 3H), 7.39-7.36 (m, 2H), 7.23 (d, 1H, J=2.4 Hz), 7.09 (d, 1H, J=8.1 Hz), 6.86 (dd, 1H, J=8.1, 2.3 Hz), 4.17 (t, 2H, J=5.6 Hz), 3.75 (t, 4H, J=4.5 Hz), 2.83 (t, 2H, J=5.6 Hz), 2.59 (t, 4H, J=4.6 Hz)

Example 8

Synthesis of 6-(2-morpholinoethoxy)-3-phenyl-2-(pyridin-4-yl)-1H-inden-1-one

The procedure of Step 7 of Example 1 was repeated except for using 4-pyridinylboronic acid (1.2 eq) instead of 3-pyridinylboronic acid, Pd(PPh₃)₄ (4 mol %), Na₂CO₃ (2.4 eq), and being purified by silica gel column chromatography (EtOAc/hexanes=1:1) to obtain the title compound (62%).

¹H NMR (CDCl₃, 300 MHz) δ8.47 (d, 2H, J=5.6 Hz), 7.46-7.44 (m, 3H), 7.37-7.34 (m, 2H), 7.21 (d, 1H, J=2.1 Hz), 7.16 (d, 2H, J=5.6 Hz), 7.06 (d, 1H, J=8.0 Hz), 6.84 (dd, 1H, J=5.9, 2.1 Hz), 4.17 (t, 2H, J=5.6 Hz), 3.74 (t, 4H, J=4.5 Hz), 2.83 (t, 2H, J=5.6 Hz), 2.59 (t, 4H, J=4.5 Hz)

Example 9

Synthesis of 6-(2-morpholinoethoxy)-2-(6-fluoropyridin-3-yl)-3-phenyl-1H-inden-1-one The procedure of Step 7 of Example 1 was repeated except for using 2-fluoro-5-pyridinylboronic acid (1.2 eq) instead of 3-pyridinylboronic acid, Pd(PPh₃)₄ (4 mol %), Na₂CO₃ (2.4 eq), and being purified by silica gel column chromatography (EtOAc/hexanes=1:1) to obtain the title compound (95%).

¹H NMR (CDCl₃, 300 MHz) δ8.06 (d, 1H, J=2.1 Hz), 7.72 (td, 1H, J=8.4, 2.4 Hz), 7.46-7.44 (m, 3H), 7.37-7.34 (m, 2H), 7.20 (d, 1H, J=2.4 Hz), 7.05 (d, 1H, J=8.1 Hz), 6.87-6.81 (m, 2H), 4.16 (t, 2H, J=5.7 Hz), 3.75 (t, 4H, J=4.5 Hz), 2.83 (t, 2H, J=5.7 Hz), 2.59 (t, 4H, J=4.8 Hz)

Example 10

Synthesis of 6-(2-morpholinoethoxy)-2-(4-(phenyl)phenyl)-3-phenyl-1H-inden-1-one The procedure of Step 7 of Example 1 was repeated except for using 4-biphenylboronic acid instead of 3-pyridinylboronic acid and being recrystallized with CH₃CN to obtain the title compound (88%).

¹H NMR (CDCl₃, 300 MHz) δ 7.57 (2H, d, J=8.0 Hz), 7.49 (2H, d, J=8.4 Hz), 7.44-7.32 (10H, m), 7.33 (3H, d, J=7.8 Hz). 7.21 (1H, d, J=2.4 Hz), 7.04 (1H, d, J=8.1 Hz), 6.81 (1H, dd, J=8.1 Hz, 2.4 Hz), 4.16 (2H, t, J=5.6 Hz), 3.75 (4H, t, J=4.7 Hz), 2.82 (2H, t, J=5.6 Hz), 2.60 (4H, t, J=4.7 Hz)

Example 11

Synthesis of 6-(2-morpholinoethoxy)-3-phenyl-2-p-tolyl-1H-inden-1-one

The procedure of Step 7 of Example 1 was repeated except for using p-tolylboronic acid instead of 3-pyridinylboronic acid and being recrystallized with CH₃CN to obtain the title compound (14%).

¹H NMR (CDCl₃, 300 MHz) δ 7.42-7.36 (5H, m), 7.18 (1H, d, J=2.4 Hz), 7.15-7.12 (2H, m), 7.09 (2H, d, J=7.8 Hz). 7.02 (1H, d, J=8.1 Hz), 6.80 (1H, dd, J=8.1 Hz, 2.4 Hz), 4.15 (2H, t, J=5.7 Hz), 3.75 (4H, t, J=4.2 Hz), 2.81 (2H, t, J=5.7 Hz), 2.59 (4H, t, J=4.7 Hz), 2.31 (3H, s)

Example 12

Synthesis of 2-(6-(2-morpholinoethoxy)-1-oxo-3-phenyl-1H-inden-2-yl)benzonitrile The procedure of Step 7 of Example 1 was repeated except for using 2-cyanophenylboronic acid instead of 3-pyridinylboronic acid to obtain the title compound (4%).

¹H NMR (CDCl₃, 300 MHz) δ 7.52 (2H, d, J=8.4 Hz), 7.46-7.44 (3H, m), 7.37-7.30 (4H, m), 7.21 (1H, d, J=2.4 Hz), 7.07 (1H, d, J=8.1 Hz), 6.84 (1H, dd, J=8.1 Hz, 2.4 Hz), 4.17 (2H, t, J=5.6 Hz), 3.74 (4H, t, J=4.7 Hz), 2.82 (2H, t, J=5.6 Hz), 2.59 (4H, t, J=4.7 Hz)

Example 13

Synthesis of 6-(2-morpholinoethoxy)-2-(4-(trifluoromethyl)phenyl)-3-phenyl-1H-inden-1-one The procedure of Step 7 of Example 1 was repeated except for using 4-(trifluoromethyl)phenylboronic acid instead of 3-pyridinylboronic acid and being recrystallized with CH₃CN to obtain the title compound (14%).

¹H NMR (CDCl₃, 300 MHz) δ 7.50 (2H, d, J=8.1 Hz), 7.45-7.42 (3H, m), 7.38-7.34 (4H, m), 7.12 (1H, d, J=2.4 Hz). 7.06 (1H, d, J=8.1 Hz), 6.83 (1H, dd, J=8.1 Hz, 2.4 Hz), 4.17 (2H, t, J=5.7 Hz), 3.75 (4H, t, J=4.7 Hz), 2.82 (2H, t, J=5.7 Hz), 2.59 (4H, t, J=4.7 Hz)

Example 14

Synthesis of N-(3-(6-(2-morpholinoethoxy)-1-oxo-3-phenyl-1H-inden-2-yl)phenyl)acetamide The procedure of Step 7 of Example 1 was repeated except for using 3-(acetamido)phenylboronic acid instead of 3-pyridinylboronic acid to obtain the title compound (27%).

¹H NMR (CDCl₃, 300 MHz) δ 7.64 (1H, d, J=8.7 Hz), 7.42-7.35 (5H, m), 7.35 (1H, s, NH), 7.23 (1H, s). 7.18 (1H, d, J=2.4 Hz), 7.14 (1H, d, J=8.1 Hz), 7.04 (1H, d, J=8.1 Hz), 6.84-6.79 (2H, m), 4.16 (2H, t, J=5.4 Hz), 3.75 (4H, t, J=4.7 Hz), 2.82 (2H, t, J=5.4 Hz), 2.59 (4H, t, J=4.7 Hz), 2.12 (3H, s)

Example 15

Synthesis of 6-(2-morpholinoethoxy)-2-(isoquinolin-4-yl)-3-phenyl-1H-inden-1-one The procedure of Step 7 of Example 1 was repeated except for using 4-isoquinolinylboronic acid instead of 3-pyridinylboronic acid to obtain the title compound (36%).

¹H NMR (CDCl₃, 300 MHz) δ 9.18 (1H, s), 8.26 (1H, s), 7.97 (1H, q, J=3.2 Hz), 7.70-7.49 (4H, m), 7.33-7.13 (6H, m), 6.91-6.80 (1H, m), 4.19 (2H, t, J=5.6 Hz), 3.76 (4H, t, J=4.5 Hz), 2.84 (2H, t, J=5.6 Hz), 2.60 (4H, t, J=4.5 Hz)

Example 16

Synthesis of 6-(2-morpholinoethoxy)-2-(naphthalen-3-yl)-3-phenyl-1H-inden-1-one

The procedure of Step 7 of Example 1 was repeated except for using 2-naphthylboronic acid instead of 3-pyridinylboronic acid to obtain the title compound (64%).

¹H NMR (CDCl₃, 300 MHz) δ 7.91 (1H, s), 7.76 (2H, dt, J=6.2 Hz, 3.2 Hz), 7.64 (1H, d, J=8.7 Hz), 7.47-7.39 (7H, m). 7.23 (1H, d, J=2.4 Hz), 7.17 (1H, dd, J=8.6 Hz, 1.7 Hz), 7.08 (1H, d, J=8.1 Hz), 6.83 (1H, dd, J=8.1 Hz, 2.4 Hz), 4.17 (2H, t, J=5.6 Hz), 3.75 (4H, t, J=4.7 Hz), 2.83 (2H, t, J=5.6 Hz), 2.60 (4H, t, J=4.7 Hz)

Example 17

Synthesis of 6-(2-morpholinoethoxy)-2-(4-fluorophenyl)-3-phenyl-1H-inden-1-one

The procedure of Step 7 of Example 1 was repeated except for using 4-fluorophenylboronic acid instead of 3-pyridinylboronic acid to obtain the title compound (80%).
¹H NMR (CDCl₃, 300 MHz) δ 7.44-7.40 (3H, m), 7.38-7.35 (2H, m), 7.26-7.20 (3H, m), 7.04 (1H, d, J=8.1 Hz). 6.95 (2H, dt, J=7.8 Hz, 2.0 Hz), 6.82 (1H, dd, J=8.1 Hz, 2.4 Hz), 4.17 (2H, t, J=5.7 Hz), 3.75 (4H, t, J=4.7 Hz), 3.50 (3H, s), 2.83 (2H, t, J=5.7 Hz), 2.59 (4H, t, J=4.7 Hz)

Example 18

Synthesis of 6-(2-morpholinoethoxy)-2-(3,4-difluorophenyl)-3-phenyl-1H-inden-1-one The procedure of Step 7 of Example 1 was repeated except for using 3,4-difluorophenylboronic acid instead of 3-pyridinylboronic acid and being recrystallized with CH₃CN to obtain the title compound (11%).
¹H NMR (CDCl₃, 300 MHz) δ 7.45-7.43 (3H, m), 7.38-7.30 (2H, m), 7.20 (1H, d, J=2.4 Hz), 7.10 (1H, ddd, J=7.8 Hz, 11.7 Hz, 2.0 Hz), 7.04 (1H, s). 7.01 (1H, d, J=2.1 Hz), 6.98-6.96 (1H, s), 6.81 (1H, dd, J=2.4 Hz, 8.1 Hz), 4.16 (2H, t, J=5.6 Hz), 3.75 (4H, t, J=4.8 Hz), 2.82 (2H, t, J=5.7 Hz), 2.59 (4H, t, J=4.7 Hz)

Example 19

Synthesis of 6-(2-morpholinoethoxy)-2-(3-fluoro-4-methylphenyl)-3-phenyl-1H-inden-1-one The procedure of Step 7 of Example 1 was repeated except for using 3-fluoro-4-methylphenylboronic acid instead of 3-pyridinylboronic acid and being recrystallized with CH₃CN to obtain the title compound (25%).
¹H NMR (CDCl₃, 300 MHz) δ 7.40 (5H, m), 7.19 (1H, d, J=2.4 Hz), 7.07-7.01 (2H, m), 6.95-6.89 (2H, m). 6.80 (1H, dd, J=2.4 Hz, 8.1 Hz), 4.15 (2H, t, J=5.7 Hz), 3.74 (4H, t J=4.7 Hz), 2.82 (2H, t, J=5.7 Hz), 2.59 (4H, t J=4.7 Hz), 2.23 (3H, s)

Example 20

Synthesis of 6-(2-morpholinoethoxy)-2-(3-aminophenyl)-3-phenyl-1H-inden-1-one

The procedure of Step 7 of Example 1 was repeated except for using 3-aminophenylboronic acid instead of 3-pyridinylboronic acid and being recrystallized with EtOAc/hexanes to obtain the title compound (49%).
¹H NMR (CDCl₃, 300 MHz) δ 7.40 (5H, m), 7.19 (1H, d, J=2.4 Hz), 7.01 (2H, dt, J=8.2 Hz, 1.3 Hz), 6.80 (1H, dd, J=2.4 Hz, 8.1 Hz), 6.64 (1H, t, J=1.8 Hz), 6.58-6.55 (1H, m), 4.15 (2H, t, J=5.7 Hz), 3.75 (4H, t, J=4.7 Hz), 2.82 (2H, t, J=5.7 Hz), 2.59 (4H, t, J=4.7 Hz)

Example 21

Synthesis of 6-(2-morpholinoethoxy)-2-(4-phenoxyphenyl)-3-phenyl-1H-inden-1-one

The procedure of Step 7 of Example 1 was repeated except for using 4-phenoxyphenylboronic acid instead of 3-pyridinylboronic acid to obtain the title compound (28%).
¹H NMR (CDCl₃, 300 MHz) δ 7.40 (5H, m), 7.33 (2H, t, J=7.8 Hz), 7.23-7.19 (3H, m), 7.11 (1H, t, J=7.1 Hz), 7.04-7.00 (3H, m), 6.88 (2H, d, J=8.3 Hz), 6.825-6.79 (1H, m), 4.16 (2H, t, J=5.6 Hz), 3.75 (4H, t, J=4.4 Hz), 2.82 (2H, t, J=5.6 Hz), 2.59 (4H, t, J=4.2 Hz)

Example 22

Synthesis of 6-(2-morpholinoethoxy)-2-(4-methoxyphenyl)-3-phenyl-1H-inden-1-one

The procedure of Step 7 of Example 1 was repeated except for using 4-methoxyphenylboronic acid instead of 3-pyridinylboronic acid to obtain the title compound (94%).
¹H NMR (CDCl₃, 300 MHz) δ 7.40 (5H, m), 7.19 (3H, d, J=8.7 Hz), 7.00 (1H, d, J=7.8 Hz), 6.79 (3H, d, J=8.7 Hz), 4.15 (2H, t, J=5.6 Hz), 3.78 (3H, s), 3.74 (4H, t, J=4.5 Hz), 2.81 (2H, t, J=5.6 Hz), 2.59 (4H, t, J=4.4 Hz)

Example 23

Synthesis of 6-(2-morpholinoethoxy)-2-(4-chlorophenyl)-3-phenyl-1H-inden-1-one

The procedure of Step 7 of Example 1 was repeated except for using 4-chlorophenylboronic acid instead of 3-pyridinylboronic acid and being purified by silica gel column chromatography (acetone/hexanes 1:1) to obtain the title compound (38%).
¹H NMR (CDCl₃, 300 MHz) δ 7.43-7.35 (5H, m), 7.24-7.16 (5H, m), 7.03 (1H, d, J=7.8 Hz), 6.81 (1H, dd, J=2.4 Hz, 8.1 Hz). 4.15 (2H, t, J=5.7 Hz), 3.75 (4H, t, J=4.7 Hz), 2.82 (2H, t, J=5.6 Hz), 2.59 (4H, t, J=4.7 Hz)

Example 24

Synthesis of 6-(2-morpholinoethoxy)-3-(4-fluorophenyl)-2-(pyridin-3-yl)-1H-inden-1-one Step 1. (E)-3-(4-Fluorophenyl)-1-(3-hydroxyphenyl)prop-2-en-1-one The procedure of Step 1 of Example 1 was repeated except for using 4-fluorobenzaldehyde as a starting material instead of benzaldehyde to obtain the title compound (99%).
¹H NMR (CDCl₃, 300 MHz) δ 7.8 (1H, s, OH), 8.0 (2H, dd, J=5.7 Hz, 8.7 Hz), 7.8 (2H, q, J=18.2 Hz), 7.6 (1H, d, J=7.8 Hz), 7.4 (1H, t, J=2.0 Hz), 7.35 (1H, J=7.9 Hz), 7.3 (2H, t, J=8.8 Hz), 7.0 (1H, dd, J=7.8 Hz, 2.1 Hz)

Step 2. 3-(4-Fluorophenyl)-2,3-dihydro-6-hydroxyinden-1-one

The procedure of Step 2 of Example 1 was repeated except for using (E)-3-(4-fluorophenyl)-1-(3-hydroxyphenyl)prop-2-en-1-one obtained in Step 1 as a starting material instead of (E)-1-(3-hydroxyphenyl)-3-phenylprop-2-en-1-one, being stirred for 5 d, and removing TFA by rotary evaporation to obtain the title compound (47%).

$^1$H NMR (DMSO, 300 MHz) δ 10.2 (1H, s, OH), 7.09-6.95 (7H, m), 4.5 (1H, dd, J=3.3 Hz, 7.8 Hz), 3.14 (1H, dd, J=7.8 Hz, 19.2 Hz), 2.45 (1H, dd, J=3.3 Hz, 19.2 Hz)

Step 3. 1-(4-Fluorophenyl)-2,3-dihydro-3-oxo-1H-inden-5-yl acetate

The procedure of Step 3 of Example 1 was repeated except for using 3-(4-fluorophenyl)-2,3-dihydro-6-hydroxyinden-1-one obtained in Step 2 as a starting material instead of 2,3-dihydro-6-hydroxy-3-phenylinden-1-one and being stirred for 2 h to obtain the title compound (99%).
$^1$H NMR (DMSO, 300 MHz) δ 7.43-7.38 (2H, m), 7.29-7.23 (3H, m), 7.14 (2H, t, J=7.8 Hz, 7.8 Hz), 4.7 (1H, dd, J=7.8 Hz, 3.8 Hz), 3.3 (1H, dd, J=7.8 Hz, 19.1 Hz), 2.7 (1H, dd, J=3.9 Hz, 19.1 Hz), 2.3 (3H, s)

Step 4. 2-Bromo-3-(4-fluorophenyl)-1-oxo-1H-inden-6-yl acetate

The procedure of Step 4 of Example 1 was repeated except for using 1-(4-fluorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 5 h under tungsten lamp irradiation (375W) to obtain the title compound (99%).
$^1$H NMR (DMSO, 300 MHz) δ 7.82-7.78 (1H, m), 7.5 (1H, dd, J=2.3 Hz, 20.1 Hz), 7.5-7.4 (1H, m), 7.41-7.36 (2H, m), 7.3 (1H, d, J=8.9 Hz), 7.21-7.20 (1H, m), 2.3 (3H, s)

Step 5. 2-Bromo-3-(4-fluorophenyl)-6-hydroxy-1H-inden-1-one

The procedure of Step 5 of Example 1 was repeated except for using 2-bromo-3-(4-fluorophenyl)-1-oxo-1H-inden-6-yl acetate obtained in Step 4 as a starting material instead of 2-bromo-1-oxo-3-phenyl-1H-inden-6-yl acetate and being stirred for 7 h to obtain the title compound (45%).
$^1$H NMR (DMSO, 300 MHz) δ 10.2 (1H, s, OH), 7.8-7.7 (1H, m), 7.4 (2H, t, J=8.9 Hz), 7.0 (2H, dd, J=5.0 Hz, 11 Hz), 6.8 (1H, dd, J=2.3 Hz, 8.0 Hz)

Step 6. 6-(2-Morpholinoethoxy)-2-bromo-3-(4-fluorophenyl)-1H-inden-1-one

The procedure of Step 6 of Example 1 was repeated except for using 2-bromo-3-(4-fluorophenyl)-6-hydroxy-1H-inden-1-one obtained in Step 5 as a starting material instead of 2-bromo-6-hydroxy-3-phenyl-1H-inden-1-one and being purified by silica gel column chromatography (EtOAc 100%) to obtain the title compound (80%).

Step 7. 6-(2-Morpholinoethoxy)-3-(4-fluorophenyl)-2-(pyridin-3-yl)-1H-inden-1-one The procedure of Step 7 of Example 1 was repeated except for using 6-(2-morpholinoethoxy)-2-bromo-3-(4-fluorophenyl)-1H-inden-1-one obtained in Step 6 as a starting material instead of 6-(2-morpholinoethoxy)-2-bromo-3-phenyl-1H-inden-1-one and being purified by silica gel column chromatography (acetone/hexanes=1:1) to obtain the title compound (52%).
$^1$H NMR (CDCl$_3$, 300 MHz) δ 8.47-8.40 (2H, m), 7.63 (1H, dt, J=7.9, 2.1 Hz), 7.39-7.35 (2H, m), 7.28-7.21 (2H, m), 7.13 (2H, t, J=8.7 Hz), 7.05 (1H, d, J=8.1 Hz), 6.84 (1H, dd, J=8.1 Hz, 2.4 Hz), 4.17 (2H, t, J=5.7 Hz), 3.75 (4H, t, J=4.7 Hz), 2.82 (2H, t, J=5.6 Hz), 2.59 (4H, t, J=4.6 Hz)

Example 25

Synthesis of 6-(2-morpholinoethoxy)-3-(4-fluorophenyl)-2-(pyrimidin-5-yl)-1H-inden-1-one The procedure of Step 7 of Example 1 was repeated except for using 6-(2-morpholinoethoxy)-2-bromo-3-(4-fluorophenyl)-1H-inden-1-one obtained in Step 6 of Example 24 as a starting material instead of 6-(2-morpholinoethoxy)-2-bromo-3-phenyl-1H-inden-1-one, 5-pyrimidinylboronic acid instead of 3-pyridinylboronic acid, and being purified by silica gel column chromatography (acetone/hexanes=1:1) to obtain the title compound (96%).
$^1$H NMR (CDCl$_3$, 300 MHz) δ 9.07 (1H, s), 8.63 (2H, s), 7.41-7.37 (2H, m), 7.23 (1H, d, J=2.4 Hz). 7.21-7.15 (2H, m), 7.07 (1H, d, J=8.1 Hz) 6.87 (1H, dd, J=8.1 Hz, 2.4 Hz), 4.11 (2H, t, J=5.6 Hz), 3.75 (4H, t, J=4.7 Hz), 2.83 (2H, t, J=5.6 Hz), 2.59 (4H, t, J=4.7 Hz)

Example 26

Synthesis of 6-(2-morpholinoethoxy)-2-(3,4-difluorophenyl)-3-(4-fluorophenyl)-1H-inden-1-one The procedure of Step 7 of Example 1 was repeated except for using 6-(2-morpholinoethoxy)-2-bromo-3-(4-fluorophenyl)-1H-inden-1-one obtained in Step 6 of Example 24 as a starting material instead of 6-(2-morpholinoethoxy)-2-bromo-3-phenyl-1H-inden-1-one, 3,4-difluorophenylboronic acid instead of 3-pyridinylboronic acid, and being purified by silica gel column chromatography (acetone/hexanes=2:3) to obtain the title compound (81%).
$^1$H NMR (CDCl$_3$, 300 MHz) δ 7.38-7.34 (2H, m), 7.20 (1H, d, J=2.4 Hz), 7.17-7.00 (5H, m), 6.97-6.91 (1H, m). 6.83 (1H, dd, J=2.0 Hz, 8.0 Hz), 4.16 (2H, t, J=5.7 Hz), 3.75 (4H, t, J=4.6 Hz), 2.82 (2H, t, J=5.6 Hz), 2.59 (4H, t, J=4.6 Hz)

Example 27

Synthesis of 6-(2-morpholinoethoxy)-2-(4-(trifluoromethyl)phenyl)-3-(4-fluorophenyl)-1H-inden-1-one The procedure of Step 7 of Example 1 was repeated except for using 6-(2-morpholinoethoxy)-2-bromo-3-(4-fluorophenyl)-1H-inden-1-one obtained in Step 6 of Example 24 as a starting material instead of 6-(2-morpholinoethoxy)-2-bromo-3-phenyl-1H-inden-1-one, 4-(trifluoromethyl)phenylboronic acid instead of 3-pyridinylboronic acid, and being purified by silica gel column chromatography (acetone/hexanes=1:4) to obtain the title compound (57%).
$^1$H NMR (CDCl$_3$, 300 MHz) δ 7.53 (2H, d, J=8.4 Hz), 7.39-7.34 (4H, m), 7.21 (1H, d, J=2.4 Hz), 7.13 (2H, t, J=8.5 Hz). 7.05 (1H, d, J=8.1 Hz), 6.83 (1H, dd, J=2.4 Hz, 8.1 Hz), 4.18 (2H, t, J=5.6 Hz), 3.76 (4H, t, J=4.6 Hz), 2.83 (2H, t, J=6.0 Hz), 2.60 (4H, t, J=4.6 Hz)

Example 28

Synthesis of 6-(2-morpholinoethoxy)-3-(4-chlorophenyl)-2-(pyridin-3-yl)-1H-inden-1-one Step 1. (E)-3-(4-Chlorophenyl)-1-(3-hydroxyphenyl)prop-2-en-1-one The procedure of Step 1 of Example 1 was repeated except for using 4-chlorobenzaldehyde (1 eq) as a starting material instead of benzaldehyde and being stirred for 36 h to obtain the title compound (99%).

¹H NMR (DMSO, 300 MHz) δ 7.9 (2H, d, J=11.1 Hz), 7.8 (1H, d, J=14 Hz), 7.7 (1H, d, J=15.6 Hz), 7.7 (1H, d, J=7.8 Hz), 7.5 (2H, d, J=4.3 Hz), 7.5 (1H, t, J=2.0 Hz), 7.3 (1H, t, J=7.2 Hz), 7.1 (1H, dd, J=8.0 Hz, 2.5 Hz)

Step 2. 3-(4-Chlorophenyl)-2,3-dihydro-6-hydroxy-inden-1-one

The procedure of Step 2 of Example 1 was repeated except for using (E)-3-(4-chlorophenyl)-1-(3-hydroxyphenyl)prop-2-en-1-one obtained in Step 1 as a starting material instead of (E)-1-(3-hydroxyphenyl)-3-phenylprop-2-en-1-one and being stirred for 4 d to obtain the title compound (48%).

¹H NMR (DMSO, 300 MHz) δ 9.9 (1H, s, OH), 7.4 (2H, dd, J=2.4 Hz, 6.7 Hz), 7.2 (2H, dd, J=1.8 Hz, 14.8 Hz), 7.09-7.08 (2H, m), 7.0 (1H, t, J=1.4 Hz), 4.6 (1H, dd, J=3.4 Hz, 7.9 Hz), 3.2 (1H, dd, J=6.7 Hz, 17.6 Hz), 2.5 (1H, dd, J=2.8 Hz, 16.5 Hz)

Step 3. 1-(4-Chlorophenyl)-2,3-dihydro-3-oxo-1H-inden-5-yl acetate

The procedure of Step 3 of Example 1 was repeated except for using 3-(4-chlorophenyl)-2,3-dihydro-6-hydroxyinden-1-one obtained in Step 2 as a starting material instead of 2,3-dihydro-6-hydroxy-3-phenylinden-1-one and being stirred for 1.5 h to obtain the title compound (99%).

¹H NMR (DMSO, 300 MHz) δ 7.4 (1H, t, J=2.0 Hz), 7.4 (2H, d, J=2.4 Hz), 7.4 (1H, d, J=2.1 Hz), 7.31-7.27 (1H, m), 7.26-7.21 (2H, m), 4.7 (1H, dd, J=3.8 Hz, 8.0 Hz), 3.3 (1H, dd, J=21 Hz, 5.7 Hz) 2.66 (1H, dd, J=2.3 Hz, 21 Hz)

Step 4. 2-Bromo-3-(4-chlorophenyl)-1-oxo-1H-inden-6-yl acetate

The procedure of Step 4 of Example 1 was repeated except for using 1-(4-chlorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 9 h under tungsten lamp irradiation (375W) to obtain the title compound (49%).

¹H NMR (DMSO, 300 MHz) δ 7.7 (4H, dd, J=8.9 Hz, 16.7 Hz), 7.41-7.39 (1H, m), 7.23-7.21 (2H, m), 7.3 (3H, s)

Step 5. 2-Bromo-3-(4-chlorophenyl)-6-hydroxy-1H-inden-1-one

The procedure of Step 5 of Example 1 was repeated except for using 2-bromo-3-(4-chlorophenyl)-1-oxo-1H-inden-6-yl acetate obtained in Step 4 as a starting material instead of 2-bromo-1-oxo-3-phenyl-1H-inden-6-yl acetate and being stirred for 7 h to obtain the title compound (57%).

¹H NMR (DMSO, 300 MHz) δ 10.3 (1H, s, OH), 7.72-7.65 (4H, m), 7.0 (1H, d, J=8.0 Hz), 7.0 (1H, d, J=2.3 Hz), 6.8 (1H, dd, J=2.4 Hz, 8.0 Hz)

Step 6. 6-(2-Morpholino ethoxy)-2-bromo-3-(4-chlorophenyl)-1H-inden-1-one

The procedure of Step 6 of Example 1 was repeated except for using 2-bromo-3-(4-chlorophenyl)-6-hydroxy-1H-inden-1-one obtained in Step 5 as a starting material instead of 2-bromo-6-hydroxy-3-phenyl-1H-inden-1-one and being purified by silica gel column chromatography (EtOAc 100%) to obtain the title compound (67%).

Step 7. 6-(2-Morpholinoethoxy)-3-(4-chlorophenyl)-2-(pyridin-3-yl)-1H-inden-1-one The procedure of Step 7 of Example 1 was repeated except for using 6-(2-morpholinoethoxy)-2-bromo-3-(4-chlorophenyl)-1H-inden-1-one obtained in Step 6 as a starting material instead of 6-(2-morpholinoethoxy)-2-bromo-3-phenyl-1H-inden-1-one and being purified by silica gel column chromatography (acetone/hexanes=1:1) to obtain the title compound (67%).

¹H NMR (CDCl₃, 300 MHz) δ 8.47 (1H, dd, J=4.9 Hz, 1.7 Hz), 8.40 (1H, d, J=2.1 Hz), 7.63 (1H, dt, J=8.0 Hz, 1.8 Hz), 7.43-7.39 (2H, m), 7.33-7.30 (2H, m), 7.24-7.21 (2H, m), 7.03 (1H, d, J=8.1 Hz), 6.84 (1H, dd, J=8.1 Hz, 2.4 Hz), 4.16 (2H, t, J=5.6 Hz), 3.74 (4H, t, J=4.8 Hz), 2.82 (2H, t, J=5.6 Hz), 2.59 (4H, t, J=4.6 Hz)

Example 29

Synthesis of 6-(2-morpholinoethoxy)-3-(4-chlorophenyl)-2-(3,4-difluorophenyl)-1H-inden-1-one The procedure of Step 7 of Example 1 was repeated except for using 6-(2-morpholinoethoxy)-2-bromo-3-(4-chlorophenyl)-1H-inden-1-one obtained in Step 6 of Example 28 as a starting material instead of 6-(2-morpholinoethoxy)-2-bromo-3-phenyl-1H-inden-1-one, 3,4-difluorophenylboronic acid instead of 3-pyridinylboronic acid, and being purified by silica gel column chromatography (acetone/hexanes=1:4) to obtain the title compound (43%).

¹H NMR (CDCl₃, 300 MHz) δ 7.44-7.41 (2H, m), 7.32-7.29 (2H, m), 7.20 (1H, d, J=2.4 Hz), 7.14-6.99 (3H, m), 6.95-6.83 (1H, m), 6.82 (1H, dd, J=2.0 Hz, 7.7 Hz), 4.16 (2H, t, J=5.6 Hz), 3.74 (4H, t, J=4.7 Hz) 2.82 (2H, t, J=5.6 Hz), 2.59 (4H, t, J=4.7 Hz)

Example 30

Synthesis of 6-(2-morpholinoethoxy)-3-(4-chlorophenyl)-2-(pyrimidin-5-yl)-1H-inden-1-one The procedure of Step 7 of Example 1 was repeated except for using 6-(2-morpholinoethoxy)-2-bromo-3-(4-chlorophenyl)-1H-inden-1-one obtained in Step 6 of Example 28 as a starting material instead of 6-(2-morpholinoethoxy)-2-bromo-3-phenyl-1H-inden-1-one, 5-pyrimidinylboronic acid instead of 3-pyridinylboronic acid, and being purified by silica gel column chromatography (acetone/hexanes=2:3) to obtain the title compound (71%).

¹H NMR (CDCl₃, 300 MHz) δ 9.07 (1H, s), 8.63 (2H, s), 7.46 (2H, d, J=8.3 Hz), 7.30 (2H, d, J=8.3 Hz), 7.24 (1H, d, J=2.3 Hz). 7.05 (1H, d, J=8.1 Hz), 6.86 (1H, dd, J=2.3 Hz, 8.1 Hz), 4.18 (2H, t, J=5.6 Hz), 3.75 (4H, t, J=4.6 Hz), 2.84 (2H, t, J=5.6 Hz) 2.66 (4H, t, J=6.1 Hz)

Example 31

Synthesis of 6-(2-morpholinoethoxy)-3-(4-chlorophenyl)-2-(4-(trifluoromethyl)phenyl)-1H-inden-1-one The procedure of Step 7 of Example 1 was repeated except for using 6-(2-morpholinoethoxy)-2-bromo-3-(4-chlorophenyl)-1H-inden-1-one obtained in Step 6 of Example 28 as a starting material instead of 6-(2-morpholinoethoxy)-2-bromo-3-phenyl-1H-inden-1-one, 4-(trifluoromethyl)phenyboronic acid instead of 3-pyridinylboronic acid, and being purified by prep HPLC (CH₃CN/H₂O=7:3) to obtain the title compound (14%).
¹H NMR (CDCl₃, 300 MHz) δ 7.53 (2H, d, J=8.3 Hz), 7.43-7.40 (2H, m), 7.30-7.29 (4H, m), 7.22 (1H, d, J=2.2 Hz). 7.03 (1H, d, J=8.1 Hz), 6.84 (1H, dd, J=2.4 Hz, 8.1 Hz), 4.17 (2H, t, J=5.6 Hz), 3.75 (4H, t, J=4.7 Hz), 2.82 (2H, t, J=5.6 Hz) 2.59 (4H, t, J=4.7 Hz)

Example 32

Synthesis of 6-(2-morpholinoethoxy)-3-(4-(trifluoromethyl)phenyl)-2-(pyridin-3-yl)-1H-inden-1-one Step 1. (E)-3-(4-(Tri fluoromethyl)phenyl)-1-(3-hydroxyphenyl)prop-2-en-1-one The procedure of Step 1 of Example 1 was repeated except for using 4-(trifluoromethyl)benzaldehyde as a starting material instead of benzaldehyde and being stirred for 28 h to obtain the title compound (99%).
¹H NMR (DMSO, 300 MHz) δ 8.1 (2H, d, J=8.1 Hz), 8.0 (1H, d, J=15.7 Hz), 7.8 (2H, d, J=10.5 Hz), 7.8 (1H, d, J=17.9 Hz), 7.67-7.64 (1H, m), 7.5 (1H, t, J=2.0 Hz), 7.4 (1H, t, J=5.3 Hz), 7.1-7.0 (1H, m)

Step 2. 3-(4-(Trifluoromethyl)phenyl)-2,3-dihydro-6-hydroxyinden-1-one

The procedure of Step 2 of Example 1 was repeated except for using (E)-3-(4-(trifluoromethyl)phenyl)-1-(3-hydroxyphenyl)prop-2-en-1-one obtained in Step 1 as a starting material instead of (E)-1-(3-hydroxyphenyl)-3-phenylprop-2-en-1-one and being stirred for 5 d to obtain the title compound (38%).
1H NMR (DMSO, 300 MHz) δ 7.7 (2H, d, J=14.8 Hz), 7.4 (2H, d, J=16.1 Hz), 7.1 (2H, d, J=6.8 Hz), 7.0-6.1 (1H, m), 4.6 (1H, dd, J=3.4 Hz, 7.9 Hz), 3.2 (1H, dd, J=6.7 Hz, 17.6 Hz), 2.5 (1H, dd, J=2.8 Hz, 16.5 Hz)

Step 3. 1-(4-(Trifluoromethyl)phenyl)-2,3-dihydro-3-oxo-1H-inden-5-yl acetate

The procedure of Step 3 of Example 1 was repeated except for using 3-(4-(trifluoromethyl)phenyl)-2,3-dihydro-6-hydroxyinden-1-one obtained in Step 2 as a starting material instead of 2,3-dihydro-6-hydroxy-3-phenylinden-1-one and being stirred for 3 h to obtain the title compound (99%).
¹H NMR (DMSO, 300 MHz) δ 7.7 (2H, d, J=8.0 Hz), 7.5-7.4 (4H, m), 7.3 (1H, d, J=8.2 Hz), 4.8 (1H, dd, J=3.7 Hz, 7.9 Hz), 3.3 (1H, dd, J=8.0 Hz, 3.7 Hz), 2.7 (1H, dd, J=3.8 Hz, 19 Hz)

Step 4. 2-Bromo-3-(4-(trifluoromethyl)phenyl)-1-oxo-1H-inden-6-yl acetate

The procedure of Step 4 of Example 1 was repeated except for using 1-(4-(trifluoromethyl)phenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 6 h under tungsten lamp irradiation (375W) to obtain the title compound (67%).
¹H NMR (DMSO, 300 MHz) δ 8.0 (4H, dd, J=8.3 Hz, 22.8 Hz), 7.43-7.42 (1H, m), 7.26-7.22 (2H, m), 2.1 (3H, s)

Step 5. 2-Bromo-3-(4-(trifluoromethyl)phenyl)-6-hydroxy-1H-inden-1-one

The procedure of Step 5 of Example 1 was repeated except for using 2-bromo-3-(4-(trifluoromethyl)phenyl)-1-oxo-1H-inden-6-yl acetate obtained in Step 4 as a starting material instead of 2-bromo-1-oxo-3-phenyl-1H-inden-6-yl acetate and being stirred for 7 h to obtain the title compound (67%).
¹H NMR (DMSO, 300 MHz) δ 10.3 (1H, s, OH), 7.9 (4H, dd, J=8.4 Hz, 16.7 Hz), 7.0-6.9 (2H, m), 6.8 (1H, dd, J=2.4 Hz, 8.3 Hz)

Step 6. 6-(2-Morpholinoethoxy)-2-bromo-3-(4-(trifluoromethyl)phenyl)-1H-inden-1-one The procedure of Step 6 of Example 1 was repeated except for using 2-bromo-3-(4-(trifluoromethyl)phenyl)-6-hydroxy-1H-inden-1-one obtained in Step 5 as a starting material instead of 2-bromo-6-hydroxy-3-phenyl-1H-inden-1-one and being purified by silica gel column chromatography (EtOAc/hexanes=4:1) to obtain the title compound (52%).
¹H NMR (CDCl₃, 300 MHz) δ 7.79 (4H, q, J=7.6 Hz), 7.21 (1H, d, J=2.4 Hz), 6.97 (1H, d, J=8.1 Hz), 6.79 (1H, dd, J=2.4 Hz, 8.1 Hz), 4.14 (2H, t, J=5.7 Hz), 3.74 (4H, t, J=4.7 Hz), 2.81 (2H, t, J=5.7 Hz), 2.58 (4H, t, J=4.7 Hz)

Step 7. 6-(2-Morpholinoethoxy)-3-(4-(trifluoromethyl)phenyl)-2-(pyridin-3-yl)-1H-inden-1-one The procedure of Step 7 of Example 1 was repeated except for using 6-(2-morpholinoethoxy)-2-bromo-3-(4-(trifluoromethyl)phenyl)-1H-inden-1-one obtained in Step 6 as a starting material instead of 6-(2-morpholinoethoxy)-2-bromo-3-phenyl-1H-inden-1-one and being purified by silica gel column chromatography (acetone/hexanes 2:1) to obtain the title compound (75%).
¹H NMR (CDCl₃, 300 MHz) δ 8.48 (2H, d, J=3.6 Hz), 8.38 (1H, s), 7.71 (2H, d, J=8.1 Hz), 7.64 (1H, td, J=2.0 Hz, 7.9 Hz), 7.50 (2H, t, J=8.1 Hz), 7.25 (2H, dd, J=3.5 Hz, 8.3 Hz), 7.00 (1H, d, J=8.1 Hz), 6.85 (1H, dd, J=2.4 Hz. 8.1 Hz), 4.17 (2H, t, J=5.6 Hz), 3.7 (4H, t, J=4.7 Hz), 2.8 (2H, t, J=5.7 Hz), 2.59 (4H, t, J=4.7 Hz)

Example 33

Synthesis of 6-(2-morpholinoethoxy)-2,3-bis(4-(trifluoromethyl)phenyl)-1H-inden-1-one The procedure of Step 7 of Example 1 was repeated except for using 6-(2-morpholinoethoxy)-2-bromo-3-(4-(trifluoromethyl)phenyl)-1H-inden-1-one obtained in Step 6 of Example 32 as a starting material instead of 6-(2-morpholinoethoxy)-2-bromo-3-phenyl-1H-inden-1-one, 4-(trifluoromethyl)phenylboronic acid instead of 3-pyridinylboronic acid, and being purified by prep HPLC (CH₃CN/H₂O=7:3) to obtain the title compound (40%).
¹H NMR (CDCl₃, 300 MHz) δ 7.71 (2H, d, J=8.1 Hz), 7.53 (2H, d, J=8.7 Hz), 7.49 (2H, d, J=8.4 Hz), 7.33 (2H, d, J=8.2 Hz), 7.23 (1H, d, J=2.4 Hz). 7.00 (1H, d, J=8.1 Hz), 6.84 (1H, dd, J=2.4 Hz, 8.1 Hz), 4.17 (2H, t, J=5.6 Hz), 3.75 (4H, t, J=4.7 Hz), 2.83 (2H, t, J=5.6 Hz) 2.60 (4H, t, J=4.6 Hz)

Example 34

Synthesis of 6-(2-morpholinoethoxy)-3-(4-(trifluoromethyl)phenyl)-2-(3,4-difluorophenyl)-1H-inden-1-one The procedure of Step 7 of Example 1 was repeated except for using 6-(2-morpholinoethoxy)-2-bromo-3-(4-(trifluoromethyl)phenyl)-1H-inden-1-one obtained in Step 6 of Example 32 as a starting material instead of 6-(2-morpholinoethoxy)-2-bromo-3-phenyl-1H-inden-1-one, 3,4-difluorophenylboronic acid instead of 3-pyridinylboronic acid, and being purified by prep HPLC (CH$_3$CN/H$_2$O=7:3) to obtain the title compound (31%).

$^1$H NMR (CDCl$_3$, 300 MHz) δ 7.71 (2H, d, J=8.1 Hz), 7.49 (2H, d, J=8.0 Hz), 7.22 (1H, d, J=2.3 Hz), 7.11-7.00 (2H, m). 6.96 (1H, d, J=8.1 Hz), 6.94-7.87 (1H, m), 6.83 (1H, dd, J=2.4 Hz, 8.1 Hz), 4.16 (2H, t, J=5.7 Hz), 3.75 (4H, t, J=4.7 Hz), 2.82 (2H, t, J=5.7 Hz), 2.59 (4H, t, J=4.7 Hz)

Example 35

Synthesis of 6-(2-morpholinoethoxy)-3-(4-(trifluoromethyl)phenyl)-2-(pyrimidin-5-yl)-1H-inden-1-one The procedure of Step 7 of Example 1 was repeated except for using 6-(2-morpholinoethoxy)-2-bromo-3-(4-(trifluoromethyl)phenyl)-1H-inden-1-one obtained in Step 6 of Example 32 as a starting material instead of 6-(2-morpholinoethoxy)-2-bromo-3-phenyl-1H-inden-1-one, 5-pyrimidinylboronic acid instead of 3-pyridinylboronic acid, and being purified by prep HPLC (CH$_3$CN/H$_2$O=7:3) to obtain the title compound (25%).

$^1$H NMR (CDCl$_3$, 300 MHz) δ 9.08 (1H, s), 8.62 (2H, s), 7.75 (2H, d, J=8.1 Hz), 7.52 (2H, d, J=8.0 Hz), 7.26 (1H, d, J=2.4 Hz). 7.02 (1H, d, J=8.1 Hz), 6.87 (1H, dd, J=2.4 Hz, 8.1 Hz), 4.18 (2H, t, J=5.6 Hz), 3.75 (4H, t, J=4.7 Hz), 2.83 (2H, t, J=5.6 Hz) 2.59 (4H, t, J=4.7 Hz)

Example 36

Synthesis of 6-(2-morpholinoethoxy)-3-(3,5-difluorophenyl)-2-(pyridin-3-yl)-1H-inden-1-one hydrochloride salt Step 1. (E)-3-(3,5-Difluorophenyl)-1-(3-hydroxyphenyl)prop-2-en-1-one The procedure of Step 1 of Example 1 was repeated except for using 3,5-difluorobenzaldehyde as a starting material instead of benzaldehyde and being stirred for 22 h to obtain the title compound (80%).

$^1$H NMR (DMSO, 300 MHz) δ 9.8 (1H, s, OH), 8.0 (1H, d, J=15.6 Hz), 7.73-7.65 (3H, m), 7.5-7.3 (3H, m), 7.2-7.0 (2H, m)

Step 2. 3-(3,5-Difluorophenyl)-2,3-dihydro-6-hydroxyinden-1-one

The procedure of Step 2 of Example 1 was repeated except for using (E)-3-(3,5-difluorophenyl)-1-(3-hydroxyphenyl)prop-2-en-1-one obtained in Step 1 as a starting material instead of (E)-1-(3-hydroxyphenyl)-3-phenylprop-2-en-1-one and being stirred for 5 d to obtain the title compound (99%).

$^1$H NMR (DMSO, 300 MHz) δ 9.9 (1H, s, OH), 7.11-7.05 (3H, m), 7.0 (1H, dd, J=1.8 Hz, 14.8 Hz), 6.9 (2H, m), 4.6 (1H, dd, J=3.6 Hz, 7.8 Hz), 3.2 (1H, dd, J=19 Hz, 7.8 Hz), 2.6 (1H, dd, J=3.8 Hz, 19 Hz),

Step 3. 1-(3,5-Difluorophenyl)-2,3-dihydro-3-oxo-1H-inden-5-yl acetate

The procedure of Step 3 of Example 1 was repeated except for using 3-(3,5-difluorophenyl)-2,3-dihydro-6-hydroxyinden-1-one obtained in Step 2 as a starting material instead of 2,3-dihydro-6-hydroxy-3-phenylinden-1-one and being stirred for 2 h to obtain the title compound (83%).

$^1$H NMR (DMSO, 300 MHz) δ 7.43-7.40 (2H, m), 7.3 (1H, d, J=8.1 Hz), 7.2-7.1 (1H, m), 7.0 (2H, dd, J=7.2 Hz, 5.4 Hz), 4.7 (1H, dd, J=6.6 Hz, 5.5 Hz), 3.2 (1H, dd, J=5.4 Hz, 16.5 Hz), 2.8 (1H, dd, J=4.1 Hz, 19.1 Hz), 2.3 (3H, s)

Step 4. 2-Bromo-3-(3,5-difluorophenyl)-1-oxo-1H-inden-6-yl acetate

The procedure of Step 4 of Example 1 was repeated except for using 1-(3,5-difluorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 2 h under tungsten lamp irradiation (375W) to obtain the title compound (67%).

$^1$H NMR (DMSO, 300 MHz) δ 7.56-7.41 (4H, m), 7.26-7.24 (2H, m), 2.3 (3H, s)

Step 5. 2-Bromo-3-(3,5-difluorophenyl)-6-hydroxy-1H-inden-1-one

The procedure of Step 5 of Example 1 was repeated except for using 2-bromo-3-(3,5-difluorophenyl)-1-oxo-1H-inden-6-yl acetate obtained in Step 4 as a starting material instead of 2-bromo-1-oxo-3-phenyl-1H-inden-6-yl acetate and being stirred for 2.5 h to obtain the title compound (64%).

$^1$H NMR (DMSO, 300 MHz) δ 7.53-7.45 (1H, m), 7.42-7.35 (2H, m), 6.99 (1H, d, J=8.1 Hz), 6.96 (1H, d, J=2.1 Hz), 6.8 (1H, dd, J=2.4 Hz, 8.1 Hz)

Step 6. 6-(2-Morpholinoethoxy)-2-bromo-3-(3,5-difluorophenyl)-1H-inden-1-one

The procedure of Step 6 of Example 1 was repeated except for using 2-bromo-3-(3,5-difluorophenyl)-6-hydroxy-1H-inden-1-one (700 mg, 2.1 mmol) obtained in Step 5 as a starting material instead of 2-bromo-6-hydroxy-3-phenyl-1H-inden-1-one and being purified by silica gel column chromatography (acetone/hexanes=1:1) to obtain the title compound (67%).

$^1$H NMR (CDCl$_3$, 300 MHz) δ 7.22-7.15 (3H, m), 7.01 (1H, d, J=8.1 Hz), 7.01-6.94 (1H, m), 6.80 (1H, dd, J=2.4 Hz, 8.1 Hz), 4.15 (2H, t, J=5.6 Hz), 3.75 (4H, t, J=4.7 Hz), 2.83 (2H, t, J=5.6 Hz), 2.60 (4H, t, J=4.7 Hz)

Step 7. 6-(2-Morpholino ethoxy)-3-(3,5-difluorophenyl)-2-(pyridin-3-yl)-1H-inden-1-one The procedure of Step 7 of Example 1 was repeated except for using 6-(2-morpholinoethoxy)-2-bromo-3-(3,5-difluorophenyl)-1H-inden-1-one obtained in Step 6 as a starting material instead of 6-(2-morpholinoethoxy)-2-bromo-3-phenyl-1H-inden-1-one and being purified by prep HPLC (CH$_3$CN/H$_2$O=7:3) to obtain the title compound (40%).

$^1$H NMR (CDCl$_3$, 300 MHz) δ 8.5 (1H, dd, J=1.5 Hz, 4.8 Hz), 8.4 (1H, d, J=1.8 Hz), 7.66-7.64 (1H, m), 7.29-7.24 (1H, m), 7.23 (2H, d, J=2.4 Hz), 7.02 (1H, d, J=8.1 Hz), 6.91-6.84 (3H, m), 4.17 (2H, t, J=5.7 Hz), 3.75 (4H, t, J=4.7 Hz), 2.83 (2H, t, J=5.7 Hz), 2.59 (4H, t, J=4.7 Hz)

Step 8. 6-(2-Morpholinoethoxy)-3-(3,5-difluorophenyl)-2-(pyridin-3-yl)-1H-inden-1-one hydrochloride salt The procedure of Step 8 of Example 1 was repeated except for using 6-(2-morpholinoethoxy)-3-(3,5-difluorophenyl)-2-

(pyridin-3-yl)-1H-inden-1-one (500 mg, 1.21 mmol) obtained in Step 7 as a starting material instead of 6-(2-morpholinoethoxy)-3-phenyl-2-(pyridin-3-yl)-1H-inden-1-one to give the title compound in quantitative yield.

$^1$H NMR (DMSO, 300 MHz) δ 8.50 (1H, dd, J=1.7, 8.0 Hz), 8.37 (1H, d, J=1.5 Hz), 7.63 (1H, td, J=2.0, 8.4 Hz), 7.43-7.41 (2H, m), 7.32 (1H, d, J=2.1 Hz), 7.18 (3H, d, J=8.1 Hz), 7.09 (1H, dd, J=2.4, 8.1 Hz), 4.52 (2H, br s), 3.96 (2H, br s), 3.83 (2H, br s), 3.57 (2H, br s), 3.49 (2H, br s), 3.23 (2H, br s)

Example 37

Synthesis of 6-(2-morpholinoethoxy)-2-(4-(trifluoromethyl)phenyl)-3-(3,5-difluorophenyl)-1H-inden-1-one The procedure of Step 7 of Example 1 was repeated except for using 6-(2-morpholinoethoxy)-2-bromo-3-(3,5-difluorophenyl)-1H-inden-1-one obtained in Step 6 of Example 36 as a starting material instead of 6-(2-morpholinoethoxy)-2-bromo-3-phenyl-1H-inden-1-one, 4-(trifluoromethyl)phenylboronic acid instead of 3-pyridinylboronic acid, and being purified by silica gel column chromatography (acetone/hexanes=1:2) to obtain the title compound (55%).

$^1$H NMR (CDCl$_3$, 300 MHz) δ 7.55 (2H, d, J=8.2 Hz), 7.35 (2H, d, J=8.0 Hz), 7.23 (1H, d, J=2.4 Hz), 7.19 (1H, d, J=8.1 Hz). 6.93-6.84 (4H, m), 4.17 (2H, t, J=5.6 Hz), 3.75 (4H, t, J=4.7 Hz), 2.83 (2H, t, J=5.6 Hz), 2.59 (4H, t, J=4.7 Hz)

Example 38

Synthesis of 6-(2-morpholinoethoxy)-2-(3,4-difluorophenyl)-3-(3,5-difluorophenyl)-1H-inden-1-one The procedure of Step 7 of Example 1 was repeated except for using 6-(2-morpholinoethoxy)-2-bromo-3-(3,5-difluorophenyl)-1H-inden-1-one obtained in Step 6 of Example 36 as a starting material instead of 6-(2-morpholinoethoxy)-2-bromo-3-phenyl-1H-inden-1-one, 3,4-difluorophenylboronic acid instead of 3-pyridinylboronic acid, and being purified by prep HPLC (CH$_3$CN/H$_2$O=7:3) to obtain the title compound (47%).

$^1$H NMR (CDCl$_3$, 300 MHz) δ 7.21 (1H, d, J=2.4 Hz), 7.14-7.06 (2H, m), 6.99 (1H, d, J=8.1 Hz), 6.96-6.90 (2H, m). 6.89 (1H, d, J=1.8 Hz), 6.87 (1H, d, J=2.1 Hz), 6.84 (1H, dd, J=2.4, 8.1 Hz), 4.16 (2H, t, J=5.8 Hz), 3.75 (4H, t, J=4.7 Hz) 2.82 (2H, t, J=5.6 Hz), 2.59 (4H, t, J=4.7 Hz)

Example 39

Synthesis of 6-(2-morpholinoethoxy)-3-(3,5-difluorophenyl)-2-(pyrimidin-5-yl)-1H-inden-1-one The procedure of Step 7 of Example 1 was repeated except for using 6-(2-morpholinoethoxy)-2-bromo-3-(3,5-difluorophenyl)-1H-inden-1-one obtained in Step 6 of Example 36 as a starting material instead of 6-(2-morpholinoethoxy)-2-bromo-3-phenyl-1H-inden-1-one, 5-pyrimidinylboronic acid instead of 3-pyridinylboronic acid, and being purified by prep HPLC (CH$_3$CN/H$_2$O=7:3) to obtain the title compound (36%).

$^1$H NMR (CDCl$_3$, 300 MHz) δ 9.10 (1H, s), 8.64 (2H, s), 7.25 (1H, d, J=2.4 Hz), 7.04 (1H, d, J=8.1 Hz), 7.00-6.87 (4H, m). 4.17 (2H, t, J=5.0 Hz), 3.74 (4H, t, J=4.7 Hz), 2.83 (2H, t, J=5.6 Hz), 2.59 (4H, t, J=4.6 Hz)

Example 40

Synthesis of 4-methyl-4-(2-{[2-(1-methylpyridin-1-ium-3-yl)-1-oxo-3-phenyl-1H-inden-6-yl]oxy}ethyl)morpholin-4-ium diiodide To a solution of 6-(2-morpholinoethoxy)-3-phenyl-2-(pyridin-3-yl)-1H-inden-1-one (40 mg, 0.097 mmol) obtained in Step 7 of Example 1 in CH$_2$Cl$_2$ (0.5 mL) was added MeI (60 μL, 0.96 mmol, 10 eq). The mixture was heated to reflux for 30 min. The precipitate was collected by a Buchner funnel, rinsed with CH$_2$Cl$_2$ (5 mL), and then dried under a high vacuum to afford the title compound (4 mg, 59%).

$^1$H NMR (DMSO, 300 MHz) δ 8.91 (1H, s), 8.88 (1H, d, J=5.8 Hz), 8.09-7.99 (2H, m), 7.62-7.46 (5H, m), 7.37 (1H, d, J=2.4 Hz), 7.30 (1H, d, J=8.2 Hz), 7.12 (1H, dd, J=2.4 Hz, 8.2 Hz), 4.66-4.60 (2H, m), 4.33 (3H, s), 3.99-3.96 (m, 6H), 3.60-3.53 (4H, m), 3.28 (3H, s)

Example 41

Synthesis of 1-methyl-3-{6-[2-(morpholin-4-yl)ethoxy]-1-oxo-3-phenyl-1H-inden-2-yl}pyridin-1-ium iodide The mother liquid collected in Example 40 was purified by silica gel column chromatography (CH$_2$Cl$_2$/MeOH=5:1) to afford the title compound (9 mg, 17%).

$^1$H NMR (CDCl$_3$, 300 MHz) δ 9.29 (1H, d, J=5.7 Hz), 8.77 (1H, s), 7.93 (1H, d, J=8.2 Hz), 7.89-7.78 (1H, m), 7.56 (5H, s), 7.25 (1H, d, J=1.8 Hz), 7.14 (1H, d, J=8.1 Hz), 6.89 (1H, dd, J=1.8 Hz, 8.1 Hz), 4.61 (3H, s), 4.19 (2H, t, J=5.5 Hz), 3.75 (4H, d, J=4.4 Hz), 2.84 (2H, t, J=5.5 Hz), 2.59 (t, J=4.3 Hz, 4H).

Example 42

Synthesis of 4-oxido-4-(2-{[1-oxo-3-phenyl-2-(pyridin-3-yl)-1H-inden-6-yl]oxy}ethyl)morpholin-4-ium To a solution of 6-(2-morpholinoethoxy)-3-phenyl-2-(pyridin-3-yl)-1H-inden-1-one (100 mg, 0.24 mmol) obtained in Step 7 of Example 1 in CH$_2$Cl$_2$ (2 mL) at 10° C. was added MCPBA (21 mg, 1 eq). The mixture was stirred at room temperature for 2 h. The reaction mixture was diluted with EtOAc and washed with sat. NaHCO$_3$, H$_2$O, and brine. The organic layer was dried over MgSO$_4$ and concentrated in vacuo. The residue was purified by silica gel column chromatography (MC/MeOH/NH$_4$OH=92:7:1) to afford the title compound (14 mg, 13%).

$^1$H NMR (CDCl$_3$, 300 MHz) δ 8.38-8.34 (2H, m), 7.56 (1H, td, J=1.9 Hz, 8.0 Hz), 7.37-7.27 (5H, m), 7.14 (2H, dd, J=5.0 Hz, 7.4 Hz), 6.99 (1H, d, J=8.0 Hz), 6.76 (1H, dd, J=2.4 Hz, 8.1 Hz), 4.10 (2H, t, J=5.6 Hz), 3.67 (4H, t, J=4.7 Hz), 2.75 (2H, t, J=5.6 Hz), 2.52 (4H, t, J=4.7 Hz)

Example 43

Synthesis of 4-oxido-4-(2-{[2-(1-oxidopyridin-1-ium-3-yl)-1-oxo-3-phenyl-1H-inden-6-yl]oxy}ethyl)morpholin-4-ium During silica gel column chromatography in Example 42, the title compound was obtained as a minor product (7 mg, 7%).

$^1$H NMR (DMSO, 300 MHz) δ 8.44 (1H, dd, J=1.6 Hz, 4.8 Hz), 8.31 (1H, d, J=1.5 Hz), 7.59 (1H, dt, J=1.8 Hz, 7.9 Hz), 7.51-7.33 (6H, m), 7.22 (1H, d, J=2.2 Hz), 7.13 (1H, d, J=8.0 Hz), 7.07 (1H, ddt, J=2.3 Hz, 7.0 Hz), 4.67 (2H, t, J=4.4 Hz), 4.16 (2H, t, J=11 Hz), 3.66 (2H, d, J=12 Hz), 3.58 (2H, t, J=4.4 Hz), 3.48 (2H, dt, J=12 Hz, 3.1 Hz), 2.89 (2H, d, J=11 Hz)

Example 44

Synthesis of tert-butyl 4-(2-(1-oxo-3-phenyl-2-(pyridin-3-yl)-1H-inden-6-yloxy)ethyl)piperazine-1-carboxylate Step 1. 6-Hydroxy-3-phenyl-2-(pyridin-3-yl)-1H-inden-1-one The procedure of Step 7 of Example 1 was repeated except for using 2-bromo-6-hydroxy-3-phenyl-1H-inden-1-one obtained in Step 5 of Example 1 as a starting material instead of 6-(2-morpholinoethoxy)-2-bromo-3-phenyl-1H-inden-1-one and being recrystallized with EtOAc to give the title compound (34%).
$^1$H NMR (DMSO, 300 MHz) δ 8.4 (1H, dd, J=2.5 Hz, 6.2 Hz), 8.2 (1H, d, J=1.6 Hz), 7.55-7.51 (1H, m), 7.44-7.29 (5H, m), 6.98-6.96 (2H, m), 6.7 (1H, dd, J=2.2 Hz, 7.9 Hz)

Step 2. tert-Butyl 4-(2-(1-oxo-3-phenyl-2-(pyridin-3-yl)-1H-inden-6-yloxy)ethyl)piperazine-1-carboxylate The procedure of Step 6 of Example 1 was repeated except for using 6-hydroxy-3-phenyl-2-(pyridin-3-yl)-1H-inden-1-one obtained in Step 1 as a starting material instead of 2-bromo-6-hydroxy-3-phenyl-1H-inden-1-one, t-butyl 4-(2-hydroxyethyl)piperazine-1-carboxylate instead of 4-(2-hydroxyethyl)morpholine, being stirred for 19 h, and being recrystallized with EtOAc to give the title compound (51%).
$^1$H NMR (CDCl$_3$, 300 MHz) δ 8.45 (1H, dd, J=4.8 Hz, 1.5 Hz), 8.42 (1H, d, J=1.5 Hz), 7.64 (1H, td, J=1.5 Hz, 7.8 Hz), 7.44-7.35 (5H, m), 7.24-7.20 (2H, m), 7.07 (1H, d, J=8.1 Hz), 6.83 (1H, dd, J=2.1 Hz, 8.1 Hz), 4.16 (2H, t, J=5.6 Hz), 3.46 (4H, t, J=4.8 Hz), 2.84 (2H, t, J=5.6 Hz), 2.53 (4H, t, J=4.8 Hz), 1.47 (9H, s)

Example 45

Synthesis of 6-[2-(4-(methylsulfonyl)piperazin-1-yl)ethoxy]-3-phenyl-2-(pyridin-3-yl)-1H-inden-1-one hydrochloride salt Step 1. 2-Bromo-6-[2-(4-methylsulfonyl)piperazin-1-yl)ethoxy]-3-phenyl-1H-inden-1-one The procedure of Step 6 of Example 1 was repeated except for using 2-((4-methylsulfonyl)piperazin-1-yl)ethan-1-ol instead of 4-(2-hydroxyethyl)morpholine, being stirred for 6 h, and being purified by silica gel column chromatography (EtOAc/hexanes=1:2) to obtain the title compound (81%).
$^1$H NMR (CDCl$_3$, 300 MHz) δ 7.65-7.53 (5H, m), 7.2 (1H, d, J=2.4 Hz), 7.04 (1H, d, J=8.1 Hz), 6.74 (1H, dd, J=2.4 Hz, 8.1 Hz), 4.12 (2H, t, J=5.4 Hz), 3.28 (4H, t, J=4.9 Hz), 2.87 (2H, t, J=5.4 Hz), 2.8 (3H, s), 2.7 (4H, t, J=4.9 Hz)

Step 2. 6-[2-(4-(Methylsulfonyl)piperazin-1-yl)ethoxy]-3-phenyl-2-(pyridin-3-yl)-1H-inden-1-one The procedure of Step 7 of Example 1 was repeated except for using 2-bromo-6-[2-(4-methylsulfonyl)piperazin-1-yl)ethoxy]-3-phenyl-1H-inden-1-one obtained in Step 1 as a starting material instead of 6-(2-morpholinoethoxy)-2-bromo-3-phenyl-1H-inden-1-one and being purified by silica gel column chromatography (acetone/hexanes=1:1) to obtain the title compound (70%).
$^1$H NMR (CDCl$_3$, 300 MHz) δ 8.5 (1H, dd, J=4.8 Hz, 1.5 Hz), 8.4 (1H, d, J=1.5 Hz), 7.6 (1H, td, J=1.5 Hz, 7.8 Hz), 7.44-7.35 (5H, m), 7.24-7.20 (2H, m), 7.1 (1H, d, J=8.1 Hz), 6.8 (1H, dd, J=2.1 Hz, 8.1 Hz), 4.2 (2H, t, J=5.6 Hz), 3.4 (4H, t, J=4.8 Hz), 2.8 (2H, t, J=5.6 Hz), 2.5 (4H, t, J=4.8 Hz), 1.5 (9H, s)

Step 3. 6-[2-(4-(Methylsulfonyl)piperazin-1-yl)ethoxy]-3-phenyl-2-(pyridin-3-yl)-1H-inden-1-one hydrochloride salt The procedure of Step 8 of Example 1 was repeated except for using 6-[2-(4-(methylsulfonyl)piperazin-1-yl)ethoxy]-3-phenyl-2-(pyridin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.
$^1$H NMR (D$_2$O, 300 MHz) δ 8.44-8.42 (2H, m), 8.03 (1H, d, J=8.4 Hz), 7.64 (1H, dd, J=8.1 Hz, 6.3 Hz), 7.44-7.34 (3H, m), 7.31-7.28 (2H, m), 7.11-7.09 (2H, m), 6.87 (1H, dd, J=8.1 Hz, 2.4 Hz), 4.31 (2H, t, J=4.35 Hz), 3.57 (2H, t, J=4.65 Hz), 3.46 (8H, m), 2.95 (3H, s)

Example 46

Synthesis of 6-(2-(piperazin-1-yl)ethoxy)-3-phenyl-2-(pyridin-3-yl)-1H-inden-1-one To a solution of tert-butyl 4-(2-(1-oxo-3-phenyl-2-(pyridin-3-yl)-1H-inden-6-yloxy)ethyl)piperazine-1-carboxylate (0.38 mmol, 200 mg) obtained in Step 2 of Example 44 in CH$_2$Cl$_2$ (0.3M) was added TFA (20 eq). The resulting mixture was stirred at room temperature for 40 min and diluted with CH$_2$Cl$_2$. The solution was basicified to pH 9 by the addition of 3N NaOH. The mixture was washed with H$_2$O, dried over MgSO$_4$, and concentrated in vacuo. The residue was purified by silica gel column chromatography (acetone/hexanes=1:1) to obtain the title compound (75%).
$^1$H NMR (CDCl$_3$, 300 MHz) δ 8.50-8.41 (2H, m), 7.64 (1H, d, J=7.3 Hz), 7.44-7.37 (5H, m), 7.27-7.21 (2H, m), 7.07 (1H, dd, J=2.8 Hz, 8.2 Hz), 6.83 (1H, dd, J=2.9 Hz, 7.8 Hz), 4.15 (2H, d, J=20 Hz), 2.94 (2H, d, J=7.6 Hz), 2.83 (2H, d, J=7.6 Hz), 2.69-2.53 (6H, m), 2.04 (1H, s)

Example 47

Synthesis of 6-[2-(4-(methylsulfonyl)piperazin-1-yl)ethoxy]-2,3-bis[4-(trifluoromethyl)phenyl]-1H-inden-1-one Step 1. 2-Bromo-6-[2-(4-(methylsulfonyl)piperazin-1-yl)ethoxy]-3-[4-(trifluoromethyl)phenyl]-1H-inden-1-one The procedure of Step 6 of Example 1 was repeated except for using 2-bromo-3-(4-(trifluoromethyl)phenyl)-6-hydroxy-1H-inden-1-one obtained in Step 5 of Example 32 as a starting material instead of 2-bromo-6-hydroxy-3-phenyl-1H-inden-1-one, 2-((4-methylsulfonyl)piperazin-1-yl)ethan-1-ol instead of 4-(2-hydroxyethyl)morpholine, being stirred for 4 d, and being purified by silica gel column chromatography (acetone/hexanes=2:1) to obtain the title compound (36%).

¹H NMR (CDCl₃, 300 MHz) δ 7.71 (2H, d, J=8.2 Hz), 7.53 (2H, d, J=8.7 Hz), 7.49 (2H, d, J=8.4 Hz), 7.33 (2H, d, J=8.4 Hz), 7.24 (1H, d, J=2.4 Hz), 7.01 (1H, d, J=8.1 Hz), 6.84 (1H, dd, J=2.4 Hz, 8.1 Hz), 4.16 (2H, t, J=5.4 Hz), 3.29 (4H, t, J=4.9 Hz), 2.89 (2H, t, J=5.4 Hz), 2.79 (3H, s), 2.72 (4H, t, J=4.9 Hz)

Step 2. 6-[2-(4-(Methylsulfonyl)piperazin-1-yl)ethoxy]-2,3-bis[4-(trifluoromethyl)phenyl]-1H-inden-1-one The procedure of Step 7 of Example 1 was repeated except for using 2-bromo-6-[2-(4-(methylsulfonyl)piperazin-1-yl)ethoxy]-3-[4-(trifluoromethyl)phenyl]-1H-inden-1-one obtained in Step 1 as a starting material instead of 6-(2-morpholinoethoxy)-2-bromo-3-phenyl-1H-inden-1-one, and 4-(trifluoromethyl)phenylboronic acid instead of 3-pyridinylboronic acid, and being purified by prep HPLC (CH₃CN/H₂O=7:3) to obtain the title compound (21%).
¹H NMR (CDCl₃, 300 MHz) δ 7.71 (2H, d, J=8.2 Hz), 7.53 (2H, d, J=8.7 Hz), 7.49 (2H, d, J=8.4 Hz), 7.33 (2H, d, J=8.4 Hz), 7.24 (1H, d, J=2.4 Hz), 7.01 (1H, d, J=8.1 Hz), 6.84 (1H, dd, J=2.4 Hz, 8.1 Hz), 4.16 (2H, t, J=5.4 Hz), 3.29 (4H, t, J=4.9 Hz), 2.89 (2H, t, J=5.4 Hz), 2.79 (3H, s), 2.72 (4H, t, J=4.9 Hz)

Example 48

Synthesis of 2-(3,4-difluorophenyl)-6-(2-(4-(methylsulfonyl)piperazin-1-yl)ethoxy)-3-(4-(trifluoromethyl)phenyl)-1H-inden-1-one The procedure of Step 7 of Example 1 was repeated except for using 2-bromo-6-[2-(4-(methylsulfonyl)piperazin-1-yl)ethoxy]-3-[4-(trifluoromethyl)phenyl]-1H-inden-1-one obtained in Step 1 of Example 47 as a starting material instead of 6-(2-morpholinoethoxy)-2-bromo-3-phenyl-1H-inden-1-one, and 3,4-difluorophenylboronic acid instead of 3-pyridinylboronic acid, and being purified by prep HPLC (CH₃CN/H₂O=7:3) to obtain the title compound (49%).
¹H NMR (CDCl₃, 300 MHz) δ 7.72 (2H, d, J=8.5 Hz), 7.49 (2H, d, J=8.4 Hz), 7.22 (1H, d, J=2.4 Hz), 7.12-7.03 (2H, m), 6.97 (1H, d, J=8.1 Hz), 6.93-6.87 (1H, m), 6.82 (1H, dd, J=2.4 Hz, 8.1 Hz), 4.15 (2H, t, J=5.5 Hz), 3.29 (4H, t, J=4.9 Hz), 2.89 (2H, t, J=5.5 Hz), 2.79 (3H, s), 2.71 (4H, t, J=4.9 Hz)

Example 49

Synthesis of 6-(2-(4-(methylsulfonyl)piperazin-1-yl)ethoxy)-2-(pyrimidin-5-yl)-3-(4-(trifluoromethyl)phenyl)-1H-inden-1-one The procedure of Step 7 of Example 1 was repeated except for using 2-bromo-6-[2-(4-(methylsulfonyl)piperazin-1-yl)ethoxy]-3-[4-(trifluoromethyl)phenyl]-1H-inden-1-one obtained in Step 1 of Example 47 as a starting material instead of 6-(2-morpholinoethoxy)-2-bromo-3-phenyl-1H-inden-1-one, and 5-pyrimidinylboronic acid instead of 3-pyridinylboronic acid, and being purified by prep HPLC (CH₃CN/H₂O=7:3) to obtain the title compound (14%).
¹H NMR (CDCl₃, 300 MHz) δ 9.09 (1H, s), 8.62 (2H, s), 7.75 d, J=8.1 Hz), 7.52 (2H, d, J=8.1 Hz), 7.26 (1H, d, J=2.4 Hz), 7.03 (1H, d, J=8.1 Hz), 6.87 (1H, dd, J=2.4 Hz, 8.1 Hz), 4.17 (2H, t, J=5.4 Hz), 3.29 (4H, t, J=4.8 Hz), 2.90 (2H, t, J=5.4 Hz), 2.80 (3H, s), 2.72 (4H, t, J=4.8 Hz)

Example 50

Synthesis of 3-(3,5-difluorophenyl)-6-(2-(4-(methylsulfonyl)piperazin-1-yl)ethoxy)-2-(4-(trifluoromethyl)phenyl)-1H-inden-1-one hydrochloride salt Step 1. 2-Bromo-3-(3,5-difluorophenyl)-6-(2-(4-(methylsulfonyl)piperazin-1-yl)ethoxy)-1H-inden-1-one The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, 2-((4-methylsulfonyl)piperazin-1-yl)ethan-1-ol instead of 4-(2-hydroxyethyl)morpholine, being stirred for 4 d, and being purified by silica gel column chromatography (acetone/hexanes=1:4) to obtain the title compound (52%).
¹H NMR (CDCl₃, 300 MHz) δ 7.21-7.17 (4H, m), 7.02 (2H, d, J=8.1 Hz), 6.98 (2H, td, J=8.0 Hz, 2.4 Hz), 6.80 (1H, dd, J=8.1 Hz, 2.4 Hz), 4.13 (2H, t, J=5.4 Hz), 3.28 (4H, t, J=4.8 Hz), 2.87 (2H, t, J=5.4 Hz), 2.79 (3H, s), 2.70 (4H, t, J=4.8 Hz)

Step 2. 3-(3,5-Difluorophenyl)-6-(2-(4-(methylsulfonyl)piperazin-1-yl)ethoxy)-2-(4-(trifluoromethyl)phenyl)-1H-inden-1-one The procedure of Step 7 of Example 1 was repeated except for using 2-bromo-3-(3,5-difluorophenyl)-6-(2-(4-(methylsulfonyl)piperazin-1-yl)ethoxy)-1H-inden-1-one obtained in Step 1 as a starting material instead of 6-(2-morpholinoethoxy)-2-bromo-3-phenyl-1H-inden-1-one, and 4-(trifluoromethyl)phenylboronic acid instead of 3-pyridinylboronic acid, and being purified by prep HPLC (CH₃CN/H₂O=7:3) to obtain the title compound (69%).
¹H NMR (CDCl₃, 300 MHz) δ 7.55 (2H, d, J=8.6 Hz), 7.35 (2H, d, J=8.7 Hz), 7.23 (1H, d, J=2.2 Hz), 7.03 (1H, d, J=8.1 Hz), 6.90-6.83 (4H, m), 4.16 (2H, t, J=5.4 Hz), 3.29 (4H, t, J=4.8 Hz), 2.89 (2H, t, J=5.4 Hz), 2.79 (3H, s), 2.72 (4H, t, J=4.8 Hz)

Step 3. 3-(3,5-Difluorophenyl)-6-(2-(4-(methylsulfonyl)piperazin-1-yl)ethoxy)-2-(4-(trifluoromethyl)phenyl)-1H-inden-1-one hydrochloride salt The procedure of Step 8 of Example 1 was repeated except for using 3-(3,5-difluorophenyl)-6-(2-(4-(methylsulfonyl)piperazin-1-yl)ethoxy)-2-(4-(trifluoromethyl)phenyl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 51

Synthesis of 2-(3,4-difluorophenyl)-3-(3,5-difluorophenyl)-6-(2-(4-(methylsulfonyl)piperazin-1-yl)ethoxy)-1H-inden-1-one hydrochloride salt Step 1. 2-(3,4-Difluorophenyl)-3-(3,5-difluorophenyl)-6-(2-(4-(methylsulfonyl)piperazin-1-yl)ethoxy)-1H-inden-1-one The procedure of Step 7 of Example 1 was repeated except for using 2-bromo-3-(3,5-difluorophenyl)-6-[2-(4-(methylsulfonyl)piperazin-1-yl)ethoxy]-1H-inden-1-one obtained in Step 1 of Example 50 as a starting material instead of 6-(2- morpholinoethoxy)-2-bromo-3-phenyl-1H-inden-1-one, and 3,4-difluorophenylboronic acid instead of 3-pyridinylboronic acid, and being purified by prep HPLC (CH₃CN/H₂O=7:3) to obtain the title compound (57%).

¹H NMR (CDCl₃, 300 MHz) δ 7.21 (1H, d, J=2.3 Hz), 7.14-7.03 (2H, m), 6.99 (1H, d, J=8.1 Hz), 6.96-6.87 (4H, m), 6.83 (1H, dd, J=2.4 Hz, 8.1 Hz), 4.15 (2H, t, J=5.4 Hz), 3.28 (4H, t, J=4.8 Hz), 2.88 (2H, t, J=5.4 Hz), 2.79 (3H, s), 2.71 (4H, t, J=4.8 Hz)

Step 2. 2-(3,4-Difluorophenyl)-3-(3,5-difluorophenyl)-6-(2-(4-(methylsulfonyl)piperazin-1-yl)ethoxy)-1H-inden-1-one hydrochloride salt The procedure of Step 8 of Example 1 was repeated except for using 2-(3,4-difluorophenyl)-3-(3,5-difluorophenyl)-6-(2-(4-(methylsulfonyl)piperazin-1-yl)ethoxy)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

Example 52

Synthesis of 3-(3,5-difluorophenyl)-6-(2-(4-(methylsulfonyl)piperazin-1-yl)ethoxy)-2-(pyrimidin-5-yl)-1H-inden-1-one hydrochloride salt Step 1. 3-(3,5-Difluorophenyl)-6-(2-(4-(methylsulfonyl)piperazin-1-yl)ethoxy)-2-(pyrimidin-5-yl)-1H-inden-1-one The procedure of Step 7 of Example 1 was repeated except for using 2-bromo-3-(3,5-difluorophenyl)-6-[2-(4-(methylsulfonyl)piperazin-1-yl)ethoxy]-1H-inden-1-one obtained in Step 1 of Example 50 as a starting material instead of 6-(2-morpholinoethoxy)-2-bromo-3-phenyl-1H-inden-1-one, and 5-pyrimidinylboronic acid instead of 3-pyridinylboronic acid, and being purified by prep HPLC (CH₃CN/H₂O=7:3) to obtain the title compound (34%).

¹H NMR (CDCl₃, 300 MHz) δ 9.11 (1H, s), 8.64 (2H, s), 7.25 (1H, d, J=2.4 Hz), 7.05 (1H, d, J=8.1 Hz), 6.94-6.86 (4H, m), 4.17 (2H, t, J=5.4 Hz), 3.29 (4H, t, J=4.9 Hz), 2.9 (2H, t, J=5.4 Hz), 2.80 (3H, s), 2.73 (4H, t, J=4.9 Hz)

Step 2. 3-(3,5-Difluorophenyl)-6-(2-(4-(methylsulfonyl)piperazin-1-yl)ethoxy)-2-(pyrimidin-5-yl)-1H-inden-1-one hydrochloride salt The procedure of Step 8 of Example 1 was repeated except for using 3-(3,5-difluorophenyl)-6-(2-(4-(methylsulfonyl)piperazin-1-yl)ethoxy)-2-(pyrimidin-5-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 53

Synthesis of 3-(4-chlorophenyl)-2-(3,4-difluorophenyl)-6-(2-(4-(methylsulfonyl)piperazin-1-yl)ethoxy)-1H-inden-1-one hydrochloride salt Step 1. 2-Bromo-3-(4-chlorophenyl)-6-(2-(4-(methylsulfonyl)piperazin-1-yl)ethoxy)-1H-inden-1-one The procedure of Step 6 of Example 1 was repeated except for using 2-bromo-3-(4-chlorophenyl)-6-hydroxy-1H-inden-1-one obtained in Step 5 of Example 28 as a starting material instead of 2-bromo-6-hydroxy-3-phenyl-1H-inden-1-one, 2-((4-methylsulfonyl)piperazin-1-yl)ethan-1-ol instead of 4-(2-hydroxyethyl)morpholine, being stirred for 20 h, and being purified by silica gel column chromatography (acetone/hexanes=2:3) to obtain the title compound (44%).

¹H NMR (CDCl₃, 300 MHz) δ 7.57 (4H, q, J=12.2 Hz), 7.20 (1H, d, J=2.4 Hz), 7.00 (1H, d, J=8.1 Hz), 6.78 (1H, dd, J=8.3 Hz, 2.3 Hz), 4.12 (2H, t, J=5.4 Hz), 3.28 (4H, t, J=4.8 Hz), 2.87 (2H, t, J=5.4 Hz), 2.79 (3H, s), 2.70 (4H, t, J=4.8 Hz)

Step 2. 3-(4-Chlorophenyl)-2-(3,4-difluorophenyl)-6-(2-(4-(methylsulfonyl)piperazin-1-yl)ethoxy)-1H-inden-1-one The procedure of Step 7 of Example 1 was repeated except for using 2-bromo-3-(4-chlorophenyl)-6-(2-(4-(methylsulfonyl)piperazin-1-yl)ethoxy)-1H-inden-1-one obtained in Step 1 as a starting material instead of 6-(2-morpholinoethoxy)-2-bromo-3-phenyl-1H-inden-1-one, 3,4-difluorophenylboronic acid instead of 3-pyridinylboronic acid, and being purified by prep HPLC (CH₃CN/H₂O=7:3) to obtain the title compound (50%).

¹H NMR (CDCl₃, 300 MHz) δ 7.43 (2H, d, J=8.7 Hz), 7.31 (2H, d, J=8.0 Hz), 7.20 (1H, d, J=2.1 Hz), 7.15-6.99 (3H, m), 6.96-6.91 (1H, m), 6.82 (1H, dd, J=8.1 Hz, 2.4 Hz), 4.15 (2H, t, J=4.8 Hz), 3.29 (4H, t, J=15.4 Hz), 2.89 (2H, t, J=4.8 Hz), 2.80 (3H, s), 2.72 (4H, t, J=5.4 Hz)

Step 3. 3-(4-Chlorophenyl)-2-(3,4-difluorophenyl)-6-(2-(4-(methylsulfonyl)piperazin-1-yl)ethoxy)-1H-inden-1-one hydrochloride salt The procedure of Step 8 of Example 1 was repeated except for using 3-(4-chlorophenyl)-2-(3,4-difluorophenyl)-6-(2-(4-(methylsulfonyl)piperazin-1-yl)ethoxy)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 54

Synthesis of 3-(4-chlorophenyl)-6-(2-(4-(methylsulfonyl)piperazin-1-yl)ethoxy)-2-(pyrimidin-5-yl)-1H-inden-1-one hydrochloride salt Step 1. 3-(4-Chlorophenyl)-6-(2-(4-(methylsulfonyl)piperazin-1-yl)ethoxy)-2-(pyrimidin-5-yl)-1H-inden-1-one The procedure of Step 7 of Example 1 was repeated except for using 2-bromo-3-(4-chlorophenyl)-6-(2-(4-(methylsulfonyl)piperazin-1-yl)ethoxy)-1H-inden-1-one obtained in Step 1 of Example 53 as a starting material instead of 6-(2-morpholinoethoxy)-2-bromo-3-phenyl-1H-inden-1-one, 5-pyrimidinylboronic acid instead of 3-pyridinylboronic acid, and being purified by prep HPLC (CH₃CN/H₂O=7:3) to obtain the title compound (50%).

¹H NMR (CDCl₃, 300 MHz) δ 9.08 (1H, s), 8.63 (2H, s), 7.46 (2H, d, J=8.7 Hz), 7.33 (2H, d, J=8.5 Hz), 7.24 (1H, d, J=2.3 Hz), 7.06 (1H, d, J=8.0 Hz), 6.86 (2H, dd, J=2.5 Hz, 8.1 Hz), 4.16 (2H, t, J=4.8 Hz), 3.29 (4H, t, J=5.4 Hz), 2.89 (2H, t, J=4.8 Hz), 2.79 (3H, s), 2.72 (4H, t, J=5.4 Hz)

Step 2. 3-(4-Chlorophenyl)-6-(2-(4-(methylsulfonyl)piperazin-1-yl)ethoxy)-2-(pyrimidin-5-yl)-1H-inden-1-one hydrochloride salt The procedure of Step 8 of Example 1 was repeated except for using 3-(4-chlorophenyl)-6-(2-(4-(methylsulfonyl)piperazin-1-yl)ethoxy)-2-(pyrimidin-5-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 55

Synthesis of tert-Butyl 4-(3-(1-oxo-3-phenyl-2-(pyridin-3-yl)-1H-inden-6-yloxy)propyl)piperazine-1-carboxylate Step 1. 6-Hydroxy-3-phenyl-2-(pyridin-3-yl)-1H-inden-1-one The procedure of Step 7 of Example 1 was repeated except for using 2-bromo-6-hydroxy-3-phenyl-1H-inden-1-one obtained in Step 1 of Example 5 as a starting material instead of 6-(2-morpholinoethoxy)-2-bromo-3-phenyl-1H-inden-1-one, and being recrystallized with EtOAc to obtain the title compound (34%).
$^1$H NMR (DMSO, 300 MHz) δ 8.4 (1H, dd, J=2.5 Hz, 6.2 Hz), 8.2 (1H, d, J=1.6 Hz), 7.55-7.51 (1H, m), 7.44-7.29 (5H, m), 6.98-6.96 (2H, m), 6.7 (1H, dd, J=2.2 Hz, 7.9 Hz)

Step 2. tert-Butyl 4-(3-(1-oxo-3-phenyl-2-(pyridin-3-yl)-1H-inden-6-yloxy)propyl)piperazine-1-carboxylate The procedure of Step 6 of Example 1 was repeated except for using 6-hydroxy-3-phenyl-2-(pyridin-3-yl)-1H-inden-1-one obtained in Step 1 as a starting material instead of 2-bromo-6-hydroxy-3-phenyl-1H-inden-1-one, tert-butyl 4-(3-hydroxypropyl)piperazine-1-carboxylate instead of 4-(2-hydroxyethyl)morpholine, being stirred for 19 h, and being recrystallized with EtOAc to obtain the title compound (45%).
$^1$H NMR (CDCl$_3$, 300 MHz) δ 8.45 (1H, dd, J=1.6 Hz, 4.9 Hz), 8.42 (1H, d, J=1.4 Hz), 7.64 (1H, td, J=2.0 Hz, 8.0 Hz), 7.44-7.37 (5H, m), 7.24-7.20 (2H, m), 7.06 (1H, d, J=8.1 Hz), 6.82 (1H, dd, J=2.4 Hz, 8.1 Hz), 4.08 (2H, t, J=6.3 Hz), 3.45 (4H, t, J=5.0 Hz), 2.53 (2H, t, J=7.2 Hz), 2.41 (4H, t, J=5.0 Hz), 2.02 (2H, t, J=8.7 Hz), 1.46 (9H, s)

Example 56

Synthesis of 6-(2-(dimethylamino)ethoxy)-3-phenyl-2-(pyridin-3-yl)-1H-inden-1-one hydrochloride salt Step 1. 6-(2-(Dimethylamino)ethoxy)-3-phenyl-2-(pyridin-3-yl)-1H-inden-1-one The procedure of Step 6 of Example 1 was repeated except for using 6-hydroxy-3-phenyl-2-(pyridin-3-yl)-1H-inden-1-one obtained in Step 1 of Example 55 as a starting material instead of 2-bromo-6-hydroxy-3-phenyl-1H-inden-1-one, 2-(dimethylamino)ethanol instead of 4-(2-hydroxyethyl)morpholine, and being recrystallized with EtOAc to obtain the title compound (45%).
$^1$H NMR (CDCl$_3$, 300 MHz) δ 8.42 (2H, s), 7.64 (1H, d, J=7.9 Hz), 7.44-7.38 (5H, m), 7.22 (2H, d, J=1.3 Hz), 7.06 (1H, d, J=8.1 Hz), 6.85 (1H, dd, J=2.5 Hz, 8.1 Hz), 4.13 (2H, t, J=5.5 Hz), 2.71 (2H, t, J=5.5 Hz), 2.36 (6H, s)

Step 2. 6-(2-(Dimethylamino)ethoxy)-3-phenyl-2-(pyridin-3-yl)-1H-inden-1-one hydrochloride salt The procedure of Step 8 of Example 1 was repeated except for using 6-(2-(dimethylamino)ethoxy)-3-phenyl-2-(pyridin-3-yl)-1H-inden-1-one obtained in Step 1 as a starting material instead of 6-(2-morpholino ethoxy)-3-phenyl-2-(pyridin-3-yl)-1H-inden-1-one to give the title compound in quantitative yield.

Example 57

Synthesis of 6-(3-(dimethylamino)propoxy)-3-phenyl-2-(pyridin-3-yl)-1H-inden-1-one hydrochloride salt Step 1. 6-(3-(Dimethylamino)propoxy)-3-phenyl-2-(pyridin-3-yl)-1H-inden-1-one The procedure of Step 6 of Example 1 was repeated except for using 6-hydroxy-3-phenyl-2-(pyridin-3-yl)-1H-inden-1-one obtained in Step 1 of Example 55 as a starting material instead of 2-bromo-6-hydroxy-3-phenyl-1H-inden-1-one, 3-(dimethylamino)propanol instead of 4-(2-hydroxyethyl)morpholine, being stirred for 4 d, and being recrystallized with EtOAc to obtain the title compound (30%).
$^1$H NMR (CDCl$_3$, 300 MHz) δ 8.44 (1H, dd, J=1.4 Hz, 4.9 Hz), 8.42 (1H, d, J=2.2 Hz), 7.64 (1H, td, J=1.7 Hz, 9.7 Hz), 7.44-7.35 (5H, m), 7.21 (2H, q, J=4.3 Hz), 7.05 (1H, d, J=8.1 Hz), 6.82 (1H, dd, J=2.3 Hz, 8.02 Hz), 4.08 (2H, t, J=6.4 Hz), 2.46 (2H, t, J=7.2 Hz), 2.26 (6H, s), 1.98 (2H, t, J=7.0 Hz)

Step 2. 6-(3-(Dimethylamino)propoxy)-3-phenyl-2-(pyridin-3-yl)-1H-inden-1-one hydrochloride salt The procedure of Step 8 of Example 1 was repeated except for using 6-(3-(dimethylamino)propoxy)-3-phenyl-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

Example 58

Synthesis of tert-Butyl 4-(2-(3-(3,5-difluorophenyl)-1-oxo-2-(pyridin-3-yl)-1H-inden-6-yloxy)ethyl)piperazine-1-carboxylate Step 1. t-Butyl 4-(2-(2-bromo-3-(3,5-difluorophenyl)-1-oxo-1H-inden-6-yl oxy)ethyl)piperazine-1-carboxylate The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, t-butyl 4-(2-hydroxyethyl)piperazine-1-carboxylate instead of 4-(2-hydroxyethyl)morpholine, being stirred for 4 d, and being purified by silica gel column chromatography (EtOAc/hexanes=1:4) to obtain the title compound.
$^1$H NMR (CDCl$_3$, 300 MHz) δ 7.18-7.16 (3H, m), 7.02-6.94 (2H, m), 6.80 (1H, dd, J=8.1 Hz, 2.5 Hz), 4.13 (1H, t, J=5.6 Hz), 3.46 (2H, t, J=5.0 Hz), 2.83 (4H, t, J=5.6 Hz), 1.47 (9H, s)

Step 2. tert-Butyl 4-(2-(3-(3,5-difluorophenyl)-1-oxo-2-(pyridin-3-yl)-1H-inden-6-yloxy)ethyl)piperazine-1-carboxylate The procedure of Step 7 of Example 1 was repeated except for using t-Butyl 4-(2-(2-bromo-3-(3,5-difluorophenyl)-1-oxo-1H-inden-6-yloxy)ethyl)piperazine-1-carboxylate obtained in Step 1 as a starting material instead of 6-(2-morpholinoethoxy)-2-bromo-3-phenyl-1H-inden-1-one, and being purified by silica gel column chromatography (acetone/hexanes=1:2) to obtain the title compound (85%).

$^1$H NMR (CDCl$_3$, 300 MHz) δ 8.50 (1H, dd, J=1.5 Hz, 4.8 Hz), 8.4 (1H, d, J=2.0 Hz), 7.65 (1H, td, J=2.0 Hz, 7.9 Hz), 7.27 (1H, d, J=4.1 Hz), 7.22 (1H, d, J=2.3 Hz), 7.02 (1H, d, J=8.1 Hz), 6.90-6.84 (4H, m), 4.16 (2H, t, J=5.6 Hz), 3.47 (4H, t, J=4.9 Hz), 2.84 (2H, t, J=5.6 Hz), 2.54 (4H, t, J=4.9 Hz), 1.47 (9H, s)

Example 59

Synthesis of 3-(3,5-difluorophenyl)-6-(2-(4-(methylsulfonyl)piperazin-1-yl)ethoxy)-2-(pyridin-3-yl)-1H-inden-1-one hydrochloride salt Step 1. 2-Bromo-3-(3,5-difluorophenyl)-6-[2-(4-(methylsulfonyl)piperazin-1-yl)ethoxy]-1H-inden-1-one The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, 2-(4-(methylsulfonyl)piperazin-1-yl)ethanol instead of 4-(2-hydroxyethyl)morpholine, being stirred for 4 d, and being purified by silica gel column chromatography (CH$_2$Cl$_2$/EtOAc=1:2) to obtain the title compound (99%)

$^1$H NMR (CDCl$_3$, 300 MHz) δ 7.19-7.17 (3H, m), 7.03-6.95 (2H, m), 6.80 (1H, dd, J=8.1 Hz, 2.4 Hz), 4.13 (2H, t, J=5.5 Hz), 3.28 (4H, t, J=4.8 Hz), 2.88 (2H, t, J=5.4 Hz), 2.79 (3H, s) 2.71 (4H, t, J=4.9 Hz)

Step 2. 3-(3,5-Difluorophenyl)-6-(2-(4-(methylsulfonyl)piperazin-1-yl)ethoxy)-2-(pyridin-3-yl)-1H-inden-1-one The procedure of Step 7 of Example 1 was repeated except for using 2-bromo-3-(3,5-difluorophenyl)-6-[2-(4-(methylsulfonyl)piperazin-1-yl)ethoxy]-1H-inden-1-one obtained in Step 1 as a starting material instead of 6-(2-morpholinoethoxy)-2-bromo-3-phenyl-1H-inden-1-one, and being purified by silica gel column chromatography (acetone/hexanes=1:1) to obtain the title compound (79%).

$^1$H NMR (CDCl$_3$, 300 MHz) δ 8.50 (1H, d, J=4.6 Hz), 8.4 (1H, s), 7.65 (1H, dd, J=1.5 Hz, 7.8 Hz), 7.29-7.23 (2H, m), 7.03 (1H, d, J=8.0 Hz), 6.89-6.87 (4H, m), 4.16 (2H, t, J=5.4 Hz), 3.29 (4H, t, J=4.8 Hz), 2.89 (2H, t, J=5.4 Hz), 2.79 (3H, s), 2.72 (4H, t, J=4.8 Hz)

Step 3. 3-(3,5-Difluorophenyl)-6-(2-(4-(methylsulfonyl)piperazin-1-yl)ethoxy)-2-(pyridin-3-yl)-1H-inden-1-one hydrochloride salt The procedure of Step 8 of Example 1 was repeated except for using 3-(3,5-difluorophenyl)-6-(2-(4-(methylsulfonyl)piperazin-1-yl)ethoxy)-2-(pyridin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 60

Synthesis of 3-(3,5-difluorophenyl)-6-(3-(dimethylamino)propoxy)-2-(pyridin-3-yl)-1H-inden-1-one hydrochloride salt Step 1. 6-(3-(Dimethylamino)propoxy)-2-bromo-3-(3,5-difluorophenyl)-1H-inden-1-one The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, 3-(dimethylamino)propanol instead of 4-(2-hydroxyethyl)morpholine, being stirred for 4 d, and being purified by silica gel column chromatography (CH$_2$Cl$_2$/EtOAc=1:1) to obtain the title compound (86%).

$^1$H NMR (CDCl$_3$, 300 MHz) δ 7.19-7.16 (3H, m), 7.00-6.94 (2H, m), 6.79 (1H, dd, J=8.1 Hz, 2.5 Hz), 4.05 (2H, t, J=6.4 Hz), 2.44 (2H, t, J=7.2 Hz), 2.25 (6H, s), 1.98-1.96 (2H, m)

Step 2. 3-(3,5-Difluorophenyl)-6-(3-(dimethylamino)propoxy)-2-(pyridin-3-yl)-1H-inden-1-one The procedure of Step 7 of Example 1 was repeated except for using 6-(3-(dimethyl amino)propoxy)-2-bromo-3-(3,5-difluorophenyl)-1H-inden-1-one obtained in Step 1 as a starting material instead of 6-(2-morpholinoethoxy)-2-bromo-3-phenyl-1H-inden-1-one, and being purified by silica gel column chromatography (CH$_2$Cl$_2$/MeOH=9:1) to obtain the title compound (52%).

$^1$H NMR (CDCl$_3$, 300 MHz) δ 8.49 (1H, dd, J=4.8 Hz, 1.6 Hz), 8.40 (1H, d, J=1.8 Hz), 7.65 (1H, td, J=1.8 Hz, 8.0 Hz), 7.29-7.25 (1H, m), 7.22 (1H, d, J=2.3 Hz), 7.01 (1H, d, J=8.1 Hz), 6.92-6.82 (4H, m), 4.08 (2H, t, J=6.4 Hz), 2.48 (2H, t, J=7.2 Hz), 2.27 (6H, s), 2.05-1.96 (2H, m)

Step 3. 3-(3,5-Difluorophenyl)-6-(3-(dimethyl amino)propoxy)-2-(pyridin-3-yl)-1H-inden-1-one hydrochloride salt The procedure of Step 8 of Example 1 was repeated except for using 3-(3,5-difluorophenyl)-6-(3-(dimethylamino)propoxy)-2-(pyridin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 61

Synthesis of 3-(3,5-difluorophenyl)-6-phenethoxy-2-(pyridin-3-yl)-1H-inden-1-one hydrochloride salt Step 1. 3-(3,5-Difluorophenyl)-6-hydroxy-2-(pyridin-3-yl)-1H-inden-1-one The procedure of Step 7 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one and being purified by silica gel column chromatography (CH$_2$Cl$_2$/EtOAc=2:1) to obtain the title compound (76%).

$^1$H NMR (DMSO, 300 MHz) δ 10.25 (1H, s, OH), 8.41 (1H, dd, J=1.5 Hz, 4.7 Hz), 8.27 (1H, d, J=1.7 Hz), 7.52 (1H, td, J=1.9 Hz, 7.9 Hz), 7.39-7.29 (2H, m), 7.10-7.07 (2H, m), 6.97-6.94 (2H, m), 6.76 (1H, dd, J=2.2 Hz, 8.1 Hz)

Step 2. 3-(3,5-Difluorophenyl)-6-phenethoxy-2-(pyridin-3-yl)-1H-inden-1-one

To a solution of 3-(3,5-difluorophenyl)-6-hydroxy-2-(pyridin-3-yl)-1H-inden-1-one (0.15 mol, 50 mg) obtained in Step 1 in $CH_3CN$ was added $K_2CO_3$(1.5 eq). 1-(2-bromoethyl)benzene (1.5 eq) was added dropwise and the resulting mixture was heated to reflux for 3 d. The reaction was cooled to room temperature and diluted with EtOAc. The organic layer was washed with $H_2O$, dried over $MgSO_4$, and concentrated in vacuo to obtain the title compound (30%).

$^1$H NMR (CDCl$_3$, 300 MHz) δ 8.50 (1H, d, J=3.7 Hz), 8.39 (1H, s), 7.65 (1H, td, J=1.8 Hz, 8.0 Hz), 7.34-7.20 (8H, m), 7.00 (1H, d, J=8.1 Hz), 6.88-6.81 (3H, m), 4.23 (2H, t, J=7.0 Hz), 3.12 (2H, t, J=7.0 Hz)

Step 3. 3-(3,5-Difluorophenyl)-6-phenethoxy-2-(pyridin-3-yl)-1H-inden-1-one hydrochloride salt The procedure of Step 8 of Example 1 was repeated except for using 3-(3,5-difluorophenyl)-6-phenethoxy-2-(pyridin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

Example 62

Synthesis of 3-(3,5-difluorophenyl)-6-(2-(pyridin-2-yl)ethoxy)-2-(pyridin-3-yl)-1H-inden-1-one hydrochloride salt

Step 1. 3-(3,5-Difluorophenyl)-6-(2-(pyridin-2-yl)ethoxy)-2-(pyridin-3-yl)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 61 as a starting material instead of 2-bromo-6-hydroxy-3-phenyl-1H-inden-1-one, 2-(pyridin-2-yl)ethanol instead of 4-(2-hydroxyethyl)morpholine, being stirred for 7 d, and being purified by silica gel column chromatography ($CH_2Cl_2$/EtOAc=1:4) to obtain the title compound (45%).

$^1$H NMR (CDCl$_3$, 300 MHz) δ 8.57 (1H, d, J=4.6 Hz), 8.5 (1H, d, J=4.4 Hz), 8.39 (1H, s), 7.67-7.63 (2H, m), 7.28-7.16 (4H, m), 7.00 (1H, d, J=8.1 Hz), 6.88-6.83 (4H, m), 4.43 (2H, t, J=6.6 Hz), 3.29 (2H, t, J=6.6 Hz)

Step 2. 3-(3,5-Difluorophenyl)-6-(2-(pyridin-2-yl)ethoxy)-2-(pyridin-3-yl)-1H-inden-1-one hydrochloride salt The procedure of Step 8 of Example 1 was repeated except for using 3-(3,5-difluorophenyl)-6-(2-(pyridin-2-yl)ethoxy)-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

Example 63

Synthesis of 3-(3,5-difluorophenyl)-6-(2-(piperidin-1-yl)ethoxy)-2-(pyridin-3-yl)-1H-inden-1-one hydrochloride salt

Step 1. 3-(3,5-Difluorophenyl)-6-(2-(piperidin-1-yl)ethoxy)-2-(pyridin-3-yl)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 61 as a starting material instead of 2-bromo-6-hydroxy-3-phenyl-1H-inden-1-one, 2-(piperidin-1-yl)ethanol instead of 4-(2-hydroxyethyl)morpholine, being stirred for 3 h, and being purified by silica gel column chromatography ($CH_2Cl_2$/EtOAc=1:4) to obtain the title compound (37%).

$^1$H NMR (CDCl$_3$, 300 MHz) δ 8.50 (1H, dd, J=4.8 Hz, 1.5 Hz), 8.40 (1H, d, J=1.7 Hz), 7.65 (1H, td, J=2.0 Hz, 7.4 Hz), 7.28-7.24 (1H, m), 7.22 (1H, d, J=2.4 Hz), 7.01 (1H, d, J=8.1 Hz), 6.90-6.83 (4H, m), 4.16 (2H, t, J=5.9 Hz), 2.79 (2H, t, J=5.9 Hz), 2.52 (4H, t, J=5.1 Hz), 1.64-1.59 (4H, m), 1.27-1.25 (2H, m)

Step 2. 3-(3,5-Difluorophenyl)-6-(2-(piperidin-1-yl)ethoxy)-2-(pyridin-3-yl)-1H-inden-1-one hydrochloride salt The procedure of Step 8 of Example 1 was repeated except for using 3-(3,5-difluorophenyl)-6-(2-(piperidin-1-yl)ethoxy)-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

Example 64

Synthesis of tert-butyl 4-(3-(3-(3,5-difluorophenyl)-1-oxo-2-(pyridin-3-yl)-1H-inden-6-yloxy)propyl)piperazine-1-carboxylate

Step 1. 3-(3,5-difluorophenyl)-6-hydroxy-2-(pyridin-3-yl)-1H-inden-1-one

To a microwave reaction vial, 2-bromo-3-(3,5-difluorophenyl)-6-hydroxy-1H-inden-1-one (302.7 mg, 0.90=01) obtained in Step 5 of Example 36, 3-pyridinylboronic acid (165.5 mg, 1.5 eq), Pd(PPh$_3$)$_4$(62.4 mg, 6 mol %), Na$_2$CO$_3$ (286.1 mg, 3.0 eq), and dioxane/H$_2$O (4:1, 5 mL) were sequentially added. The mixture was placed into a microwave reactor and irradiated at 150° C. for 20 min. The reaction mixture was cooled to room temperature and diluted with EtOAc. The mixture was dried over MgSO$_4$ and filtered through a Celite pad. The liquid was concentrated by rotary evaporation under reduced pressure. The residue was dissolved with CH$_2$Cl$_2$ and the insoluble solid was removed by the filtration. The solution was concentrated in vacuo to provide the title compound (230 mg, 76%).

$^1$H NMR (DMSO, 300 MHz) δ 8.41 (1H, d, J=5.1 Hz), 8.27 (1H, d, 0.1=2.4 Hz), 7.53 (1H, d, J=8.1 Hz), 7.35-7.30 (2H, m), 7.10 (2H, d, J=3.6 Hz), 6.97-6.93 (2H, m), 6.78-6.73 (1H, m)

Step 2. tert-Butyl 4-(3-(3-(3,5-difluorophenyl)-1-oxo-2-(pyridin-3-yl)-1H-inden-6-yloxy)propyl)piperazine-1-carboxylate The procedure of Step 6 of Example 1 was repeated except for using 3-(3,5-difluorophenyl)-6-hydroxy-2-(pyridin-3-yl)-1H-inden-1-one obtained in Step 1 as a starting material instead of 2-bromo-6-hydroxy-3-phenyl-1H-inden-1-one, t-butyl 4-(3-hydroxypropyl)piperazine-1-carboxylate (2.0 eq) instead of 4-(2-hydroxyethyl)morpholine, using 2 equivalents of PPh$_3$ and DIAD, and being stirred for 19 h to obtain the title compound (85%).

$^1$H NMR (CDCl$_3$, 300 MHz) δ 8.50 (1H, dd, J=4.65 Hz, 1.35 Hz), 8.40 (1H, d, J=2.1 Hz), 7.65 (2H, d, J=8.1 Hz), 7.25-7.22 (1H, m), 7.22 (1H, d, J=3 Hz), 7.02 (1H, d, J=7.8

Hz), 6.91-6.83 (3H, m), 4.09 (2H, t, J=6 Hz), 3.45 (4H, t, J=4.95 Hz), 2.54 (2H, t, J=7.2 Hz), 2.42 (4H, t, J=4.8 Hz), 2.04-1.95 (2H, m), 1.47 (9H, s)

Example 65

Synthesis of 3-(3,5-difluorophenyl)-6-(3-(4-methylpiperazin-1-yl)propoxy)-2-(pyridin-3-yl)-1H-inden-1-one hydrochloride salt The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, t-butyl 3-(4-methylpiperazin-1-yl)propan-1-ol (2.0 eq) instead of 4-(2-hydroxyethyl)morpholine, using 2 equivalents of $PPh_3$ and DIAD, being stirred for 34 h, and being purified by prep. HPLC (20% $H_2O/CH_3CN$) to provide 3-(3,5-difluorophenyl)-6-(3-(4-methylpiperazin-1-yl)propoxy)-2-(pyridin-3-yl)-1H-inden-1-one, which was treated with HCl/dioxane following the same procedure in Step 8 of Example 1 (50% for 2 steps).

$^1$H NMR ($CDCl_3$, 300 MHz) δ 8.52 (1H, s), 8.40 (1H, d, J=5.7 Hz), 7.98 (1H, d, J=8.1 Hz), 7.65-7.55 (1H, m), 7.25-7.20 (1H, m), 7.10-7.00 (2H, m), 6.91-6.85 (3H, m), 4.17 (2H, t, J=5.7 Hz), 3.52-3.38 (6H, m), 3.11 (2H, m), 2.93-2.85 (5H, m), 2.23 (2H, m)

Example 66

Synthesis of 3-(3,5-difluorophenyl)-6-(3-(piperazin-1-yl)propoxy)-2-(pyridin-3-yl)-1H-inden-1-one hydrochloride salt Step 1. 3-(3,5-Difluorophenyl)-6-(3-(piperazin-1-yl)propoxy)-2-(pyridin-3-yl)-1H-inden-1-one To a 10 mL round-bottomed flask, tert-butyl 4-(3-(3-(3,5-difluorophenyl)-1-oxo-2-(pyridin-3-yl)-1H-inden-6-yloxy)propyl)piperazine-1-carboxylate (107.5 mg, 0.19 mmol) obtained in Step 2 of Example 64 and $CH_2Cl_2$ (2 mL, 0.1M) were charged. Trifluoroacetic acid (0.6 mL, 40.0 eq) was added dropwise over 5 min at 0° C. After being stirred for 2 h, the mixture was quenched with $H_2O$ and washed with $CH_2Cl_2$. The aqueous layer was basicified to pH 9 with a 15% NaOH solution and extracted with $CH_2Cl_2$. The extracts were concentrated in vacuo to provide the title compound (80 mg, 93%).

Step 2. 3-(3,5-Difluorophenyl)-6-(3-(piperazin-1-yl)propoxy)-2-(pyridin-3-yl)-1H-inden-1-one hydrochloride salt The procedure of Step 8 of Example 1 was repeated except for using 3-(3,5-difluorophenyl)-6-(3-(piperazin-1-yl)propoxy)-2-(pyridin-3-yl)-1H-inden-1-one (4.7 mg, 0.01 mmol) obtained in Step 1 as a starting material instead of 6-(2-morpholinoethoxy)-3-phenyl-2-(pyridin-3-yl)-1H-inden-1-one to give the title compound (4.7 mg, 93%).

$^1$H NMR ($D_2O$, 300 MHz) δ 8.46 (1H, s), 8.42 (1H, d, J=3.6 Hz), 8.00 (1H, d, J=8.4 Hz), 7.64 (1H, dd, J=8.3 Hz, 5.6 Hz), 7.01-6.99 (2H, m), 6.94-6.77 (4H, m), 4.00 (2H, t, J=5.6 Hz), 3.43 (s, 7H), 3.25 (2H, t, J=7.8 Hz), 2.12-2.07 (2H, m), 1.07-1.02 (3H, m)

Example 67

Synthesis of 6-(3-(4-acetylpiperazin-1-yl)propoxy)-3-(3,5-difluorophenyl)-2-(pyridin-3-yl)-1H-inden-1-one hydrochloride salt Step 1. 6-(3-(4-Acetylpiperazin-1-yl)propoxy)-3-(3,5-difluorophenyl)-2-(pyridin-3-yl)-1H-inden-1-one To a 10 mL round-bottomed flask, 6-(3-(piperazin-1-yl)propoxy)-3-(3,5-difluorophenyl)-2-(pyridin-3-yl)-1H-inden-1-one (40 mg, 0.09 mmol) obtained in Step 1 of Example 66 and $CH_2Cl_2$ (2 mL, 0.05M) were charged. Pyridine (0.01 mL, 1.2 eq) was added and then the mixture was cooled to 0° C. and treated with acetic anhydride (0.01 mL, 1.2 eq). After being stirred for 15 h, the mixture was diluted with $CH_2Cl_2$ and washed with $H_2O$ and brine. The organic layer was dried over $MgSO_4$ and concentrated in vacuo. The residue was purified by being purified by silica gel column chromatography ($CH_2Cl_2$/MeOH=9:1) and being purified by prep. HPLC (20% $H_2O/CH_3CN$) to provide the title compound (25.9 mg, 59%).

$^1$H NMR ($CDCl_3$, 300 MHz) δ 8.51 (1H, dd, J=5.0 Hz, 1.35 Hz), 8.40 (1H, s), 7.66 (1H, d, J=8.4 Hz), 7.29-7.25 (1H, m), 7.22 (1H, s), 7.02 (1H, dd, J=8.1 Hz, 0.9 Hz), 6.91-6.83 (4H, m), 4.10 (2H, t, J=6.5 Hz) 3.64 (2H, t, J=4.8 Hz), 3.49 (2H, t, J=4.7 Hz), 2.56 (2H, t, J=7.2 Hz), 2.49-2.42 (4H, m), 2.10 (3H, s), 2.00 (2H, t, J=6.5 Hz)

Step 2. 6-(3-(4-Acetylpiperazin-1-yl)propoxy)-3-(3,5-difluorophenyl)-2-(pyridin-3-yl)-1H-inden-1-one hydrochloride salt The procedure of Step 8 of Example 1 was repeated except for using 6-(3-(4-acetylpiperazin-1-yl)propoxy)-3-(3,5-difluorophenyl)-2-(pyridin-3-yl)-1H-inden-1-one (4.7 mg, 0.01 mmol) obtained in Step 1 as a starting material instead of 6-(2-morpholinoethoxy)-3-phenyl-2-(pyridin-3-yl)-1H-inden-1-one to give the title compound (24.6 mg, 89%).

$^1$H NMR ($CDCl_3$, 300 MHz) δ 8.52 (1H, d, J=4.8 Hz), 8.42 (1H, s), 7.66 (1H, d, J=8.1 Hz), 7.31-7.23 (1H, m), 7.17 (1H, s), 7.05 (1H, d, J=8.1 Hz), 6.93-6.83 (4H, m), 4.75 (1H, brs) 4.17 (2H, t, J=5.6 Hz), 3.93 (2H, brs), 3.59 (2H, brs), 3.22 (2H, brs), 2.77 (2H, brs), 2.50 (2H, brs), 2.17 (3H, s), 1.64 (2H, brs)

Example 68

Synthesis of 3-(3,5-difluorophenyl)-6-(3-(4-(methylsulfonyl)piperazin-1-yl)propoxy)-2-(pyridin-3-yl)-1H-inden-1-one hydrochloride salt Step 1. 3-(3,5-Difluorophenyl)-6-(3-(4-(methylsulfonyl)piperazin-1-yl)propoxy)-2-(pyridin-3-yl)-1H-inden-1-one To a 10 mL round-bottomed flask, 6-(3-(piperazin-1-yl)propoxy)-3-(3,5-difluorophenyl)-2-(pyridin-3-yl)-1H-inden-1-one (30 mg, 1.2 eq) obtained in Step 1 of Example 66 and $CH_2Cl_2$ (1 mL, 0.05M) were charged. Triethylamine (0.02 mL, 1.5 eq) was added and then the mixture was cooled to 0° C. and treated with a solution of methylsulfonyl chloride (6.2 mg, 0.05 mmol) in $CH_2Cl_2$ (1 mL) over 5 min. After being stirred for 3 h, the mixture was diluted with $CH_2Cl_2$ and washed with $H_2O$ and brine. The organic layer was dried over $MgSO_4$ and concentrated in vacuo. The residue was purified by silica gel column chromatography ($CH_2Cl_2$/MeOH=9:1)

and being purified by prep. HPLC (20% H$_2$O/CH$_3$CN) to provide the title compound (19.8 mg, 68%).

$^1$H NMR (CDCl$_3$, 300 MHz) δ 8.50 (1H, dd, J=4.6 Hz, 1.7 Hz), 8.40 (1H, d, J=0.9 Hz), 7.66-7.63 (1H, m), 7.29-7.25 (1H, m), 7.24 (1H, d, J=2.4 Hz), 7.02 (1H, d, J=8.1 Hz), 6.92-6.83 (4H, m), 4.09 (2H, t, J=6.2 Hz), 3.27 (4H, t, J=4.5 Hz), 2.80 (3H, s), 2.61-2.57 (6H, m), 2.04-1.95 (2H, m)

Step 2. 3-(3,5-Difluorophenyl)-6-(3-(4-(methylsulfonyl)piperazin-1-yl)propoxy)-2-(pyridin-3-yl)-1H-inden-1-one hydrochloride salt The procedure of Step 8 of Example 1 was repeated except for using 3-(3,5-difluorophenyl)-6-(3-(4-(methylsulfonyl)piperazin-1-yl)propoxy)-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 8.52 (1H, d, J=4.2 Hz), 8.42 (1H, s), 7.71-7.65 (1H, m), 7.32-7.26 (1H, m), 7.19 (1H, d, J=2.1 Hz), 7.05 (1H, d, J=8.1 Hz), 6.93-6.83 (4H, m), 4.18 (2H, t, J=5.1 Hz), 3.82 (4H, brs), 3.22 (4H, brs), 2.91 (3H, s), 2.47 (2H, brs), 1.63 (2H, brs)

Example 69

Synthesis of tert-butyl 4-(2-(3-(3,5-difluorophenyl)-1-oxo-2-(pyridin-3-yl)-1H-inden-6-yloxy)ethyl)piperidine-1-carboxylate The procedure of Step 6 of Example 1 was repeated for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, t-butyl 4-(2-hydroxyethyl)piperidin-1-carboxylate (2.0 eq) instead of 4-(2-hydroxyethyl)morpholine, using 2 equivalents of PPh$_3$ and DIAD, and being stirred for 13 h to provide the title compound (80 mg, 66%).

$^1$H NMR (CDCl$_3$, 300 MHz) δ 8.50 (1H, td, J=4.7 Hz, 1.5 Hz), 8.40 (1H, s), 7.65 (1H, d, J=7.6 Hz), 7.33-7.23 (1H, m), 7.21 (1H, s), 7.02 (1H, d, J=8.0 Hz), 6.95-6.80 (4H, m), 4.14-4.01 (4H, m), 2.72 (2H, t, J=12.2 Hz), 1.78-1.68 (5H, m), 1.46 (9H, s), 1.21 (2H, t, J=10.5 Hz)

Example 70

Synthesis of 3-(3,5-difluorophenyl)-6-(2-(piperidin-4-yl)ethoxy)-2-(pyridin-3-yl)-1H-inden-1-one hydrochloride salt Step 1. 3-(3,5-Difluorophenyl)-6-(2-(piperidin-4-yl)ethoxy)-2-(pyridin-3-yl)-1H-inden-1-one The procedure of Step 1 of Example 66 was repeated except for using tert-butyl 4-(2-(3-(3,5-difluorophenyl)-1-oxo-2-(pyridin-3-yl)-1H-inden-6-yloxy)ethyl)piperidine-1-carboxylate obtained in Example 69 as a starting material instead of tert-butyl 4-(3-(3-(3,5-difluorophenyl)-1-oxo-2-(pyridin-3-yl)-1H-inden-6-yloxy)propyl)piperazine-1-carboxylate and being stirred for 30 min to provide the title compound.

$^1$H NMR (CDCl$_3$, 300 MHz) δ 8.50 (1H, td, J=4.9 Hz, 1.3 Hz), 8.40 (1H, s), 7.65 (1H, td, J=8.2 Hz, 1.6 Hz), 7.29-725 (1H, m), 7.21 (1H, s), 7.02 (1H, d, J=8.1 Hz), 6.89-6.82 (4H, m), 4.07 (2H, t, J=5.4 Hz), 3.24 (2H, d, J=12.6 Hz), 2.74 (2H, t, J=11.8 Hz), 1.85-1.78 (6H, m), 1.39 (2H, q, J=10.6 Hz)

Step 2. 3-(3,5-Difluorophenyl)-6-(2-(piperidin-4-yl)ethoxy)-2-(pyridin-3-yl)-1H-inden-1-one hydrochloride salt The procedure of Step 8 of Example 1 was repeated except for using 3-(3,5-difluorophenyl)-6-(2-(piperidin-4-yl)ethoxy)-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound (99% for two steps).

$^1$H NMR (CDCl$_3$, 300 MHz) δ 8.69 (2H, s), 8.10 (1H, d, J=8.1 Hz), 7.73 (1H, t, J=6.5 Hz), 7.23 (1H, d, J=2.1 Hz), 7.07 (1H, d, J=8.1 Hz), 7.00 (1H, tt, J=8.7 Hz, 2.0 Hz), 6.94-6.86 (3H, m), 4.10 (2H, t, J=5.4 Hz), 3.55-3.45 (3H, m), 3.27 (brs, 1H), 2.90 (2H, q, J=11.8 Hz), 2.00-1.96 (2H, m), 1.86-1.75 (5H, m).

Example 71

Synthesis of 3-(3,5-difluorophenyl)-6-(2-(1-methylpiperidin-4-yl)ethoxy)-2-(pyridin-3-yl)-1H-inden-1-one hydrochloride salt Step 1. 3-(3,5-Difluorophenyl)-6-(2-(piperidin-4-yl)ethoxy)-2-(pyridin-3-yl)-1H-inden-1-one To a 10 mL round-bottomed flask, 3-(3,5-difluorophenyl)-6-(2-(piperidin-4-yl)ethoxy)-2-(pyridin-3-yl)-1H-inden-1-one (40.0 mg, 0.09 mmol) obtained in Step 1 of Example 70, formaldehyde (aq. 37% solution, 7.3 mg, 1.0 eq), and CH$_2$Cl$_2$ (2 mL, 0.05M) were charged. Sodium triacetoxyborohydride (76.3 mg, 4.0 eq) was added and then the mixture was stirred for 2 h at room temperature. The mixture was diluted with CH$_2$Cl$_2$ and washed with H$_2$O and sat. NaHCO$_3$. The organic layer was dried over MgSO$_4$ and concentrated in vacuo. The residue was purified by silica gel column chromatography (CH$_2$Cl$_2$/MeOH=9:1 to CH$_2$Cl$_2$/MeOH=1:1) followed by prep. HPLC (20% H$_2$O/CH$_3$CN) to provide the title compound (5 mg, 12%).

$^1$H NMR (CDCl$_3$, 300 MHz) δ 8.50 (1H, m), 8.41 (1H, s), 7.64 (1H, d, J=8.1 Hz), 7.29-7.26 (1H, m), 7.19 (1H, d, J=2.4 Hz), 7.03 (1H, d, J=8.1 Hz), 6.93-6.81 (4H, m), 4.07 (2H, t, J=5.55 Hz), 3.43 (2H, d, J=11.4 Hz), 2.71 (3H, s), 2.65 (2H, brs), 1.96 (5H, brs) 1.86-1.88 (2H, m)

Step 2. 3-(3,5-Difluorophenyl)-6-(2-(piperidin-4-yl)ethoxy)-2-(1-methylpyridin-3-yl)-1H-inden-1-one hydrochloride salt The procedure of Step 8 of Example 1 was repeated except for using 3-(3,5-difluorophenyl)-6-(2-(piperidin-4-yl)ethoxy)-2-(pyridin-3-yl)-1H-inden-1-one obtained in Step 1 as a starting material instead of 6-(2-morpholinoethoxy)-3-phenyl-2-(pyridin-3-yl)-1H-inden-1-one to give the title compound (5.5 mg, 99%).

$^1$H NMR (CDCl$_3$, 300 MHz) δ 8.69 (1H, s), 8.62 (1H, d, J=5.1 Hz), 8.17 (1H, d, J=7.8 Hz), 7.78 (1H, t, J=6.9 Hz), 7.24 (1H, s), 7.09 (1H, d, J=7.8 Hz), 7.02 (1H, t, J=8.25 Hz), 6.90 (3H, s), 4.11 (2H, t, J=5.1 Hz), 3.55 (5H, t, J=11.4 Hz), 2.79-2.65 (5H, m), 2.18-2.07 (2H, m), 1.97-1.88 (6H, m)

Example 72

Synthesis of 6-(2-(1-acetylpiperidin-4-yl)ethoxy)-3-(3,5-difluorophenyl)-2-(pyridin-3-yl)-1H-inden-1-one hydrochloride salt The procedure of Example 67 was repeated except for using 3-(3,5-difluorophenyl)-6-(2-(piperidin-4-yl)ethoxy)-

2-(pyridin-3-yl)-1H-inden-1-one obtained in Example 70 as a starting material instead of 6-(3-(piperazin-1-yl)propoxy)-3-(3,5-difluorophenyl)-2-(pyridin-3-yl)-1H-inden-1-one and being stirred for 20 h to give the title compound (50% for 2 steps).

$^1$H NMR (CDCl$_3$, 300 MHz) δ 8.68 (1H, s), 8.63 (1H, d, J=5.1 Hz), 8.21 (1H, d, J=7.8 Hz), 7.81 (1H, t, J=6.8 Hz), 7.26 (1H, s), 7.10-7.00 (2H, m), 6.91-6.85 (3H, m), 4.64 (1H, d, J=11.1 Hz), 4.10 (2H, t, J=5.6 Hz), 3.84 (1H, d, J=12.3 Hz), 3.07 (1H, t, J=12.45 Hz), 2.57 (1H, t, J=11.85 Hz), 2.11 (3H, s), 1.80 (6H, brs), 1.26-1.19 (2H, m)

Example 73

Synthesis of 3-(3,5-difluorophenyl)-6-(2-(1-(methylsulfonyl)piperidin-4-yl)ethoxy)-2-(pyridin-3-yl)-1H-inden-1-one hydrochloride salt The procedure of Example 68 was repeated except for using 3-(3,5-difluorophenyl)-6-(2-(piperidin-4-yl)ethoxy)-2-(pyridin-3-yl)-1H-inden-1-one obtained in Step 1 of Example 70 as a starting material instead of 6-(3-(piperazin-1-yl)propoxy)-3-(3,5-difluorophenyl)-2-(pyridin-3-yl)-1H-inden-1-one and being stirred for 18 h to give 3-(3,5-difluorophenyl)-6-(2-(1-(methylsulfonyl)piperidin-4-yl)ethoxy)-2-(pyridin-3-yl)-1H-inden-1-one, which was treated with HCl/dioxane following the same procedure in Step 8 of Example 1 (62% for 2 steps).

$^1$H NMR (CDCl$_3$, 300 MHz) δ 8.64 (1H, s), 8.60 (1H, d, J=4.5 Hz), 8.12 (1H, d, J=7.8 Hz), 7.75-7.68 (1H, m), 7.27-7.25 (1H, m), 7.07 (1H, d, J=8.1 Hz), 7.00 (1H, t, J=8.9 Hz), 6.90-6.81 (3H, m), 4.10 (1H, t, J=6.0 Hz), 3.83 (2H, d, J=12.0 Hz), 2.78 (3H, s), 2.68 (1H, t, J=11.0 Hz), 1.81-1.79 (6H, m), 1.44-1.31 (2H, m)

Example 74

Synthesis of 6-[2-(1,1-dioxothiomorpholin-4-yl)ethoxy]-3-(3,5-difluorophenyl)-2-(pyridin-3-yl)-1H-inden-1-one hydrochloride salt The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, 4-(2-hydroxyethyl)thiomorpholine-1,1-dioxide (2.0 eq) instead of 4-(2-hydroxyethyl)morpholine, using 2 equivalents of PPh$_3$ and DIAD, and being stirred for 13 h to provide 6-[2-(1,1-dioxothiomorpholin-4-yl)ethoxy]-3-(3,5-difluorophenyl)-2-(pyridin-3-yl)-1H-inden-1-one, which was treated with HCl/dioxane following the same procedure in Step 8 of Example 1 (40% for 2 steps).

$^1$H NMR (CDCl$_3$, 300 MHz) δ 8.59-8.57 (2H, m), 7.99 (1H, d, J=6.9 Hz), 7.62-7.50 (m, 2H), 7.26-7.24 (m, 1H), 7.10-6.88 (m, 4H), 4.29 (2H, brs), 3.34 (4H, brs), 3.25 (4H, brs), 3.17 (2H, brs)

Example 75

Synthesis of 3-(3,5-difluorophenyl)-6-(isopentyloxy)-2-(pyridin-3-yl)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, 3-methylbutan-1-ol (2.0 eq) instead of 4-(2-hydroxyethyl)morpholine, using 2 equivalents of PPh$_3$ and DIAD, being stirred for 4 h, and being purified by prep. HPLC (20% H$_2$O/CH$_3$CN) to provide the title compound (59%).

$^1$H NMR (CDCl$_3$, 300 MHz) δ 8.50 (1H, dd, J=4.95 Hz, 1.05 Hz), 8.40 (1H, d, J=2.1 Hz), 7.65 (1H, d, J=7.8 Hz), 7.29-7.25 (1H, m), 7.22 (1H, d, J=2.1 Hz), 7.01 (1H, d, J=7.8 Hz), 6.91-6.82 (4H, m), 4.05 (2H, t, J=6.9 Hz), 1.89-1.80 (1H, m), 1.70 (2H, $_q$, J=6.6 Hz), 0.98 (6H, d, J=6.6 Hz)

Example 76

Synthesis of 6-(2-cyclohexylethoxy)-3-(3,5-difluorophenyl)-2-(pyridin-3-yl)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, 2-cyclohexylethanol (2.0 eq) instead of 4-(2-hydroxyethyl)morpholine, using 2 equivalents of PPh$_3$ and DIAD, being stirred for 48 h, and being purified by prep. HPLC (20% H$_2$O/CH$_3$CN) to provide the title compound (26%).

$^1$H NMR (CDCl$_3$, 300 MHz) δ 8.50 (1H, dd, J=5.0 Hz, 1.7 Hz), 8.40 (1H, s), 7.65 (1H, d, J=7.7 Hz), 7.28-7.24 (1H, m), 7.21 (1H, d, J=2.4 Hz), 7.01 (1H, d, J=8.1 Hz), 6.92-6.81 (4H, m), 4.05 (2H, t, J=6.6 Hz), 1.78-1.67 (7H, m), 1.29-1.19 (4H, m), 1.04-0.96 (2H, m)

Example 77

Synthesis of 6-(2-cyclopentylethoxy)-3-(3,5-difluorophenyl)-2-(pyridin-3-yl)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, 2-cyclopentylethanol (2.0 eq) instead of 4-(2-hydroxyethyl)morpholine, using 2 equivalents of PPh$_3$ and DIAD, being stirred for 21 h, and being purified by prep. HPLC (20% H$_2$O/CH$_3$CN) to provide the title compound (23%).

$^1$H NMR (CDCl$_3$, 300 MHz) δ 8.50 (1H, dd, J=4.95 Hz, 1.65 Hz), 8.40 (1H, d, J=1.5 Hz), 7.67-7.63 (1H, m), 7.29-7.24 (1H, m), 7.21 (1H, d, J=2.4 Hz), 7.01 (1H, d, J=8.1 Hz), 6.92-6.82 (4H, m), 4.03 (2H, t, J=6.75 Hz), 2.00-1.93 (1H, m), 1.88-1.80 (4H, m), 1.68-1.51 (4H, m), 1.23-1.14 (2H, m).

Example 78

Synthesis of 3-(3,5-difluorophenyl)-2-(pyridin-3-yl)-6-(2-(tetrahydro-2H-pyran-4-yl)ethoxy)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, 2-(tetrahydro-2H-pyran-4-yl)ethanol (2.0 eq) instead of 4-(2-hydroxyethyl)morpholine, using 2 equivalents of PPh$_3$ and DIAD, being stirred for 17 h, and being purified by prep. HPLC (20% H$_2$O/CH$_3$CN) to provide the title compound (33%).

$^1$H NMR (CDCl$_3$, 300 MHz) δ 8.50 (1H, dd, J=4.8 Hz, 1.8 Hz), 8.40 (1H, d, J=2.1 Hz), 7.67-7.63 (1H, m), 7.29-7.24 (1H, m), 7.21 (1H, d, J=2.7 Hz), 7.02 (1H, d, J=8.1 Hz), 6.92-6.82 (4H, m), 4.07 (2H, t, J=6 Hz), 3.98 (2H, dd, J=11.5 Hz, 4.05 Hz), 3.42 (2H, t, J=11.85 Hz), 1.80-1.74 (3H, m), 1.67 (2H, d, J=12 Hz), 1.44-1.31 (2H, m).

Example 79

Synthesis of 3-(3,5-difluorophenyl)-2-(pyridin-3-yl)-6-((tetrahydrofuran-2-yl)methoxy)-1H-inden-1-one The procedure of Step 6 of Example 1 was repeated except for using 3-(3,5-difluorophenyl)-6-hydroxy-2-(pyridin-3-yl)-1H-inden-1-one obtained in Step 1 of Example 64 as a starting material instead of 2-bromo-6-hydroxy-3-phenyl-1H-inden-1-one, (tetrahydrofuran-2-yl)methanol (2.0 eq) instead of 4-(2-hydroxyethyl)morpholine, using 2 equivalents of $PPh_3$ and DIAD, being stirred for 17 h, and being purified by prep. HPLC (20% $H_2O/CH_3CN$ and 30% $H_2O/CH_3CN$) to provide the title compound (7%).

$^1$H NMR (CDCl$_3$, 300 MHz) δ 8.50 (1H, dd, J=4.95 Hz, 1.65 Hz), 8.40 (1H, d, J=1.5 Hz), 7.67-7.63 (1H, m), 7.29-7.24 (2H, m), 7.02 (1H, d, J=8.1 Hz), 6.91-6.87 (4H, m), 4.34-4.25 (1H, m), 4.06-4.02 (2H, m), 4.00-3.82 (2H, m), 2.16-2.05 (1H, m), 2.03-1.93 (2H, m), 1.83-1.74 (1H, m).

Example 80

Synthesis of 6-(2-morpholinoethoxy)-3-(2-fluorophenyl)-2-(pyridin-3-yl)-1H-inden-1-one Step 1. (E)-3-(2-Fluorophenyl)-1-(3-hydroxyphenyl)prop-2-en-1-one The procedure of Step 1 of Example 1 was repeated except for using 2-fluorobenzaldehyde as a starting material instead of benzaldehyde and being stirred for 4.5 h to obtain the title compound (90%).

$^1$H NMR (300 MHz, CDCl$_3$) δ 7.88 (1H, d, J=15.9 Hz), 7.62-7.65 (2H, m), 7.56-7.60 (2H, m), 7.35-7.39 (2H, m), 7.18 (1H, d, J=8.7 Hz), 7.09-7.14 (2H, m)

Step 2. 3-(2-Fluorophenyl)-2,3-dihydro-6-hydroxy-inden-1-one

The procedure of Step 2 of Example 1 was repeated except for using (E)-3-(2-fluorophenyl)-1-(3-hydroxyphenyl)prop-2-en-1-one obtained in Step 1 as a starting material instead of (E)-1-(3-hydroxyphenyl)-3-phenylprop-2-en-1-one, being stirred for 16 h to obtain the title compound (83%).

$^1$H NMR (300 MHz, CDCl$_3$) δ 7.27 (s, 1H), 7.19-7.23 (m, 1H), 7.14-7.17 (m, 2H), 7.02-7.08 (m, 2H), 6.94-6.99 (m, 2H), 4.80 (q, 1H), 3.26 (dd, J=19.5 Hz, 7.8 Hz, 1H), 2.71 (dd, J=19.5 Hz, 3.3 Hz, 1H)

Step 3. 1-(2-Fluorophenyl)-2,3-dihydro-3-oxo-1H-inden-5-yl acetate

The procedure of Step 3 of Example 1 was repeated except for using 3-(2-fluorophenyl)-2,3-dihydro-6-hydroxyinden-1-one obtained in Step 2 as a starting material instead of 2,3-dihydro-6-hydroxy-3-phenylinden-1-one to obtain the title compound (85%).

$^1$H NMR (300 MHz, CDCl$_3$) δ 7.51 (s, 1H), 7.17-7.29 (m, 2H), 6.97-7.09 (m, 4H), 4.86 (q, 1H), 3.24 (dd, J=19.2 Hz, 8.1 Hz, 1H), 2.78 (dd, J=19.2 Hz, 3.6 Hz, 1H), 2.32 (s, 3H)

Step 4. 2-Bromo-3-(2-fluorophenyl)-1-oxo-1H-inden-6-yl acetate

The procedure of Step 4 of Example 1 was repeated except for using 1-(2-fluorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 2 h to obtain the title compound (91%).

$^1$H NMR (300 MHz, CDCl$_3$) δ 7.47-7.56 (m, 2H), 7.23-7.34 (m, 3H), 7.06 (dd, J=7.8 Hz, 2.1 Hz, 1H), 6.96 (dd, J=7.8 Hz, 2.4 Hz, 1H), 2.31 (s, 3H)

Step 5. 2-Bromo-3-(2-fluorophenyl)-6-hydroxy-1H-inden-1-one

The procedure of Step 5 of Example 1 was repeated except for using 2-bromo-3-(2-fluorophenyl)-1-oxo-1H-inden-6-yl acetate obtained in Step 4 as a starting material instead of 2-bromo-1-oxo-3-phenyl-1H-inden-6-yl acetate to obtain the title compound (93%).

$^1$H NMR (300 MHz, CDCl$_3$) δ 7.47-7.54 (m. 2H), 7.19-7.35 (m, 2H), 7.09 (d, 1H), 6.80 (dd, J=7.8 Hz, 2.1 Hz, 1H), 6.72 (dd, J=7.8 Hz, 2.4 Hz, 1H)

Step 6. 6-(2-Morpholinoethoxy)-2-bromo-3-(2-fluorophenyl)-1H-inden-1-one

The procedure of Step 6 of Example 1 was repeated except for using 2-bromo-3-(2-fluorophenyl)-6-hydroxy-1H-inden-1-one obtained in Step 5 as a starting material instead of 2-bromo-6-hydroxy-3-phenyl-1H-inden-1-one and being stirred for 3 h to obtain the title compound (62%).

$^1$H NMR (300 MHz, CDCl$_3$) δ 7.64-7.67 (m, 1H), 7.45-7.56 (m. 2H), 7.24-7.30 (m, 1H), 7.17 (d, J=2.1 Hz, 1H), 6.84 (dd, J=8.1 Hz, 2.1 Hz, 1H), 6.75 (dd, J=8.1 Hz, 2.4 Hz, 1H), 4.12 (t, 2H), 3.70 (m, 4H), 2.79 (t, 2H), 2.55 (m, 4H)

Step 7. 6-(2-Morpholinoethoxy)-3-(2-fluorophenyl)-2-(pyridin-3-yl)-1H-inden-1-one The procedure of Step 7 of Example 1 was repeated except for using 6-(2-morpholinoethoxy)-2-bromo-3-(2-fluorophenyl)-1H-inden-1-one obtained in Step 6 as a starting material instead of 6-(2-morpholinoethoxy)-2-bromo-3-phenyl-1H-inden-1-one and being stirred for 15 min to obtain the title compound (47%).

$^1$H NMR (300 MHz, CDCl$_3$) δ 8.45 (dd, J=4.8 Hz, 1.2 Hz, 1H), 8.41 (m. 1H), 7.67-7.69 (m, 1H), 7.43-7.45 (m, 1H), 7.29-7.35 (m, 1H), 7.14-7.25 (m, 4H), 6.92 (d, J=8.1 Hz, 1H), 6.83 (dd, J=8.1 Hz, 2.4 Hz, 1H), 4.16 (t, 2H), 3.75 (m, 4H), 2.82 (t, 2H), 2.59 (m, 4H);
MS (m/e, M$^+$): 430.48.

Example 81

Synthesis of 6-(2-morpholinoethoxy)-3-(3-fluorophenyl)-2-(pyridin-3-yl)-1H-inden-1-one Step 1. (E)-3-(3-Fluorophenyl)-1-(3-hydroxyphenyl)prop-2-en-1-one The procedure of Step 1 of Example 1 was repeated except for using 3,5-difluorobenzaldehyde as a starting material instead of benzaldehyde and being stirred for 4 h to obtain the title compound (91%).

$^1$H NMR (300 MHz, CDCl$_3$) δ 7.76 (d, J=15.9 Hz, 1H), 7.58 (d, J=2.4 Hz 1H), 7.53 (d, J=12.9 Hz, 1H), 7.40-7.48 (m, 2H), 7.30-7.39 (m, 3H), 7.10-7.13 (m, 2H)

Step 2. 3-(3-Fluorophenyl)-2,3-dihydro-6-hydroxy-inden-1-one

The procedure of Step 2 of Example 1 was repeated except for using (E)-3-(3-fluorophenyl)-1-(3-hydroxyphenyl)prop- 2-en-1-one obtained in Step 1 as a starting material instead of (E)-1-(3-hydroxyphenyl)-3-phenylprop-2-en-1-one and being stirred for 16 h to obtain the title compound (86%).

$^1$H NMR (300 MHz, CDCl$_3$) δ 7.46 (s, 1H), 7.27-7.30 (m, 1H), 7.07-7.16 (m, 3H), 6.94 (dd, J=8.4 Hz, 2.4 Hz, 1H), 6.88-6.90 (m, 1H), 6.77-6.81 (m, 1H), 4.50 (q, 1H), 3.27 (dd, J=19.5 Hz, 7.8 Hz, 1H), 2.71 (dd, J=19.5 Hz, 3.3 Hz, 1H)

Step 3. 1-(3-Fluorophenyl)-2,3-dihydro-3-oxo-1H-inden-5-yl acetate

The procedure of Step 3 of Example 1 was repeated except for using 3-(3-fluorophenyl)-2,3-dihydro-6-hydroxyinden-1-one obtained in Step 2 as a starting material instead of 2,3-dihydro-6-hydroxy-3-phenylinden-1-one to obtain the title compound (92%).

$^1$H NMR (300 MHz, CDCl$_3$) δ 7.53 (s, 1H), 7.40-7.46 (m, 1H), 7.25-7.32 (m, 3H), 6.91-6.98 (m, 1H), 6.81-6.85 (m, 1H), 4.55 (q, 1H), 3.27 (dd, J=19.5 Hz, 8.1 Hz, 1H), 2.70 (dd, J=19.5 Hz, 4.2 Hz, 1H), 2.32 (s, 3H)

Step 4. 2-Bromo-3-(3-fluorophenyl)-1-oxo-1H-inden-6-yl acetate

The procedure of Step 4 of Example 1 was repeated except for using 1-(3-fluorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 2 h to obtain the title compound (88%).

$^1$H NMR (300 MHz, CDCl$_3$) δ 7.48-7.57 (m, 2H), 7.32-7.42 (m, 2H), 7.20-7.25 (m, 1H), 7.14 (d, J=8.1 Hz, 1H), 7.08 (dd, J=8.1 Hz, 2.4 Hz, 1H), 2.32 (s, 3H)

Step 5. 2-Bromo-3-(3-fluorophenyl)-6-hydroxy-1H-inden-1-one

The procedure of Step 5 of Example 1 was repeated except for using 2-bromo-3-(3-fluorophenyl)-1-oxo-1H-inden-6-yl acetate obtained in Step 4 as a starting material instead of 2-bromo-1-oxo-3-phenyl-1H-inden-6-yl acetate to obtain the title compound (96%).

$^1$H NMR (300 MHz, CDCl$_3$) δ 7.48-7.57 (m, 2H), 7.33 (d, 1H), 7.14-7.20 (m, 1H), 7.11 (d, 1H), 6.96 (d, J=8.1 Hz, 1H), 6.75 (dd, J=8.1 Hz, 2.4 Hz, 1H)

Step 6. 6-(2-Morpholinoethoxy)-2-bromo-3-(3-fluorophenyl)-1H-inden-1-one

The procedure of Step 6 of Example 1 was repeated except for using 2-bromo-3-(3-fluorophenyl)-6-hydroxy-1H-inden-1-one obtained in Step 5 as a starting material instead of 2-bromo-6-hydroxy-3-phenyl-1H-inden-1-one and being stirred for 3 h to obtain the title compound (71%).

$^1$H NMR (300 MHz, CDCl$_3$) δ 7.64-7.68 (m, 1H), 7.47-7.56 (m, 2H), 7.34-7.37 (m, 1H), 7.18 (d, J=2.4 Hz, 1H), 7.02 (d, J=8.1 Hz, 1H), 6.77 (dd, J=8.1 Hz, 2.4 Hz, 1H), 4.15 (t, 2H), 3.73 (m, 4H), 2.78 (t, 2H), 2.57 (m, 4H)

Step 7. 6-(2-Morpholinoethoxy)-3-(3-fluorophenyl)-2-(pyridin-3-yl)-1H-inden-1-one The procedure of Step 7 of Example 1 was repeated except for using 6-(2-morpholinoethoxy)-2-bromo-3-(3-fluorophenyl)-1H-inden-1-one obtained in Step 6 as a starting material instead of 6-(2-morpholinoethoxy)-2-bromo-3-phenyl-1H-inden-1-one and being stirred for 15 min to obtain the title compound (55%).

$^1$H NMR (300 MHz, CDCl$_3$) δ 8.46 (dd, J=8.4 Hz, 1.5 Hz, 1H), 8.40 (m, 1H), 7.62-7.66 (m, 1H), 7.37-7.44 (m, 1H), 7.23-7.27 (m, 2H), 7.06-7.16 (m, 2H), 7.03 (d, J=8.1 Hz, 1H), 6.84 (dd, J=8.1 Hz, 2.4 Hz, 1H), 4.16 (t, 2H), 3.74 (m, 4H), 2.82 (t, 2H), 2.59 (m, 4H)

MS (m/e, M$^+$): 430.48

Example 82

Synthesis of 6-(2-morpholinoethoxy)-3-(2,4-difluorophenyl)-2-(pyridin-3-yl)-1H-inden-1-one Step 1. (E)-3-(2,4-Difluorophenyl)-1-(3-hydroxyphenyl)prop-2-en-1-one The procedure of Step 1 of Example 1 was repeated except for using 2,4-difluorobenzaldehyde as a starting material instead of benzaldehyde and being stirred for 4 h to obtain the title compound (90%).

$^1$H NMR (300 MHz, CDCl$_3$) δ 7.82 (d, J=15.9 Hz, 1H), 7.49-7.62 (m, 4H), 7.33-7.36 (m, 1H), 7.11-7.14 (m, 1H), 6.81-6.93 (m, 2H)

Step 2. 3-(2,4-Difluorophenyl)-2,3-dihydro-6-hydroxyinden-1-one

The procedure of Step 2 of Example 1 was repeated except for using (E)-3-(2,4-difluorophenyl)-1-(3-hydroxyphenyl)prop-2-en-1-one obtained in Step 1 as a starting material instead of (E)-1-(3-hydroxyphenyl)-3-phenylprop-2-en-1-one and being stirred for 16 h to obtain the title compound (83%).

$^1$H NMR (300 MHz, CDCl$_3$) δ 7.31 (s, 1H), 7.11-7.16 (m, 1H), 6.89-6.97 (m, 2H), 6.79-6.89 (m, 2H), 4.77 (q, 1H), 3.27 (dd, J=19.5 Hz, 6.6 Hz, 1H), 2.71 (dd, J=19.5 Hz, 3.6 Hz, 1H)

Step 3. 1-(2,4-Difluorophenyl)-2,3-dihydro-3-oxo-1H-inden-5-yl acetate

The procedure of Step 3 of Example 1 was repeated except for using 3-(2,4-difluorophenyl)-2,3-dihydro-6-hydroxyinden-1-one obtained in Step 2 as a starting material instead of 2,3-dihydro-6-hydroxy-3-phenylinden-1-one to obtain the title compound (90%).

$^1$H NMR (300 MHz, CDCl$_3$) δ 7.51 (s, 1H), 7.12-7.32 (m, 2H), 6.91-6.97 (m, 2H), 6.80-6.83 (m, 1H), 4.56 (q, 1H), 3.29 (dd, J=19.2 Hz, 8.1 Hz, 1H), 2.70 (dd, J=19.2 Hz, 3.9 Hz, 1H), 2.32 (s, 3H)

Step 4. 2-Bromo-3-(2,4-difluorophenyl)-1-oxo-1H-inden-6-yl acetate

The procedure of Step 4 of Example 1 was repeated except for using 1-(2,4-difluorophenyl)-2,3-dihydro-3-oxo-1H-inden-5-yl acetate obtained in Step 3 as a starting material instead of 2,3-dihydro-1-oxo-3-phenyl-1H-inden-6-yl acetate and being heated to reflux for 2 h to obtain the title compound (91%).

$^1$H NMR (300 MHz, CDCl$_3$) δ 7.47-7.57 (m, 2H), 7.27-7.31 (m, 1H), 6.95-7.06 (m, 2H), 6.81-6.90 (m, 1H), 2.32 (s, 3H)

Step 5. 2-Bromo-3-(2,4-difluorophenyl)-6-hydroxy-1H-inden-1-one

The procedure of Step 5 of Example 1 was repeated except for using 2-bromo-3-(2,4-difluorophenyl)-1-oxo-1H-inden- 6-yl acetate obtained in Step 4 as a starting material instead of 2-bromo-1-oxo-3-phenyl-1H-inden-6-yl acetate to obtain the title compound (90%).

$^1$H NMR (300 MHz, CDCl$_3$) δ 7.44-7.56 (m, 2H), 7.27-7.33 (m, 1H), 6.97-7.05 (m, 2H), 6.71-6.89 (m, 1H)

Step 6. 6-(2-Morpholinoethoxy)-2-bromo-3-(2,4-difluorophenyl)-1H-inden-1-one

The procedure of Step 6 of Example 1 was repeated except for using 2-bromo-3-(2,4-difluorophenyl)-6-hydroxy-1H-inden-1-one (700 mg, 2.1 mmol) obtained in Step 5 as a starting material instead of 2-bromo-6-hydroxy-3-phenyl-1H-inden-1-one and being stirred for 3 h to obtain the title compound (70%).

$^1$H NMR (300 MHz, CDCl$_3$) δ 7.66-7.69 (m, 1H), 7.47-7.51 (m. 2H), 7.16 (d, J=2.1 Hz, 1H), 6.79-6.84 (m, 2H), 4.12 (t, 2H), 3.73 (m, 4H), 2.78 (t, 2H), 2.57 (m, 4H)

Step 7. 6-(2-Morpholino ethoxy)-3-(2,4-difluorophenyl)-2-(pyridin-3-yl)-1H-inden-1-one The procedure of Step 7 of Example 1 was repeated except for using 642-morpholinoethoxy)-2-bromo-3-(2,4-difluorophenyl)-1H-inden-1-one obtained in Step 6 as a starting material instead of 6-(2-morpholinoethoxy)-2-bromo-3-phenyl-1H-inden-1-one and being stirred for 15 min to obtain the title compound (52%).

$^1$H NMR (300 MHz, CDCl$_3$) δ 8.46 (dd, J=4.5 Hz, 1.5 Hz, 1H), 8.40 (m. 1H), 7.66-7.69 (m, 1H), 7.30-7.35 (m, 1H), 7.21-7.28 (m, 2H), 6.91-7.01 (m, 2H), 6.89 (d, J=3.9 Hz, 1H) 6.84 (dd, J=8.1 Hz, 2.4 Hz, 1H), 4.16 (t, 2H), 3.74 (m, 4H), 2.82 (t, 2H), 2.59 (m, 4H);

MS (m/e, M$^+$): 448.47.

Example 83

Synthesis of 6-(2-morpholinoethoxy)-3-phenyl-2-(pyridin-2-yl)-1H-inden-1-one

The procedure of Step 7 of Example 1 was repeated except for using 2-pyridinylboronic acid instead of 3-pyridinylboronic acid and being stirred for 15 min to obtain the title compound (58%).

$^1$H NMR (300 MHz, CDCl$_3$) δ 2.61 (t, 4H), 2.84 (t, 214), 3.76 (t, 4H), 4.18 (t, 2H), 6.83 (dd, 1H, J=2.4, 8.1 Hz), 7.11 (d, 1H, J=8.1 Hz), 7.14 (m, 1H), 7.22 (d, 1H, J=2.4 Hz), 7.32 (dd, 1H, J=0.9, 7.9 Hz), 7.39 (m, 5H), 7.61 (m, 1H), 8.54 (dd, 1H, J=0.9, 4.8 Hz);

MS (m/e, M$^+$): 412

Example 84

Synthesis of 2-(benzo[b]thiophen-3-yl)-6-(2-morpholinoethoxy)-3-phenyl-1H-inden-1-one The procedure of Step 7 of Example 1 was repeated except for using 3-benzo[b]thiophenylboronic acid instead of 3-pyridinylboronic acid and being stirred for 10 min to obtain the title compound (65%).

$^1$H NMR (300 MHz, CDCl$_3$) δ 2.61 (t, 4H), 2.84 (t, 2H), 3.75 (t, 4H), 4.12 (t, 2H), 6.87 (dd, 1H, J=2.4, 8.1 Hz), 7.09 (m, 1H), 7.21 (s, 1H), 7.24 (m, 2H), 7.31 (m, 3H), 7.38 (m, 3H) 7.80 (dd, 1H, J=1.0, 7.8 Hz);

MS (m/e, M$^+$): 467.

Example 85

Synthesis of 2-(benzo[1,3]dioxol-5-yl)-6-(2-morpholinoethoxy)-3-phenyl-1H-inden-1-one The procedure of Step 7 of Example 1 was repeated except for using 5-benzo[1,3]dioxolylboronic acid instead of 3-pyridinylboronic acid and being stirred for 10 min to obtain the title compound (63%).

$^1$H NMR (300 MHz, CDCl$_3$) δ 2.59 (t, 4H), 2.82 (t, 2H), 3.75 (t, 4H), 4.15 (t, 2H), 5.92 (s, 2H), 6.75 (m, 4H), 7.01 (d, 1H, J=8.04 Hz), 7.18 (d, 1H, J=2.3 Hz), 7.39 (m, 5H);

MS (m/e, M$^+$): 455

Example 86

Synthesis of 2-(5-chlorothiophen-2-yl)-6-(2-morpholinoethoxy)-3-phenyl-1H-inden-1-one The procedure of Step 7 of Example 1 was repeated except for using 5-chloro-2-thiophenylboronic acid instead of 3-pyridinylboronic acid and being stirred for 10 min to obtain the title compound (71%).

$^1$H NMR (300 MHz, CDCl$_3$) δ 2.59 (t, 4H), 2.81 (t, 2H), 3.74 (t, 4H), 4.12 (t, 2H), 6.72 (d, 1H, J=4.0), 6.76 (m, 2H), 7.12 (d, 1H, J=4.0 Hz), 7.14 (m, 1H), 7.45 (m, 2H), 7.52 (m, 3H);

MS (m/e, M$^+$): 451.

Example 87

Synthesis of 2-(1-methyl-1H-indol-5-yl)-6-(2-morpholinoethoxy)-3-phenyl-1H-inden-1-one The procedure of Step 7 of Example 1 was repeated except for using 1-methyl-1H-indol-5-ylboronic acid instead of 3-pyridinylboronic acid and being stirred for 10 min to obtain the title compound (67%).

$^1$H NMR (300 MHz, CDCl$_3$) δ 2.58 (t, 4H), 2.81 (t, 2H), 3.74 (s, 3H), 3.75 (t, 4H), 4.15 (t, 2H), 6.43 (d, 1H, J=3.2 Hz), 6.80 (d, 1H, J=8.2 Hz), 7.02 (m, 3H), 7.18 (m, 2H), 7.38 (m, 5H), 7.62 (s, 1H);

MS (m/e, M$^+$): 464

Example 88

Synthesis of 2-(1H-indol-2-yl)-6-(2-morpholinoethoxy)-3-phenyl-1H-inden-1-one

The procedure of Step 7 of Example 1 was repeated except for using 2-1H-indolylboronic acid instead of 3-pyridinylboronic acid and being stirred for 10 min to obtain the title compound (73%).

$^1$H NMR (300 MHz, CDCl$_3$) δ 2.59 (t, 4H), 2.82 (t, 2H), 3.75 (t, 4H), 4.14 (t, 2H), 6.36 (s, 1H), 6.76 (d, 1H, J=8.1 Hz), 6.82 (d, 1H, J=8.1 Hz), 7.03 (m, 1H), 7.13 (d, 1H, J=8.1 Hz), 7.17 (d, 1H, J=2.0 Hz), 7.35 (d, 1H, J=8.1 Hz), 7.42 (d, 1H, J=7.8 Hz), 7.57 (m, 5H), 9.89 (s, 1H, —NH);

MS (m/e, M$^+$): 450

Example 89

Synthesis of 6-(2-morpholinoethoxy)-2-(6-(morpholin-4-yl)pyridin-3-yl)-3-phenyl-1H-inden-1-one The procedure of Step 7 of Example 1 was repeated except for using 6-morpholino-3-pyridinylboronic acid instead of 3-pyridinylboronic acid and being stirred for 10 min to obtain the title compound (61.7%).

¹H NMR (300 MHz, CDCl₃) δ 2.59 (t, 4H), 2.78 (t, 2H), 3.50 (t, 4H), 3.75 (t, 4H), 3.80 (t, 4H), 4.15 (t, 2H), 6.54 (d, 1H, J=8.8 Hz), 6.79 (dd, 1H, J=2.0, 8.1 Hz), 6.99 (d, 1H, J=8.1 Hz), 7.18 (d, 1H, J=2.0 Hz), 7.42 (m, 5H), 7.46 (m, 1H), 8.13 (s, 1H);
MS (m/e, M⁺): 497

Example 90

Synthesis of 6-(2-morpholinoethoxy)-3-phenyl-2-(1H-pyrrol-2-yl)-1H-inden-1-one

The procedure of Step 7 of Example 1 was repeated except for using 2-1H-pyrrolylboronic acid instead of 3-pyridinylboronic acid and being stirred for 10 min to obtain the title compound (76%).
¹H NMR (300 MHz, CDCl₃) δ 2.58 (t, 4H), 2.82 (t, 2H), 3.74 (t, 4H), 4.12 (t, 2H), 6.06 (m, 2H), 6.71 (s, 2H), 6.81 (s, 1H), 7.08 (s, 1H), 7.47-7.56 (m, 5H), 10.2 (s, 1H, —NH); MS (m/e, M⁺): 400

Example 91

Synthesis of 6-(2-morpholinoethoxy)-2-(benzofuran-2-yl)-3-phenyl-1H-inden-1-one

The procedure of Step 7 of Example 1 was repeated except for using 2-benzofuranylboronic acid instead of 3-pyridinylboronic acid and being stirred for 10 min to obtain the title compound (72%).
¹H NMR (300 MHz, CDCl₃) δ 7.56-7.58 (m, 3H), 7.50-7.52 (m, 3H), 7.44 (brs, 1H), 7.17-7.20 (m, 4H), 7.00 (dd, J=8.1 Hz, 1.5 Hz, 1H), 6.80 (d, J=8.1 Hz, 1H), 4.16 (t, 2H), 3.75 (m, 4H), 2.82 (t, 2H), 2.59 (m, 4H);
MS (m/e, M⁺): 451.51.

Example 92

Synthesis of 3-(3,5-difluorophenyl)-6-[2-(1,1-dioxothiomorpholin-4-yl)ethoxy]-2-(quinolin-3-yl)-1H-inden-1-one hydrochloride salt Step 1. 2-Bromo-3-(3,5-difluorophenyl)-6-[2-(1,1-dioxothiomorpholin-4-yl)ethoxy]-1H-inden-1-one The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, 2-(1,1-dioxothiomorpholin-4-yl)ethanol instead of 4-(2-hydroxyethyl)morpholine, being stirred for 2 h to obtain the title compound (29%).
¹H NMR (CDCl₃, 300 MHz) δ 7.20-7.13 (3H, m), 7.04-6.96 (2H, m), 6.79 (1H, dd, J=3.0 Hz, 9.0 Hz), 4.12 (3H, t, J=6.0 Hz), 3.14 (8H, dd, J=7.5 Hz, 20 Hz), 3.02 (4H, t, J=4.5 Hz)

Step 2. 3-(3,5-Difluorophenyl)-6-[2-(1,1-dioxothiomorpholin-4-yl)ethoxy]-2-(quinolin-3-yl)-1H-inden-1-one The procedure of Step 7 of Example 1 was repeated except for using 2-bromo-3-(3,5-difluorophenyl)-6-[2-(1,1-dioxothiomorpholin-4-yl)ethoxy]-1H-inden-1-one obtained in Step 1 as a starting material instead of 6-(2-morpholinoethoxy)-2-bromo-3-phenyl-1H-inden-1-one, 3-quinolinylboronic acid instead of 3-pyridinylboronic acid and being purified by silica gel column chromatography (acetone/hexanes=1:3) to obtain the title compound (95%).
¹H NMR (CDCl₃, 300 MHz) δ 8.53 (1H, d, J=3.0 Hz), 8.32 (1H, s), 8.03 (1H, d, J=9.0 Hz), 7.85 (1H, d, J=9.0 Hz), 7.75-7.69 (m, 1H), 7.57 (1H, t, J=7.5 Hz), 7.24 (1H, d, J=3.0 Hz). 7.08 (1H, d, J=9.0 Hz), 7.00-6.80 (4H, m), 4.17 (2H, t, J=4.5 Hz), 3.19 (4H, d, J=6.0 Hz), 3.11 (4H, d, J=6.0 Hz), 3.04 (2H, t, J=4.5 Hz)

Step 3. 3-(3,5-Difluorophenyl)-6-[2-(1,1-dioxothiomorpholin-4-yl)ethoxy]-2-(quinolin-3-yl)-1H-inden-1-one hydrochloride salt The procedure of Step 8 of Example 1 was repeated except for using 3-(3,5-difluorophenyl)-6-[2-(1,1-dioxothiomorpholin-4-yl)ethoxy]-2-(quinolin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.
¹H NMR (CDCl₃, 300 MHz) δ 8.86-8.82 (m, 2H), 8.70 (s, 1H), 8.03 (t, 2H, J=9.0 Hz), 7.86 (t, 1H, J=7.5 Hz), 7.30-7.29 (m, 1H), 7.15 (d, 1H, J=6.0 Hz), 7.02-6.91 (m, 4H), 4.59 (brs, 2H), 3.75-3.52 (m, 10H)

Example 93

Synthesis of 3-(3,5-difluorophenyl)-2-(6-methoxypyridin-3-yl)-6-[2-(1,1-dioxothiomorpholin-4-yl)ethoxy]-1H-inden-1-one hydrochloride salt Step 1. 3-(3,5-Difluorophenyl)-2-(6-methoxypyridin-3-yl)-6-[2-(1,1-dioxothiomorpholin-4-yl)ethoxy]-1H-inden-1-one The procedure of Step 7 of Example 1 was repeated except for using 2-bromo-3-(3,5-difluorophenyl)-6-[2-(1,1-dioxothiomorpholin-4-yl)ethoxy]-1H-inden-1-one obtained in Step 1 of Example 92 as a starting material instead of 6-(2-morpholinoethoxy)-2-bromo-3-phenyl-1H-inden-1-one, 6-methoxy-3-pyridinylboronic acid instead of 3-pyridinylboronic acid, and being purified by silica gel column chromatography (EtOAc/CH₂Cl₂=1:1) to obtain the title compound (68%).
¹H NMR (CDCl₃, 300 MHz) δ 8.11 (1H, d, J=3.0 Hz), 7.54 (1H, dd, J=3.0 Hz, 9.0 Hz), 7.19 (1H, d, J=3.0 Hz), 6.99 (1H, d, J=6.0 Hz), 6.83-6.80 (m, 4H), 6.71 (1H, d, J=9.0 Hz), 4.14 (2H, t, J=6.0 Hz), 3.93 (3H, s), 3.17-3.09 (8H, m), 3.01 (2H, t, J=4.5 Hz)

Step 2. 3-(3,5-Difluorophenyl)-2-(6-methoxypyridin-3-yl)-6-[2-(1,1-dioxothiomorpholin-4-yl)ethoxy]-1H-inden-1-one hydrochloride salt The procedure of Step 8 of Example 1 was repeated except for using 3-(3,5-difluorophenyl)-2-(6-methoxypyridin-3-yl)-6-[2-(1,1-dioxothiomorpholin-4-yl)ethoxy]-1H-inden-1-one obtained in Step 1 as a starting material instead of 6-(2-morpholinoethoxy)-3-phenyl-2-(pyridin-3-yl)-1H-inden-1-one to give the title compound in quantitative yield.
¹H NMR (CDCl₃, 300 MHz) δ 8.11 (1H, d, J=3.0 Hz), 7.54 (1H, dd, J=3.0 Hz, 9.0 Hz), 7.19 (1H, d, J=3.0 Hz), 7.04 (1H, d, J=9.0 Hz), 6.91-6.87 (4H, m), 6.76 (1H, d, J=9.0 Hz), 4.63 (2H, t, J=6.0 Hz), 3.99 (3H, s), 3.86 (5H, brs), 3.56 (3H, t, J=3.0 Hz), 2.05-2.01 (m, 2H), 1.74 (brs, 3H)

Example 94

Synthesis of 3-(3,5-difluorophenyl)-6-[2-(1,1-dioxothiomorpholin-4-yl)ethoxy]-2-p-tolyl-1H-inden-1-one hydrochloride salt

Step 1. 3-(3,5-Difluorophenyl)-6-[2-(1,1-dioxothiomorpholin-4-yl)ethoxy]-2-p-tolyl-1H-inden-1-one The procedure of Step 7 of Example 1 was repeated except for using 2-bromo-3-(3,5-difluorophenyl)-6-[2-(1,1-dioxothiomorpholin-4-yl)ethoxy]-1H-inden-1-one obtained in Step 1 of Example 92 as a starting material instead of 6-(2-morpholinoethoxy)-2-bromo-3-phenyl-1H-inden-1-one, p-tolylboronic acid instead of 3-pyridinylboronic acid, and being purified by silica gel column chromatography (EtOAc/hexanes=1:1) to obtain the title compound (71%).

$^1$H NMR (CDCl$_3$, 300 MHz) δ 7.26 (1H, m), 7.18 (1H, d, J=3.0 Hz), 7.11 (3H, s), 6.99 (1H, d, J=6.0 Hz), 6.91-6.80 (4H, m), 4.13 (2H, t, J=6.0 Hz), 3.16-3.09 (m, 8H), 3.01 (2H, t, J=4.5 Hz), 2.33 (3H, s)

Step 2. 3-(3,5-Difluorophenyl)-6-[2-(1,1-dioxothiomorpholin-4-yl)ethoxy]-2-p-tolyl-1H-inden-1-one hydrochloride salt The procedure of Step 8 of Example 1 was repeated except for using 3-(3,5-difluorophenyl)-6-[2-(1,1-dioxothiomorpholin-4-yl)ethoxy]-2-p-tolyl-1H-inden-1-one obtained in Step 1 as a starting material instead of 6-(2-morpholinoethoxy)-3-phenyl-2-(pyridin-3-yl)-1H-inden-1-one to give the title compound (97%).

$^1$H NMR (CDCl$_3$, 300 MHz) δ 7.17 (1H, brs), 7.11 (4H, brs), 7.01 (1H, brs), 6.89-6.87 (4H, m), 4.6 (2H, brs), 3.84-3.45 (10H, m), 2.34 (3H, s)

Example 95

Synthesis of 2-(3-fluoro-4-methoxyphenyl)-3-(3,5-difluorophenyl)-6-[2-(1,1-dioxothiomorpholin-4-yl)ethoxy]-1H-inden-1-one hydrochloride salt

Step 1. 2-(3-Fluoro-4-methoxyphenyl)-3-(3,5-difluorophenyl)-6-[2-(1,1-dioxothiomorpholin-4-yl)ethoxy]-1H-inden-1-one The procedure of Step 7 of Example 1 was repeated except for using 2-bromo-3-(3,5-difluorophenyl)-6-[2-(1,1-dioxothiomorpholin-4-yl)ethoxy]-1H-inden-1-one obtained in Step 1 of Example 92 as a starting material instead of 6-(2-morpholinoethoxy)-2-bromo-3-phenyl-1H-inden-1-one, 3-fluoro-4-methoxyphenylboronic acid instead of 3-pyridinylboronic acid, and being purified by silica gel column chromatography (EtOAc/hexanes=1:1) to obtain the title compound (94%).

$^1$H NMR (CDCl$_3$, 300 MHz) δ 7.17 (1H, s), 7.01-6.96 (3H, m), 6.91-6.86 (4H, m). 6.81 (1H, d, J=6.0 Hz), 4.14 (2H, t, J=4.5 Hz), 3.89 (3H, s), 3.16-3.09 (8H, m), 3.01 (2H, t, J=6.0 Hz)

Step 2. 2-(3-Fluoro-4-methoxyphenyl)-3-(3,5-difluorophenyl)-6-[2-(1,1-dioxothiomorpholin-4-yl)ethoxy]-1H-inden-1-one hydrochloride salt The procedure of Step 8 of Example 1 was repeated except for using 2-(3-fluoro-4-methoxyphenyl)-3-(3,5-difluorophenyl)-6-[2-(1,1-dioxothiomorpholin-4-yl)ethoxy]-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 7.2 (1H, s), 7.2 (3H, d, J=9.0 Hz), 6.9-6.8 (5H, m), 4.7 (2H, s), 3.9 (3H, s), 3.8-3.5 (10H, m)

Example 96

Synthesis of 3-(3,5-difluorophenyl)-6-{2-[4-(methylsulfonyl)piperazin-1-yl]ethoxy}-2-(quinolin-3-yl)-1H-inden-1-one hydrochloride salt

Step 1. 2-Bromo-3-(3,5-difluorophenyl)-6-{2-[4-(methylsulfonyl)piperazin-1-yl]ethoxy}-1H-inden-1-one The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, 2-(4-(methylsulfonyl)piperazin-1-yl)ethanol instead of 4-(2-hydroxyethyl)morpholine, being stirred for 2 h, and being purified by silica gel column chromatography (acetone/hexanes=2:1) to obtain the title compound (73%).

$^1$H NMR (CDCl$_3$, 300 MHz) δ 7.16 (2H, dd, J=3.0 Hz, J=9.0 Hz), 7.1 (1H, d, J=3.0 Hz), 6.7 (1H, d, J=9.0 Hz), 6.94-6.84 (1H, m), 6.8 (1H, d, J=1.5 Hz, J=7.5 Hz), 4.26 (1H, t, J=6.0 Hz), 4.10 (1H, t, J=4.5 Hz), 3.25 (4H, t, J=6.0 Hz), 2.87 (1H, t, J=3.0 Hz), 2.78 (3H, s), 2.72-2.58 (4H, m)

Step 2. 3-(3,5-Difluorophenyl)-6-{2-[4-(methylsulfonyl)piperazin-1-yl]ethoxy}-2-(quinolin-3-yl)-1H-inden-1-one The procedure of Step 7 of Example 1 was repeated except for using 2-bromo-3-(3,5-difluorophenyl)-6-{2-[4-(methylsulfonyl)piperazin-1-yl]ethoxy}-1H-inden-1-one obtained in Step 1 as a starting material instead of 6-(2-morpholinoethoxy)-2-bromo-3-phenyl-1H-inden-1-one, 3-quinolinylboronic acid instead of 3-pyridinylboronic acid, and being purified by silica gel column chromatography (EtOAc/CH$_2$Cl$_2$=1:1) to obtain the title compound (62%).

$^1$H NMR (CDCl$_3$, 300 MHz) δ 8.53 (1H, d, J=3.0 Hz), 8.32 (1H, d, J=3.0 Hz), 8.03 (1H, d, J=9.0 Hz), 7.85 (1H, d, J=9.0 Hz), 7.75-7.69 (2H, m), 7.59-7.54 (2H, m), 7.07 (1H, d, J=9.0 Hz). 6.93-6.85 (3H, m), 4.17 (2H, t, J=4.5 Hz), 3.29 (4H, t, J=4.5 Hz), 2.90 (2H, t, J=6.0 Hz), 2.80 (3H, s), 2.73 (4H, t, J=4.5 Hz)

Step 3. 3-(3,5-Difluorophenyl)-6-{2-[4-(methylsulfonyl)piperazin-1-yl]ethoxy}-2-(quinolin-3-yl)-1H-inden-1-one hydrochloride salt The procedure of Step 8 of Example 1 was repeated except for using 3-(3,5-difluorophenyl)-6-{2-[4-(methylsulfonyl)piperazin-1-yl]ethoxy}-2-(quinolin-3-yl)-1H-inden-1-one obtained in Step 2 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 8.84-8.81 (2H, m), 8.72 (1H, s), 8.03-8.01 (2H, m), 7.86 (1H, t, J=7.6 Hz), 7.30-7.28 (1H, m), 7.17-6.91 (5H, m), 4.89 (4H, brs), 4.73 (2H, brs), 3.86 (4H, brs), 3.56 (2H, brs), 2.91 (s, 3H)

Example 97

Synthesis of 3-(3,5-difluorophenyl)-2-(6-methoxypyridin-3-yl)-6-{2-[4-(methylsulfonyl)piperazin-1-yl]ethoxy}-1H-inden-1-one hydrochloride salt Step 1. 3-(3,5-Difluorophenyl)-2-(6-methoxypyridin-3-yl)-6-{2-[4-(methylsulfonyl)piperazin-1-yl]ethoxy}-1H-inden-1-one The procedure of Step 7 of Example 1 was repeated except for using 2-bromo-3-(3,5-difluorophenyl)-6-{2-[4-(methylsulfonyl)piperazin-1-yl]ethoxy}-1H-inden-1-one obtained in Step 1 of Example 96 as a starting material instead of 6-(2-morpholinoethoxy)-2-bromo-3-phenyl-1H-inden-1-one, 6-methoxy-3-pyridinylboronic acid instead of 3-pyridinylboronic acid, and being purified by silica gel column chromatography (EtOAc/CH$_2$Cl$_2$=1:1) to obtain the title compound (68%).

$^1$H NMR (CDCl$_3$, 300 MHz) δ 8.05-8.04 (1H, m), 7.49 (1H, dd, J=3.0 Hz, 9.0 Hz), 7.21 (1H, d, J=3.0 Hz), 6.99 (1H, d, J=9.0 Hz), 6.92-6.83 (3H, m), 6.83 (1H, dd, J=6.0 Hz, 3.0 Hz), 6.71 (1H, d, J=9.0 Hz), 4.15 (2H, t, J=6.0 Hz), 3.93 (3H, s), 3.29 (4H, t, J=6.0 Hz), 2.89 (2H, t, J=6.0 Hz), 2.79 (3H, s), 2.72 (4H, t, J=4.5 Hz)

Step 2. 3-(3,5-Difluorophenyl)-2-(6-methoxypyridin-3-yl)-6-{2-[4-(methylsulfonyl)piperazin-1-yl]ethoxy}-1H-inden-1-one hydrochloride salt The procedure of Step 8 of Example 1 was repeated except for using 3-(3,5-difluorophenyl)-2-(6-methoxypyridin-3-yl)-6-{2-[4-(methylsulfonyl)piperazin-1-yl]ethoxy}-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 8.15 (1H, s), 7.61 (1H, d, J=6.0 Hz), 7.20 (1H, s), 7.04 (1H, d, J=8.1 Hz), 6.91-6.89 (4H, m), 6.80 (1H, d, J=8.1 Hz), 4.66 (2H, brs), 4.06 (3H, s), 4.00-3.77 (6H, m), 3.52 (2H, brs), 3.19 (2H, brs), 2.91 (3H, s)

Example 98

Synthesis of 3-(3,5-difluorophenyl)-6-{2-[4-(methylsulfonyl)piperazin-1-yl]ethoxy}-2-p-tolyl-1H-inden-1-one hydrochloride salt Step 1. 3-(3,5-Difluorophenyl)-6-{2-[4-(methylsulfonyl)piperazin-1-yl]ethoxy}-2-p-tolyl-1H-inden-1-one The procedure of Step 7 of Example 1 was repeated except for using 2-bromo-3-(3,5-difluorophenyl)-6-{2-[4-(methylsulfonyl)piperazin-1-yl]ethoxy}-1H-inden-1-one obtained in Step 1 of Example 96 as a starting material instead of 6-(2-morpholinoethoxy)-2-bromo-3-phenyl-1H-inden-1-one, p-tolylboronic acid instead of 3-pyridinylboronic acid, and being purified by silica gel column chromatography (EtOAc/CH$_2$Cl$_2$=1:1) to obtain the title compound (52%).

$^1$H NMR (CDCl$_3$, 300 MHz) δ 7.20 (1H, d, J=3.0 Hz), 7.14-7.11 (5H, m), 7.00 (1H, d, J=9.0 Hz), 6.88-6.85 (2H, m), 6.85-6.81 (1H, m), 4.15 (2H, t, J=4.5 Hz), 3.28 (4H, t, J=4.5 Hz), 2.90 (2H, t, J=6.0 Hz), 2.73 (3H, s), 2.70 (4H, t, J=4.5 Hz), 2.33 (3H, s)

Step 2. 3-(3,5-Difluorophenyl)-6-{2-[4-(methylsulfonyl)piperazin-1-yl]ethoxy}-2-p-tolyl-1H-inden-1-one hydrochloride salt The procedure of Step 8 of Example 1 was repeated except for using 3-(3,5-difluorophenyl)-6-{2-[4-(methylsulfonyl)piperazin-1-yl]ethoxy}-2-p-tolyl-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 7.25 (1H, brs), 7.16 (1H, brs), 7.11 (3H, brs), 7.02 (1H, d, J=7.5 Hz), 6.90-6.87 (m, 4H), 4.64 (2H, brs), 3.86 (4H, brs), 3.49 (2H, brs), 2.91 (s, 3H), 2.34 (s, 3H), 1.66 (4H, brs)

Example 99

Synthesis of 2-(3-fluoro-4-methoxyphenyl)-3-(3,5-difluorophenyl)-6-{2-[4-(methylsulfonyl)piperazin-1-yl]ethoxy}-1H-inden-1-one hydrochloride salt Step 1. 2-(3-Fluoro-4-methoxyphenyl)-3-(3,5-difluorophenyl)-6-{2-[4-(methylsulfonyl)piperazin-1-yl]ethoxy}-1H-inden-1-one The procedure of Step 7 of Example 1 was repeated except for using 2-bromo-3-(3,5-difluorophenyl)-6-{2-[4-(methylsulfonyl)piperazin-1-yl]ethoxy}-1H-inden-1-one obtained in Step 1 of Example 96 as a starting material instead of 6-(2-morpholinoethoxy)-2-bromo-3-phenyl-1H-inden-1-one, 3-fluoro-4-methoxyphenylboronic acid instead of 3-pyridinylboronic acid, and being purified by silica gel column chromatography (EtOAc/CH$_2$Cl$_2$=1:1) to obtain the title compound (71%).

$^1$H NMR (CDCl$_3$, 300 MHz) δ 7.22-7.15 (2H, m), 7.01-6.80 (7H, m), 4.14 (2H, t, J=6.0 Hz), 3.88 (3H, s), 3.28 (4H, t, J=4.5 Hz), 2.90 (2H, t, J=6.0 Hz), 2.79 (3H, s), 2.71 (4H, t, J=6.0 Hz)

Step 2. 2-(3-Fluoro-4-methoxyphenyl)-3-(3,5-difluorophenyl)-6-{2-[4-(methylsulfonyl)piperazin-1-yl]ethoxy}-1H-inden-1-one hydrochloride salt The procedure of Step 8 of Example 1 was repeated except for using 2-(3-fluoro-4-methoxyphenyl)-3-(3,5-difluorophenyl)-6-{2-[4-(methylsulfonyl)piperazin-1-yl]ethoxy}-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 7.16-7.12 (2H, m), 7.01-6.86 (7H, m), 4.64 (2H, brs), 3.88 (3H, s), 3.75 (4H, brs), 3.50 (2H, brs), 3.17 (2H, brs), 2.91 (s, 3H), 1.72 (2H, brs)

Example 100

Synthesis of 3-(3,5-difluorophenyl)-2-(6-methoxypyridin-3-yl)-6-{2-[1-(methylsulfonyl)piperidin-4-yl]ethoxy}-1H-inden-1-one hydrochloride salt Step 1. t-Butyl 4-(2-(2-bromo-3-(3,5-difluorophenyl)-1-oxo-1H-inden-6-yloxy)ethyl)piperidine-1-carboxylate The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden- 1-one, t-butyl 4-(2-hydroxyethyl)piperidine-1-carboxylate instead of 4-(2-hydroxyethyl)morpholine, being stirred for 2 h, and being purified by silica gel column chromatography (EtOAc/hexanes=1:3) to obtain the title compound.

$^1$H NMR (CDCl$_3$, 300 MHz) δ 7.21-7.11 (3H, m), 7.02-6.91 (2H, m), 6.83-6.76 (1H, m), 4.11-3.99 (2H, m), 2.72 (2H, t, J=12 Hz), 2.10-2.16 (7H, m), 1.44 (9H, s), 1.28-1.17 (2H, m)

Step 2. 6-(2-(Piperidin-4-yl)ethoxy)-2-bromo-3-(3,5-difluorophenyl)-1H-inden-1-one To a solution of t-Butyl 4-(2-(2-bromo-3-(3,5-difluorophenyl)-1-oxo-1H-inden-6-yloxy)ethyl)piperidine-1-carboxylate (700 mg, 1.4 mmol) obtained in Step 1 in CH$_2$Cl$_2$ was added TFA (20 eq, 27 mmol). The solution was stirred for 1 h at room temperature and diluted with CH$_2$Cl$_2$. The mixture was basicified to with 3N aq. NaOH. The organic layer was washed with H$_2$O and brine, dried over MgSO$_4$, and concentrated to obtain the title compound (99%).

$^1$H NMR (CDCl$_3$, 300 MHz) δ 7.21-7.11 (3H, m), 7.02-6.91 (2H, m), 6.83-6.76 (1H, m), 4.05-3.94 (2H, m), 3.42-3.32 (2H, m), 2.82-2.65 (2H, m), 2.10-2.16 (7H, m)

Step 3. 2-Bromo-3-(3,5-difluorophenyl)-6-{2-[1-(methylsulfonyl)piperidin-4-yl]ethoxy}-1H-inden-1-one To a solution of t-butyl 6-(2-(piperidin-4-yl)ethoxy)-2-bromo-3-(3,5-difluorophenyl)-1H-inden-1-one (211 mg, 1.2 eq, 1.03 mmol) obtaind in Step 2 in CH$_2$Cl$_2$ at 0° C. was added triethylamine (1.5 eq) and methylsulfonyl chloride (1.0 eq). The mixture was stirred for 1 h at room temperature and diluted with CH$_2$Cl$_2$. The mixture was washed with H$_2$O and brine, dried over MgSO$_4$, and concentrated in vacuo. The residue was purified by silica gel column chromatography (EtOAc/hexanes=1:1) to obtain the title compound (58%).

$^1$H NMR (CDCl$_3$, 300 MHz) δ 7.22-7.11 (3H, m), 7.02-6.95 (2H, m), 6.82-6.76 (1H, m), 4.18-4.03 (2H, m), 3.8 (2H, d, J=12 Hz), 2.8 (3H, s), 2.7 (2H, t, J=11 Hz), 1.80-1.67 (5H, m), 1.38-1.17 (2H, m)

Step 4. 3-(3,5-Difluorophenyl)-2-(6-methoxypyridin-3-yl)-6-{2-[1-(methylsulfonyl)piperidin-4-yl]ethoxy}-1H-inden-1-one The procedure of Step 7 of Example 1 was repeated except for using 2-bromo-3-(3,5-difluorophenyl)-6-{2-[1-(methylsulfonyl)piperidin-4-yl]ethoxy}-1H-inden-1-one obtained in Step 3 as a starting material instead of 6-(2-morpholinoethoxy)-2-bromo-3-phenyl-1H-inden-1-one, 6-methoxypyridinylboronic acid instead of 3-pyridinylboronic acid, and being purified by silica gel column chromatography (EtOAc/CH$_2$Cl$_2$=1:1) to obtain the title compound (59%).

$^1$H NMR (CDCl$_3$, 300 MHz) δ 8.06 (1H, s), 7.50 (1H, dd, J=3.0 Hz, 9.0 Hz), 7.19 (1H, d, J=3.0 Hz), 6.99 (1H, d, J=9.0 Hz), 6.91 (2H, d, J=6.0 Hz), 6.81 (1H, dd, J=3.0 Hz, 9.0 Hz), 6.71 (2H, d, J=9.0 Hz), 4.07 (2H, t, J=6.0 Hz), 3.93 (3H, s), 3.83 (2H, t, J=12.0 Hz), 2.79 (3H, s), 2.67 (2H, t, J=1.05 Hz), 1.89-1.79 (5H, m), 1.48-1.38 (2H, m)

Step 5. 3-(3,5-Difluorophenyl)-2-(6-methoxypyridin-3-yl)-6-{2-[1-(methylsulfonyl)piperidin-4-yl]ethoxy}-1H-inden-1-one hydrochloride salt The procedure of Step 8 of Example 1 was repeated except for using 3-(3,5-difluorophenyl)-2-(6-methoxypyridin-3-yl)-6-{2-[1-(methylsulfonyl)piperidin-4-yl]ethoxy}-1H-inden-1-one obtained in Step 4 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 8.11 (1H, s), 7.61 (1H, dd, J=3.0 Hz, 9.0 Hz), 7.18 (1H, d, J=3.0 Hz), 6.98 (1H, d, J=9.0 Hz), 6.94-6.84 (3H, m), 6.80 (2H, dd, J=3.0 Hz, 9.0 Hz), 4.07 (2H, t, J=6.0 Hz), 4.01 (3H, s), 3.82 (2H, td, J=3.0 Hz, 12.0 Hz), 2.78 (3H, s), 2.67 (2H, t, J=11 Hz), 1.89-1.73 (7H, m)

Example 101

Synthesis of 3-(3,5-difluorophenyl)-6-{2-[1-(methylsulfonyl)piperidin-4-yl]ethoxy}-2-(quinolin-3-yl)-1H-inden-1-one hydrochloride salt

Step 1. 3-(3,5-Difluorophenyl)-6-{2-[1-(methylsulfonyl)piperidin-4-yl]ethoxy}-2-(quinolin-3-yl)-1H-inden-1-one The procedure of Step 7 of Example 1 was repeated except for using 2-bromo-3-(3,5-difluorophenyl)-6-{2-[1-(methylsulfonyl)piperidin-4-yl]ethoxy}-1H-inden-1-one obtained in Step 3 of Example 100 as a starting material instead of 6-(2-morpholinoethoxy)-2-bromo-3-phenyl-1H-inden-1-one, 3-quinolinylboronic acid instead of 3-pyridinylboronic acid, and being purified by silica gel column chromatography (EtOAc/hexanes=1:1) to obtain the title compound (79%).

$^1$H NMR (CDCl$_3$, 300 MHz) δ 8.53 (1H, s), 8.32 (1H, s), 8.04-7.63 (4H, m), 7.27-7.23 (2H, m), 7.07 (1H, d, J=6.0 Hz), 6.95-6.84 (3H, m), 4.10 (2H, t, J=4.5 Hz), 3.84 (2H, t, J=12.0 Hz), 2.79 (3H, s), 2.68 (2H, t, J=10.5 Hz), 1.90-1.81 (5H, m), 1.47-1.41 (2H, m)

Step 2. 3-(3,5-Difluorophenyl)-6-{2-[1-(methylsulfonyl)piperidin-4-yl]ethoxy}-2-(quinolin-3-yl)-1H-inden-1-one hydrochloride salt The procedure of Step 8 of Example 1 was repeated except for using 3 (3,5-difluorophenyl)-6-{2-[1-(methylsulfonyl)piperidin-4-yl]ethoxy}-2-(quinolin-3-yl)-1H-inden-1-one obtained in Step 1 as a starting material instead of 6-(2-morpholinoethoxy)-3-phenyl-2-(pyridin-3-yl)-1H-inden-1-one to give the title compound in quantitative yield.

$^1$H NMR (CDCl$_3$, 300 MHz) δ 8.91-8.80 (1H, m), 8.75 (1H, s), 8.02 (2H, d, J=6.0 Hz), 7.86 (1H, t, J=8.0 Hz), 7.25-7.20 (1H, m), 7.11 (1H, d, J=9.0 Hz), 7.02-6.85 (5H, m), 4.12 (2H, t, J=4.5 Hz), 3.85-3.82 (2H, m), 2.79 (3H, s), 2.69 (2H, t, J=11 Hz), 2.05-1.70 (7H, m)

Example 102

Synthesis of 3-(3,5-difluorophenyl)-2-(3-fluoro-4-methoxyphenyl)-6-{2-[1-(methylsulfonyl)piperidin-4-yl]ethoxy}-1H-inden-1-one The procedure of Step 7 of Example 1 was repeated except for using 2-bromo-3-(3,5-difluorophenyl)-6-{2-[1-(methylsulfonyl)piperidin-4-yl]ethoxy}-1H-inden-1-one obtained in Step 3 of Example 100 as a starting material instead of 6-(2-morpholino ethoxy)-2-bromo-3-phenyl-1H-inden-1-one, 3-fluoro-4-methoxyphenylboronic acid instead of 3-pyridinylboronic acid, and being purified by silica gel column chromatography (EtOAc/hexanes=1:1) to obtain the title compound (67%).

¹H NMR (CDCl₃, 300 MHz) δ 7.22-7.12 (2H, m), 7.01-6.78 (7H, m), 4.08 (2H, t, J=7.5 Hz), 3.80-3.66 (5H, m), 2.78 (3H, s), 2.67 (2H, t, J=12.0 Hz), 1.89-1.78 (5H, m), 1.42-1.39 (2H, m)

Example 103

Synthesis of 3-(3,5-difluorophenyl)-6-{2-[1-(methylsulfonyl)piperidin-4-yl]ethoxy}-2-p-tolyl-1H-inden-1-one The procedure of Step 7 of Example 1 was repeated except for using 2-bromo-3-(3,5-difluorophenyl)-6-{2-[1-(methylsulfonyl)piperidin-4-yl]ethoxy}-1H-inden-1-one obtained in Step 3 of Example 100 as a starting material instead of 6-(2-morpholinoethoxy)-2-bromo-3-phenyl-1H-inden-1-one, p-tolylboronic acid instead of 3-pyridinylboronic acid, and being purified by silica gel column chromatography (EtOAc/hexanes=2:1) to obtain the title compound (66%).

¹H NMR (CDCl₃, 300 MHz) δ 7.16 (1H, d, J=3.0 Hz), 7.15-7.11 (5H, m), 6.98 (1H, d, J=9.0 Hz), 6.95-6.87 (2H, m), 6.81-6.76 (1H, m), 4.06 (2H, t, J=6.0 Hz), 3.82 (2H, d, J=12.0 Hz), 2.78 (3H, s), 2.68 (2H, t, J=11.3 Hz), 2.33 (3H, s), 1.97-1.67 (5H, m), 1.41-1.29 (2H, m)

Example 104

Synthesis of 3-(3,5-difluorophenyl)-6-{3-[4-(methylsulfonyl)piperazin-1-yl]propoxy}-2-(quinolin-3-yl)-1H-inden-1-one hydrochloride salt Step 1. t-Butyl 4-(3-(2-bromo-3-(3,5-difluorophenyl)-1-oxo-1H-inden-6-yl oxy)propyl)piperazine-1-carboxylate The procedure of Step 6 of Example 1 was repeated except for using 2-bromo-3-(3,5-difluorophenyl)-6-hydroxy-1H-inden-1-one obtained in Step 5 of Example 36 as a starting material instead of 2-bromo-6-hydroxy-3-phenyl-1H-inden-1-one, t-butyl 4-(3-hydroxypropyl)piperazine-1-carboxylate instead of 4-(2-hydroxyethyl)morpholine, being stirred for 2 h, and being purified by silica gel column chromatography (EtOAc/CH₂Cl₂=1:1) to obtain the title compound (48%).

¹H NMR (CDCl₃, 300 MHz) δ 8.53 (s, 1H), 8.34 (s, 1H), 8.03 (1H, d, J=9.0 Hz), 7.84 (1H, d, J=6.0 Hz), 7.72 (1H, t, J=7.5 Hz), 7.56 (1H, t, J=7.5 Hz), 7.24 (1H, s), 7.06 (1H, d, J=9.0 Hz), 6.94 (1H, d, J=6.0 Hz), 6.87 (3H, t, J=7.5 Hz), 4.10 (2H, t, J=6.0 Hz), 3.50-3.40 (4H, m), 2.56 (2H, t, J=6.0 Hz), 2.51-2.35 (7H, m), 2.09-1.95 (2H, m)

Step 2. t-Butyl 4-(3-(3-(3,5-difluorophenyl)-1-oxo-2-(quinolin-3-yl)-1H-inden-6-yloxy)propyl)piperazine-1-carboxylate The procedure of Step 7 of Example 1 was repeated except for using t-butyl 4-(3-(2-bromo-3-(3,5-difluorophenyl)-1-oxo-1H-inden-6-yloxy)propyl)piperazine-1-carboxylate obtained in Step 1 as a starting material instead of 6-(2-morpholinoethoxy)-2-bromo-3-phenyl-1H-inden-1-one, 3-quinolinylboronic acid instead of 3-pyridinylboronic acid, and being purified by silica gel column chromatography (EtOAc/hexanes=1:1) to obtain the title compound (39%).

Step 3. 3-(3,5-Difluorophenyl)-6-(3-(piperazin-1-yl)propoxy)-2-(quinolin-3-yl)-1H-inden-1-one To a solution of tert-butyl 4-(3-(3-(3,5-difluorophenyl)-1-oxo-2-(quinolin-3-yl)-1H-inden-6-yloxy)propyl)piperazine-1-carboxylate (42 mg, 0.1 mmol) obtained in Step 2 in CH₂Cl₂ was added trifluoroacetic acid (20 eq, 1.0 mmol). After being stirred for 1 h, the mixture was diluted with CH₂Cl₂ and basicified to pH 9 with a 3N NaOH solution. The organic layer was washed with H₂O and brine, dried over MgSO₄, and concentrated in vacuo to provide the title compound, which was used in the next step without further purification.

Step 4. 3-(3,5-Difluorophenyl)-6-{3-[4-(methylsulfonyl)piperazin-1-yl]propoxy}-2-(quinolin-3-yl)-1H-inden-1-one To a solution of 3-(3,5-difluorophenyl)-6-(3-(piperazin-1-yl)propoxy)-2-(quinolin-3-yl)-1H-inden-1-one (40 mg, 1.2 eq, 0.1 mmol) obtained in Step 3 in CH₂Cl₂ at 0° C. was added triethylamine (1.5 eq) and methylsulfonyl chloride (1.0 eq). The mixture was stirred for 1 h at room temperature and diluted with CH₂Cl₂. The mixture was washed with H₂O and brine, dried over MgSO₄, and concentrated in vacuo. The residue was purified by silica gel column chromatography (EtOAc/hexanes=1:1) to obtain the title compound (53%).

¹H NMR (CDCl₃, 300 MHz) δ 8.53 (1H, s), 8.32 (1H, s), 8.03 (1H, d, J=9.0 Hz), 7.84 (1H, d, J=6.0 Hz), 7.72 (1H, t, J=7.5 Hz), 7.56 (1H, t, J=7.5 Hz), 7.26 (1H, d, J=9.0 Hz), 7.06 (1H, d, J=9.0 Hz), 6.94 (1H, d, J=6.0 Hz), 6.87 (3H, t, J=7.5 Hz), 4.10 (2H, t, J=6.0 Hz), 3.46 (4H, s), 2.56 (2H, t, J=6.0 Hz), 2.51-2.35 (7H, m), 2.09-1.95 (2H, m)

Step 5. 3-(3,5-Difluorophenyl)-6-{3-[4-(methylsulfonyl)piperazin-1-yl]propoxy}-2-(quinolin-3-yl)-1H-inden-1-one hydrochloride salt The procedure of Step 8 of Example 1 was repeated except for using 3-(3,5-difluorophenyl)-6-{3-[4-(methylsulfonyl)piperazin-1-yl]propoxy}-2-(quinolin-3-yl)-1H-inden-1-one obtained in Step 4 as a starting material instead of 6-(2-morpholinoethoxy)-3-phenyl-2-(pyridin-3-yl)-1H-inden-1-one to give the title compound in quantitative yield.

¹H NMR (CDCl₃, 300 MHz) δ 8.85 (2H, d, J=6.0 Hz), 8.73 (1H, s), 8.04 (2H, t, J=9.0 Hz), 7.87-7.80 (1H, m), 7.24-6.94 (6H, m), 4.93 (2H, t, J=6.0 Hz), 4.23 (4H, brs), 3.60-3.20 (m, 6H), 2.76 (3H, brs), 2.55 (2H, brs)

Example 105

3-(3,5-Difluorophenyl)-6-{3-[4-(methylsulfonyl)piperazin-1-yl]propoxy}-2-p-tolyl-1H-inden-1-one hydrochloride salt Step 1. t-Butyl 4-(3-(3-(3,5-difluorophenyl)-1-oxo-2-p-olyl-1H-inden-6-yloxy)propyl)piperazine-1-carboxylate The procedure of Step 7 of Example 1 was repeated except for using t-butyl 4-(3-(2-bromo-3-(3,5-difluorophenyl)-1-oxo-1H-inden-6-yloxy)propyl)piperazine-1-carboxylate obtained in Step 1 of Example 104 as a starting material instead of 6-(2-morpholinoethoxy)-2-bromo-3-phenyl-1H-inden-1-one, p-tolylboronic acid instead of 3-pyridinylboronic acid, and being purified by silica gel column chromatography (EtOAc/hexanes=1:1) to obtain the title compound (75%).

Step 2. 3-(3,5-Difluorophenyl)-6-(3-(piperazin-1-yl)propoxy)-2-p-tolyl-1H-inden-1-one To a solution of tert-butyl 4-(3-(3-(3,5-difluorophenyl)-1-oxo-2-p-tolyl-1H-inden-6-yloxy)propyl)piperazine-1-carboxylate (24 mg, 0.04 mmol) obtained in Step 1 in CH$_2$Cl$_2$ was added trifluoroacetic acid (20 eq, 0.6 mmol). After being stirred for 1 h, the mixture was diluted with CH$_2$Cl$_2$ and basicified to pH 9 with a 3N NaOH solution. The organic layer was washed with H$_2$O and brine, dried over MgSO$_4$, and concentrated in vacuo to provide the title compound.

Step 3. 3-(3,5-Difluorophenyl)-6-{3-[4-(methylsulfonyl)piperazin-1-yl]propoxy}-2-p-tolyl-1H-inden-1-one To a solution of 3-(3,5-difluorophenyl)-6-(3-(piperazin-1-yl)propoxy)-2-p-tolyl-1H-inden-1-one (30 mg, 1.2 eq, 0.063 mmol) obtained in Step 2 in CH$_2$Cl$_2$ at 0° C. was added triethylamine (11 mL, 1.5 eq) and methylsulfonyl chloride (4.0 mL, 1.0 eq). The mixture was stirred for 1 h at room temperature and diluted with CH$_2$Cl$_2$. The mixture was washed with H$_2$O and brine, dried over MgSO$_4$, and concentrated in vacuo. The residue was purified by silica gel column chromatography (EtOAc/hexanes=1:1) to obtain the title compound (17 mg, 74% for 2 steps).
$^1$H NMR (CDCl$_3$, 300 MHz) δ 7.23-7.17 (1H, m), 7.17-7.07 (4H, m), 6.99-6.79 (5H, m), 4.07 (2H, t, J=6.0 Hz), 3.52-3.40 (4H, m), 2.54 (2H, t, J=6.0 Hz), 2.48-2.39 (5H, m), 2.33 (3H, s), 2.06-1.95 (4H, m)

Step 4. 3-(3,5-Difluorophenyl)-6-{3-[4-(methylsulfonyl)piperazin-1-yl]propoxy}-2-p-tolyl-1H-inden-1-one hydrochloride salt The procedure of Step 8 of Example 1 was repeated except for using 3-(3,5-difluorophenyl)-6-{3-[4-(methylsulfonyl)piperazin-1-yl]propoxy}-2-p-tolyl-1H-inden-1-one obtained in Step 3 as a starting material instead of 6-(2-morpholinoethoxy)-3-phenyl-2-(pyridin-3-yl)-1H-inden-1-one to give the title compound in quantitative yield.
$^1$H NMR (CDCl$_3$, 300 MHz) δ 7.72-7.70 (1H, m), 7.5 (1H, q, J=4.5 Hz), 7.13-7.08 (4H, m), 7.00-6.83 (4H, m), 4.29-4.15 (5H, m), 3.75 (2H, brs), 3.55 (2H, brs), 3.22 (2H, brs), 2.77 (2H, brs), 2.50 (2H, brs), 2.33 (3H, s), 2.04-2.02 (2H, m)

Example 106

Synthesis of 2-(3-fluoro-4-methoxyphenyl)-3-(3,5-difluorophenyl)-6-{3-[4-(methylsulfonyl)piperazin-1-yl]propoxy}-1H-inden-1-one hydrochloride salt Step 1. t-Butyl 4-(3-(2-(3-fluoro-4-methoxyphenyl)-3-(3,5-difluorophenyl)-1-oxo-1H-inden-6-yloxy)propyl)piperazine-1-carboxylate The procedure of Step 7 of Example 1 was repeated except for using t-butyl 4-(3-(2-bromo-3-(3,5-difluorophenyl)-1-oxo-1H-inden-6-yloxy)propyl)piperazine-1-carboxylate obtained in Step 1 of Example 104 as a starting material instead of 6-(2-morpholino ethoxy)-2-bromo-3-phenyl-1H-inden-1-one, 3-fluoro-4-methoxyphenylboronic acid instead of 3-pyridinylboronic acid, and being purified by silica gel column chromatography (EtOAc/hexanes=1:1) to obtain the title compound.

Step 2. 3-(3,5-Difluorophenyl)-2-(3-fluoro-4-methoxyphenyl)-6-(3-(piperazin-1-yl)propoxy)-1H-inden-1-one To a solution of tert-butyl 4-(3-(2-(3-fluoro-4-methoxyphenyl)-3-(3,5-difluorophenyl)-1-oxo-1H-inden-6-yloxy)propyl)piperazine-1-carboxylate (96 mg, 0.2 mmol) obtained in Step 1 in CH$_2$Cl$_2$ was added trifluoroacetic acid (20 eq, 2.4 mmol). After being stirred for 1 h, the mixture was diluted with CH$_2$Cl$_2$ and basicified to pH 9 with a 3N NaOH solution. The organic layer was washed with H$_2$O and brine, dried over MgSO$_4$, and concentrated in vacuo to provide the title compound.

Step 3. 3-(3,5-Difluorophenyl)-2-(3-fluoro-4-methoxyphenyl)-6-{3-[4-(methylsulfonyl)piperazin-1-yl]propoxy}-1H-inden-1-one To a solution of 3-(3,5-difluorophenyl)-2-(3-fluoro-4-methoxyphenyl)-6-(3-(piperazin-1-yl)propoxy)-1H-inden-1-one (70 mg, 1.2 eq, 0.1 mmol) obtained in Step 2 in CH$_2$Cl$_2$ at 0° C. was added triethylamine (1.5 eq) and methylsulfonyl chloride (1.0 eq). The mixture was stirred for 1 h at room temperature and diluted with CH$_2$Cl$_2$. The mixture was washed with H$_2$O and brine, dried over MgSO$_4$, and concentrated in vacuo. The residue was purified by silica gel column chromatography (EtOAc/hexanes=1:1) to obtain the title compound (47%).
$^1$H NMR (CDCl$_3$, 300 MHz) δ 7.26-7.18 (2H, m), 7.13-7.08 (1H, m), 7.00-6.95 (2H, m), 6.90 (2H, d, J=6.0 Hz), 6.85-6.79 (2H, m), 4.07 (2H, t, J=6.0 Hz), 3.89 (3H, s), 3.27-3.21 (4H, m), 2.80 (3H, s), 2.65-2.51 (6H, m), 2.03-1.97 (2H, m)

Step 4. 3-(3,5-Difluorophenyl)-2-(3-fluoro-4-methoxyphenyl)-6-{3-[4-(methylsulfonyl)piperazin-1-yl]propoxy}-1H-inden-1-one hydrochloride salt The procedure of Step 8 of Example 1 was repeated except for using 3-(3,5-difluorophenyl)-2-(3-fluoro-4-methoxyphenyl)-6-{3-[4-(methylsulfonyl)piperazin-1-yl]propoxy}-1H-inden-1-one obtained in Step 3 as a starting material instead of 6-(2-morpholinoethoxy)-3-phenyl-2-(pyridin-3-yl)-1H-inden-1-one to give the title compound in quantitative yield.
$^1$H NMR (CDCl$_3$, 300 MHz) δ 7.2-7.1 (3H, m), 7.0 (2H, d, J=12 Hz), 6.9 (2H, d, J=6.0 Hz), 6.9-6.8 (2H, m), 4.2 (2H, m), 3.9 (3H, s), 3.9-3.8 (2H, m), 2.9 (3H, s), 2.1-2.0 (4H, m), 1.7-1.5 (2H, m), 1.3-1.2 (4H, m)

Example 107

Synthesis of 3-(3,5-difluorophenyl)-2-(6-methoxypyridin-3-yl)-6-{3-[4-(methylsulfonyl)piperazin-1-yl]propoxy}-1H-inden-1-one hydrochloride salt Step 1. t-Butyl 4-(3-(3-(3,5-difluorophenyl)-2-(6-methoxypyridin-3-yl)-1-oxo-1H-inden-6-yloxy)propyl)piperazine-1-carboxylate The procedure of Step 7 of Example 1 was repeated except for using t-butyl 4-(3-(2-bromo-3-(3,5-difluorophenyl)-1-oxo-1H-inden-6-yloxy)propyl)piperazine-1-carboxylate obtained in Step 1 of Example 104 as a starting material instead of 6-(2-morpholinoethoxy)-2-bromo-3-phenyl-1H-inden-1-one, 6-methoxy-3-pyridinylboronic acid instead of 3-pyridinylboronic acid, and being purified by silica gel column chromatography (EtOAc/hexanes=1:1) to obtain the title compound.

Step 2. 3-(3,5-Difluorophenyl)-2-(6-methoxypyridin-3-yl)-6-(3-(piperazin-1-yl)propoxy)-1H-inden-1-one To a solution of tert-butyl 4-(3-(3-(3,5-difluorophenyl)-2-(6-methoxypyridin-3-yl)-1-oxo-1H-inden-6-yloxy)propyl)

piperazine-1-carboxylate (115 mg, 0.2 mmol) obtained in Step 1 in CH₂Cl₂ was added trifluoroacetic acid (20 eq, 3.0 mmol). After being stirred for 1.5 h, the mixture was diluted with CH₂Cl₂ and basicified to pH 9 with a 3N NaOH solution. The organic layer was washed with H₂O and brine, dried over MgSO₄, and concentrated in vacuo to provide the title compound.

Step 3. 3-(3,5-Difluorophenyl)-2-(6-methoxypyridin-3-yl)-6-{3-[4-(methylsulfonyl)piperazin-1-yl]propoxy}-1H-inden-1-one To a solution of 3-(3,5-difluorophenyl)-2-(6-methoxypyridin-3-yl)-6-(3-(piperazin-1-yl)propoxy)-1H-inden-1-one (90 mg, 1.2 eq, 0.2 mmol) obtained in Step 2 in CH₂Cl₂ at 0° C. was added triethylamine (1.5 eq) and methylsulfonyl chloride (1.0 eq). The mixture was stirred for 1 h at room temperature and diluted with CH₂Cl₂. The mixture was washed with H₂O and brine, dried over MgSO₄, and concentrated in vacuo. The residue was purified by silica gel column chromatography (EtOAc/hexanes=1:1) to obtain the title compound (20%).
¹H NMR (CDCl₃, 300 MHz) δ 7.22-7.08 (3H, m), 6.98-6.76 (6H, m), 4.08 (2H, t, J=4.5 Hz), 3.89 (3H, s), 3.34-3.19 (4H, m), 2.80 (3H, s), 2.63-2.52 (6H, m), 2.05-1.99 (2H, m)

Step 4. 3-(3,5-Difluorophenyl)-2-(6-methoxypyridin-3-yl)-6-{3-[4-(methylsulfonyl)piperazin-1-yl]propoxy}-1H-inden-1-one hydrochloride salt The procedure of Step 8 of Example 1 was repeated except for using 3-(3,5-difluorophenyl)-2-(6-methoxypyridin-3-yl)-6-{3-[4-(methylsulfonyl)piperazin-1-yl]propoxy}-1H-inden-1-one obtained in Step 3 as a starting material instead of 6-(2-morpholinoethoxy)-3-phenyl-2-(pyridin-3-yl)-1H-inden-1-one to give the title compound in quantitative yield.
¹H NMR (CDCl₃, 300 MHz) δ 7.6-7.5 (1H, m), 7.2-7.1 (3H, m), 7.1-7.0 (2H, m), 6.9 (2H, d, J=6.0 Hz), 6.9-6.8 (1H, m), 4.2 (2H, t, J=6.0 Hz), 4.0 (3H, s), 3.9-3.8 (2H, m), 3.3-3.2 (2H, s), 3.1-3.0 (2H, m), 2.9 (3H, s), 2.5-2.4 (2H, m), 2.1-2.0 (4H, m)

Example 108

Synthesis of 3-(2,4-difluorophenyl)-6-{3-[4-(methylsulfonyl)piperazin-1-yl]propoxy}-2-p-tolyl-1H-inden-1-one Step 1. 2-Bromo-3-(2,4-difluorophenyl)-6-[3-(4-(methylsulfonyl)piperazin-1-yl)propoxy]-1H-inden-1-one

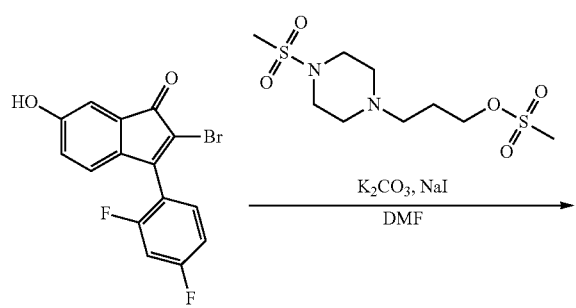

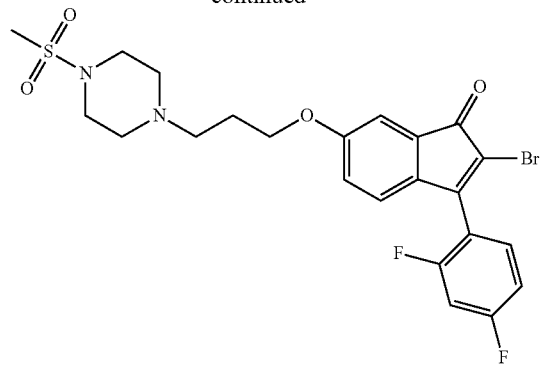

To a solution of 2-bromo-3-(2,4-difluorophenyl)-6-hydroxy-1H-inden-1-one (500 mg, 1.48 mmol) obtained in Step 5 of Example 82 in DMF was added K₂CO₃ (3 eq), 3-[4-(methylsulfonyl)piperazin-1-yl]propyl methanesulfonate (669 mg, 2.23 mmol, 1.5 eq), and NaI (0.3 eq) sequentially. The mixture was heated to 60° C. for 16 h. The reaction mixture was quenched with H₂O and extracted with EtOAc. The organic layer was washed with H₂O and brine, dried over MgSO₄, and concentrated in vacuo. The residue was purified by silica gel column chromatography (2% MeOH/CH₂Cl₂) to obtain the title compound (66%).
¹H NMR (300 MHz, CDCl₃): δ 1.98 (m, 2H), 2.57 (m, 6H), 2.80 (s, 3H), 3.25 (m, 4H), 4.05 (t, 2H), 6.80 (m, 2H), 7.03 (m, 2H), 7.20 (s, 1H), 7.51 (m, 1H)

Step 2. 3-(2,4-Difluorophenyl)-6-{3-[4-(methylsulfonyl)piperazin-1-yl]propoxy}-2-p-tolyl-1H-inden-1-one The procedure of Step 7 of Example 1 was repeated except for using 2-bromo-3-(2,4-difluorophenyl)-6-[3-(4-(methylsulfonyl)piperazin-1-yl)propoxy]-1H-inden-1-one obtained in Step 1 as a starting material instead of 6-(2-morpholinoethoxy)-2-bromo-3-phenyl-1H-inden-1-one and p-tolylboronic acid instead of 3-pyridinylboronic acid to obtain the title compound (76%).
¹H NMR (300 MHz, CDCl₃): δ 1.97 (m, 2H), 2.32 (s, 3H), 2.57 (m, 6H), 2.80 (s, 3H), 3.27 (m, 4H), 4.05 (t, 2H), 6.81 (m, 2H), 6.95 (m, 2H), 7.11 (m, 4H), 7.20 (d, 1H, J=1.9 Hz), 7.26 (m, 1H)

Example 109

Synthesis of 3-(2,4-difluorophenyl)-6-{3-[4-(methylsulfonyl)piperazin-1-yl]propoxy}-2-(6-methoxypyridin-3-yl)-1H-inden-1-one The procedure of Step 7 of Example 1 was repeated except for using 2-bromo-3-(2,4-difluorophenyl)-6-[3-(4-(methylsulfonyl)piperazin-1-yl)propoxy]-1H-inden-1-one obtained in Step 1 of Example 108 as a starting material instead of 6-(2-morpholino ethoxy)-2-bromo-3-phenyl-1H-inden-1-one and 6-methoxy-3-pyridinylboronic acid instead of 3-pyridinylboronic acid to obtain the title compound (77%).
¹H NMR (300 MHz, CDCl₃): δ 1.98 (m, 2H), 2.58 (m, 6H), 2.80 (s, 3H), 3.27 (m, 4H), 3.91 (s, 3H), 4.07 (t, 2H), 6.70 (dd, 1H, J=0.7, 8.7 Hz), 6.82 (m, 2H), 6.95 (m, 2H), 7.20 (d, 1H, J=1.8 Hz), 7.31 (m, 1H), 7.53 (dd, 1H, J=2.4, 8.7 Hz), 8.06 (dd, 1H, J=0.7, 2.4 Hz)

Example 110

Synthesis of 2-(3-fluoro-4-methoxyphenyl)-3-(2,4-difluorophenyl)-6-{3-[4-(methylsulfonyl)piperazin-1-yl]propoxy}-1H-inden-1-one The procedure of Step 7 of Example 1 was repeated except for using 2-bromo-3-(2,4-difluorophenyl)-6-[3-(4-(methylsulfonyl)piperazin-1-yl)propoxy]-1H-inden-1-one obtained in Step 1 of Example 108 as a starting material instead of 6-(2-morpholinoethoxy)-2-bromo-3-phenyl-1H-inden-1-one and 3-fluoro-4-methoxyphenylboronic acid instead of 3-pyridinylboronic acid to obtain the title compound (77%).
$^1$H NMR (300 MHz, CDCl$_3$): δ 1.98 (m, 2H), 2.58 (m, 6H), 2.79 (s, 3H), 3.25 (m, 4H), 3.87 (s, 3H), 4.06 (t, 2H), 6.82 (m, 3H), 7.00 (m, 3H), 7.18 (s, 1H), 7.29 (m, 2H)

Example 111

Synthesis of 3-(2,4-difluorophenyl)-6-{3-[4-(methylsulfonyl)piperazin-1-yl]propoxy}-2-(quinolin-3-yl)-1H-inden-1-one The procedure of Step 7 of Example 1 was repeated except for using 2-bromo-3-(2,4-difluorophenyl)-6-[3-(4-(methylsulfonyl)piperazin-1-yl)propoxy]-1H-inden-1-one obtained in Step 1 of Example 108 as a starting material instead of 6-(2-morpholinoethoxy)-2-bromo-3-phenyl-1H-inden-1-one and 3-quinolinylboronic acid instead of 3-pyridinylboronic acid to obtain the title compound (83%).
$^1$H NMR (300 MHz, CDCl$_3$): δ 2.03 (m, 2H), 2.06 (m, 6H), 2.80 (s, 3H), 3.27 (m, 4H), 4.09 (t, 2H), 6.86 (m, 1H), 6.96 (m, 3H), 7.26 (m, 1H), 7.35 (m, 1H), 7.56 (m, 1H), 7.84 (d, 1H, J=8.2 Hz), 8.03 (d, 1H, J=8.2 Hz), 8.32 (s, 1H), 8.57 (s, 1H)

Example 112

Synthesis of 3-(2,4-difluorophenyl)-6-[2-(1,1-dioxothiomorpholin-4-yl)ethoxy]-2-p-tolyl-1H-inden-1-one

Step 1. 2-Bromo-3-(2,4-difluorophenyl)-6-[2-(1,1-dioxothiomorpholin-4-yl)ethoxy]-1H-inden-1-one The procedure of Step 6 of Example 1 was repeated except for using 2-bromo-3-(2,4-difluorophenyl)-6-hydroxy-1H-inden-1-one obtained in Step 5 of Example 82 as a starting material instead of 2-bromo-6-hydroxy-3-phenyl-1H-inden-1-one, 2-(1,1-dioxothiomorpholin-4-yl)ethanol instead of 4-(2-hydroxyethyl)morpholine to obtain the title compound (65%).
$^1$H NMR (300 MHz, CDCl$_3$): δ 3.00 (t, 2H), 3.14 (m, 4H), 3.17 (m, 4H), 4.11 (t, 2H), 6.78 (m, 1H), 6.83 (m, 1H), 7.05 (m, 2H), 7.16 (d, 1H, J=Hz), 7.68 (m, 1H)

Step 2. 3-(2,4-Difluorophenyl)-6-[2-(1,1-dioxothiomorpholin-4-yl)ethoxy]-2-p-tolyl-1H-inden-1-one The procedure of Step 7 of Example 1 was repeated except for using 2-bromo-3-(2,4-difluorophenyl)-6-[2-(1,1-dioxothiomorpholin-4-yl)ethoxy]-1H-inden-1-one obtained in Step 1 as a starting material instead of 6-(2-morpholinoethoxy)-2-bromo-3-phenyl-1H-inden-1-one and p-tolylboronic acid instead of 3-pyridinylboronic acid to obtain the title compound (70%).
$^1$H NMR (300 MHz, CDCl$_3$): δ 2.32 (s, 3H), 3.00 (t, 2H), 3.10 (m, 4H), 3.16 (m, 4H), 4.13 (t, 2H), 6.83 (m, 2H), 6.93 (m, 2H), 7.13 (m, 5H), 7.28 (m, 1H)

Example 113

Synthesis of 3-(2,4-difluorophenyl)-2-(6-methoxypyridin-3-yl)-6-[2-(1,1-dioxothiomorpholin-4-yl)ethoxy]-1H-inden-1-one The procedure of Step 7 of Example 1 was repeated except for using 2-bromo-3-(2,4-difluorophenyl)-6-[2-(1,1-dioxothiomorpholin-4-yl)ethoxy]-1H-inden-1-one obtained in Step 1 of Example 112 as a starting material instead of 6-(2-morpholinoethoxy)-2-bromo-3-phenyl-1H-inden-1-one and 6-methoxy-3-pyridinylboronic acid instead of 3-pyridinylboronic acid to obtain the title compound (67%).
$^1$H NMR (300 MHz, CDCl$_3$): δ 3.01 (t, 2H), 3.12 (m, 4H), 3.16 (m, 4H), 3.91 (s, 3H), 4.12 (t, 2H), 6.69 (d, 1H, J=8.2 Hz), 6.85 (m, 2H), 6.97 (m, 2H), 7.17 (d, 1H, J=2.0 Hz), 7.32 (m, 1H), 7.53 (dd, 1H, J=2.3, 8.7 Hz), 8.06 (d, 1H, J=1.5 Hz)

Example 114

Synthesis of 2-(3-fluoro-4-methoxyphenyl)-3-(2,4-difluorophenyl)-6-[2-(1,1-dioxothiomorpholin-4-yl)ethoxy]-1H-inden-1-one The procedure of Step 7 of Example 1 was repeated except for using 2-bromo-3-(2,4-difluorophenyl)-6-[2-(1,1-dioxothiomorpholin-4-yl)ethoxy]-1H-inden-1-one obtained in Step 1 of Example 112 as a starting material instead of 6-(2-morpholinoethoxy)-2-bromo-3-phenyl-1H-inden-1-one and 3-fluoro-4-methoxyphenylboronic acid instead of 3-pyridinylboronic acid to obtain the title compound (74%).
$^1$H NMR (300 MHz, CDCl$_3$): δ 3.00 (t, 2H), 3.10 (m, 4H), 3.18 (m, 4H), 3.87 (s, 3H), 4.12 (t, 2H), 6.83 (m, 3H), 7.00 (m, 4H), 7.16 (s, 1H), 7.28 (m, 1H)

Example 115

Synthesis of 3-(2,4-difluorophenyl)-6-[2-(1,1-dioxothiomorpholin-4-yl)ethoxy]-2-(quinolin-3-yl)-1H-inden-1-one The procedure of Step 7 of Example 1 was repeated except for using 2-bromo-3-(2,4-difluorophenyl)-6-[2-(1,1-dioxothiomorpholin-4-yl)ethoxy]-1H-inden-1-one obtained in Step 1 of Example 112 as a starting material instead of 6-(2-morpholinoethoxy)-2-bromo-3-phenyl-1H-inden-1-one and 3-quinolinylboronic acid instead of 3-pyridinylboronic acid to obtain the title compound (74%).
$^1$H NMR (300 MHz, CDCl$_3$): δ 3.03 (m, 2H), 3.10 (m, 4H), 3.19 (m, 4H), 4.16 (t, 2H), 6.86 (m, 1H), 6.97 (m, 3H), 7.23 (m, 1H), 7.35 (m, 1H), 7.56 (m, 1H), 7.70 (m, 1H), 7.83 (d, 1H, J=8.3 Hz), 8.01 (d, 1H, J=8.3 Hz), 8.32 (d, 1H, J=1.5 Hz), 8.57 (d, 1H, J=2.0 Hz)

Example 116

Synthesis of 3-(2,4-difluorophenyl)-6-{2-[4-(methylsulfonyl)piperazin-1-yl]ethoxy}-2-p-tolyl-1H-inden-1-one

Step 1. 2-Bromo-3-(2,4-difluorophenyl)-6-{2-[4-(methylsulfonyl)piperazin-1-yl]ethoxy}-1H-inden-1-one The procedure of Step 1 of Example 108 was repeated except for using 2-[4-(methylsulfonyl)piperazin-1-yl]ethyl methanesulfonate instead of 3-[4-(methylsulfonyl)piperazin-1-yl]propyl methanesulfonate to obtain the title compound (65%).

¹H NMR (300 MHz, CDCl₃): δ 7.47-7.54 (m, 1H), 7.18 (d, 1H), 6.97-7.09 (m, 2H), 6.75-6.85 (m, 2H), 4.03 (t, 2H), 3.27 (m, 4H), 2.86 (t, 2H), 2.78 (s, 3H), 2.69 (m, 4H)

Step 2. 3-(2,4-Difluorophenyl)-6-{2-[4-(methylsulfonyl)piperazin-1-yl]ethoxy}-2-p-tolyl-1H-inden-1-one The procedure of Step 7 of Example 1 was repeated except for using 2-bromo-3-(2,4-difluorophenyl)-6-{2-[4-(methylsulfonyl)piperazin-1-yl]ethoxy}-1H-inden-1-one obtained in Step 1 as a starting material instead of 6-(2-morpholinoethoxy)-2-bromo-3-phenyl-1H-inden-1-one and p-tolylboronic acid instead of 3-pyridinylboronic acid to obtain the title compound (73%).

¹H NMR (300 MHz, CD₃OD): δ 7.28 (m, 1H), 7.06-7.18 (m, 5H), 6.89-6.95 (m, 2H), 6.78-6.83 (m, 2H), 4.13 (t, 2H), 3.27 (m, 4H), 2.86 (t, 2H), 2.78 (s, 3H), 2.70 (m, 4H), 2.31 (s, 3H)

Example 117

Synthesis of 3-(2,4-difluorophenyl)-2-(6-methoxypyridin-3-yl)-6-{2-[4-(methylsulfonyl)piperazin-1-yl]ethoxy}-1H-inden-1-one The procedure of Step 7 of Example 1 was repeated except for using 2-bromo-3-(2,4-difluorophenyl)-6-{2-[4-(methylsulfonyl)piperazin-1-yl]ethoxy}-1H-inden-1-one obtained in Step 1 of Example 116 as a starting material instead of 6-(2-morpholinoethoxy)-2-bromo-3-phenyl-1H-inden-1-one and 6-methoxy-3-pyridinylboronic acid instead of 3-pyridinylboronic acid to obtain the title compound (68%).

¹H NMR (200 MHz, CD₃OD): δ 8.07 (s, 1H), 7.52-7.58 (m, 2H), 7.21 (d, 1H), 6.91-6.99 (m, 2H), 6.85-6.90 (m, 2H), 6.69 (d, 1H), 4.16 (t, 2H), 3.73 (s, 3H), 3.30 (m, 4H), 2.90 (t, 2H), 2.81 (s, 3H), 2.73 (m, 4H)

Example 118

Synthesis of 2-(3-fluoro-4-methoxyphenyl)-3-(2,4-difluorophenyl)-6-{2-[4-(methylsulfonyl)piperazin-1-yl]ethoxy}-1H-inden-1-one The procedure of Step 7 of Example 1 was repeated except for using 2-bromo-3-(2,4-difluorophenyl)-6-{2-[4-(methylsulfonyl)piperazin-1-yl]ethoxy}-1H-inden-1-one obtained in Step 1 of Example 116 as a starting material instead of 6-(2-morpholinoethoxy)-2-bromo-3-phenyl-1H-inden-1-one and 3-fluoro-4-methoxyphenylboronic acid instead of 3-pyridinylboronic acid to obtain the title compound (68%).

¹H NMR (300 MHz, CDCl₃): δ 7.28 (d, 1H), 7.18 (d, 1H), 6.97-7.03 (m, 4H), 6.79-6.85 (m, 3H), 4.14 (t, 2H), 3.87 (s, 3H), 3.28 (m, 4H), 2.87 (t, 2H), 2.79 (s, 3H), 2.71 (m, 4H)

Example 119

Synthesis of 3-(2,4-difluorophenyl)-6-{2-[4-(methylsulfonyl)piperazin-1-yl]ethoxy}-2-(quinolin-3-yl)-1H-inden-1-one The procedure of Step 7 of Example 1 was repeated except for using 2-bromo-3-(2,4-difluorophenyl)-6-{2-[4-(methylsulfonyl)piperazin-1-yl]ethoxy}-1H-inden-1-one obtained in Step 1 of Example 116 as a starting material instead of 6-(2-morpholinoethoxy)-2-bromo-3-phenyl-1H-inden-1-one and 3-quinolinylboronic acid instead of 3-pyridinylboronic acid to obtain the title compound (71%).

¹H NMR (300 MHz, CDCl₃): δ 8.56 (d, J=1.8 Hz, 1H), 8.32 (d, 1H), 8.01 (d, J=8.4 Hz, 1H), 7.83 (d, J=7.8 Hz, 1H), 7.68-7.73 (m, 1H), 7.53-7.58 (m, 1H), 7.32-7.40 (m, 1H), 7.25 (m, 1H), 6.92-7.00 (m, 3H), 6.85 (dd, J=8.1 Hz, 2.4 Hz, 1H), 4.17 (t, 2H), 3.28 (s, 3H), 2.90 (t, 2H), 2.79 (s, 3H), 2.72 (m, 4H)

Example 120

Synthesis of 3-(2,4-difluorophenyl)-6-{2-[1-(methylsulfonyl)piperidin-4-yl]ethoxy}-2-p-tolyl-1H-inden-1-one Step 1. 2-Bromo-3-(2,4-difluorophenyl)-6-{2-[4-(methylsulfonyl)piperidin-4-yl]ethoxy}-1H-inden-1-one The procedure of Step 1 of Example 108 was repeated except for using 2-[4-(methylsulfonyl)piperidin-4-yl]ethyl methanesulfonate instead of 3-[4-(methylsulfonyl)piperazin-1-yl]propyl methanesulfonate to obtain the title compound (63%).

¹H NMR (300 MHz, CDCl₃): δ 7.47-7.54 (m, 1H), 7.15 (d, J=2.1 Hz, 1H), 6.96-7.11 (m, 2H), 6.83 (dd, J=8.1 Hz, 2.4 Hz, 1H), 6.73 (dd, J=8.1 Hz, 2.4 Hz, 1H), 4.03 (t, 2H), 3.81 (m, 2H), 2.70 (s, 3H), 2.60-2.66 (m, 2H), 1.70-1.87 (m, 4H), 1.64-1.67 (m, 1H), 1.33-1.46 (m, 2H)

Step 2. 3-(2,4-Difluorophenyl)-6-{2-[1-(methylsulfonyl)piperidin-4-yl]ethoxy}-2-p-tolyl-1H-inden-1-one The procedure of Step 7 of Example 1 was repeated except for using 2-bromo-3-(2,4-difluorophenyl)-6-{2-[4-(methylsulfonyl)piperidin-4-yl]ethoxy}-1H-inden-1-one obtained in Step 1 as a starting material instead of 6-(2-morpholinoethoxy)-2-bromo-3-phenyl-1H-inden-1-one and p-tolylboronic acid instead of 3-pyridinylboronic acid to obtain the title compound (68%).

¹H NMR (300 MHz, CDCl₃): δ 7.30 (d, 1H), 7.06-7.15 (m, 5H), 6.85-6.95 (m, 2H), 6.76-6.82 (m, 2H), 4.05 (t, 2H), 3.81 (m, 2H), 2.77 (s, 3H), 2.63 (t, 2H), 2.31 (s, 3H), 1.81-1.88 (m, 2H), 1.75-1.79 (m, 2H), 1.58-1.68 (m, 1H), 1.34-1.44 (m, 2H)

Example 121

Synthesis of 3-(2,4-difluorophenyl)-2-(6-methoxypyridin-3-yl)-6-{2-[1-(methylsulfonyl)piperidin-4-yl]ethoxy}-1H-inden-1-one The procedure of Step 7 of Example 1 was repeated except for using 2-bromo-3-(2,4-difluorophenyl)-6-{2-[4-(methylsulfonyl)piperidin-4-yl]ethoxy}-1H-inden-1-one obtained in Step 1 of Example 120 as a starting material instead of 6-(2-morpholinoethoxy)-2-bromo-3-phenyl-1H-inden-1-one and 6-methoxy-3-pyridinylboronic acid instead of 3-pyridinylboronic acid to obtain the title compound (68%).

¹H NMR (300 MHz, CDCl₃): δ 8.06 (s, 1H), 7.53 (d, J=8.7 Hz, 1H), 7.31-7.36 (m, 1H), 7.17 (s, 1H), 6.92-7.01 (m, 2H), 6.78-6.88 (m, 2H), 6.69 (d, J=8.7 Hz, 1H), 4.08 (t, 2H), 3.92 (s, 3H), 3.83 (m, 2H), 2.79 (s, 3H), 2.64 (t, 2H), 1.90-2.06 (m, 2H), 1.77-1.85 (m, 2H), 1.67-1.69 (m, 1H), 1.39-1.46 (m, 2H)

Example 122

Synthesis of 2-(3-fluoro-4-methoxyphenyl)-3-(2,4-difluorophenyl)-6-{2-[1-(methylsulfonyl)piperidin-4-yl]ethoxy}-1H-inden-1-one The procedure of Step 7 of Example 1 was repeated except for using 2-bromo-3-(2,4-difluorophenyl)-6-{2-[4-(methylsulfonyl)piperidin-4-yl]ethoxy}-1H-inden-1-one obtained in Step 1 of Example 120 as a starting material instead of 6-(2-morpholinoethoxy)-2-bromo-3-phenyl-1H-inden-1-one and 3-fluoro-4-methoxyphenylboronic acid instead of 3-pyridinylboronic acid to obtain the title compound (68%).

$^1$H NMR (300 MHz, CDCl$_3$): δ 7.30 (d, 1H), 7.14 (d, 1H), 6.94-7.02 (m, 4H), 6.76-6.86 (m, 3H), 4.05 (t, 2H), 3.87 (s, 3H), 3.79 (m, 2H), 2.77 (s, 3H), 2.66 (t, 2H), 1.84-1.89 (m, 2H), 1.77-1.79 (m, 2H), 1.68-1.76 (m, 1H), 1.38-1.45 (m, 2H)

Example 123

Synthesis of 3-(2,4-difluorophenyl)-6-{2-[1-(methylsulfonyl)piperidin-4-yl]ethoxy}-2-(quinolin-3-yl)-1H-inden-1-one The procedure of Step 7 of Example 1 was repeated except for using 2-bromo-3-(2,4-difluorophenyl)-6-{2-[4-(methylsulfonyl)piperidin-4-yl]ethoxy}-1H-inden-1-one obtained in Step 1 of Example 120 as a starting material instead of 6-(2-morpholinoethoxy)-2-bromo-3-phenyl-1H-inden-1-one and 3-quinolinylboronic acid instead of 3-pyridinylboronic acid to obtain the title compound (70%).

$^1$H NMR (300 MHz, CDCl$_3$): δ 8.56 (s, 1H), 8.31 (s, 1H), 8.01 (d, J=8.1 Hz, 1H), 7.82 (d, J=7.8 Hz, 1H), 7.67-7.72 (m, 1H), 7.52-7.57 (m, 1H), 7.31-7.36 (m, 1H), 7.21 (m, 1H), 6.93-6.99 (m, 3H), 6.82 (d, J=7.8 Hz, 1H), 4.08 (t, 2H), 3.83 (m, 2H), 2.71 (s, 3H), 2.67 (t, 2H), 1.79-2.04 (m, 4H), 1.70-1.77 (m, 1H), 1.35-1.46 (m, 2H)

Example 124

Synthesis of 3-(2,4-difluorophenyl)-6-[2-(morpholin-4-yl)ethoxy]-2-p-tolyl-1H-inden-1-one Step 1. 2-Bromo-3-(2,4-difluorophenyl)-6-{2-(morpholin-4-yl)ethoxy}-1H-inden-1-one The procedure of Step 1 of Example 108 was repeated except for using 4-(2-chloroethyl)morpholine hydrochloride instead of 3-[4-(methylsulfonyl)piperazin-1-yl]propyl methanesulfonate, not adding NaI, and being stirred at 70° C. for 4 h to obtain the title compound (68%).

$^1$H NMR (300 MHz, CDCl$_3$): δ 2.57 (m, 4H), 2.80 (t, 2H), 3.74 (m, 4H), 4.12 (t, 2H), 6.80 (m, 2H), 7.04 (m, 2H), 7.17 (s, 1H), 7.51 (m, 1H)

Step 2. 3-(2,4-Difluorophenyl)-6-[2-(morpholin-4-yl)ethoxy]-2-p-tolyl-1H-inden-1-one The procedure of Step 7 of Example 1 was repeated except for using 2-bromo-3-(2,4-difluorophenyl)-6-{2-(morpholin-4-yl)ethoxy}-1H-inden-1-one obtained in Step 1 as a starting material instead of 6-(2-morpholinoethoxy)-2-bromo-3-phenyl-1H-inden-1-one and p-tolylboronic acid instead of 3-pyridinylboronic acid to obtain the title compound (80%).

$^1$H NMR (300 MHz, CDCl$_3$): δ 2.32 (s, 3H), 2.59 (m, 4H), 2.82 (t, 2H), 3.74 (m, 4H), 4.15 (t, 2H), 6.83 (m, 2H), 6.93 (m, 2H), 7.13 (m, 5H), 7.56 (m, 1H)

Example 125

Synthesis of 3-(2,4-difluorophenyl)-2-(6-methoxypyridin-3-yl)-6-[2-(morpholin-4-yl)ethoxy]-1H-inden-1-one The procedure of Step 7 of Example 1 was repeated except for using 2-bromo-3-(2,4-difluorophenyl)-6-{2-(morpholin-4-yl)ethoxy}-1H-inden-1-one obtained in Step 1 of Example 124 as a starting material instead of 6-(2-morpholinoethoxy)-2-bromo-3-phenyl-1H-inden-1-one and 6-methoxy-3-pyridinylboronic acid instead of 3-pyridinylboronic acid to obtain the title compound (81%).

$^1$H NMR (300 MHz, CDCl$_3$): δ 2.59 (m, 4H), 2.82 (t, 2H), 3.74 (m, 4H), 3.91 (s, 3H), 4.15 (t, 2H), 6.69 (d, 1H, J=8.6 Hz), 6.83 (m, 2H), 6.97 (m, 2H), 7.19 (s, 1H), 7.32 (m, 1H), 7.54 (dd, 1H, J=2.4, 8.6 Hz), 8.05 (s, 1H)

Example 126

Synthesis of 2-(3-fluoro-4-methoxyphenyl)-3-(2,4-difluorophenyl)-6-[2-(morpholin-4-yl)ethoxy]-1H-inden-1-one The procedure of Step 7 of Example 1 was repeated except for using 2-bromo-3-(2,4-difluorophenyl)-6-{2-(morpholin-4-yl)ethoxy}-1H-inden-1-one obtained in Step 1 of Example 124 as a starting material instead of 6-(2-morpholinoethoxy)-2-bromo-3-phenyl-1H-inden-1-one and 3-fluoro-4-methoxyphenylboronic acid instead of 3-pyridinylboronic acid to obtain the title compound (81%).

$^1$H NMR (300 MHz, CDCl$_3$): δ 2.58 (t, 4H), 2.82 (t, 2H), 3.75 (t, 4H), 3.87 (s, 3H), 4.15 (t, 2H), 6.84 (m, 3H), 7.00 (m, 4H), 7.18 (s, 1H), 7.58 (m, 1H)

Example 127

Synthesis of 3-(2,4-difluorophenyl)-6-[2-(morpholin-4-yl)ethoxy]-2-(quinolin-3-yl)-1H-inden-1-one The procedure of Step 7 of Example 1 was repeated except for using 2-bromo-3-(2,4-difluorophenyl)-6-{2-(morpholin-4-yl)ethoxy}-1H-inden-1-one obtained in Step 1 of Example 124 as a starting material instead of 6-(2-morpholinoethoxy)-2-bromo-3-phenyl-1H-inden-1-one and 3-quinolinylboronic acid instead of 3-pyridinylboronic acid to obtain the title compound (85%).

$^1$H NMR (300 MHz, CDCl$_3$): δ 2.60 (t, 4H), 2.84 (t, 2H), 3.75 (t, 4H), 4.18 (t, 2H), 6.87 (m, 1H), 6.96 (m, 3H), 7.25 (m, 1H), 7.36 (m, 1H), 7.56 (m, 1H), 7.70 (m, 1H), 7.83 (d, 1H, J=7.9 Hz), 8.02 (d, 1H, J=8.2 Hz), 8.32 (s, 1H), 8.57 (d, 1H, J=2.0 Hz)

Example 128

Synthesis of 3-(3,5-difluorophenyl)-5-[2-(morpholin-4-yl)ethoxy]-2-(pyridin-3-yl)-1H-inden-1-one

Step 1. 3-Bromo-5-methoxy-1H-inden-1-one

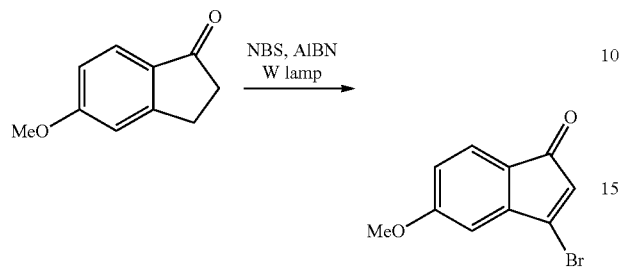

5-Methoxy-1H-indan-1-one (1.3 g, 8.01 mmol) was placed into a flask and dissolved in $CCl_4$ (10 mL). To the resulting solution, NBS (3.14 g, 17.62 mmol) and AIBN (394 mg, 2.40 mmol) were added. The resulting mixture was allowed to reflux for 3 h, while being irradiated by a tungsten lamp (375W). After cooling to room temperature, triethylamine (4.05 g, 40.05 mmol) was added and stirred for 16 h at room temperature. The reaction mixture was quenched with sat. $Na_2S_2O_3$, extracted with $CH_2Cl_2$ (20 mL×3). The organic layers were washed $H_2O$ and brine, dried over $MgSO_4$ and concentrated in vacuo to give the desired product (1.55 g, 80%).

$^1$H NMR (300 MHz, $CDCl_3$) δ 3.89 (s, 3H), 6.21 (s, 1H), 6.71 (dd, 1H, J=2.0, 8.0 Hz), 6.77 (d, 1H, J=2.0 Hz), 7.38 (d, 1H J=8.0H); MS (m/e, M$^+$): 239

Step 2. 3-(3,5-Difluorophenyl)-5-methoxy-1H-inden-1-one

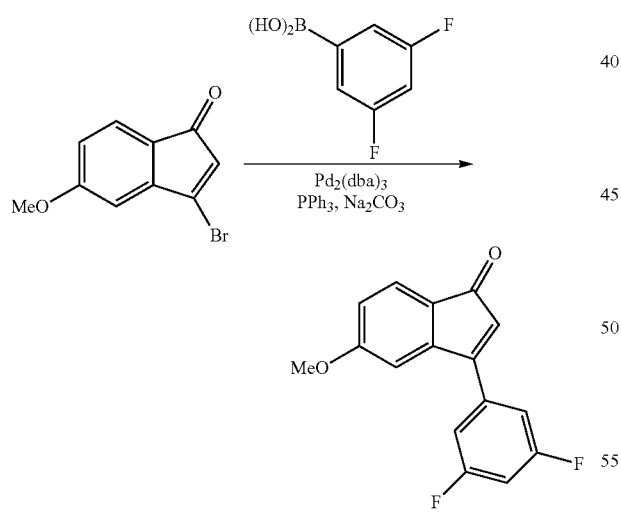

To a reaction vial, 3-bromo-5-methoxy-1H-inden-1-one (1.5 g, 6.27 mmol) obtained in Step 1, 3,5-difluorophenylboronic acid (1.19 g, 7.52 mmol), $Pd_2(dba)_3$ (284 mg, 0.31 mmol), $PPh_3$ (329 mg, 1.25 mmol), 2M $Na_2CO_3$ (7.84 mL, 15.68 mmol), and ethyleneglycol dimethyl ether (15 mL) were sequentially charged. The reaction vial was heated to reflux for 3 h. After cooling to room temperature, the reaction was diluted with EtOAc and filtered through a Celite pad. The solution was washed with $H_2O$ and brine, dried over $MgSO_4$, and concentrated in vacuo. The residue was purified by silica gel column chromatography (EtOAc/hexanes=1:10) to afford the desired product (1.12 g, 65%).

$^1$H NMR (300 MHz, $CDCl_3$) δ 3.87 (s, 3H), 6.03 (s, 1H), 6.71 (dd, 1H, J=2.0, 8.0 Hz), 6.85 (d, 1H, J=2.0 Hz), 6.94 (m, 1H), 7.10-7.17 (m, 2H), 7.51 (d, 1H J=8.0H); MS (m/e, M$^+$): 272

Step 3. 2-Bromo-3-(3,5-difluorophenyl)-5-methoxy-1H-inden-1-one

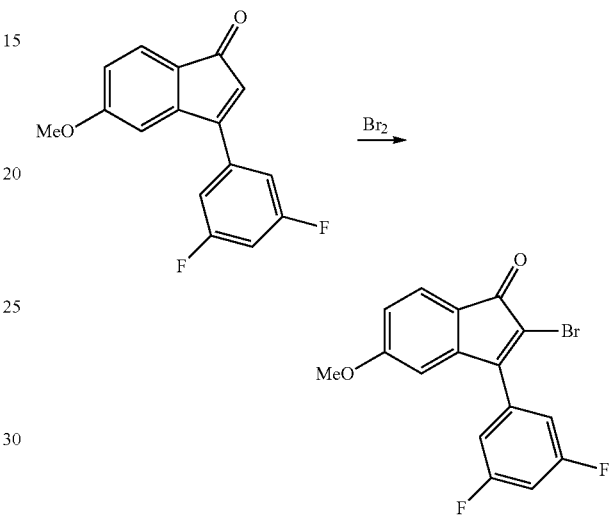

To a solution of 3-(3,5-difluorophenyl)-5-methoxy-1H-inden-1-one (810 mg, 2.98 mmol) obtained in Step 2 in $CH_2Cl_2$ (10 mL) at 0° C. was added dropwise a solution of $Br_2$ (571 mg, 3.57 mmol) in $CH_2Cl_2$ (3 mL). The mixture was stirred for 3 h at room temperature. The reaction was diluted with $H_2O$ (10 mL) and extracted with $CH_2Cl_2$. The extracts were washed with $H_2O$ and brine, dried over $MgSO_4$, and concentrated in vacuo. The residue was purified by silica gel column chromatography ($CH_2Cl_2$/hexanes) to afford the desired product (1.0 g, 95%).

$^1$H NMR (300 MHz, $CDCl_3$) δ 3.86 (s, 3H), 6.67 (m, 2H), 6.97 (m, 1H), 7.16 (m, 2H), 7.57 (d, 1H, J=8.6 Hz); MS (m/e, M$^+$): 351

Step 4. 3-(3,5-Difluorophenyl)-5-methoxy-2-(pyridin-3-yl)-1H-inden-1-one

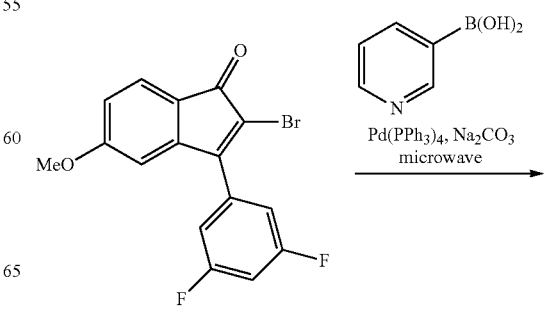

-continued

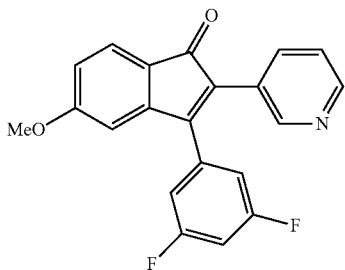

To a microwave reaction vial, 2-bromo-3-(3,5-difluorophenyl)-5-methoxy-1H-inden-1-one (300 mg, 0.85 mmol) obtained in Step 3,3-pyridinylboronic acid (126 mg, 1.03 mmol), Pd(PPh$_3$)$_4$ (50 mg, 0.043 mmol), 3M Na$_2$CO$_3$ (0.85 mL, 1.44 mmol), and dioxane (5 mL) were sequentially charged. The reaction vial was placed into a microwave reactor and irradiated at 150° C. for 10 min. After cooling to room temperature, the reaction was diluted with EtOAc and dried over MgSO$_4$. The mixture was filtered through a Celite pad while rinsing with EtOAc and then concentrated in vacuo. The residue was purified by silica gel column chromatography (EtOAc/hexanes=1:3) to afford the desired product (220 mg, 75%).

$^1$H NMR (300 MHz, CDCl$_3$) δ 3.88 (s, 3H), 6.67 (d, 1H, J=2.1 Hz), 6.74 (dd, 1H, J=2.1, 8.0 Hz), 6.89 (m, 3H), 7.30 (d, 1H, J=4.8 Hz), 7.61 (d, 1H, J=8.0 Hz), 7.69 (dd, 1H, J=1.7, 8.0 Hz), 8.42 (d, 1H, J=1.7 Hz), 8.52 (dd, 1H, J=1.7, 4.8 Hz); MS (m/e, M$^+$): 349

Step 5. 3-(3,5-Difluorophenyl)-5-hydroxy-2-(pyridin-3-yl)-1H-inden-1-one

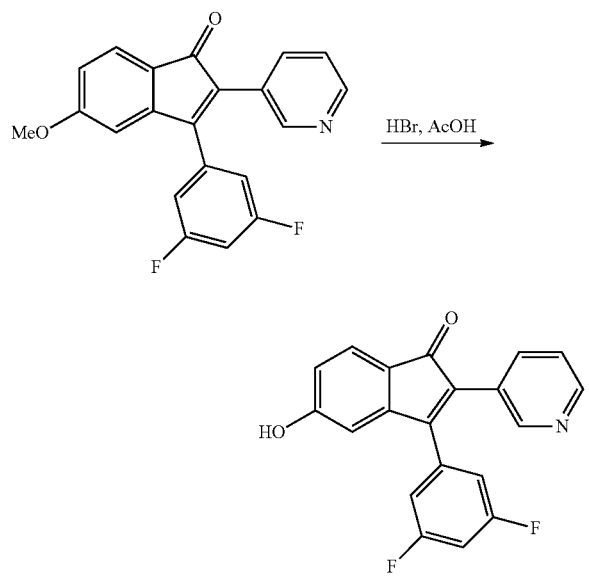

To a solution of 3-(3,5-difluorophenyl)-5-methoxy-2-(pyridin-3-yl)-1H-inden-1-one (210 mg, 0.60 mmol) obtained in Step 4 in AcOH (6 mL) was added HBr (3 mL). The mixture was heated to reflux at 120° C. for 16 h. The reaction mixture was cooled to room temperature and neutralized with 3N—NaOH. The resulting solution was extracted with EtOAc (10 mL). The extracts were washed with H$_2$O and brine, dried over MgSO$_4$, and concentrated in vacuo. The residue was purified by recrystallization with CH$_2$Cl$_2$/hexanes to afford the desired product (200 mg, 99%).

$^1$H NMR (300 MHz, DMSO) δ 6.58 (d, 1H, J=1.8 Hz), 6.68 (dd, 1H, J=1.6, 7.9 Hz), 7.18 (m, 2H), 7.40 (m, 2H), 7.48 (d, 1H, J=7.9 Hz), 7.62 (dd, 1H, J=1.8, 8.1 Hz), 8.35 (m, 1H), 8.49 (dd, 1H, J=1.6, 4.9 Hz); MS (m/e, M$^+$): 335

Step 6. 3-(3,5-Difluorophenyl)-5-[2-(morpholin-4-yl)ethoxy]-2-(pyridin-3-yl)-1H-inden-1-one To a solution of 3-(3,5-difluorophenyl)-5-hydroxy-2-(pyridin-3-yl)-1H-inden-1-one (60 mg, 0.18 mmol) obtained in Step 5 in DMF (2 mL) was added K$_2$CO$_3$ (75 mg, 0.54 mmol) and 4-(2-chloroethyl)morpholine hydrochloride (50 mg, 0.27 mmol). The mixture was heated to 80° C. for 3 h and cooled to room temperature. The resulting solution was diluted with H$_2$O and extracted with EtOAc (5 mL×3). The extracts were washed with H$_2$O and brine, dried over MgSO$_4$, and concentrated in vacuo. The residue was purified by silica gel column chromatography (2% MeOH/CH$_2$Cl$_2$) to afford the title compound (55 mg, 68%).

$^1$H NMR (300 MHz, CDCl$_3$) δ 2.57 (t, 4H), 2.82 (t, 2H), 3.74 (t, 4H), 4.16 (t, 2H), 6.69 (d, 1H, J=1.9 Hz), 6.73 (dd, 1H, J=2.1, 8.0 Hz), 6.89 (m, 3H), 7.29 (d, 1H, J=4.9 Hz), 7.59 (d, 1H, J=8.0 Hz), 7.68 (dd, 1H, J=2.1, 8.0 Hz), 8.42 (d, 1H, J=1.6 Hz), 8.52 (dd, 1H, J=1.6, 4.9 Hz); MS (m/e, M$^+$): 448

Example 129

Synthesis of 5-(2-morpholinoethoxy)-3-phenyl-2-(pyridin-3-yl)-1H-inden-1-one

Step 1. 1-(2-Bromo-4-methoxyphenyl)ethanone

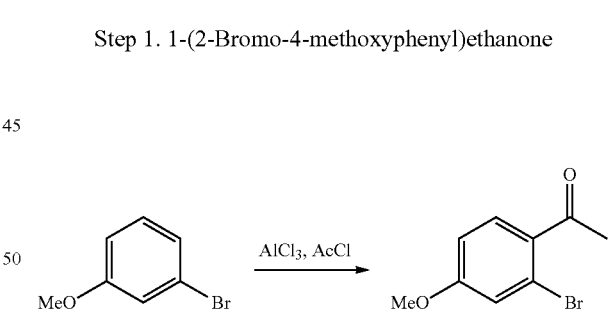

A round-bottomed flask was charged acetyl chloride (4.20 g, 53.56 mmol, 1 eq), AlCl$_3$ (7.13 g, 53.56 mmol, 1 eq), and carbon disulfide (80 mL). To the mixture was added dropwise a solution of 3-bromoanisole (9.75 g, 52.13 mmol) in carbon disulfide (20 mL) and stirred for 16 h. The resulting solution was diluted with ice water (100 mL) and extracted with CH$_2$Cl$_2$ (50 mL×3). The extracts were washed with H$_2$O, brine, and 1N NaOH (30 mL). The organic layer was dried over MgSO$_4$ and concentrated in vacuo. The residue was purified by silica gel column chromatography (EtOAc/hexanes=1:10) to afford the title compound (6.2 g, 51%).

$^1$H NMR (300 MHz, CDCl$_3$) δ 7.48 (dd, J=8.4 Hz, 1.2 Hz, 1H), 7.04 (brs. 1H), 6.76 (dd, 1H), 3.74 (s, 3H), 2.52 (s, 3H)

Step 2. (E)-1-(2-Bromo-4-methoxyphenyl)-3-phenyl-2-propen-1-one

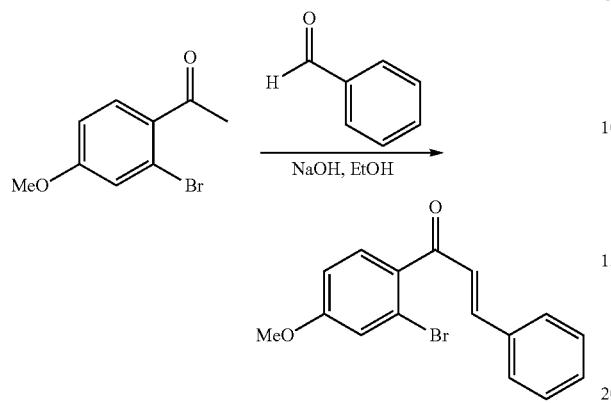

To a solution of 1-(2-bromo-4-methoxyphenyl)ethanone (6.2 g, 27.06 mmol) obtained in Step 1 in EtOH (50 mL) at 0° C. was added sequentially aq. NaOH solution (8.12 mL, 81.19 mmol, 3 eq) and benzaldehyde (3.3 mL, 32.48 mmol, 1.2 eq). After being stirred for additional 4 h at room temperature, the mixture was diluted with H$_2$O and neutralized with 3N HCl. The resulting mixture was extracted with EtOAc (20 mL×3). The extracts were washed with brine, dried over MgSO$_4$, and concentrated in vacuo to obtain the desired product (6 g, 70%).

$^1$H NMR (300 MHz, CDCl$_3$) δ 7.54-7.59 (m, 2H), 7.46-7.49 (m, 2H), 7.39-7.42 (m, 3H), 7.15-7.21 (m, 2H), 6.93 (dd, 1H), 3.85 (s, 3H)

Step 3. 5-Methoxy-3-phenyl-1H-inden-1-one

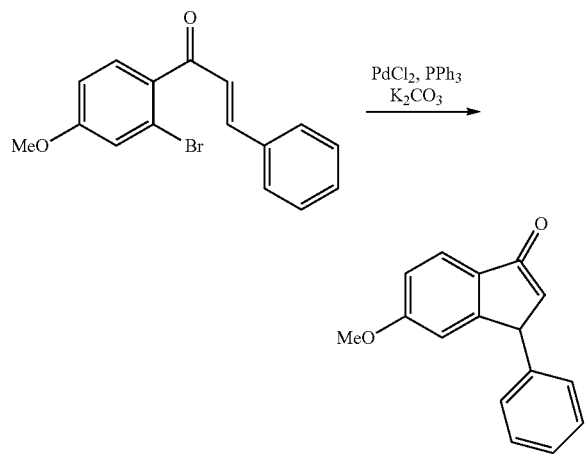

To a solution of (E)-1-(2-bromo-4-methoxyphenyl)-3-phenyl-2-propen-1-one (6.0 g, 18.91 mmol) obtained in Step 2 in DMF (15 mL) was added PPh$_3$ (1.46 g, 5.68 mmol, 0.3 eq), K$_2$CO$_3$ (5.23 g, 37.83 mmol, 2 eq), and PdCl$_2$ (335 mg, 1.89 mmol, 0.1 eq). The reaction vial was heated to 110° C. for 3 h. After cooling to room temperature, the reaction mixture was diluted with EtOAc and filtered through a Celite pad. The solution was washed with H$_2$O and brine, dried over MgSO$_4$, and concentrated in vacuo. The residue was purified by silica gel column chromatography (EtOAc/hexanes=1:5) to afford the desired product (2.8 g, 63%).

$^1$H NMR (300 MHz, CDCl$_3$) δ 7.61-7.64 (m, 2H), 7.47-7.51 (m, 4H), 6.91 (d, J=1.8 Hz, 1H), 6.69 (dd, J=8.1 Hz, 1.8 Hz, 1H), 6.01 (s, 1H), 3.86 (s, 3H)

Step 4. 2-Bromo-5-methoxy-3-phenyl-1H-inden-1-one

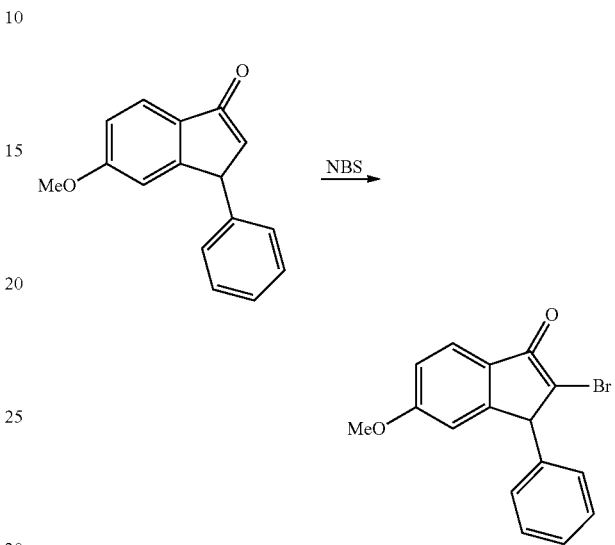

5-Methoxy-3-phenyl-1H-inden-1-one (2.8 g, 11.85 mmol) obtained in Step 3 was placed into a flask and dissolved in CCl$_4$ (20 mL). To the resulting solution, NBS (2.53 g, 14.22 mmol, 1.2 eq) and AIBN (280 mg, 10%/w) were added. The resulting mixture was allowed to reflux for 2 h. After cooling to room temperature, the reaction mixture was quenched with sat. Na$_2$S$_2$O$_3$ (20 mL) extracted with CH$_2$Cl$_2$ (20 mL×3). The organic layers were washed H$_2$O and brine, dried over MgSO$_4$ and concentrated in vacuo to give the desired product (2.45 g, 66%).

$^1$H NMR (300 MHz, CDCl$_3$) δ 7.2-7.64 (m, 2H), 7.52-7.57 (m, 4H), 6.70 (d, J=2.1 Hz, 1H), 6.65 (dd, J=8.01, 2.1 Hz, 1H), 3.83 (s, 3H)

Step 5. 5-Methoxy-3-phenyl-2-(pyridin-3-yl)-1H-inden-1-one

The procedure of Step 7 of Example 1 was repeated except for using 2-bromo-5-methoxy-3-phenyl-1H-inden-1-one obtained in Step 4 as a starting material instead of 6-(2-morpholinoethoxy)-2-bromo-3-phenyl-1H-inden-1-one and being stirred for 10 min to obtain the title compound (72%).

$^1$H NMR (300 MHz, CDCl$_3$) δ 8.46 (d, J=1.8 Hz, 1H), 8.44 (dd, J=3.3 Hz, 2.1 Hz, 1H), 7.64-7.68 (m, 1H), 7.57 (dd, J=7.2 Hz, 1.8 Hz, 1H), 7.41-7.44 (m, 3H), 7.34-7.38 (m, 2H), 7.22 (dd, J=8.1 Hz, 4.8 Hz, 1H), 6.71 (d, J=1.5 Hz, 6.69 (d, J=2.1 Hz, 1H), 3.85 (s, 3H)

Step 6. 5-Hydroxy-3-phenyl-2-(pyridin-3-yl)-1H-inden-1-one

The procedure of Step 5 of Example 128 was repeated except for using 5-methoxy-3-phenyl-2-(pyridin-3-yl)-1H-inden-1-one obtained in Step 5 as a starting material instead of 3-(3,5-difluorophenyl)-5-methoxy-2-(pyridin-3-yl)-1H-inden-1-one to obtain the title compound (93%).

¹H NMR (300 MHz, CDCl₃) δ 8.46 (d, J=1.8 Hz, 1H), 8.43 (m, 1H), 7.68-7.72 (m, 1H), 7.50 (d, J=7.8 Hz, 1H), 7.40-7.44 (m, 3H), 7.32-7.37 (m, 2H), 6.66 (dd, J=5.1 Hz, 1.8 Hz, 1H) 6.63 (d, J=2.1 Hz, 1H)

Step 7. 5-(2-Morpholinoethoxy)-3-phenyl-2-(pyridin-3-yl)-1H-inden-1-one

The procedure of Step 6 of Example 128 was repeated except for using 5-hydroxy-3-phenyl-2-(pyridin-3-yl)-1H-inden-1-one obtained in Step 5 as a starting material instead of 3-(3,5-difluorophenyl)-5-hydroxy-2-(pyridin-3-yl)-1H-inden-1-one to obtain the title compound (72%).
¹H NMR (300 MHz, CDCl₃) δ 8.46 (dd, J=5.1 Hz, 1.5 Hz, 1H), 8.43 (d, J=1.5 Hz, 1H), 7.66 (dd, J=8.1 Hz, 2.1 Hz 1H), 7.56 (d, J=7.8 Hz, 1H), 7.41-7.45 (m, 3H), 7.33-7.37 (m, 2H), 7.20-7.24 (m, 1H), 6.72 (dd, J=5.4 Hz, 2.1 Hz, 1H), 6.69 (d, J=2.1 Hz, 1H), 4.14 (t, 2H), 3.71 (m, 4H), 2.80 (t, 2H), 2.56 (m, 4H); MS (m/e, M⁺): 412

Example 130

Synthesis of 5-(2-morpholinoethoxy)-3-phenyl-2-(pyridin-4-yl)-1H-inden-1-one

Step 1. 5-Methoxy-3-phenyl-2-(pyridin-4-yl)-1H-inden-1-one

The procedure of Step 7 of Example 1 was repeated except for using 2-bromo-5-methoxy-3-phenyl-1H-inden-1-one obtained in Step 4 of Example 129 as a starting material instead of 6-(2-morpholinoethoxy)-2-bromo-3-phenyl-1H-inden-1-one, 4-pyridinylboronic acid instead of 3-pyridinylboronic acid, and being stirred for 10 min to obtain the title compound (74%).
¹H NMR (300 MHz, CDCl₃) δ 8.49 (dd, J=4.8 Hz, 1.5 Hz, 2H), 7.59 (dd, J=8.4 Hz, 1.5 Hz, 1H), 7.42-7.46 (m, 3H), 7.32-7.37 (m, 2H), 7.18 (dd, J=4.8 Hz, 1.5 Hz, 2H), 6.74 (d, J=2.4 Hz, 1H), 6.72 (brs, 1H), 3.85 (s, 3H)

Step 2. 5-Hydroxy-3-phenyl-2-(pyridin-4-yl)-1H-inden-1-one

The procedure of Step 5 of Example 128 was repeated except for using 5-methoxy-3-phenyl-2-(pyridin-4-yl)-1H-inden-1-one obtained in Step 1 as a starting material instead of 3-(3,5-difluorophenyl)-5-methoxy-2-(pyridin-3-yl)-1H-inden-1-one to obtain the title compound (88%).
¹H NMR (300 MHz, CDCl₃) δ 8.49 (dd, J=4.8 Hz, 1.5 Hz, 2H), 7.59 (dd, J=8.4 Hz, 1.5 Hz, 1H), 7.42-7.46 (m, 3H), 7.32-7.37 (m, 2H), 7.18 (dd, J=4.8 Hz, 1.5 Hz, 2H), 6.74 (d, J=2.4 Hz, 1H), 6.72 (brs, 1H)

Step 3. 5-(2-Morpholinoethoxy)-3-phenyl-2-(pyridin-4-yl)-1H-inden-1-one

The procedure of Step 6 of Example 128 was repeated except for using 5-hydroxy-3-phenyl-2-(pyridin-4-yl)-1H-inden-1-one obtained in Step 2 as a starting material instead of 3-(3,5-difluorophenyl)-5-hydroxy-2-(pyridin-3-yl)-1H-inden-1-one to obtain the title compound (70%).
¹H NMR (300 MHz, CDCl₃) δ 8.48-8.50 (m, 2H), 7.56 (dd, J=8.7 Hz, 2.1 Hz, 1H), 7.44-7.47 (m, 3H), 7.32-7.35 (m, 2H), 7.16-7.18 (m, 2H), 6.71-6.74 (m, 2H), 4.14 (t, 2H), 3.72 (m, 4H), 2.80 (t, 2H), 2.55 (m, 4H); MS (m/e, M⁺): 412

Example 131

Synthesis of 5-(2-morpholinoethoxy)-3-phenyl-2-p-tolyl-1H-inden-1-one

Step 1. 5-Methoxy-3-phenyl-2-(p-tolyl)-1H-inden-1-one

The procedure of Step 7 of Example 1 was repeated except for using 2-bromo-5-methoxy-3-phenyl-1H-inden-1-one obtained in Step 4 of Example 129 as a starting material instead of 6-(2-morpholinoethoxy)-2-bromo-3-phenyl-1H-inden-1-one, p-tolylboronic acid instead of 3-pyridinylboronic acid, and being stirred for 10 min to obtain the title compound (70%).
¹H NMR (300 MHz, CDCl₃) δ 7.53 (dd. J=7.8 Hz, 0.6 Hz, 1H), 7.34-7.42 (m, 5H), 7.16 (d, 2H), 7.06 (dd, J=7.8 Hz, 0.3 Hz, 2H), 6.67 (dd, J=2.1 Hz, 1.2 Hz, 1H), 6.64 (d, J=2.4 Hz, 1H) 3.83 (s, 3H), 2.31 (s, 3H)

Step 2. 5-Hydroxy-3-phenyl-2-(p-tolyl)-1H-inden-1-one

The procedure of Step 5 of Example 128 was repeated except for using 5-methoxy-3-phenyl-2-(p-tolyl)-1H-inden-1-one obtained in Step 1 as a starting material instead of 3-(3,5-difluorophenyl)-5-methoxy-2-(pyridin-3-yl)-1H-inden-1-one to obtain the title compound (90%).
¹H NMR (300 MHz, CDCl₃) δ 7.48 (dd. J=7.5 Hz, 0.6 Hz, 1H), 7.34-7.42 (m, 5H), 7.16 (d, 2H), 7.06 (dd, J=7.8 Hz, 0.6 Hz, 2H), 6.63 (dd, J=3.6 Hz, 1.5 Hz, 1H), 6.60 (d, J=2.1 Hz, 1H), 5.58 (s. 1H, OH), 2.31 (s, 3H)

Step 3. 5-(2-Morpholinoethoxy)-3-phenyl-2-(p-tolyl)-1H-inden-1-one

The procedure of Step 6 of Example 128 was repeated except for using 5-hydroxy-3-phenyl-2-(p-tolyl)-1H-inden-1-one obtained in Step 2 as a starting material instead of 3-(3,5-difluorophenyl)-5-hydroxy-2-(pyridin-3-yl)-1H-inden-1-one to obtain the title compound (78%).
¹H NMR (300 MHz, CDCl₃) δ 7.52 (d, J=7.8 Hz, 1H), 7.39-7.42 (m, 3H), 7.34-7.39 (m, 2H), 7.14-7.17 (m, 2H), 7.05-7.07 (m, 2H), 6.64-6.69 (m, 2H), 4.13 (t, 2H), 3.72 (m, 4H), 2.79 (t, 2H), 2.55 (m, 4H), 2.26 (s, 3H); MS (m/e, M⁺): 425

Example 132

Synthesis of 5-(2-morpholinoethoxy)-2-(3-fluoro-4-methylphenyl)-3-phenyl-1H-inden-1-one Step 1. 2-(3-Fluoro-4-methylphenyl)-5-Methoxy-3-phenyl-1H-inden-1-one The procedure of Step 7 of Example 1 was repeated except for using 2-bromo-5-methoxy-3-phenyl-1H-inden-1-one obtained in Step 4 of Example 129 as a starting material instead of 6-(2-morpholinoethoxy)-2-bromo-3-phenyl-1H-inden-1-one, 3-fluoro-4-methylphenylboronic acid instead of 3-pyridinylboronic acid, and being stirred for 10 min to obtain the title compound (65%).
¹H NMR (300 MHz, CDCl₃) δ 7.54 (dd. J=4.8 Hz, 3.6 Hz, 1H), 7.38-7.43 (m, 3H), 7.33-7.36 (m, 2H), 7.04 (m, 1H), 6.91-6.97 (m, 2H), 6.65-6.68 (m, 2H), 3.83 (s, 3H), 2.23 (s, 3H)

Step 2. 2-(3-Fluoro-4-methylphenyl)-5-hydroxy-3-phenyl-1H-inden-1-one

The procedure of Step 5 of Example 128 was repeated except for using 2-(3-fluoro-4-methylphenyl)-5-methoxy-3-phenyl-1H-inden-1-one obtained in Step 1 as a starting material instead of 3-(3,5-difluorophenyl)-5-methoxy-2-(pyridin-3-yl)-1H-inden-1-one to obtain the title compound (88%).

$^1$H NMR (300 MHz, CDCl$_3$) δ 7.52 (dd. 0.1=4.8 Hz, 3.6 Hz, 1H), 7.41-7.46 (m, 3H), 7.32-7.39 (m, 2H), 7.04 (m, 1H), 6.91-6.97 (m, 2H), 6.65-6.68 (m, 2H), 2.23 (s, 3H)

Step 3. 5-(2-Morpholino ethoxy)-2-(3-fluoro-4-methylphenyl)-3-phenyl-1H-inden-1-one The procedure of Step 6 of Example 128 was repeated except for using 2-(3-fluoro-4-methylphenyl)-5-hydroxy-3-phenyl-1H-inden-1-one obtained in Step 2 as a starting material instead of 3-(3,5-difluorophenyl)-5-hydroxy-2-(pyridin-3-yl)-1H-inden-1-one to obtain the title compound (71%).

$^1$H NMR (300 MHz, CDCl$_3$) δ 7.53 (d, J=8.1 Hz, 1H), 7.42-7.43 (m, 3H), 7.33-7.36 (m, 2H), 7.02-7.07 (m, 1H), 6.91-6.96 (m, 2H), 6.66-6.69 (m, 2H), 4.13 (t, 2H), 3.72 (m, 4H), 2.79 (t, 2H), 2.55 (m, 4H), 2.20 (s, 3H); MS (m/e, M$^+$): 443

Example 133

Synthesis of 3-(3,5-difluorophenyl)-5-[2-(4-(methylsulfonyl)piperazin-1-yl)ethoxy]-2-(pyridin-3-yl)-1H-inden-1-one

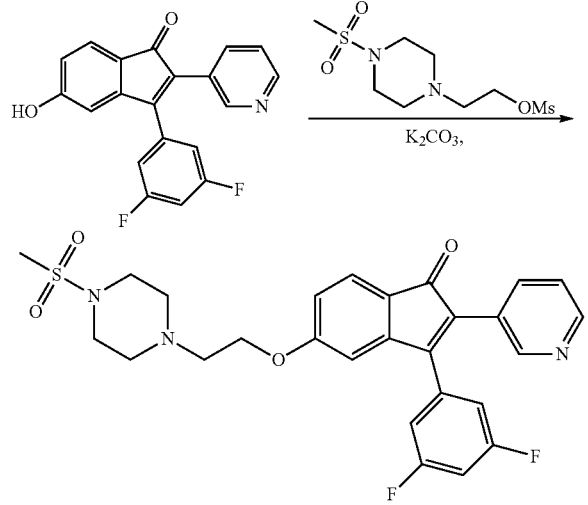

To a solution of 3-(3,5-difluorophenyl)-5-hydroxy-2-(pyridin-3-yl)-1H-inden-1-one (60 mg, 0.18 mmol) obtained in Step 5 of Example 128 in DMF (2 mL) was added K$_2$CO$_3$ (75 mg, 0.54 mmol) and methylsulfonyl 2-(4-(methylsulfonyl)piperazin-1-yl)ethyl ether (77 mg, 0.27 mmol). The mixture was heated to 80° C. for 3 h and cooled to room temperature. The resulting solution was diluted with H$_2$O (5 mL) and extracted with EtOAc (5 mL×3). The extracts were washed with H$_2$O and brine, dried over MgSO$_4$, and concentrated in vacuo. The residue was purified by silica gel column chromatography (2% MeOH/CH$_2$Cl$_2$) to afford the title compound (65 mg, 69%).

$^1$H NMR (300 MHz, CDCl$_3$) δ 2.68 (t, 4H), 2.77 (s, 3H), 2.86 (t, 2H), 3.26 (t, 4H), 4.13 (t, 2H), 6.67 (d, 1H, J=2.1 Hz), 6.72 (dd, 1H, J=2.1, 8.1 Hz), 6.90 (m, 3H), 7.29 (d, 1H, J=4.9 Hz), 7.59 (d, 1H, J=8.0), 7.69 (dd, 1H, J=1.7, 8.0 Hz), 8.42 (d, 1H, J=2.1 Hz) 8.52 (dd, 1H, J=1.7, 4.9 Hz); MS (m/e, M$^+$): 525

Example 134

Synthesis of 5-[2-(4-(methylsulfonyl)piperazin-1-yl)ethoxy]-3-phenyl-2-(pyridin-3-yl)-1H-inden-1-one The procedure of Example 133 was repeated except for using 5-hydroxy-3-phenyl-2-(pyridin-3-yl)-1H-inden-1-one obtained in Step 6 of Example 129 as a starting material instead of 3-(3,5-difluorophenyl)-5-hydroxy-2-(pyridin-3-yl)-1H-inden-1-one to obtain the title compound (78%).

$^1$H NMR (300 MHz, CDCl$_3$) δ 8.45 (dd, J=5.1 Hz, 1.8 Hz, 1H), 8.43 (d, J=1.5 Hz, 1H), 7.67 (dd, J=8.1 Hz, 1.8 Hz, 1H), 7.56 (d, J=7.8 Hz, 1H), 7.42-7.46 (m, 3H), 7.33-7.36 (m, 2H), 7.20-7.24 (m, 1H), 6.71 (dd, J=4.8 Hz, 2.4 Hz, 1H), 6.68 (d, J=2.1 Hz, 1H), 4.13 (t, 2H), 3.24 (m, 4H), 2.86 (t, 2H), 2.78 (s, 3H), 2.67 (m, 4H); MS (m/e, M$^+$): 489

Example 135

Synthesis of 5-[2-(4-(methylsulfonyl)piperazin-1-yl)ethoxy]-3-phenyl-2-(p-tolyl)-1H-inden-1-one The procedure of Example 133 was repeated except for using 5-hydroxy-3-phenyl-2-(p-tolyl)-1H-inden-1-one obtained in Step 2 of Example 131 as a starting material instead of 3-(3,5-difluorophenyl)-5-hydroxy-2-(pyridin-3-yl)-1H-inden-1-one to obtain the title compound (73%).

$^1$H NMR (300 MHz, CDCl$_3$) δ 7.53 (d, J=7.8 Hz, 1H), 7.40-7.43 (m, 3H), 7.34-7.37 (m, 2H), 7.14-7.17 (m, 2H), 7.05-7.08 (m, 2H), 6.66 (dd, J=5.1 Hz, 1.8 Hz, 1H), 6.64 (d, J=2.1 Hz, 1H), 4.11 (t, 2H), 3.23 (m, 4H), 2.85 (t, 2H), 2.74 (s, 3H), 2.63 (m, 4H), 2.28 (s, 3H); MS (m/e, M$^+$): 502

Example 136

Synthesis of 5-[2-(4-(methylsulfonyl)piperazin-1-yl)ethoxy]-2-(3-fluoro-4-methylphenyl)-3-phenyl-1H-inden-1-one The procedure of Example 133 was repeated except for using 2-(3-fluoro-4-methylphenyl)-5-hydroxy-3-phenyl-1H-inden-1-one obtained in Step 2 of Example 132 as a starting material instead of 3-(3,5-difluorophenyl)-5-hydroxy-2-(pyridin-3-yl)-1H-inden-1-one to obtain the title compound (76%).

$^1$H NMR (300 MHz, CDCl$_3$) δ 7.53 (dd, J=7.5 Hz, 0.9 Hz, 1H), 7.42-7.44 (m, 3H), 7.33-7.36 (m, 2H), 7.02-7.07 (m, 1H), 6.91-6.97 (m, 2H), 6.65-6.68 (m, 2H), 4.12 (t, 2H), 3.25 (m, 4H), 2.85 (t, 2H), 2.76 (s, 3H), 2.65 (m, 4H), 2.20 (s, 3H); MS (m/e, M$^+$): 489

EXPERIMENTAL EXAMPLE

Experimental Example 1

Effects of the Inventive Indenone Derivatives on Differentiation of Osteoblast Cells To examine the effects of the inventive indenone derivatives on the differentiation and activation of osteoblast cells, the activity and expression of alkaline phosphatase (ALP), a marker for the differentiation of osteoblast cells, and the bone nodule formation using a mouse derived osteoblast-like cells, MC3T3-E1 (ATCC, Japan) or a primary mouse calvaria derived preosteoblastic cells were observed.

MC3T3-E 1 cells were seeded in a medium containing osteogenic factors (OF) such as ascorbic acids and β-glycerophosphates (b-GP), and each compound of Examples was added thereto at a concentration of 0.1, 1 and 10 μM. The cells were incubated for 6 days (MC3T3-E1 cells) or 7 days (primary mouse calvaria derived preosteoblastic cells) in a 37° C. $CO_2$ incubator. Then, the culture medium was replaced with a fresh medium together with the test compound every two or three days. On the last day, the medium was centrifuged to remove the supernatant, and the cells were washed with PBS. The washed cells were subjected to a 3-cycle freege-thaw treatment using a –70° C. deep freezer to allow enzymes elute in a lysis buffer. The lysed protein was quantified, followed by measurement of ALP activity using 4-nitrophenylphosphate. The results are shown in Table 1.

Further, a group treated only with DMSO or OF was tested for ALP activities for comparison. The group treated only with DMSO did not show any ALP activity. In addition, the group treated only with OF showed an ALP activity, which was lower than that of the group treated with the inventive compound together with OF. In contrast, a group treated with the inventive compound together with OF showed more than 100% of activity, based on the ALP activity of the group treated with only OF, the activity being dependent on the concentration of the compound.

Meanwhile, the bone nodule formation involving osteogenesis was evaluated using the Alizarin red-S staining method in which coloring occurs due to the reaction of accumulated calcium as well as the coloring due to the reaction with arenazo III by way of measuring the value of absorbance. As a result, red cells formed by the reaction with alizarin red-S were minor degree for the group treated only with OF, while markedly increased red cells were observed for the group treated with the inventive compound and OF, the degree of increase being dependent on the concentration of the treated compound. In absorbance results, the groups treated with the inventive compounds showed more than 100%, based on the group treated only with OF, the absorbance being dependent on the concentration of treated compound.

Experimental Example 2

Effects of the Indenone Derivatives on Formation and Activity of the Osteoclast Cells To investigate the effects of the indenone derivatives on the osteoclast formation, the TRAP (tartrate-resistant acid phosphatase) activity was measured using mouse primary bone marrow cells and Raw264.7 cells (TIB-71™, ATCC, U.S).

RANKL (receptor activator of NF-kappa B ligand), which is essential to mouse primary bone marrow cells and Raw264.7 cells, is known to control the differentiation of osteoclast cells. To evaluate the inhibitory effects of the indenone derivative on osteoclast cells, TRAP staining and measurement of TRAP activity were conducted on day 5 after treatment of the inventive indenone derivative at various concentrations of 0.1, 1, 10, and 100 μM together with RNAKL. The results are shown in FIG. 1 and Table 1.

TABLE 1

| Example No. | Activity ALP[1] | TRAP[2] |
|---|---|---|
| 01 | 455 | 61 |
| 02 | 221 | 48 |
| 03 | 216 | 60 |
| 04 | 128 | 29 |
| 05 | 44 | 48 |
| 06 | 63 | 47 |
| 07 | — | — |
| 08 | — | — |
| 09 | 87 | 37 |
| 10 | 172 | 53 |
| 11 | 649 | 10 |
| 12 | 365 | 46 |
| 13 | 151 | 60 |
| 14 | 131 | 45 |
| 15 | 65 | 57 |
| 16 | 713 | 76 |
| 17 | 236 | 32 |
| 18 | 349 | 39 |
| 19 | 220 | 36 |
| 20 | 283 | 54 |
| 21 | 130 | 23 |
| 22 | 169 | 47 |
| 23 | 162 | 41 |
| 24 | 121 | 106 |
| 25 | 105 | 77 |
| 26 | 79 | 79 |
| 27 | 75 | 83 |
| 28 | 134 | 100 |
| 29 | 84 | 84 |
| 30 | 150 | 67 |
| 31 | — | — |
| 32 | — | — |
| 33 | 65 | 60 |
| 34 | 78 | 42 |
| 35 | 79 | 51 |
| 36 | 224 | 98 |
| 37 | 80 | 66 |
| 38 | 77 | 88 |
| 39 | 92 | 45 |
| 40 | 291 | 63 |
| 41 | 329 | 145 |
| 42 | — | — |
| 43 | 125 | 22 |
| 44 | 710 | 39 |
| 45 | 192 | 98 |
| 46 | 107 | 4 |
| 47 | — | — |
| 48 | 67 | 65 |
| 49 | 37 | 14 |
| 50 | — | — |
| 51 | 33 | 22 |
| 52 | 50 | 12 |
| 53 | 27 | 14 |
| 54 | 62 | 30 |
| 55 | 129 | 62 |
| 56 | 71 | 2 |
| 57 | 62 | 2 |
| 58 | 19 | 16 |
| 59 | 254 | 12 |
| 60 | 19 | 2 |
| 61 | 113 | 67 |
| 62 | 90 | 47 |
| 63 | 53 | 2 |
| 64 | 34 | 16 |
| 65 | 19 | 3 |
| 66 | 70 | 7 |
| 67 | 116 | 44 |
| 68 | 164 | 31 |
| 69 | 72 | 47 |
| 70 | 19 | 2 |
| 71 | 19 | 2 |
| 72 | 58 | 29 |
| 73 | 150 | 41 |
| 74 | 206 | 57 |
| 75 | — | — |
| 76 | — | — |

TABLE 1-continued

| Example No. | Activity ALP[1] | TRAP[2] |
|---|---|---|
| 77 | — | — |
| 78 | 187 | 86 |
| 79 | 110 | 82 |
| 80 | 74 | 75 |
| 81 | 116 | 61 |
| 82 | 178 | 84 |
| 83 | 18 | 10 |
| 84 | — | — |
| 85 | 77 | 76 |
| 86 | 77 | 74 |
| 87 | 71 | 82 |
| 88 | — | — |
| 89 | — | — |
| 90 | 63 | 81 |
| 91 | 67 | 71 |
| 92 | 262 | 90 |
| 93 | 155 | 87 |
| 94 | 109 | 51 |
| 95 | 203 | 76 |
| 96 | 152 | 119 |
| 97 | 179 | 35 |
| 98 | 146 | 18 |
| 99 | 212 | 12 |
| 100 | 185 | 118 |
| 101 | 216 | 105 |
| 102 | 220 | 20 |
| 103 | 209 | 91 |
| 104 | 124 | 123 |
| 105 | 99 | 86 |
| 106 | 133 | 88 |
| 107 | 286 | 64 |
| 108 | 111 | 4 |
| 109 | 177 | 4 |
| 110 | 207 | 43 |
| 111 | 117 | 27 |
| 112 | 70 | 32 |
| 113 | 217 | 41 |
| 114 | 286 | 59 |
| 115 | 199 | 36 |
| 116 | 71 | 43 |
| 117 | 98 | 70 |
| 118 | 311 | 70 |
| 119 | 170 | 74 |
| 120 | 169 | 110 |
| 121 | 207 | 111 |
| 122 | 203 | 54 |
| 123 | 164 | 90 |
| 124 | — | — |
| 125 | 63 | 77 |
| 126 | 73 | 66 |
| 127 | 55 | 61 |

[1]ALP activity - MC3T3E1 cells treated with 10 μM of the compound of Example 1 and OF
[2]TRAP activity - Raw264.7 cells treated with 10 μM of the compound of Example 1 and RANKL In Table 1, the ALP activity refers to osteoclast activity involving osteogenesis, of which the higher value indicates the treat compound being more efficacious, and the TRAP activity means osteoclast activity facilitating the bone resorption, of which the lower value indicates the treated compound being more efficacious.

As shown in FIG. 1, the inhibitory effects of the compounds on the bone resorption by the osteoclastic cells are dependent on the concentration of the treated compound.

Experimental Example 3

Effects of the Indenone Derivatives on Osteogenesis In Vivo

The bone formation is regulated via the synthesis of bone matrix formed upon differentiation of osteoclast cells. To evaluate the effects of the indenone derivatives of the present invention on osteogenesis, the skull of SD rat was exposed in a size of 6 mm diameter and to the collagen sponge thereof, 0.5 mg of compound of Example 1 was treated, followed by suturing the epidermis. Two weeks later, the rat was sacrificed, and the skull was extracted to observe the bone formation using micro-CT. Further, the skull treated with a vehicle as a control and the skull treated with 2 μg of BMP-2, which facilitates bone formation, as a positive control were observed according to the same procedure.

Figure 2:
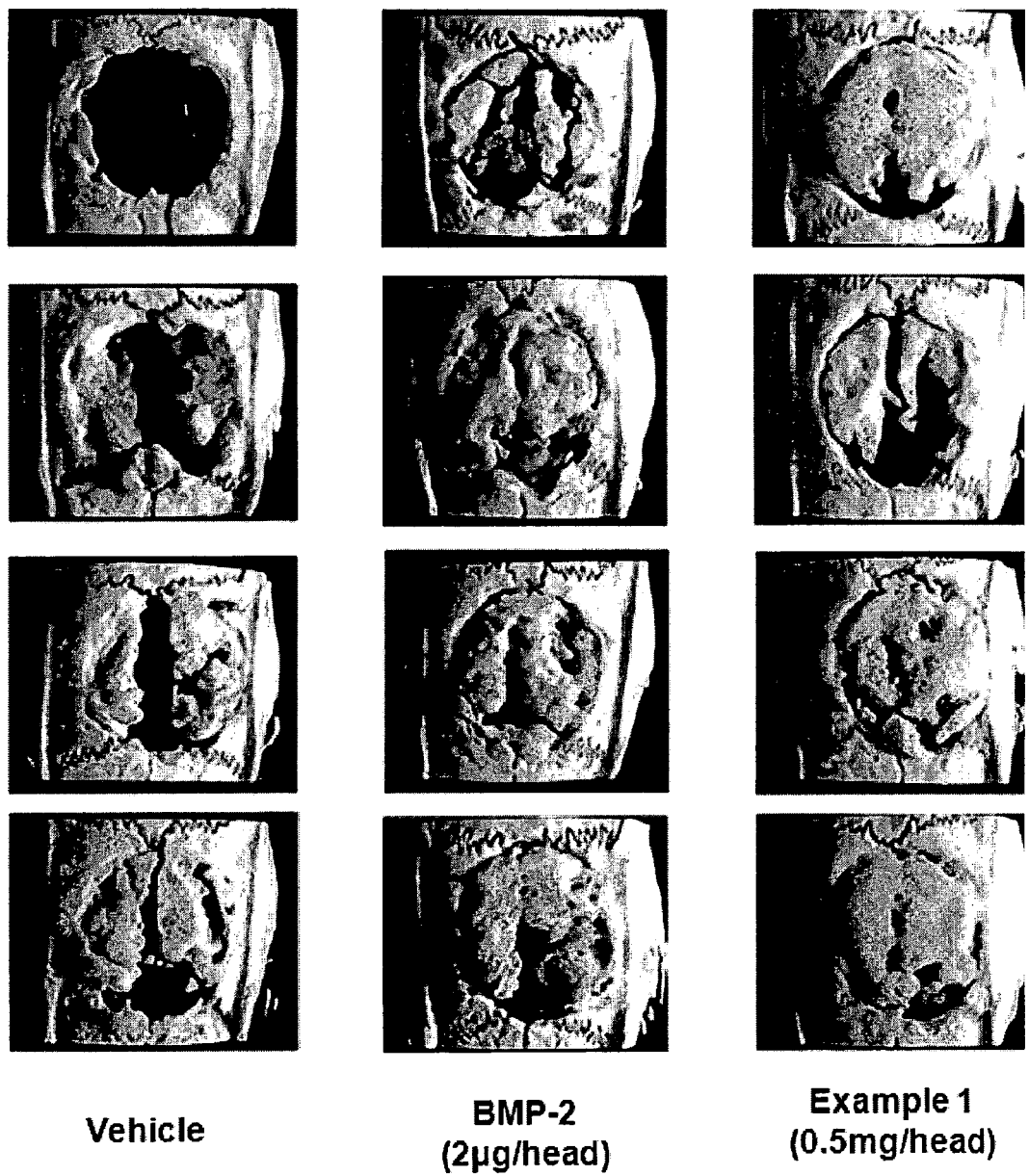
FIG. 2: Micro-CT images showing the effects of the indenone derivatives on osteogenesis in vivo.

The results are shown in FIG. 2. As shown in FIG. 2, the indenone derivatives of the present invention is effective in bone formation, compared to the controls.

Experimental Example 4

Effects of the Indenone Derivatives on the Bone Resorption In Vivo

Most pharmacological effectiveness of therapeutic agents for osteoporosis has been evaluated using an animal, rather than a human. Particularly, as a model animal for osteoporosis occurring after menopause, ovariectomized female rats have been used for its similarity to women after menopause. To examine the effects of the indenone derivatives on the bone resorption, female SD rats and female DDY mice were subjected to ovariectomy. After the rats or mice were anesthetized by abdominally injecting 25 mg/kg of sodium pentobarbital (Choongwae pharma coporation), the fur of the abdominal region was shaved and the operation area was sterilized. About 1.5 cm of abdominal skin, abdominal muscle, and peritoneum were cut in the middle under aseptic condition, and ovary was exposed, followed by removal of both left and right ovaries after ligaturing of oviducts using silk threads. Then, peritoneum, abdominal muscle and skin were sutured with silk threads. The Sham group, animals operated upon for the surgery as in the ovariectomized rats except for removing ovary, was employed to compare the effects.

To examine whether the indenone derivative have the effect on osteoporosis models, the compound of Example 1 was orally administered once a day for 4 weeks in a various concentrations, followed by analysis of the bone density, using high resolution in-vivo micro-CT system (explore Locus scanner, GE Health Care, U.S.; scan resolution: 45 μm).

Figure 3A:
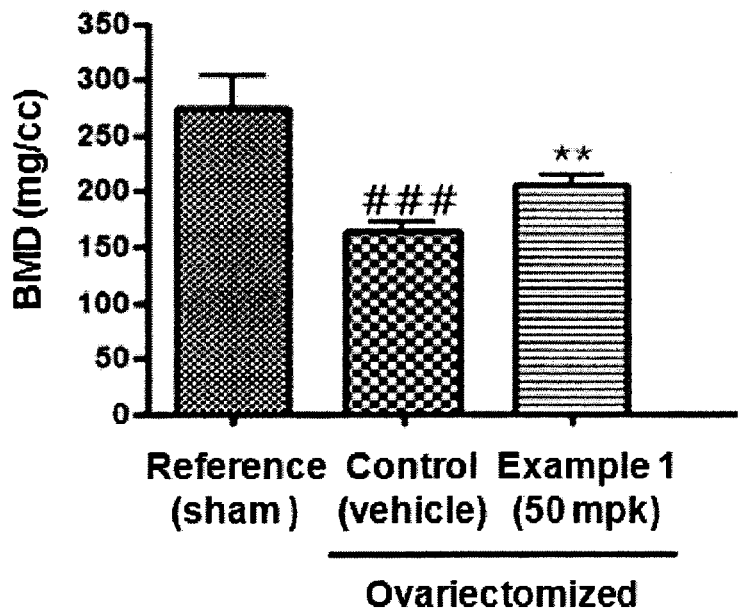
FIG. 3A: Bone densities of DDY mice measured using high resolution in-vivo micro-CT system (** P<0.01 vs. Control (vehicle), #### P<0.01 vs. reference (sham operation), n=5)
Figure 3B:
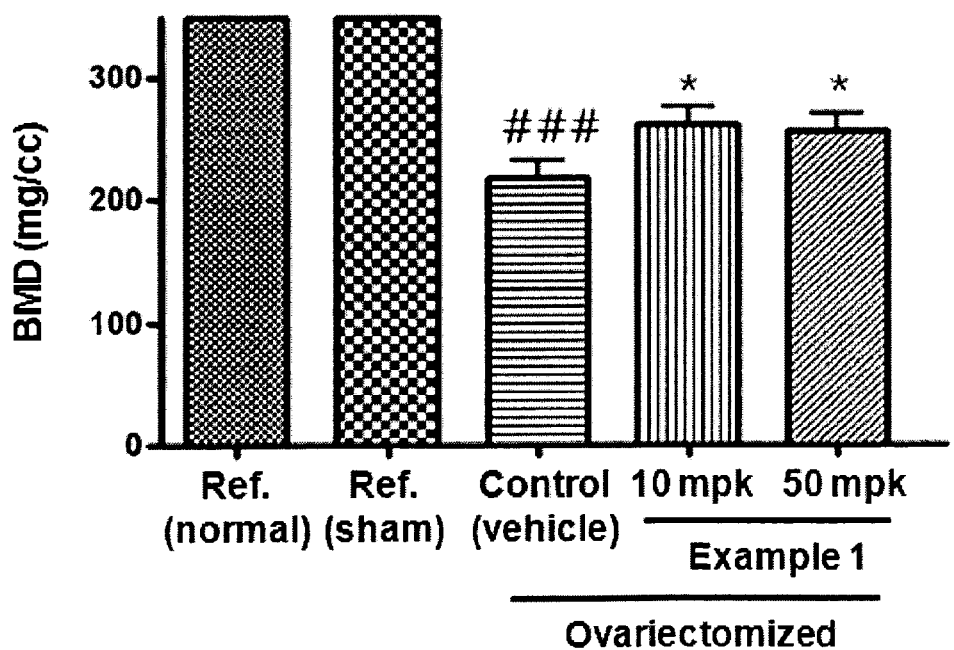
FIG. 3B: Bone densities of SD rats measured using high resolution in-vivo micro-CT system (* P<0.05 vs. Control (vehicle), #### P<0.01 vs. reference (sham operation), n=5).

As shown in FIGS. 3A and 3B, the bone densities decreased by ovariectomy were significantly increased by the 4 weeks-administration of the indenone derivative of Example 1.

While the invention has been described with respect to the above specific embodiments, it should be recognized that various modifications and changes may be made to the invention by those skilled in the art which also fall within the scope of the invention as defined by the appended claims.

What is claimed is:

1. An indenone derivative of formula (I) or a pharmaceutically acceptable salt thereof:

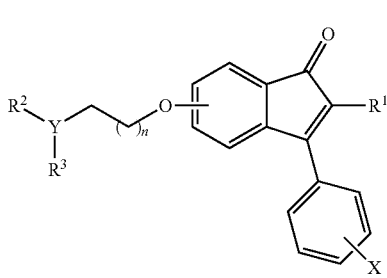

(1)

wherein, n is 0, 1 or 2;

X is one or more substituents introduced to the ortho-, meta- or para-position of the phenyl group, each selected independently from the group consisting of hydrogen, halogen, —CN, —CF$_3$, C$_{1-6}$alkyl, C$_{1-6}$alkoxy, C$_{3-10}$cycloalkyl, and C$_{3-8}$cycloalkoxy;

R$^1$ is C$_{6-10}$aryl substituted with at least one substituent selected from the group consisting of halogen, oxo, —CF$_3$, —CN, amino, hydroxy, carboxy, carbamoyl, nitro, thiol, C$_{1-6}$alkyl, C$_{2-6}$alkenyl, C$_{1-6}$alkoxy, C$_{3-10}$cycloalkyl, C$_{3-8}$cycloalkoxy, C$_{6-10}$aryl, C$_{6-10}$aryloxy, —C(O)R$^4$, —C(O)OR$^4$, —C(O)NR$^4$R$^5$, —S(O)R$^4$, —S(O$_2$)R$^4$, —S(O$_2$)NR$^4$R$^5$, —NR$^4$R$^5$, and —NR$^4$C(O)R$^5$, R$^4$ and R$^5$ being each independently hydrogen, C$_{1-6}$alkyl, or C$_{3-10}$cycloalkyl; or 5 to 10-membered heteroaryl;

Y is CH, N, N$^+$(—C$_{1-6}$alkyl), or N$^+$(—O$^-$); and

R$^2$ and R$^3$ are each independently hydrogen, C$_{1-6}$alkyl, C$_{1-6}$alkoxy, C$_{6-10}$aryl, or 5 to 10-membered heteroaryl, or are fused together with Y to form C$_{3-10}$cycloalkyl or 5 to 10-membered heterocycloalkyl, in which the C$_{6-10}$aryl of R$^2$ and R$^3$, 5 to 10-membered heteroaryl, C$_{3-10}$cycloalkyl, and 5 to 10-membered heterocycloalkyl are each independently and optionally substituted with at least one substituent selected from the group consisting of halogen, oxo, —CF$_3$, —CN, amino, hydroxy, carboxy, carbamoyl, nitro, thiol, C$_{1-6}$alkyl, C$_{2-6}$alkenyl, C$_{1-6}$alkoxy, C$_{3-10}$cycloalkyl, C$_{3-8}$cycloalkoxy, C$_{6-10}$aryl, C$_{6-10}$aryloxy, —C(O)R$^4$, —C(O)OR$^4$, —C(O)NR$^4$R$^5$, —S(O)R$^4$, —S(O$_2$)R$^4$, —S(O$_2$)NR$^4$R$^5$, —NR$^4$R$^5$, and —NR$^4$C(O)R$^5$, R$^4$ and R$^5$ being each independently hydrogen, C$_{1-6}$alkyl, or C$_{3-10}$cycloalkyl.

2. The compound of claim 1, wherein R$^1$ is C$_6$-aryl which is substituted with at least one selected from halogen and C$_{1-6}$alkoxy, or 6 to 10-membered heteroaryl, which is unsubstituted or substituted with at least one substituent selected from halogen and C$_{1-6}$alkoxy.

3. The compound of claim 2, wherein R$^1$ is phenyl substituted with at least one substituent selected from fluoro and methoxy; or pyridyl, pyrimidyl, quinolyl, or isoquinolyl, each of which is unsubstituted or substituted with at least one substituent selected from fluoro and methoxy.

4. The compound of claim 1, wherein R$^2$ and R$^3$ are fused together with Y to form a 5 to 10-membered heterocycloalkyl group which is unsubstituted or substituted with —S(O$_2$)R$^4$, R$^4$ being C$_{1-6}$alkyl.

5. The compound of claim 4, wherein R$^2$ and R$^3$ are fused together with Y to form morpholinyl;

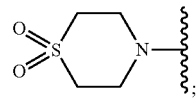 [SMILES: *N1CCS(=O)(=O)CC1]

or a piperidinyl or piperazinyl group substituted with —S(O$_2$)CH$_3$.

6. The compound of claim 1, wherein X is one or more substituents introduced to the ortho-, meta-, or para-position of the phenyl group, each selected independently from hydrogen and halogen.

7. The compound of claim 6, wherein X is hydrogen, 2,4-difluoro, or 3,5-difluoro.

8. The compound of claim 1, wherein n is 1 or 2.

9. The compound of claim 1, wherein Y is CH or N.

10. The compound of claim 1, which is an indenone derivative of formula (Ia) or a pharmaceutically acceptable salt thereof:

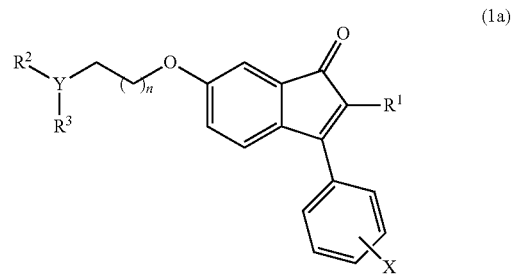

(Ia)

wherein, n, X, Y, R$^1$, R$^2$, and R$^3$ have the same meanings as defined in claim 1.

11. The compound of claim 10, wherein R1 is C6-aryl or 6 to 10-membered heteroaryl, which is unsubstituted or substituted with at least one substituent selected from halogen and C1-6alkoxy.

12. The compound of claim 11, wherein R$^1$ is phenyl which is substituted with at least one substituent selected from fluoro and methoxy; or pyridyl, pyrimidyl, quinolyl, or isoquinolyl, each of which is unsubstituted or substituted with at least one substituent selected from fluoro and methoxy.

13. The compound of claim 11, wherein R$^2$ and R$^3$ are fused together with Y to form a 5 to 10-membered heterocycloalkyl group, which is unsubstituted or substituted with —S(O$_2$)R$^4$, R$^4$ being C$_{1-6}$alkyl.

14. The compound of claim 13, wherein R$^2$ and R$^3$ are fused together with Y to form morpholinyl;

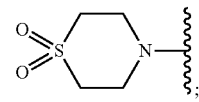 [SMILES: *N1CCS(=O)(=O)CC1]

or a piperidinyl or piperazinyl group substituted with —S(O$_2$)CH$_3$.

15. The compound of claim 11, wherein X is one or more substituents introduced to the ortho-, meta-, or para-position of the phenyl group, each selected independently from hydrogen and halogen.

16. The compound of claim 15, wherein X is hydrogen, 2,4-difluoro, or 3,5-difluoro.

17. The compound of claim 1, which is an indenone derivative selected from the compounds listed below or a pharmaceutically acceptable salt thereof:
1) 6-(2-morpholinoethoxy)-3-phenyl-2-(pyridin-3-yl)-1H-inden-1-one;
2) 6-(2-morpholinoethoxy)-2-(3-fluoro-4-methoxyphenyl)-3-phenyl-1H-inden-1-one;
3) 6-(2-morpholinoethoxy)-3-phenyl-2-(quinolin-3-yl)-1H-inden-1-one;
4) 4-(6-(2-morpholinoethoxy)-1-oxo-3-phenyl-1H-inden-2-yl)benzamide;
5) 3-(6-(2-morpholinoethoxy)-1-oxo-3-phenyl-1H-inden-2-yl)benzonitrile;
6) 6-(2-morpholinoethoxy)-2-(6-methoxypyridin-3-yl)-3-phenyl-1H-inden-1-one;
7) 6-(2-morpholinoethoxy)-3-phenyl-2-(pyrimidin-5-yl)-1H-inden-1-one;
8) 6-(2-morpholinoethoxy)-3-phenyl-2-(pyridin-4-yl)-1H-inden-1-one;
9) 6-(2-morpholinoethoxy)-2-(6-fluoropyridin-3-yl)-3-phenyl-1H-inden-1-one;
10) 6-(2-morpholinoethoxy)-2-(4-(phenyl)phenyl)-3-phenyl-1H-inden-1-one;
11) 6-(2-morpholinoethoxy)-3-phenyl-2-p-tolyl-1H-inden-1-one;
12) 2-(6-(2-morpholinoethoxy)-1-oxo-3-phenyl-1H-inden-2-yl)benzonitrile;
13) 6-(2-morpholinoethoxy)-2-(4-(trifluoromethyl)phenyl)-3-phenyl-1H-inden-1-one;
14) N-(3-(6-(2-morpholinoethoxy)-1-oxo-3-phenyl-1H-inden-2-yl)phenyl)acetamide;
15) 6-(2-morpholinoethoxy)-2-(isoquinolin-4-yl)-3-phenyl-1H-inden-1-one;
17) 6-(2-morpholinoethoxy)-2-(4-fluorophenyl)-3-phenyl-1H-inden-1-one;
18) 6-(2-morpholinoethoxy)-2-(3,4-difluorophenyl)-3-phenyl-1H-inden-1-one;
19) 6-(2-morpholinoethoxy)-2-(3-fluoro-4-methylphenyl)-3-phenyl-1H-inden-1-one;
20) 6-(2-morpholinoethoxy)-2-(3-aminophenyl)-3-phenyl-1H-inden-1-one;
21) 6-(2-morpholinoethoxy)-2-(4-phenoxyphenyl)-3-phenyl-1H-inden-1-one;
22) 6-(2-morpholinoethoxy)-2-(4-methoxyphenyl)-3-phenyl-1H-inden-1-one;
23) 6-(2-morpholinoethoxy)-2-(4-chlorophenyl)-3-phenyl-1H-inden-1-one;
24) 6-(2-morpholinoethoxy)-3-(4-fluorophenyl)-2-(pyridin-3-yl)-1H-inden-1-one;
25) 6-(2-morpholinoethoxy)-3-(4-fluorophenyl)-2-(pyrimidin-5-yl)-1H-inden-1-one;
26) 6-(2-morpholinoethoxy)-2-(3,4-difluorophenyl)-3-(4-fluorophenyl)-1H-inden-1-one;
27) 6-(2-morpholinoethoxy)-2-(4-(trifluoromethyl)phenyl)-3-(4-fluorophenyl)-1H-inden-1-one;
28) 6-(2-morpholinoethoxy)-3-(4-chlorophenyl)-2-(pyridin-3-yl)-1H-inden-1-one;
29) 6-(2-morpholinoethoxy)-3-(4-chlorophenyl)-2-(3,4-difluorophenyl)-1H-inden-1-one;
30) 6-(2-morpholinoethoxy)-3-(4-chlorophenyl)-2-(pyrimidin-5-yl)-1H-inden-1-one;
31) 6-(2-morpholinoethoxy)-3-(4-chlorophenyl)-2-(4-(trifluoromethyl)phenyl)-1H-inden-1-one;
32) 6-(2-morpholinoethoxy)-3-(4-(trifluoromethyl)phenyl)-2-(pyridin-3-yl)-1H-inden-1-one;
33) 6-(2-morpholinoethoxy)-2,3-bis(4-(trifluoromethyl)phenyl)-1H-inden-1-one;
34) 6-(2-morpholinoethoxy)-3-(4-(trifluoromethyl)phenyl)-2-(3,4-difluorophenyl)-1H-inden-1-one;
35) 6-(2-morpholinoethoxy)-3-(4-(trifluoromethyl)phenyl)-2-(pyrimidin-5-yl)-1H-inden-1-one;
36) 6-(2-morpholinoethoxy)-3-(3,5-difluorophenyl)-2-(pyridin-3-yl)-1H-inden-1-one;
37) 6-(2-morpholinoethoxy)-2-(4-(trifluoromethyl)phenyl)-3-(3,5-difluorophenyl)-1H-inden-1-one;
38) 6-(2-morpholinoethoxy)-2-(3,4-difluorophenyl)-3-(3,5-difluorophenyl)-1H-inden-1-one;
39) 6-(2-morpholinoethoxy)-3-(3,5-difluorophenyl)-2-(pyrimidin-5-yl)-1H-inden-1-one;
40) 4-methyl-4-(2-{[2-(1-methylpyridin-1-ium-3-yl)-1-oxo-3-phenyl-1H-inden-6-yl]oxy}ethyl)morpholin-4-ium diiodide;
41) 1-methyl-3-{6-[2-(morpholin-4-yl)ethoxy]-1-oxo-3-phenyl-1H-inden-2-yl}pyridin-1-ium iodide;
42) 4-oxido-4-(2-{[1-oxo-3-phenyl-2-(pyridin-3-yl)-1H-inden-6-yl]oxy}ethyl)morpholin-4-ium;
43) 4-oxido-4-(2-{[2-(1-oxidopyridin-1-ium-3-yl)-1-oxo-3-phenyl-1H-inden-6-yl]oxy}ethyl)morpholin-4-ium;
44) tert-butyl 4-(2-(1-oxo-3-phenyl-2-(pyridin-3-yl)-1H-inden-6-yloxy)ethyl)piperazine-1-carboxylate;
45) 6-[2-(4-(methylsulfonyl)piperazin-1-yl)ethoxy]-3-phenyl-2-(pyridin-3-yl)-1H-inden-1-one;
46) 6-(2-(piperazin-1-yl)ethoxy)-3-phenyl-2-(pyridin-3-yl)-1H-inden-1-one;
47) 6-[2-(4-(methylsulfonyl)piperazin-1-yl)ethoxy]-2,3-bis[4-(trifluoromethyl)phenyl]-1H-inden-1-one;
48) 2-(3,4-difluorophenyl)-6-(2-(4-(methylsulfonyl)piperazin-1-yl)ethoxy)-3-(4-(trifluoromethyl)phenyl)-1H-inden-1-one;
49) 6-(2-(4-(methylsulfonyl)piperazin-1-yl)ethoxy)-2-(pyrimidin-5-yl)-3-(4-(trifluoromethyl)phenyl)-1H-inden-1-one;
50) 3-(3,5-difluorophenyl)-6-(2-(4-(methylsulfonyl)piperazin-1-yl)ethoxy)-2-(4-(trifluoromethyl)phenyl)-1H-inden-1-one;
51) 2-(3,4-difluorophenyl)-3-(3,5-difluorophenyl)-6-(2-(4-(methylsulfonyl)piperazin-1-yl)ethoxy)-1H-inden-1-one;
52) 3-(3,5-difluorophenyl)-6-(2-(4-(methylsulfonyl)piperazin-1-yl)ethoxy)-2-(pyrimidin-5-yl)-1H-inden-1-one;
53) 3-(4-chlorophenyl)-2-(3,4-difluorophenyl)-6-(2-(4-(methylsulfonyl)piperazin-1-yl)ethoxy)-1H-inden-1-one;
54) 3-(4-chlorophenyl)-6-(2-(4-(methylsulfonyl)piperazin-1-yl)ethoxy)-2-(pyrimidin-5-yl)-1H-inden-1-one;
55) tert-butyl 4-(3-(1-oxo-3-phenyl-2-(pyridin-3-yl)-1H-inden-6-yloxy)propyl)piperazine-1-carboxylate;
56) 6-(2-(dimethylamino)ethoxy)-3-phenyl-2-(pyridin-3-yl)-1H-inden-1-one;
57) 6-(3-(dimethylamino)propoxy)-3-phenyl-2-(pyridin-3-yl)-1H-inden-1-one;
58) tert-butyl 4-(2-(3-(3,5-difluorophenyl)-1-oxo-2-(pyridin-3-yl)-1H-inden-6-yloxy)ethyl)piperazine-1-carboxylate;
59) 3-(3,5-difluorophenyl)-6-(2-(4-(methylsulfonyl)piperazin-1-yl)ethoxy)-2-(pyridin-3-yl)-1H-inden-1-one;
60) 3-(3,5-difluorophenyl)-6-(3-(dimethylamino)propoxy)-2-(pyridin-3-yl)-1H-inden-1-one;
61) 3-(3,5-difluorophenyl)-6-phenethoxy-2-(pyridin-3-yl)-1H-inden-1-one;
62) 3-(3,5-difluorophenyl)-6-(2-(pyridin-2-yl)ethoxy)-2-(pyridin-3-yl)-1H-inden-1-one;

63) 3-(3,5-difluorophenyl)-6-(2-(piperidin-1-yl)ethoxy)-2-(pyridin-3-yl)-1H-inden-1-one;
64) tert-butyl 4-(3-(3-(3,5-difluorophenyl)-1-oxo-2-(pyridin-3-yl)-1H-inden-6-yloxy)propyl)piperazine-1-carboxylate;
65) 6-(3-(4-methylpiperazin-1-yl)propoxy)-3-(3,5-difluorophenyl)-2-(pyridin-3-yl)-1H-inden-1-one;
66) 6-(3-(piperazin-1-yl)propoxy)-3-(3,5-difluorophenyl)-2-(pyridin-3-yl)-1H-inden-1-one;
67) 6-(3-(4-acetylpiperazin-1-yl)propoxy)-3-(3,5-difluorophenyl)-2-(pyridin-3-yl)-1H-inden-1-one;
68) 3-(3,5-difluorophenyl)-6-(3-(4-(methylsulfonyl)piperazin-1-yl)propoxy)-2-(pyridin-3-yl)-1H-inden-1-one;
69) tert-butyl 4-(2-(3-(3,5-difluorophenyl)-1-oxo-2-(pyridin-3-yl)-1H-inden-6-yloxy)ethyl)piperidine-1-carboxylate;
70) 3-(3,5-difluorophenyl)-6-(2-(piperidin-4-yl)ethoxy)-2-(pyridin-3-yl)-1H-inden-1-one;
71) 3-(3,5-difluorophenyl)-6-(2-(1-methylpiperidin-4-yl)ethoxy)-2-(pyridin-3-yl)-1H-inden-1-one;
72) 6-(2-(1-acetylpiperidin-4-yl)ethoxy)-3-(3,5-difluorophenyl)-2-(pyridin-3-yl)-1H-inden-1-one;
73) 3-(3,5-difluorophenyl)-6-(2-(1-(methylsulfonyl)piperidin-4-yl)ethoxy)-2-(pyridin-3-yl)-1H-inden-1-one;
74) 6-[2-(1,1-dioxothiomorpholin-4-yl)ethoxy]-3-(3,5-difluorophenyl)-2-(pyridin-3-yl)-1H-inden-1-one;
75) 3-(3,5-difluorophenyl)-6-(isopentyloxy)-2-(pyridin-3-yl)-1H-inden-1-one;
76) 6-(2-cyclohexylethoxy)-3-(3,5-difluorophenyl)-2-(pyridin-3-yl)-1H-inden-1-one;
77) 6-(2-cyclopentylethoxy)-3-(3,5-difluorophenyl)-2-(pyridin-3-yl)-1H-inden-1-one;
78) 3-(3,5-difluorophenyl)-2-(pyridin-3-yl)-6-(2-(tetrahydro-2H-pyran-4-yl)ethoxy)-1H-inden-1-one;
79) 3-(3,5-difluorophenyl)-2-(pyridin-3-yl)-6-((tetrahydrofuran-2-yl)methoxy)-1H-inden-1-one;
80) 6-(2-morpholinoethoxy)-3-(2-fluorophenyl)-2-(pyridin-3-yl)-1H-inden-1-one;
81) 6-(2-morpholinoethoxy)-3-(3-fluorophenyl)-2-(pyridin-3-yl)-1H-inden-1-one;
82) 6-(2-morpholinoethoxy)-3-(2,4-difluorophenyl)-2-(pyridin-3-yl)-1H-inden-1-one;
83) 6-(2-morpholinoethoxy)-3-phenyl-2-(pyridin-2-yl)-1H-inden-1-one;
84) 2-(benzo[b]thiophen-3-yl)-6-(2-morpholinoethoxy)-3-phenyl-1H-inden-1-one;
85) 2-(benzo[1,3]dioxol-5-yl)-6-(2-morpholinoethoxy)-3-phenyl-1H-inden-1-one;
86) 2-(5-chlorothiophen-2-yl)-6-(2-morpholinoethoxy)-3-phenyl-1H-inden-1-one;
87) 2-(1-methyl-1H-indol-5-yl)-6-(2-morpholinoethoxy)-3-phenyl-1H-inden-1-one;
88) 2-(1H-indol-2-yl)-6-(2-morpholinoethoxy)-3-phenyl-1H-inden-1-one;
89) 6-(2-morpholinoethoxy)-2-(6-(morpholin-4-yl)pyridin-3-yl)-3-phenyl-1H-inden-1-one;
90) 6-(2-morpholinoethoxy)-3-phenyl-2-(1H-pyrrol-2-yl)-1H-inden-1-one;
91) 6-(2-morpholinoethoxy)-2-(benzofuran-2-yl)-3-phenyl-1H-inden-1-one;
92) 3-(3,5-difluorophenyl)-6-[2-(1,1-dioxothiomorpholin-4-yl)ethoxy]-2-(quinolin-3-yl)-1H-inden-1-one;
93) 3-(3,5-difluorophenyl)-2-(6-methoxypyridin-3-yl)-6-[2-(1,1-dioxothiomorpholin-4-yl)ethoxy]-1H-inden-1-one;
94) 3-(3,5-difluorophenyl)-6-[2-(1,1-dioxothiomorpholin-4-yl)ethoxy]-2-p-tolyl-1H-inden-1-one;
95) 2-(3-fluoro-4-methoxyphenyl)-3-(3,5-difluorophenyl)-6-[2-(1,1-dioxothiomorpholin-4-yl)ethoxy]-1H-inden-1-one;
96) 3-(3,5-difluorophenyl)-6-{2-[4-(methylsulfonyl)piperazin-1-yl]ethoxy}-2-(quinolin-3-yl)-1H-inden-1-one;
97) 3-(3,5-difluorophenyl)-2-(6-methoxypyridin-3-yl)-6-{2-[4-(methylsulfonyl)piperazin-1-yl]ethoxy}-1H-inden-1-one;
98) 3-(3,5-difluorophenyl)-6-{2-[4-(methylsulfonyl)piperazin-1-yl]ethoxy}-2-p-tolyl-1H-inden-1-one;
99) 2-(3-fluoro-4-methoxyphenyl)-3-(3,5-difluorophenyl)-6-{2-[4-(methylsulfonyl)piperazin-1-yl]ethoxy}-1H-inden-1-one;
100) 3-(3,5-difluorophenyl)-2-(6-methoxypyridin-3-yl)-6-{2-[1-(methylsulfonyl)piperidin-4-yl]ethoxy}-1H-inden-1-one;
101) 3-(3,5-difluorophenyl)-6-{2-[1-(methylsulfonyl)piperidin-4-yl]ethoxy}-2-(quinolin-3-yl)-1H-inden-1-one;
102) 2-(3-fluoro-4-methoxyphenyl)-3-(3,5-difluorophenyl)-6-{2-[1-(methylsulfonyl)piperidin-4-yl]ethoxy}-1H-inden-1-one;
103) 3-(3,5-difluorophenyl)-6-{2-[1-(methylsulfonyl)piperidin-4-yl]ethoxy}-2-p-tolyl-1H-inden-1-one;
104) 3-(3,5-difluorophenyl)-6-{3-[4-(methylsulfonyl)piperazin-1-yl]propoxy}-2-(quinolin-3-yl)-1H-inden-1-one;
105) 3-(3,5-difluorophenyl)-6-{3-[4-(methylsulfonyl)piperazin-1-yl]propoxy}-2-p-tolyl-1H-inden-1-one;
106) 2-(3-fluoro-4-methoxyphenyl)-3-(3,5-difluorophenyl)-6-{3-[4-(methylsulfonyl)piperazin-1-yl]propoxy}-1H-inden-1-one;
107) 3-(3,5-difluorophenyl)-2-(6-methoxypyridin-3-yl)-6-{3-[4-(methylsulfonyl)piperazin-1-yl]propoxy}-1H-inden-1-one;
108) 3-(2,4-difluorophenyl)-6-{3-[4-(methylsulfonyl)piperazin-1-yl]propoxy}-2-p-tolyl-1H-inden-1-one;
109) 3-(2,4-difluorophenyl)-2-(6-methoxypyridin-3-yl)-6-{3-[4-(methylsulfonyl)piperazin-1-yl]propoxy}-1H-inden-1-one;
110) 2-(3-fluoro-4-methoxyphenyl)-3-(2,4-difluorophenyl)-6-{3-[4-(methylsulfonyl)piperazin-1-yl]propoxy}-1H-inden-1-one;
111) 3-(2,4-difluorophenyl)-6-{3-[4-(methylsulfonyl)piperazin-1-yl]propoxy}-2-(quinolin-3-yl)-1H-inden-1-one;
112) 3-(2,4-difluorophenyl)-6-[2-(1,1-dioxothiomorpholin-4-yl)ethoxy]-2-p-tolyl-1H-inden-1-one;
113) 3-(2,4-difluorophenyl)-2-(6-methoxypyridin-3-yl)-6-[2-(1,1-dioxothiomorpholin-4-yl)ethoxy]-1H-inden-1-one;
114) 2-(3-fluoro-4-methoxyphenyl)-3-(2,4-difluorophenyl)-6-[2-(1,1-dioxothiomorpholin-4-yl)ethoxy]-1H-inden-1-one;
115) 3-(2,4-difluorophenyl)-6-[2-(1,1-dioxothiomorpholin-4-yl)ethoxy]-2-(quinolin-3-yl)-1H-inden-1-one;
116) 3-(2,4-difluorophenyl)-6-{2-[4-(methylsulfonyl)piperazin-1-yl]ethoxy}-2-p-tolyl-1H-inden-1-one;
117) 3-(2,4-difluorophenyl)-2-(6-methoxypyridin-3-yl)-6-{2-[4-(methylsulfonyl)piperazin-1-yl]ethoxy}-1H-inden-1-one;
118) 2-(3-fluoro-4-methoxyphenyl)-3-(2,4-difluorophenyl)-6-{2-[4-(methylsulfonyl)piperazin-1-yl]ethoxy}-1H-inden-1-one;

119) 3-(2,4-difluorophenyl)-6-{2-[4-(methylsulfonyl)piperazin-1-yl]ethoxy}-2-(quinolin-3-yl)-1H-inden-1-one;
120) 3-(2,4-difluorophenyl)-6-{2-[1-(methylsulfonyl)piperidin-4-yl]ethoxy}-2-p-tolyl-1H-inden-1-one;
121) 3-(2,4-difluorophenyl)-2-(6-methoxypyridin-3-yl)-6-{2-[1-(methylsulfonyl)piperidin-4-yl]ethoxy}-1H-inden-1-one;
122) 2-(3-fluoro-4-methoxyphenyl)-3-(2,4-difluorophenyl)-6-{2-[1-(methylsulfonyl)piperidin-4-yl]ethoxy}-1H-inden-1-one;
123) 3-(2,4-difluorophenyl)-6-{2-[1-(methylsulfonyl)piperidin-4-yl]ethoxy}-2-(quinolin-3-yl)-1H-inden-1-one;
124) 3-(2,4-difluorophenyl)-6-[2-(morpholin-4-yl)ethoxy]-2-p-tolyl-1H-inden-1-one;
125) 3-(2,4-difluorophenyl)-2-(6-methoxypyridin-3-yl)-6-[2-(morpholin-4-yl)ethoxy]-1H-inden-1-one;
126) 2-(3-fluoro-4-methoxyphenyl)-3-(2,4-difluorophenyl)-6-[2-(morpholin-4-yl)ethoxy]-1H-inden-1-one;
127) 3-(2,4-difluorophenyl)-6-[2-(morpholin-4-yl)ethoxy]-2-(quinolin-3-yl)-1H-inden-1-one;
128) 3-(3,5-difluorophenyl)-5-[2-(morpholin-4-yl)ethoxy]-2-(pyridin-3-yl)-1H-inden-1-one;
129) 5-(2-morpholinoethoxy)-3-phenyl-2-(pyridin-3-yl)-1H-inden-1-one;
130) 5-(2-morpholinoethoxy)-3-phenyl-2-(pyridin-4-yl)-1H-inden-1-one;
131) 5-(2-morpholinoethoxy)-3-phenyl-2-p-tolyl-1H-inden-1-one;
132) 5-(2-morpholinoethoxy)-2-(3-fluoro-4-methylphenyl)-3-phenyl-1H-inden-1-one;
133) 3-(3,5-difluorophenyl)-5-[2-(4-(methylsulfonyl)piperazin-1-yl)ethoxy]-2-(pyridin-3-yl)-1H-inden-1-one;
134) 5-[2-(4-(methylsulfonyl)piperazin-1-yl)ethoxy]-3-phenyl-2-(pyridin-3-yl)-1H-inden-1-one;
135) 5-[2-(4-(methylsulfonyl)piperazin-1-yl)ethoxy]-3-phenyl-2-p-tolyl-1H-inden-1-one; and
136) 5-[2-(4-(methylsulfonyl)piperazin-1-yl)ethoxy]-2-(3-fluoro-4-methylphenyl)-3-phenyl-1H-inden-1-one.

18. The compound of claim 1, which is an indenone derivative selected from the compounds listed below or a pharmaceutically acceptable salt thereof:
1) 6-(2-morpholinoethoxy)-3-phenyl-2-(pyridin-3-yl)-1H-inden-1-one;
45) 6-[2-(4-(methylsulfonyl)piperazin-1-yl)ethoxy]-3-phenyl-2-(pyridin-3-yl)-1H-inden-1-one;
73) 3-(3,5-difluorophenyl)-6-(2-(1-(methylsulfonyl)piperidin-4-yl)ethoxy)-2-(pyridin-3-yl)-1H-inden-1-one;
74) 6-[2-(1,1-dioxothiomorpholin-4-yl)ethoxy]-3-(3,5-difluorophenyl)-2-(pyridin-3-yl)-1H-inden-1-one;
82) 6-(2-morpholinoethoxy)-3-(2,4-difluorophenyl)-2-(pyridin-3-yl)-1H-inden-1-one;
97) 3-(3,5-difluorophenyl)-2-(6-methoxypyridin-3-yl)-6-{2-[4-(methylsulfonyl)piperazin-1-yl]ethoxy}-1H-inden-1-one;
102) 2-(3-fluoro-4-methoxyphenyl)-3-(3,5-difluorophenyl)-6-{2-[1-(methylsulfonyl)piperidin-4-yl]ethoxy}-1H-inden-1-one;
113) 3-(2,4-difluorophenyl)-2-(6-methoxypyridin-3-yl)-6-[2-(1,1-dioxothiomorpholin-4-yl)ethoxy]-1H-inden-1-one;
114) 2-(3-fluoro-4-methoxyphenyl)-3-(2,4-difluorophenyl)-6-[2-(1,1-dioxothiomorpholin-4-yl)ethoxy]-1H-inden-1-one; and
122) 2-(3-fluoro-4-methoxyphenyl)-3-(2,4-difluorophenyl)-6-{2-[1-(methylsulfonyl)piperidin-4-yl]ethoxy}-1H-inden-1-one.

19. A pharmaceutical composition comprising the compound according to claim 1 or pharmaceutically acceptable salt thereof as an active ingredient and a pharmaceutically acceptable carrier.

20. A method for treating a bone disease selected from the group consisting of osteoporosis, bone growth disorder, bone fractures, periodontal disease, Paget's disease, metastatic carcinoma, and rheumatoid arthritis, comprising administering a therapeutically effective amount of the compound of claim 1 or a pharmaceutically acceptable salt thereof.

* * * * *